United States Patent [19]

Jadhav et al.

[11] Patent Number: 5,760,028
[45] Date of Patent: Jun. 2, 1998

[54] INTEGRIN RECEPTOR ANTAGONISTS

[75] Inventors: Prabhakar Kondaji Jadhav, Wilmington, Del.; Joseph James Petraitis, Glenmoore, Pa.; Douglas Guy Batt, Wilmington, Del.

[73] Assignee: The DuPont Merck Pharmaceutical Company, Wilmington, Del.

[21] Appl. No.: 770,538

[22] Filed: Dec. 20, 1996

Related U.S. Application Data

[60] Provisional application Nos. 60/009,088, Dec. 22, 1995, and 60/025,699, Aug. 9, 1996.

[51] Int. Cl.⁶ .................... C07D 403/14; C07D 401/14; A61K 31/54; A61K 31/535
[52] U.S. Cl. .................... 514/211; 544/238; 544/262; 544/350; 544/67; 544/224; 544/333; 544/295; 544/337; 544/371; 544/361; 544/96; 544/98; 544/182; 544/179; 546/119; 546/244; 546/278.1; 546/268.1; 546/272.4; 548/361.1; 548/122; 548/127; 548/128; 548/131; 548/134; 548/136; 548/146; 548/254; 548/255; 548/262.2; 548/312.1; 540/545; 540/554; 540/575; 540/596; 540/597; 540/598; 540/599; 540/600; 540/601; 540/602; 540/603; 514/212; 514/228.2; 514/229.2; 514/227; 514/253; 514/256; 514/258; 514/242
[58] Field of Search .................... 514/211, 212, 514/228.2, 229.2, 227, 253, 258, 256, 242; 540/596–603, 575, 554, 545; 548/361.1, 122, 128, 127, 131, 134, 136, 146, 254, 255, 262.2, 312.1; 544/238, 262, 350, 67, 224, 333, 295, 337, 371, 361, 96, 98, 179, 182

[56] References Cited

U.S. PATENT DOCUMENTS

| | | | |
|---|---|---|---|
| 4,808,405 | 2/1989 | Smith et al. | 424/94.3 |
| 4,950,764 | 8/1990 | Nakamura et al. | 248/243 |
| 5,187,157 | 2/1993 | Kettner et al. | 514/64 |
| 5,288,707 | 2/1994 | Metternich | 514/19 |
| 5,444,038 | 8/1995 | James et al. | 504/253 |

FOREIGN PATENT DOCUMENTS

| | | |
|---|---|---|
| 0655439 | 5/1995 | European Pat. Off. |
| 9309795 | 5/1993 | WIPO |
| 9408962 | 4/1994 | WIPO |
| 9504531 | 2/1995 | WIPO |
| 9514683 | 6/1995 | WIPO |
| 9517397 | 6/1995 | WIPO |
| 9620192 | 7/1996 | WIPO |
| 9637492 | 11/1996 | WIPO |

*Primary Examiner*—Matthew V. Grumbling
*Attorney, Agent, or Firm*—Blair Q. Ferguson

[57] ABSTRACT

This invention relates to novel heterocycles including 3-[1-[3-(imidazolin-2-ylamino)propyl]indazol-5-ylcarbonylamino]-2-(benzyloxycarbonylamino)propionic acid, which are useful as antagonists of the $\alpha_v\beta_3$ integrin and related cell surface adhesive protein receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

16 Claims, No Drawings

INTEGRIN RECEPTOR ANTAGONISTS

FIELD OF THE INVENTION

This application claims priority under 35 U.S.C. 119 (e) from provisional application Ser. No. 60/009,088, filed Dec. 22, 1995 and 60/025,699 filed Aug. 9, 1996.

This invention relates to novel heterocycles which are useful as antagonists of the $\alpha_v\beta_3$ integrin and related cell surface adhesive protein receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

BACKGROUND OF THE INVENTION

Angiogenesis or neovascularization is critical for normal physiological processes such as embryonic development and wound repair (Folkman and Shing, J. Biol. Chem. 1992, 26:10931–10934; D'Amore and Thompson, Ann. Rev. Physiol. 1987, 49:453–464). However, angiogenesis also occurs pathologically, for example, in ocular neovascularization (leading to diabetic retinopathy, neovascular glaucoma, retinal vein occlusion and blindness), in rheumatoid arthritis and in solid tumors (Folkman and Shing, J. Biol. Chem., 1992, 267:10931–10934; Blood and Zetter, Biochim. Biophys. Acta., 1990, 1032:118–128).

Tumor dissemination, or metastasis, involves several distinct and complementary components, including the penetration and traversing of tumor cells through basement membranes and the establishment of self-sustaining tumor foci in diverse organ systems. To this end, angiogenesis is critical to tumor survival. Without neovascularization, tumor cells lack the nourishment to divide and will not be able to leave the primary tumor site (Folkman and Shing, J. Biol. Chem., 1992, 267:10931–10934).

Inhibition of angiogenesis in animal models of cancer has been shown to result in tumor growth suppression and prevention of metastatic growth (Herblin et al., Exp. Opin. Ther. Patents, 1994, 1–14). Many angiogenic inhibitors have been directed toward blocking initial cytokine-dependent induction of new vessel growth, e.g. antibodies to endothelial cell growth factors. However, these approaches are problematic because tumor and inflammatory cells can secrete multiple activators of angiogenesis (Brooks et al., Cell, 1994, 79:1157–1164). Therefore, a more general approach that would allow inhibition of angiogenesis due to a variety of stimuli would be of benefit.

The integrin $\alpha_v\beta_3$, sometimes called the vitronectin receptor, is preferentially expressed on angiogenic blood vessels in chick and man (Brooks et al., Science, 1994, 264:569–571; Enenstein and Kramer, J. Invest. Dermatol., 1994, 103:381–386). $\alpha_v\beta_3$ is the most promiscuous member of the integrin family, allowing endothelial cells to interact with a wide variety of extracellular matrix components (Hynes, Cell, 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley et al., J. Cell Biol., 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$, the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell and smooth muscle cell migration and, therefore, may play a fundamental role in vascular cell biology.

Recently, an antibody to the $\alpha_v\beta_3$ integrin has been developed that inhibits the interaction of this integrin with agonists such as vitronectin (Brooks et al., Science, 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks et al., Cell, 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis and are recognized as being useful as therapeutic agents for the treatment of human diseases such as cancer, restenosis, thromoembolic disorders, rheumatoid arthritis and ocular vasculopathies (Folkman and Shing, J. Biol. Chem., 1992, 267:10931–10934).

Increasing numbers of other cell surface receptors have been identified which bind to extracellular matrix ligands or other cell adhesion ligands thereby mediating cell-cell and cell-matrix adhesion processes. Like the $\alpha_v\beta_3$ integrin, these receptors belong to the integrin gene superfamily and are composed of heterodimeric transmembrane glycoproteins containing α- and β-subunits. Integrin subfamilies contain a common β-subunit combined with different α-subunits to form adhesion receptors with unique specificity. The genes for eight distinct β-subunits have been cloned and sequenced to date.

The integrin $\alpha_v\beta_3$ is a member of the $\beta_3$ integrin subfamily and has been described on platelets, endothelial cells, melanoma, smooth muscle cells, and osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like the major platelet integrin GPIIb/IIIa, the vitronectin receptor binds a variety of RGD-containing adhesive proteins such as vitronectin, fibronectin, von Willibrand factor, fibrinogen, osteopontin, bone sialoprotein II and thrombospondin in a manner mediated by the RGD sequence.

A key event in bone resorption is the adhesion of osteoclasts to the matrix of bone. Studies with monoclonal antibodies have implicated the $\alpha_v\beta_3$ receptor in this process and suggest that a selective $\alpha_v\beta_3$ antagonist would have utility in blocking bone resorption in diseases such as osteoporosis (Horton et al., J. Bone Miner. Res., 1993, 8:239–247; Helfrich et al., J. Bone Miner. Res., 1992, 7:335–343).

PCT Patent Application Publication Number WO94/08962, published Apr. 28, 1994 discloses fibrinogen receptor antagonists of the general formula shown below:

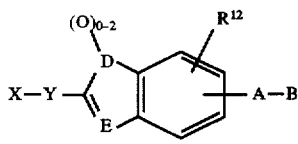

European Patent Application Publication Number 655,439, published May 31, 1995 discloses fibrinogen receptor antagonists of the general formula shown below:

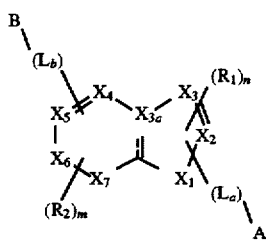

PCT Patent Application Publication Number WO95/17397, published Jun. 29, 1995, discloses fibrinogen receptor antagonists of the general formula shown below:

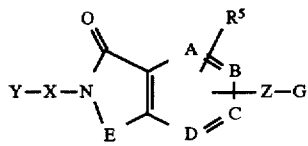

PCT Patent Application Publication Number WO96/20192, published Jul. 4, 1996, discloses fibrinogen receptor antagonists of the general formula shown below:

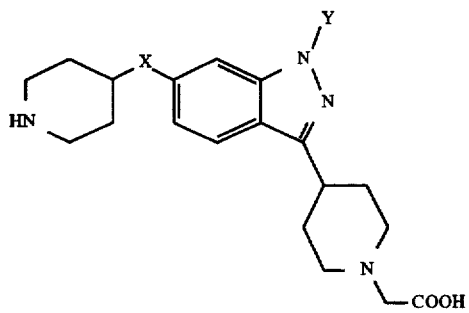

Co-pending, commonly assigned U.S. patent application Ser. No. 08/455,768 filed May 31, 1995 discloses integrin inhibitors of the general formula shown below:

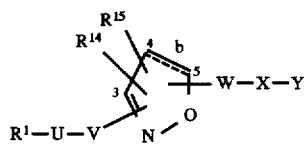

None of the above references discloses or suggests the compounds of the present invention which are described in detail below.

SUMMARY OF THE INVENTION

The present invention provides novel nonpeptide compounds which bind to integrin receptors thereby altering cell-matrix and cell-cell adhesion processes. The compounds of the present invention are useful for the inhibition of cell adhesion and the treatment (including prevention) of angiogenic disorders, inflammation, bone degradation, cancer metastases, diabetic retinopathy, thrombosis, restenosis, macular degeneration, and other conditions mediated by cell adhesion and/or cell migration and/or angiogenesis.

One aspect of this invention provides novel compounds of Formula Ia, Ib or Ic (described below) which are useful as antagonists of the $\alpha_v\beta_3$ integrin. The $\alpha_v\beta_3$ integrin is also referred to as the $\alpha_v\beta_3$ receptor or the vitronectin receptor. The compounds of the present invention inhibit the binding of vitronectin or other RGD-containing ligands to $\alpha_v\beta_3$ and inhibit cell adhesion. The present invention also includes pharmaceutical compositions containing such compounds, and methods of using such compounds for the inhibition of angiogenesis, and/or for the treatment of disorders mediated by angiogenesis.

Another aspect of the present invention comprises agents that inhibit the binding of vitronectin to the $\alpha_v\beta_3$ receptor for the treatment (including prevention) of thrombosis, which do not significantly alter hemostatic balance and do not significantly inhibit platelet aggregation and do not significantly inhibit coagulation. Also, the compounds of the current invention can be used for the treatment or prevention of restenosis.

The present invention also provides novel compounds, pharmaceutical compositions and methods which may be used in the treatment or prevention of other diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, inflammatory bowel disease and other autoimmune diseases.

Also included in the present invention are pharmaceutical kits comprising one or more containers containing pharmaceutical dosage units comprising a compound of Formula Ia, Ib or Ic, for the therapeutic inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

DETAILED DESCRIPTION OF THE INVENTION

The present invention provides novel compounds of Formula Ia, Ib or Ic (described below) which bind to integrin receptors thereby altering cell-matrix and cell-cell adhesion processes. The compounds of the present invention are useful for the inhibition of cell adhesion and the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis, in a mammal.

One aspect of this invention provides novel compounds of Formula Ia, Ib or Ic (described below) which are, useful as antagonists of the $\alpha_v\beta_3$ integrin. The $\alpha_v\beta_3$ integrin is also referred to as the $\alpha_v\beta_3$ receptor or the vitronectin receptor. The compounds of the present invention inhibit the binding of vitronectin or other RGD-containing ligands to $\alpha_v\beta_3$ and inhibit cell adhesion. The present invention also includes pharmaceutical compositions containing such compounds of Formula Ia, Ib or Ic, and methods of using such compounds for the inhibition of angiogenesis, and/or for the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis, in a mammal.

[1] One aspect of the present invention comprises compounds of Formula Ia:

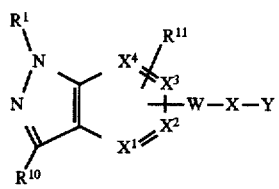

including stereoisomeric forms thereof, or mixtures of stereoisomeric forms thereof, or pharmaceutically acceptable salt or prodrug forms thereof, wherein:

$X^1$, $X^2$, $X^3$, and $X^4$ are independently selected from nitrogen or carbon provided that at least two of $X^1$, $X^2$, $X^3$ and $X^4$ are carbon; $R^1$ is selected from:

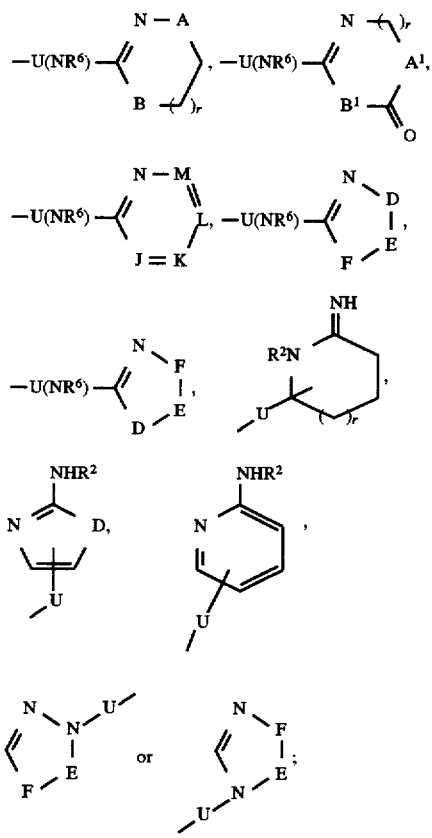

A and B are independently —$CH_2$—, —O—, —$N(R^2)$—, or —C(=O)—;

$A^1$ and $B^1$ are independently —$CH_2$— or —$N(R^3)$—;

D is —$N(R^2)$—, —O—, —S—, —C(=O)— or —$SO_2$—;

E—F is —$C(R^4)=C(R^5)$—, —$N=C(R^4)$—, —$C(R^4)=N$—, or —$C(R^4)_2C(R^5)_2$—;

J, K, L and M are independently selected from —$C(R^4)$—, —$C(R^5)$— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl($C_1$–$C_6$ alkyl)-, ($C_1$–$C_6$ alkyl)carbonyl—, arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl)carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—,
—$(CH_2)_n(C\equiv C)(CH_2)_m$—,
—$(CH_2)_nQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—,
—$(CH_2)_nC(=O)N(R^6)(CH_2)_m$—
—$(CH_2)_nN(R^6)(C=O)(CH^2)_m$—, or
—$(CH_2)_nS(O)_p(CH_2)_m$—;

wherein one or more of the methylene groups in U is optionally substituted with $R^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl; $R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl ($C_1$–$C_6$ alkyl)-, or heteroaryl($C_0$–$C_6$ alkyl)-;

$R^{10}$ is selected from: H, $C_1$–$C_4$ alkoxy substituted with 0–1 $R^{21}$, $N(R^6)_2$, halogen, $NO_2$, CN, $CF_3$, $CO_2R^{17}$, C(=O)$R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)-substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:
—$(C(R^{12})_2)_qC(=O)N(R^{13})$—, or —$C(=O)$—$N(R^{13})$—$(C(R^{12})_2)_q$—;

X is —$C(R^{12})(R^{14})$—$C(R^{12})(R^{15})$—; or
alternatively, W and X can be taken together to be

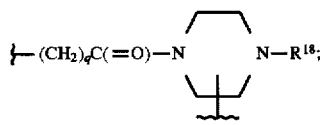

$R^{12}$ is selected from H, halogen, $C_1$–$C_6$ alkyl $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from H, $C_1$–$C_6$ alkyl, $C_3$–$C_7$ cycloalkylmethyl, or aryl($C_1$–$C_6$ alkyl)-;

$R^{14}$ is selected from:
H, $C_1$–$C_6$ alkylthio ($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from:
H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:
—$COR^{19}$, —$SO_3H$, —$PO_3H$, tetrazolyl, —$CONHNHSO_2CF_3$, —$CONHSO_2R^{17}$, —$CONHSO_2NHR^{17}$, —$NHCOCF_3$, —$NHCONHSO_2R^{17}$, —$NHSO_2R^{17}$, —$OPO_3H_2$, —$OSO_3H$, —$PO_3H_2$, —$SO_3H$, $SO_2NHCOR^{17}$, —$SO_2NHCO_2R^{17}$,

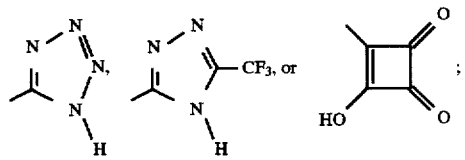

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from:
—$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo,cyano, amino, $CF_3$, and $NO_2$;

$R^{18}$ is selected from:
H, —$C(=O)$—$O$—$R^{17}$, —$C(=O)$—$R^{17}$, —$C(=O)$—$NH$—$R^{17}$, —$SO_2$—$R^{17}$, or —$SO_2$—$NR^{20}R^{17}$;

$R^{19}$ is selected from: hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5alkyl-1,3-dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N$—($C_1$–$C_{10}$ alkoxy)-;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from: COOH or $NR^6_2$;

m is 0–4;

n is 0–4;

t is 0–4;

p is 0–2;

q is 0–2; and r is 0–2;

with the following provisos:

(1) t, n, m and q are chosen such that the number of atoms connecting $R^1$ and Y is in the range of 10–14; and (2) n and m are chosen such that the value of n plus m is greater than one unless U is —$(CH_2)_tQ(CH_2)_m$—.

[2] Preferred compounds of the invention as described above are compounds of the Formula Ia:

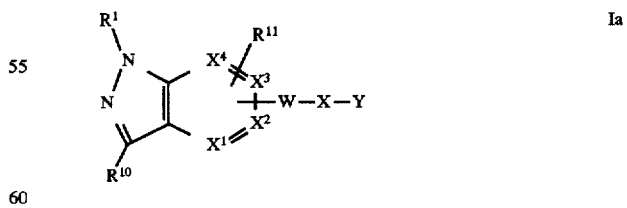

including stereoisomeric forms thereof, or mixtures of stereoisomeric forms thereof, or pharmaceutically acceptable salt or prodrug forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

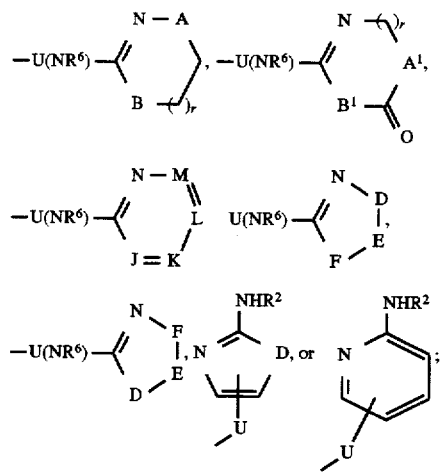

A and B are independently —$CH_2$—, —O—, —$N(R^2)$—, or —$C(=O)$—;

$A^1$ and $B^1$ are independently —$CH_2$— or —$N(R^3)$—;

D is —$N(R^2)$—, —O—, —S—, —$C(=O)$— or —$SO_2$—;

E—F is —$C(R^4)=C(R^5)$—, —$N=C(R^4)$—, —$C(R^4)=N$—, or —$C(R^4)_2(R^5)_2$—;

J, K, L and M are independently selected from —$C(R^4)$—, —$C(R^5)$— or —N—, provided that at least one of J, K, L and M is not —N—;

$R^2$ is selected from: H, $C_1$-$C_6$ alkyl, ($C_1$-$C_6$ alkyl)carbonyl, ($C_1$-$C_6$ alkoxy)carbonyl, $C_1$-$C_6$ alkylaminocarbonyl, $C_3$-$C_6$ alkenyl, $C_3$-$C_7$ cycloalkyl, $C_4$-$C_{11}$ cycloalkylalkyl, aryl, heteroaryl($C_1$-$C_6$ alkyl)carbonyl, heteroarylcarbonyl, aryl($C_1$-$C_6$ alkyl)-, ($C_1$-$C_6$ alkyl)carbonyl, arylcarbonyl, alkylsulfonyl, arylsulfonyl, aryl($C_1$-$C_6$ alkyl)sulfonyl, heteroarylsulfonyl, heteroaryl($C_1$-$C_6$ alkyl)sulfonyl, aryloxycarbonyl, or aryl($C_1$-$C_6$ alkoxy)carbonyl, wherein said aryl groups are substituted with 0–2 substituents selected from the group consisting of $C_1$-$C_4$ alkyl, $C_1$-$C_4$ alkoxy, halo, $CF_3$, and nitro;

$R^3$ is selected from: H, $C_1$-$C_6$ alkyl, $C_3$-$C_7$ cycloalkyl, $C_4$-$C_{11}$ cycloalkylalkyl, aryl, aryl($C_1$-$C_6$ alkyl)-, or heteroaryl($C_1$-$C_6$ alkyl)-;

$R^4$ and $R^5$ are independently selected from: H, $C_1$-$C_4$ alkoxy, $NR^2R^3$, halogen, $NO_2$, CN, $CF_3$, $C_1$-$C_6$ alkyl, $C_3$-$C_6$ alkenyl, $C_3$-$C_7$ cycloalkyl, $C_4$-$C_{11}$ cycloalkylalkyl, aryl, aryl($C_1$-$C_6$ alkyl)-, $C_2$-$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$-$C_4$ alkyl, $C_1$-$C_4$ alkoxy, halo, cyano, amino, $CF_3$, or $NO_2$;

U is selected from:

—$(CH_2)_n$—,
—$(CH_2)_n(CR^7=CR^8)(CH_2)_m$—,
—$(CH_2)_nQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—, or
—$(CH_2)_nS(O)_p(CH_2)_m$—;

wherein one or more of the methylene groups in U is optionally substituted with $R^7$;

Q is selected from 1,2-phenylene, 1,3-phenylene, 2,3-pyridinylene, 3,4-pyyrdinylene, or 2,4-pyridinylene;

$R^6$ is selected from: H, $C_1$-$C_4$ alkyl, or benzyl;

$R^7$ and $R^8$ are independently selected from: H, $C_1$-$C_6$ alkyl, $C_3$-$C_7$ cycloalkyl, $C_4$-$C_{11}$ cycloalkylalkyl, aryl, aryl($C_1$-$C_6$ alkyl)-, or heteroaryl($C_0$-$C_6$ alkyl)-;

$R^{10}$ is selected from: H, $C_1$-$C_4$ alkoxy substituted with 0–1 $R^{21}$, $N(R^6)_2$, halogen, $NO_2$, CN, $CF_3$, $CO_2R^{17}$, $C(=O)R^{17}$, $CONR^{17}R^{20}$, —$SO_2R^{17}$, —$SO_2NR^{17}R^{20}$, $C_1$-$C_6$ alkyl substituted with 0–1 $R^{15}$ or 0–1 $R^{21}$, $C_3$-$C_6$ alkenyl substituted with 0–1 $R^{15}$ or 0–1 $R^{21}$, $C_3$-$C_7$ cycloalkyl substituted with 0–1 $R^{15}$ or 0–1 $R^{21}$, $C_4$-$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$-$C_6$ alkyl)-substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$-$C_4$ alkyl substituted with 0–1 $R^{21}$, $C_1$-$C_4$ alkoxy substituted with 0–1 $R^{21}$, aryl substituted with 0–1 $R^{21}$, aryl($C_1$-$C_6$ alkyl)-substituted with 0–1 $R^{21}$, ($C_1$-$C_4$ alkoxy)carbonyl substituted with 0–1 $R^{21}$, ($C_1$-$C_4$ alkyl)carbonyl substituted with 0–1 $R^{21}$ $C_1$-$C_4$ alkylsulfonyl substituted with 0–1 $R^{21}$, or $C_1$-$C_4$ alkylaminosulfonyl substituted with 0–1 $R^{21}$;

W is —$C(=O)$—$N(R^{13})$—$(C(R^{12})_2)_q$—;

X is —$C(R^{12})(R^{14})$—$C(R^{12})(R^{15})$—;

alternatively, W and X can be taken together to be

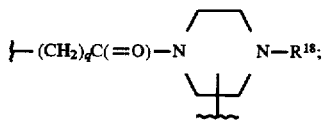

$R^{12}$ is H or $C_1$-$C_6$ alkyl;

$R^{13}$ is selected from: H, $C_1$-$C_6$ alkyl, $C_3$-$C_7$ cycloalkylmethyl, or aryl($C_1$-$C_6$ alkyl)-;

$R^{14}$ is selected from:

H, $C_1$-$C_6$ alkylthioalkyl, aryl($C_1$-$C_{10}$ alkylthioalkyl)-, aryl($C_1$-$C_{10}$ alkoxyalkyl)-, $C_1$-$C_{10}$ alkyl, $C_1$-$C_{10}$ alkoxyalkyl, $C_1$-$C_6$ hydroxyalkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl($C_1$-$C_6$ alkyl)-, heteroaryl($C_1$-$C_6$ alkyl)-, aryl, heteroaryl, $CO_2R^{17}$, $C(=O)R^{17}$, or $CONR^{17}R^{20}$, or provided that any of the above alkyl, cycloalkyl, aryl or heteroaryl groups may be substituted independently with 0–1 $R^{16}$ or 0–2 $R^{11}$;

$R^{15}$ is selected from:

H, $R^{16}$, $C_1$-$C_{10}$ alkyl, $C_1$-$C_{10}$ alkoxyalkyl, $C_1$-$C_{10}$ alkylaminoalkyl, $C_1$-$C_{10}$ dialkylaminoalkyl, $C_1$-$C_{10}$ alkylcarbonyl, aryl($C_0$-$C_6$ alkyl)carbonyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl($C_1$-$C_6$ alkyl)-, heteroaryl($C_1$-$C_6$ alkyl)-, aryl, heteroaryl, $CO_2R^{17}$, $C(=O)R^{17}$, $CONR^{17}R^{20}$, $SO_2R^{17}$ or $SO_2NR^{17}R^{20}$, provided that any of the above alkyl, cycloalkyl, aryl or heteroaryl groups may be substituted independently with 0–2 $R^{11}$;

Y is selected from:

−COR$^{19}$, −SO$_3$H,

[triazole structure with methyl group and NH]

[pyrazole-like structure with CF$_3$ and methyl, NH]

or

[squaric acid derivative: cyclobutenedione with methyl and HO];

R$^{16}$ is selected from:
—N(R$^{20}$)—C(=O)—O—R$^{17}$,
—N(R$^{20}$)—C(=O)—R$^{17}$,
—N(R$^{20}$)—C(=O)—NH—R$^{17}$,
—N(R$^{20}$)SO$_2$—R$^{17}$, or
—N(R$^{20}$)SO$_2$—NR$^{20}$R$^{17}$;

R$^{17}$ is selected from:
C$_1$–C$_{10}$ alkyl, C$_3$–C$_{11}$ cycloalkyl, aryl(C$_1$–C$_6$ alkyl)-, (C$_1$–C$_6$ alkyl)aryl, heteroaryl(C$_1$–C$_6$ alkyl)-, (C$_1$–C$_6$ alkyl)heteroaryl, biaryl(C$_1$–C$_6$ alkyl)-, heteroaryl, or aryl, wherein said aryl or heteroaryl groups are optionally substituted with 0–3 substituents selected from the group consisting of: C$_1$–C$_4$ alkyl, C$_1$–C$_4$ alkoxy, aryl, heteroaryl, halo, cyano, amino, CF$_3$, and NO$_2$;

R$^{18}$ is selected from:
H,
—C(=O)—O—R$^{17}$,
—C(=O)—R$^{17}$,
—C(=O)—NH—R$^{17}$,
—SO$_2$—R$^{17}$, or
—SO$_2$—NR$^{20}$R$^{17}$;

R$^{19}$ is selected from: hydroxy, C$_1$–C$_{10}$ alkyloxy,
C$_3$–C$_{11}$ cycloalkyloxy, C$_6$–C$_{10}$ aryloxy,
C$_7$–C$_{11}$ aralkyloxy, C$_3$–C$_{10}$ alkylcarbonyloxyalkyloxy,
C$_3$–C$_{10}$ alkoxycarbonyloxyalkyloxy,
C$_2$–C$_{10}$ alkoxycarbonylalkyloxy,
C$_5$–C$_{10}$ cycloalkylcarbonyloxyalkyloxy,
C$_5$–C$_{10}$ cycloalkoxycarbonyloxyalkyloxy,
C$_5$–C$_{10}$ cycloalkoxycarbonylalkyloxy,
C$_7$–C$_{11}$ aryloxycarbonylalkyloxy,
C$_8$–C$_{12}$ aryloxycarbonyloxyalkyloxy,
C$_8$–C$_{12}$ arylcarbonyloxyalkyloxy,
C$_5$–C$_{10}$ alkoxyalkylcarbonyloxyalkyloxy,
C$_5$–C$_{10}$ (5-alkyl-1,3-dioxa-cyclopenten-2-one-yl)methyloxy, C$_{10}$–C$_{14}$ (5-aryl-1,3-dioxa-cyclopenten-2-one-yl)methyloxy, or (R$^{11}$)(R$^{12}$)N—(C$_1$–C$_{10}$ alkoxy)-;

R$^{20}$ selected from: H, C$_1$–C$_6$ alkyl, C$_3$–C$_7$ cycloalkyl, C$_4$–C$_{11}$ cycloalkylalkyl, aryl(C$_1$–C$_6$ alkyl)-, or heteroaryl(C$_1$–C$_6$ alkyl)-;

R$^{21}$ is selected from COOH or NR$^6{}_2$;
m is 0–4;
n is 0–4;
p is 0–2;
q is 0–2;
t is 0–4; and
r is 0–2.

[3] Further preferred compounds of the invention as described above are compounds of the Formula IIa or IIb:

[Structure IIa: pyrazole ring with R$^1$, R$^{10}$, X$_1$, X$_3$, W—X—Y]

or

[Structure IIb: similar pyrazole-containing structure with R$^1$, R$^{10}$, X$_3$, W, X, Y]

including stereoisomeric forms thereof, or mixtures of stereoisomeric forms thereof, or pharmaceutically acceptable salt or prodrug forms thereof wherein:

X$^1$ and X$_3$ are independently selected from nitrogen or carbon;

R$^1$ is selected from:

[Various heterocyclic structures shown, including imidazolines, pyridines, thiazoles, benzimidazoles, thiazolopyridines, imidazopyridines, pyrimidines, benzothiazoles, aminothiazoles, and aminopyridines, with —UNR$^6$— or —U— linkers, and substituents R$^4$, R$^5$]

-continued

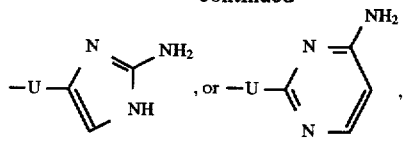

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_tQ(CH_2)_m$— or —C(=O)$(CH_2)_{n-1}$—, wherein one of the methylene groups is optionally substituted with $R^7$; Q is selected from 1,2-phenylene, 1,3-phenylene, 2,3-pyridinylene, 3,4-pyrrdinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, $C_1$–$C_4$ alkoxy substituted with 0–1 $R^{21}$, halogen, $CO_2R^{17}$, $CONR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl ($C_1$–$C_6$ alkyl)-substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH ($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$) $R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy, methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6_2$;

m is 0 or 1;

n is 1–4; and t is 0 or 1.

[4] Still further preferred compounds of the above invention are compounds of the Formula IIa or IIb:

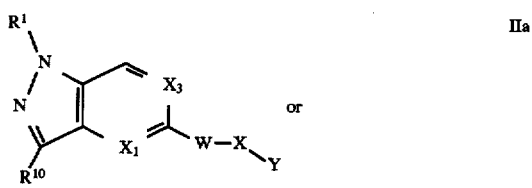

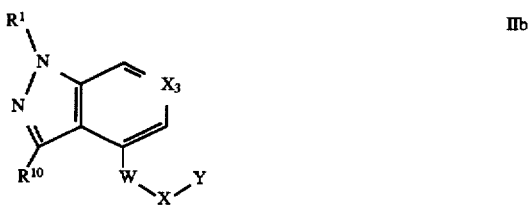

including stereoisomeric forms thereof, or mixtures of stereoisomeric forms thereof, or pharmaceutically acceptable salt or prodrug forms thereof wherein: $X_1$ and $X_3$ are independently selected from nitrogen or carbon, provided that at least one of $X_1$ and $X_3$ is carbon;

$R^1$ is selected from:

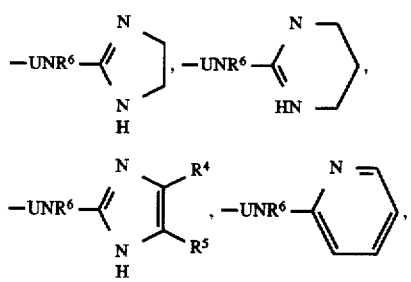

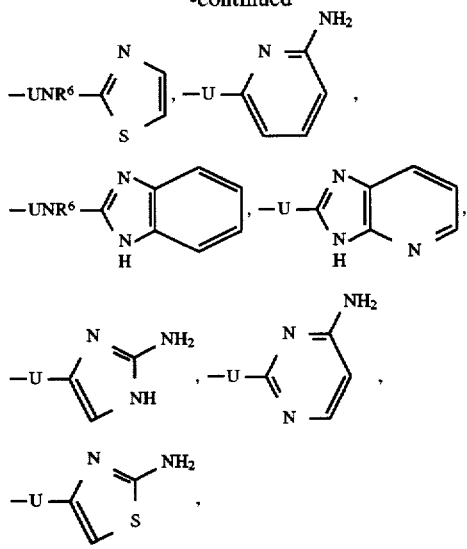

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_t$Q $(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, $C_1$–$C_4$ alkoxy substituted with 0–1 $R^{21}$, halogen, $CO_2R^{17}$, $CONR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl ($C_1$–$C_6$ alkyl)-substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$ $C_1$–$C_4$ alkoxy substituted with 0–1 $R^{21}$, aryl substituted with 0–1 $R^{21}$, aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;W is —C(=O)—N($R^{13}$)—;

W is —C(=O)-N($R^{13}$)—;

X is —CH($R^{14}$)—CH($R^{15}$)—;

$R^{13}$ is H or $CH_3$;

$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—N($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
methylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6{}_2$;

m is 0 or 1;

n is 1–4; and t is 0 or 1.

[5] Specifically preferred compounds of the invention as described above are compounds of Formula Ia, including enantiomeric or diasteriomeric forms thereof, or mixtures of enantiomeric or diasteriomeric forms thereof, or pharmaceutically acceptable salt or prodrug forms thereof, selected from the group consisting of:

3-[1-[3-(imidazolin-2-ylamino)propyl]indazol-5-ylcarbonylamino]-2-(benzyloxycarbonylamino)-propionic acid, 3-[1-[3-(imidazolin-2-ylamino)propyl]indazol-5-ylcarbonylamino]-2-(2,4,6-trimethylbenzenesulfonylamino)propionic acid, 3-[1-[3-(imidazolin-2-ylamino)propyl]indazol-5-ylcarbonylamino]-2-(benzenesulfonylamino)propionic acid, 3-[1-[3-(imidazolin-2-ylamino)propyl]indazol-5-ylcarbonylamino]-2-(2,6-dichlorobenzenesulfonylamino) propionic acid, 3-[1-[3-(imidazolin-2-ylamino)propyl]indazol-5-ylcarbonylamino]-2-(3,5-dimethylisoxazol-4-ylsulfonylamino)propionic acid, 3-[1-[3-(imidazolin-2-ylamino)propyl]indazol-5-ylcarbonylamino]-2-(2,6-dimethylbenzenesulfonylamino)propionic acid, 3-[1-[3-(imidazolin-2-ylamino)propyl]indazol-5-ylcarbonylamino]-2-(2,6-dimethyl-4-phenylbenzenesulfonylamino)propionic acid, 3-[1-[3-(imidazolin-2-ylamino)propyl]indazol-5-ylcarbonylamino]-2-(4-phenylbenzenesulfonylamino)propionic acid, 3-[1-[3-(tetrahydropyrimid-2-ylamino)propyl]indazol-5-ylcarbonylamino]-2-(benzyloxycarbonylamino)propionic acid, 3-[1-[3-(tetrahydropyrimid-2-ylamino)propyl]indazol-5-ylcarbonylamino]-2-(2,4,6-trimethylbenzenesulfonylamino)propionic acid, 3-[1-[3-(tetrahydropyrimid-2-ylamino)propyl]indazol-5-ylcarbonylamino]-2-(benzenesulfonylamino)propionic acid, 3-[1-[3-(tetrahydropyrimid-2-ylamino)propyl]indazol-5-ylcarbonylamino]-2-(2,6-dichlorobenzenesulfonylamino)propionic acid, 3-[1-[3-(tetrahydropyrimid-2-ylamino)propyl]indazol-5-ylcarbonylamino]-2-(3,5-dimethylisoxazol-4-ylsulfonylamino)propionic acid, 3-[1-[3-(tetrahydropyrimid-2-ylamino)propyl]indazol-5-ylcarbonylamino]-2-(2,6-dimethylbenzenesulfonylamino)propionic acid, 3-[1-[3-(tetrahydropyrimid-2-ylamino)propyl]indazol-5-ylcarbonylamino]-2-(2,6-dimethyl-4-phenylbenzenesulfonylamino)propionic acid, 3-[1-[3-(tetrahydropyrimid-2-ylamino)propyl]indazol-5-ylcarbonylamino]-2-(4-phenylbenzenesulfonylamino)propionic acid, 3-[1-[3-(imidazol-2-ylamino)propyl]indazol-5-ylcarbonylamino]-2-(benzyloxycarbonylamino)propionic acid, 3-[1-[3-(imidazol-2-ylamino)propyl]indazol-5-ylcarbonylamino]-2-(2,4,6-trimethylbenzenesulfonylamino)propionic acid, 3-[1-[3-(imidazol-2-ylamino)propyl]indazol-5-ylcarbonylamino]-2-(benzenesulfonylamino)propionic acid, 3-[1-[3-(imidazol-2-ylamino)propyl]indazol-5-ylcarbonylamino]-2-(2,6-dichlorobenzenesulfonylamino)propionic acid, 3-[1-[3-(imidazol-2-ylamino)propyl]indazol-5-ylcarbonylamino]-2-(3,5-dimethylisoxazol-4-ylsulfonylamino)propionic acid, 3-[1-[3-(imidazol-2-ylamino)propyl]indazol-5-ylcarbonylamino]-2-(2,6-dimethylbenzenesulfonylamino)propionic acid, 3-[1-[3-(imidazol-2-ylamino)propyl]indazol-5-ylcarbonylamino]-2-(2,6-dimethyl-4-phenylbenzenesulfonylamino)propionic acid, 3-[1-[3-(imidazol-2-ylamino)propyl]indazol-5-ylcarbonylamino]-2-(4-phenylbenzenesulfonylamino)propionic acid, 3-[1-[3-(pyridin-2-ylamino)propyl]indazol-5-ylcarbonylamino]-2-(benzyloxycarbonylamino)propionic acid, 3-[1-[3-(pyridin-2-ylamino)propyl]indazol-5-ylcarbonylamino]-2-(2,4,6-trimethylbenzenesulfonylamino)propionic acid, 3-[1-[3-(pyridin-2-ylamino)propyl]indazol-5-ylcarbonylamino]-2-(benzenesulfonylamino)propionic acid, 3-[1-[3-(pyridin-2-ylamino)propyl]indazol-5-ylcarbonylamino]-2-(2,6-dichlorobenzenesulfonylamino)propionic acid, 3-[1-[3-(pyridin-2-ylamino)propyl]indazol-5-ylcarbonylamino]-2-(3,5-dimethylisoxazol-4-ylsulfonylamino)propionic acid, 3-[1-[3-(pyridin-2-ylamino)propyl]indazol-5-ylcarbonylamino]-2-(2,6-dimethylbenzenesulfonylamino)propionic acid, 3-[1-[3-(pyridin-2-ylamino)propyl]indazol-5-ylcarbonylamino]-2-(2,6-dimethyl-4-phenylbenzenesulfonylamino)propionic acid, 3-[1-[3-(pyridin-2-ylamino)propyl]indazol-5-ylcarbonylamino]-2-(4-phenylbenzenesulfonylamino)propionic acid, 3-[1-[3-(imidazolin-2-ylamino)propyl]indazol-4-ylcarbonylamino]-2-(benzyloxycarbonylamino)propionic acid, 3-[1-[3-(imidazolin-2-ylamino)propyl]indazol-4-ylcarbonylamino]-2-(2,4,6-trimethylbenzenesulfonylamino)propionic acid, 3-[1-[3-(imidazolin-2-ylamino)propyl]indazol-4-ylcarbonylamino]-2-(benzenesulfonylamino)propionic acid, 3-[1-[3-(imidazolin-2-ylamino)propyl]indazol-4-ylcarbonylamino]-2-(2,6-dichlorobenzenesulfonylamino)propionic acid, 3-[1-[3-(imidazolin-2-ylamino)propyl]indazol-4-ylcarbonylamino]-2-(3,5-dimethylisoxazol-4-ylsulfonylamino)propionic acid, 3-[1-[3-(imidazolin-2-ylamino)propyl]indazol-4-ylcarbonylamino]-2-(2,6-dimethylbenzenesulfonylamino)propionic acid, 3-[1-[3-(imidazolin-2-ylamino)propyl]indazol-4-ylcarbonylamino]-2-(2,6-dimethyl-4-phenylbenzenesulfonylamino)propionic acid, 3-[1-[3-(imidazolin-2-ylamino)propyl]indazol-4-ylcarbonylamino]-2-(4-phenylbenzenesulfonylamino)propionic acid, 3-[1-[3-(tetrahydropyrimid-2-ylamino)propyl]indazol-4-ylcarbonylamino]-2-(benzyloxycarbonylamino)propionic acid, 3-[1-[3-(tetrahydropyrimid-2-ylamino)propyl]indazol-4-ylcarbonylamino]-2-(2,4,6-trimethylbenzenesulfonylamino)propionic acid, 3-[1-[3-(tetrahydropyrimid-2-ylamino)propyl]indazol-4-ylcarbonylamino]-2-(benzenesulfonylamino)propionic acid, 3-[1-[3-(tetrahydropyrimid-2-ylamino)propyl]indazol-4-ylcarbonylamino]-2-(2,6-dichlorobenzenesulfonylamino)propionic acid, 3-[1-[3-(tetrahydropyrimid-2-ylamino)propyl]indazol-4-ylcarbonylamino]-2-(3,5-dimethylisoxazol-4-ylsulfonylamino)propionic acid, 3-[1-[3-(tetrahydropyrimid-2-ylamino)propyl]indazol-4-ylcarbonylamino]-2-(2,6-dimethylbenzenesulfonylamino)propionic acid, 3-[1-[3-(tetrahydropyrimid-2-ylamino)propyl]indazol-4-ylcarbonylamino]-2-(2,6-dimethyl-4-phenylbenzenesulfonylamino)propionic acid, 3-[1-[3-(tetrahydropyrimid-2-ylamino)propyl]indazol-4-ylcarbonylamino]-2-(4-phenylbenzenesulfonylamino)propionic acid, 3-[1-[3-(imidazol-2-ylamino)propyl]indazol-4-ylcarbonylamino]-2-(benzyloxycarbonylamino)propionic acid, 3-[1-[3-(imidazol-2-ylamino)propyl]indazol-4-ylcarbonylamino]-2-(2,4,6-trimethylbenzenesulfonylamino)propionic acid, 3-[1-[3-(imidazol-2-ylamino)propyl]indazol-4-ylcarbonylamino]-2-(benzenesulfonylamino)propionic acid, 3-[1-[3-(imidazol-2-ylamino)propyl]indazol-4-ylcarbonylamino]-2-(2,6-dichlorobenzenesulfonylamino)propionic acid, 3-[1-[3-(imidazol-2-ylamino)propyl]indazol-4-ylcarbonylamino]-2-(3,5-dimethylisoxazol-4-ylsulfonylamino)propionic acid, 3-[1-[3-(imidazol-2-ylamino)propyl]indazol-4-ylcarbonylamino]-2-(2,6-dimethylbenzenesulfonylamino)propionic acid, 3-[1-8 3-(imidazol-2-ylamino)propyl]indazol-4-ylcarbonylamino]-2-(2,6-dimethyl-4-phenylbenzenesulfonylamino)propionic acid, 3-[1-[3-(imidazol-2-ylamino)propyl]indazol-4-ylcarbonylamino]-2-(4-phenylbenzenesulfonylamino)propionic acid, 3-[1-[3-(pyridin-2-ylamino)propyl]indazol-4-ylcarbonylamino]-2-(benzyloxycarbonylamino)propionic acid, 3-[1-[3-(pyridin-2-ylamino)propyl]indazol-4-ylcarbonylamino]-2-(2,4,6-trimethylbenzenesulfonylamino)propionic acid, 3-[1-[3-(pyridin-2-ylamino)propyl]indazol-4-ylcarbonylamino]-2-(benzenesulfonylamino)propionic acid, 3-[1-[3-(pyridin-2-ylamino)propyl]indazol-4-ylcarbonylamino]-2-(2,6-dichlorobenzenesulfonylamino)propionic acid, 3-[1-[3-(pyridin-2-ylamino)propyl]indazol-4-ylcarbonylamino]-2-(3,5-dimethylisoxazol-4-ylsulfonylamino)propionic acid, 3-[1-[3-(pyridin-2-ylamino)propyl]indazol-4-ylcarbonylamino]-2-(2,6-dimethylbenzenesulfonylamino)propionic acid, 3-[1-[3-(pyridin-2-ylamino)propyl]indazol-4-ylcarbonylamino]-2-(2,6-dimethyl-4-phenylbenzenesulfonylamino)propionic acid, and 3-[1-[3-(pyridin-2-ylamino)propyl]indazol-4-ylcarbonylamino]-2-(4-phenylbenzenesulfonylamino)propionic acid.

Also specifically preferred are ester prodrugs of the specifically preferred compounds of Formula Ia, said esters being chosen from the group consisting of:

methyl,
ethyl,
isopropyl,
n-butyl,
isobutyl,
benzyl,
methylcarbonyloxymethyl,
ethylcarbonyloxymethyl,
tert-butylcarbonyloxymethyl,
cyclohexylcarbonyloxymethyl,
tert-butyloxycarbonyloxymethyl,
dimethylaminoethyl,
diethylaminoethyl,
morpholinoethyl, pyrrolidinoethyl, and
trimethylanimonioethyl.

[6] Another aspect of the present invention comprises compounds of Formula Ib:

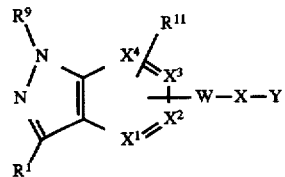

including stereoisomeric forms thereof, or mixtures of stereoisomeric forms thereof, or pharmaceutically acceptable salt or prodrug forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

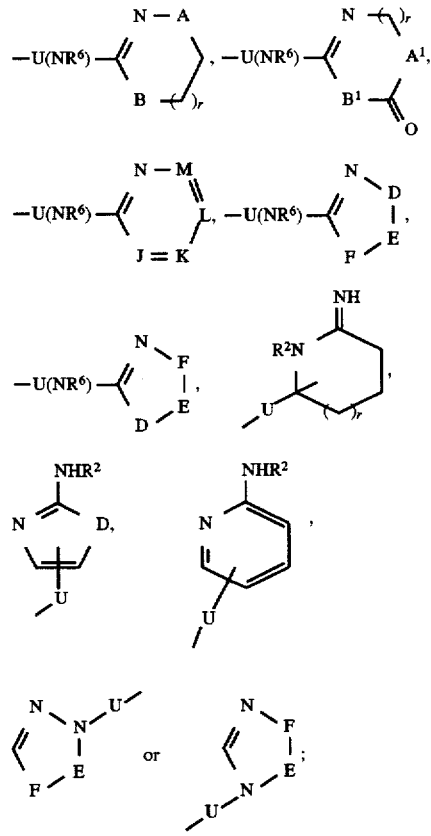

A and B are independently —$CH_2$—, —O—, —$N(R^2)$—, or —C(=O)—;

$A^1$ and $B^1$ are independently —$CH_2$— or —$N(R^3)$—;

D is —$N(R^2)$—, —O—, —S—, —C(=O)— or —$SO_2$—;

E—F is —$C(R^4)=C(R^5)$—, —$N=C(R^4)$—, —$C(R^4)=N$—, or —$C(R^4)_2C(R^5)_2$—;

J, K, L and M are independently selected from: —$C(R^4)$—, —$C(R^5)$— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl, ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl $C_1$–$C_6$ alkyl, ($C_1$–$C_6$ alkyl)carbonyl, or arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroalry ($C_1$–$C_6$ alkyl);

$R^4$ and $R^5$ are independently selected from: H, $C_1$–$C_4$ alkoxy, $NR^2R^3$ halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)($C_1$–$C_6$ alkyl)carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7{=}CR^8)(CH_2)_m$—
—$(CH_2)_n(C{\equiv}C)(CH_2)_m$—
—$(CH_2)_nQ(CH_2)_m$—
—$(CH_2)_nO(CH_2)_m$—,
—$(CH_2)_nN(R^6)(CH_2)_m$—,
—$(CH_2)_nC({=}O)(CH_2)_m$—,
—$(CH_2)_n(C{=}O)N(R^6)(CH_2)_m$—
—$(CH_2)_nN(R^6)(C{=}O)(CH_2)_m$—, or
—$(CH_2)_nS(O)_p(CH_2)_m$—;
wherein one of the methylene groups is optionally substituted with $R^7$;

Q is selected from: 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C({=}O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)substituted with 0–1 $R^{15}$ or 0–2 $R^{11}$ or 0–1 $R^{21}$; $R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:
—$(C(R^{12})_2)_qC({=}O)N(R^{13})$—, or
—$C({=}O)$—$N(R^{13})$—$(C(R^{12})_2)_q$—;

X is —$C(R^{12})(R^{14})$—$C(R^{12})(R^{15})$—; or alternatively, W and X can be taken together to be

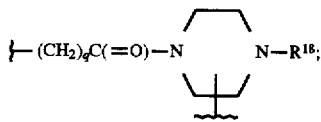

$R^{12}$ is selected from: H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl($C_1$–$C_6$ alkyl)-;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from:
H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C({=}O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from:
H, $R^{16}C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C({=}O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:
—$COR^{19}$, —$SO_3H$, —$PO_3H$, tetrazolyl, —$CONHNHSO_2CF_3$, —$CONHSO_2R^{17}$, —$CONHSO_2NHR^{17}$, —$NHCOCF_3$, —$NHCONHSO_2R^{17}$, —$NHSO_2R^{17}$, —$OPO_3H_2$, —$OSO_3H$, —$PO_3H_2$, —$SO_3H$, —$SO_2NHCOR^{17}$, —$SO_2NHCO_2R^{17}$,

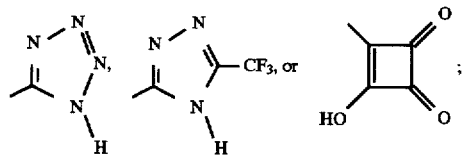

$R^{16}$ is selected from:
—$N(R^{20})$—$C({=}O)$—$O$—$R^{17}$,
—$N(R^{20})$—$C({=}O)$—$R^{17}$,
—$N(R^{20})$—$C({=}O)$—$NH$—$R^{17}$,
—$N(R^{20})SO_2$—$R^{17}$, or
—$N(R^{20})SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:
H,
—$C({=}O)$—$O$—$R^{17}$,
—$C({=}O)$—$R^{17}$,
—$C({=}O)$—$NH$—$R^{17}$,
—$SO_2$—$R^{17}$, or
—$SO_2$—$NR^{20}R^{17}$;

$R^{19}$ is selected from hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$ arylcarbonyloxyalkyloxy, $C_5-C_{10}$ alkoxyalkylcarbonyloxyalkyloxy, $C_5-C_{10}$ (5-alkyl-1,3-dioxa-cyclopenten-2-one-yl)methyloxy, $C_{10}-C_{14}$ (5-aryl-1,3-dioxa-cyclopenten-2-one-yl)methyloxy, or $(R^{11})(R^{12})N-(C_1-C_{10}$ alkoxy)-;

$R^{20}$ is selected from: H, $C_1-C_6$ alkyl, $C_3-C_7$ cycloalkyl, $C_4-C_{11}$ cycloalkylalkyl, aryl, aryl($C_1-C_6$ alkyl)-, or heteroaryl($C_1-C_6$ alkyl)-;

$R^{21}$ is selected from COOH or $NR^6_2$;

m is 0–4;

n is 0–4;

t is 0–4;

p is 0–2;

q is 0–2; and r is 0–2;

with the following provisos:

(1) t, n, m and q are chosen such that the number of atoms connecting $R^1$ and Y is in the range of 10–14; and (2) n and m are chosen such that the value of n plus m is greater than one unless U is $-(CH_2)_nQ(CH_2)_m-$.

[7] Preferred compounds of the invention as described above are compounds of the Formula Ib:

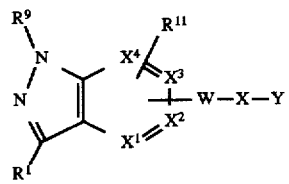

Ib including stereoisomeric forms thereof, or mixtures of stereoisomeric forms thereof, or pharmaceutically acceptable salt or prodrug forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

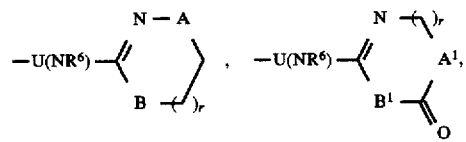

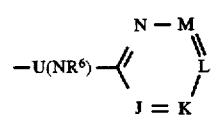

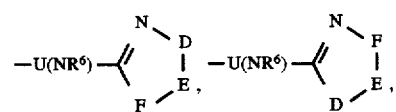

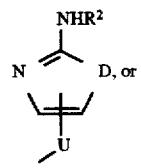

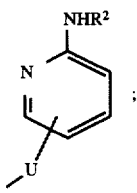

A and B are independently $-CH_2-$, $-O-$, $-N(R^2)-$, or $-C(=O)-$;

$A^1$ and $B^1$ are independently $-CH_2-$ or $-N(R^3)-$;

D is $-N(R^2)-$, $-O-$, $-S-$, $-C(=O)-$ or $-SO_2-$;

E—F is $-C(R^4)=C(R^5)-$, $-N=C(R^4)-$, $-C(R^4)=N-$, or $-C(R^4)_2C(R^5)_2-$;

J, K, L and M are independently selected from $-C(R^4)-$, $-C(R^5)-$ or $-N-$, provided that at least one of J, K, L and M is not $-N-$;

$R^2$ is selected from: H, $C_1-C_6$ alkyl, ($C_1-C_6$ alkyl)carbonyl, ($C_1-C_6$ alkoxy)carbonyl, $C_1-C_6$ alkylaminocarbonyl, $C_3-C_6$ alkenyl, $C_3-C_7$ cycloalkyl, $C_4-C_{11}$ cycloalkylalkyl, aryl, heteroaryl($C_1-C_6$ alkyl) carbonyl, heteroarylcarbonyl, aryl($C_1-C_6$ alkyl)-, ($C_1-C_6$ alkyl)carbonyl, arylcarbonyl, alkylsulfonyl, arylsulfonyl, aryl($C_1-C_6$ alkyl)sulfonyl, heteroarylsulfonyl, heteroaryl($C_1-C_6$ alkyl)sulfonyl, aryloxycarbonyl, aryl($C_1-C_6$ alkoxy)carbonyl, wherein said aryl groups are substituted with 0-2 substituents selected from the group consisting of $C_1-C_4$ alkyl, $C_1-C_4$ alkoxy, halo, $CF_3$, and nitro;

$R^3$ is selected from: H, $C_1-C_6$ alkyl, $C_3-C_7$ cycloalkyl, $C_4-C_{11}$ cycloalkylalkyl, aryl, aryl($C_1-C_6$ alkyl)-, or heteroaryl($C_1-C_6$ alkyl)-;

$R^4$ and $R^5$ are independently selected from: H, $C_1-C_4$ alkoxy, $NR^2R^3$, halogen, $NO_2$, CN, $CF_3$, $C_1-C_6$ alkyl, $C_3-C_6$ alkenyl, $C_3-C_7$ cycloalkyl, $C_4-C_{11}$ cycloalkylalkyl, aryl, aryl($C_1-C_6$ alkyl)-, $C_2-C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1-C_4$ alkyl, $C_1-C_4$ alkoxy, halo, cyano, amino, $CF_3$, or $NO_2$;

U is selected from:

$-(CH_2)_n-$,
$-(CH_2)_n(CR^7=CR^8)(CH_2)_m-$
$-(CH_2)_nQ(CH_2)_m-$,
$-(CH_2)_nO(CH_2)_m-$,
$-(CH_2)_nN(R^6)(CH_2)_m-$,
$-(CH_2)_nC(=O)(CH_2)_m-$, or
$-(CH_2)_nS(O)_p(CH_2)_m-$;

wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1-C_4$ alkyl, or benzyl;

$R^7$ and $R^8$ are independently selected from: H, $C_1-C_6$ alkyl, $C_3-C_7$ cycloalkyl, $C_4-C_{11}$ cycloalkylalkyl, aryl, aryl($C_1-C_6$ alkyl)-, or heteroaryl($C_0-C_6$ alkyl)-;

$R^9$ is selected from: H, $CO_2R^{17}$, $C(=O)R^{17}$, $CONR^{17}R^{20}$, $-SO_2R^{17}$, $-SO_2NR^{17}R^{20}$, $C_1-C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$aryl substituted with 0–1 $R^{15}$ or 0–2 $R^{11}$ or 0–1 $R^{21}$, or aryl ($C_1$–$C_6$ alkyl)substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is $-C(=O)-N(R^{13})-(C(R^{12})_2)_q-$;

X is $-C(R^{12})(R^{14})-C(R^{12})(R^{15})-$;

alternatively, W and X can be taken together to be

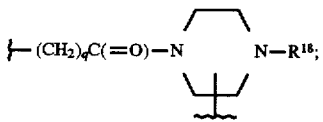

$R^{12}$ is H or $C_1$–$C_6$ alkyl;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from:
H, $C_1$–$C_6$ alkylthioalkyl, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_0$–$C_6$ alkyl)-, heteroaryl ($C_1$–$C_6$ alkyl)-, aryl, heteroaryl, $CO_2R^{17}$, $C(=O)R^{17}$ or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from:
H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:

$-COR^{19}$, $-SO_3H$,

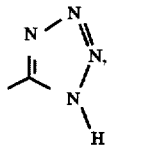

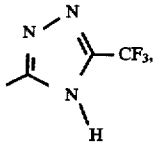

or

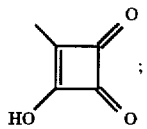

$R^{16}$ is selected from:
$-N(R^{20})-C(=O)-O-R^{17}$,
$-N(R^{20})-C(=O)-R^{17}$,
$-N(R^{20})-C(=O)-NH-R^{17}$,
$-N(R^{20})SO_2-R^{17}$ or
$-N(R^{20})SO_2-NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_0$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:
H,
$-C(=O)-O-R^{17}$,
$-C(=O)-R^{17}$,
$-C(=O)-NH-R^{17}$,
$-SO_2-R^{17}$, or
$-SO_2-NR^{20}R^{17}$;

$R^{19}$ is selected from hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N-(C_1$–$C_{10}$ alkoxy)-;

$R^{20}$ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

$R^{21}$ is selected from COOH or $NR^6_2$;

m is 0–4;

n is 0–4;

t is 0–4;

p is 0–2;

q is 0–2; and r is 0–2.

[8] Further preferred compounds of the invention as described above are compounds of the Formula IIc or IId:

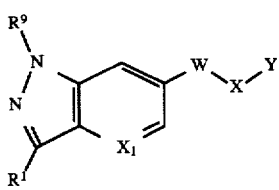

IIc

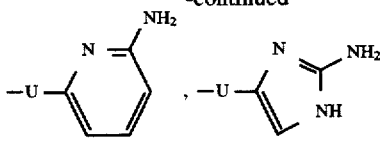

or

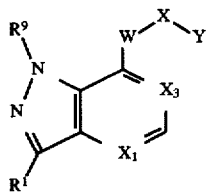

IId

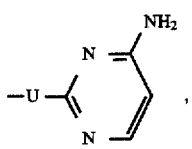

or

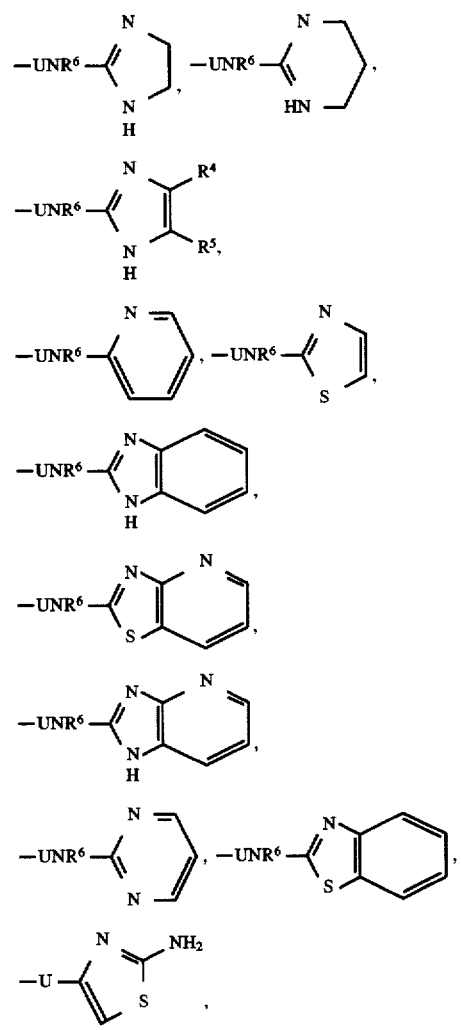

including stereoisomeric forms thereof, or mixtures of stereoisomeric forms thereof, or pharmaceutically acceptable salt or prodrug forms thereof, wherein:

$X^1$ and $X_3$ are independently selected from nitrogen or carbon;

$R^1$ is selected from:

wherein the above heterocycles are optionally substituted with 0–2 substituents selected from the group consisting of: $NH_2$, halogen, $NO_2$, CN, $CF_3$, $C_1-C_4$ alkoxy, $C_1-C_6$ alkyl, and $C_3-C_7$ cycloalkyl;

U is $—(CH_2)_n—$, $—(CH_2)_rQ(CH_2)_m—$ or $—C(=O)(CH_2)_{n-1}—$, wherein one of the methylene groups is optionally substituted with $R^7$;

Q is selected from 1,2-phenylene, 1,3-phenylene, 2,3-pyridinylene, 3,4-pyrdinylene, or 2,4-pyridinylene;

$R^6$ is selected from: H, $C_1-C_4$ alkyl, or benzyl;

$R^7$ is selected from: $C_1-C_6$ alkyl, $C_3-C_7$ cycloalkyl, $C_4-C_{11}$ cycloalkylalkyl, aryl, aryl($C_1-C_6$ alkyl), heteroaryl, or heteroaryl($C_1-C_6$ alkyl);

$R^9$ is selected from: H, $—SO_2R^{17}$, $—SO_2NR^{17}R^{20}$, $C_1-C_6$ alkyl substituted with 0–1 $R^{15}$ or 0–1 $R^{21}$, $C_3-C_7$ cycloalkyl substituted with 0–1 $R^{15}$ or 0–1 $R^{21}$, $C_4-C_{11}$ cycloalkylalkyl substituted with 0–1 $R^{15}$ or 0–1 $R^{21}$, aryl substituted with 0–1 $R^{15}$ or 0–2 $R^1$1 or 0–1 $R^{21}$, or aryl($C_1-C_6$ alkyl)-substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1-C_4$ alkyl substituted with 0–1 $R^{21}$, $C_1-C_4$ alkoxy substituted with 0–1 $R^{21}$, aryl substituted with 0–1 $R^{21}$, aryl($C_1-C_6$ alkyl)-substituted with 0–1 $R^{21}$ ($C_1-C_4$ alkoxy)carbonyl substituted with 0–1 $R^{21}$ ($C_1-C_4$ alkyl)carbonyl substituted with 0–1 $R^{21}$, $C_1-C_4$ alkylsulfonyl substituted with 0–1 $R^{21}$, or $C_1-C_4$ alkylaminosulfonyl substituted with 0–1 $R^{21}$;

W is $—C(=O)—N(R^{13})—$;

X is $—CH(R^{14})—CH(R^{15})—$;

$R^{13}$ is H or $CH_3$;

$R^{14}$ is selected from:
H, $C_1-C_{10}$ alkyl, aryl, or heteroaryl, wherein said aryl or heteroaryl groups are optionally substituted with 0–3 substituents selected from the group consisting of: $C_1-C_4$ alkyl, $C_1-C_4$ alkoxy, aryl, halo, cyano, amino, $CF_3$, and $NO_2$;

$R^{15}$ is H or $R^{16}$;

Y is $—COR^{19}$;

$R^{16}$ is selected from:
$—NH(R^{20})—C(=O)—O—R^{17}$,
$—N(R^{20})—C(=O)—R^{17}$,
$—N(R^{20})—C(=O)—NH—R^{17}$,
$—N(R^{20})SO_2—R^{17}$, or
$—N(R^{20})SO_2—N(R^{20})R^{17}$;

$R^{17}$ is selected from:
$C_1-C_{10}$ alkyl, $C_3-C_{11}$ cycloalkyl, aryl($C_1-C_6$ alkyl)-, ($C_1-C_6$ alkyl)aryl, heteroaryl($C_1-C_6$ alkyl)-, ($C_1-C_6$ alkyl)heteroaryl, biaryl($C_1-C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6{}_2$; and m is 0 or 1;

n is 1–4; and t is 0 or 1.

[9] Still further preferred compounds of the above invention are compounds of the Formula IIc or IId:

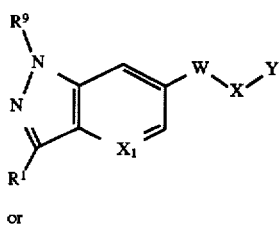

IIc or

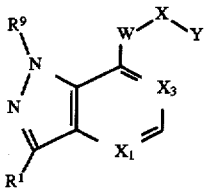

IId including stereoisomeric forms thereof, or mixtures of stereoisomeric forms thereof, or pharmaceutically acceptable salt or prodrug forms thereof, wherein:

$X_1$ and $X_3$ are independently selected from nitrogen or carbon, provided that at least one of $X_1$ and $X_3$ is carbon;

$R^1$ is selected from:

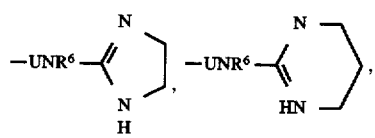

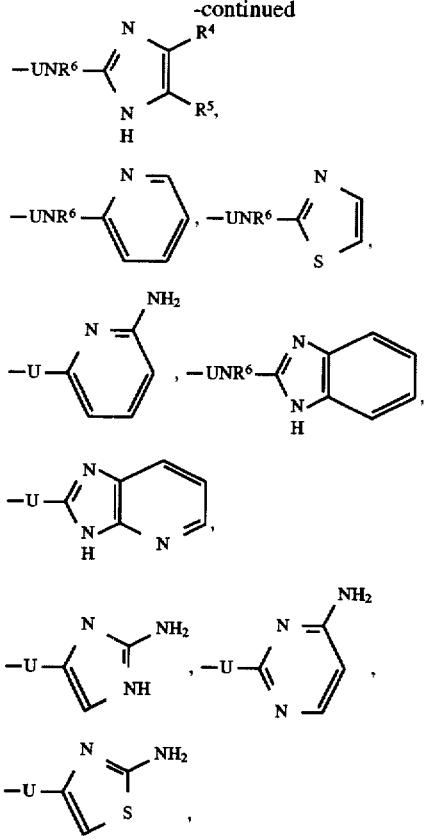

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl and $C_3$–$C_7$ cycloalkyl;

U is —$(CH_2)_n$—, —$(CH_2)_rQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)-substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from:
  H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
  —$N(R^{20})$—C(=O)—O—$R^{17}$,
  —$N(R^{20})$—C(=O)—$R^{17}$,
  —$N(R^{20})$—C(=O)—NH—$R^{17}$,
  —$N(R^{20})SO_2$—$R^{17}$, or
  —$N(R^{20})SO_2$—$NR^{20}R^{17}$;

$R^{17}$ is selected from:
  $C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
  hydroxy, $C_1$–$C_{10}$ alkoxy,
  methylcarbonyloxymethoxy-,
  ethylcarbonyloxymethoxy-,
  t-butylcarbonyloxymethoxy-,
  cyclohexylcarbonyloxymethoxy-,
  1-(methylcarbonyloxy)ethoxy-,
  1-(ethylcarbonyloxy)ethoxy-,
  1-(t-butylcarbonyloxy)ethoxy-,
  1-(cyclohexylcarbonyloxy)ethoxy-,
  i-propyloxycarbonyloxymethoxy-,
  t-butyloxycarbonyloxymethoxy-,
  1-(i-propyloxycarbonyloxy)ethoxy-,
  1-(cyclohexyloxycarbonyloxy)ethoxy-,
  1-(t-butyloxycarbonyloxy)ethoxy-,
  dimethylaminoethoxy-,
  diethylaminoethoxy-,
  (5-methyl-1,3-dioxacyclopenten-2-on-4-yl)methoxy-,
  (5-(t-butyl)-1,3-dioxacyclopenten-2-on-4-yl)methoxy-,
  (1,3-dioxa-5-phenyl-cyclopenten-2-on-4-yl)methoxy-, or
  1-(2-(2-methoxypropyl)carbonyloxy)ethoxy-;

$R^{20}$ is H or $CH_3$;

$R^{21}$ is selected from COOH or $NR^6{}_2$; and m is 0 or 1;

n is 1–4; and t is 0 or 1.

[10] Specifically preferred compounds of the invention as described above are compounds of Formula Ib, including enantiomeric or diasteriomeric forms thereof, or mixtures of enantiomeric or diasteriomeric forms thereof, or pharmaceutically acceptable salt or prodrug forms thereof, selected from the group consisting of:

3-[3-[3-(imidazolin-2-ylamino)propyl]indazol-6-ylcarbonylamino]-2-(benzyloxycarbonylamino)propionic acid, 3-[1-methyl-3-[3-(imidazolin-2-ylamino)propyl]-indazol-6-ylcarbonylamino]-2-(2,4,6-trimethylbenzenesulfonylamino)propionic acid, 3-[3-[3-(imidazolin-2-ylamino)propyl]indazol-6-ylcarbonylamino]-2-(benzenesulfonylamino)propionic acid, 3-[1-methyl-3-[3-(imidazolin-2-ylamino)propyl]indazol-6-ylcarbonylamino]-2-(2,6-dichlorobenzenesulfonylamino)propionic acid, 3-[3-[3-(imidazolin-2-ylamino)propyl]indazol-6-ylcarbonylamino]-2-(3,5-dimethylisoxazol-4-ylsulfonylamino)propionic acid, 3-[1-methyl-3-[3-(imidazolin-2-ylamino)propyl]indazol-6-ylcarbonylamino]-2-(2,6-dimethylbenzenesulfonylamino)propionic acid, 3-[3-[3-(imidazolin-2-ylamino)propyl]indazol-6-ylcarbonylamino]-2-(2,6-dimethyl-4-phenylbenzenesulfonylamino)propionic acid, 3-[1-methyl-3-[3-(imidazolin-2-ylamino)propyl]indazol-6-ylcarbonylamino]-2-(4-phenylbenzenesulfonylamino)propionic acid, 3-[3-[3-(tetrahydropyrimid-2-ylamino)propyl]indazol-6-ylcarbonylamino]-2-(benzyloxycarbonylamino)propionic acid, 3-[1-methyl-3-[3-(tetrahydropyrimid-2-ylamino)propyl]indazol-6-ylcarbonylamino]-2-(2,4,6-trimethylbenzenesulfonylamino)propionic acid, 3-[3-[3-(tetrahydropyrimid-2-ylamino)propyl]indazol-6-ylcarbonylamino]-2-(benzenesulfonylamino)propionic acid, 3-[1-methyl-3-[3-(tetrahydropyrimid-2-ylamino)propyl]indazol-6-ylcarbonylamino]-2-(2,6-dichlorobenzenesulfonylamino)propionic acid, 3-[3-[3-(tetrahydropyrimid-2-ylamino)propyl]indazol-6-ylcarbonylamino]-2-(3,5-dimethylisoxazol-4-ylsulfonylamino)propionic acid, 3-[1-methyl-3-[3-(tetrahydropyrimid-2-ylamino)propyl]indazol-6-ylcarbonylamino]-2-(2,6-dimethylbenzenesulfonylamino)propionic acid, 3-[3-[3-(tetrahydropyrimid-2-ylamino)propyl]indazol-6-ylcarbonylamino]-2-(2,6-dimethyl-4-phenylbenzenesulfonylamino)propionic acid, 3-[1-methyl-3-[3-(tetrahydropyrimid-2-ylamino)propyl]-indazol-6-ylcarbonylamino]-2-(4-phenylbenzenesulfonylamino)propionic acid, 3-[3-[3-(imidazol-2-ylamino)propyl]indazol-6-ylcarbonylamino]-2-(benzyloxycarbonylamino)propionic acid, 3-[1-methyl-3-[3-(imidazol-2-ylamino)propyl]indazol-6-ylcarbonylamino]-2-(2,4,6-trimethylbenzenesulfonylamino)propionic acid, 3-[3-[3-(imidazol-2-ylamino)propyl]indazol-6-ylcarbonylamino]-2-(benzenesulfonylamino)propionic acid, 3-[1-methyl-3-[3-(imidazol-2-ylamino)propyl]indazol-6-ylcarbonylamino]-2-(2,6-dichlorobenzenesulfonylamino)propionic acid, 3-[3-[3-(imidazol-2-ylamino)propyl]indazol-6-ylcarbonylamino]-2-(3,5-dimethylisoxazol-4-ylsulfonylamino)propionic acid, 3-[1-methyl-3-[3-(imidazol-2-ylamino)propyl]indazol-6-ylcarbonylamino]-2-(2,6-dimethylbenzenesulfonylamino)propionic acid, 3-[3-[3-(imidazol-2-ylamino)propyl]indazol-6-ylcarbonylamino]-2-(2,6-dimethyl-4-phenylbenzenesulfonylamino)propionic acid, 3-[1-methyl-3-[3-(imidazol-2-ylamino)propyl]indazol-6-ylcarbonylamino]-2-(4-phenylbenzenesulfonylamino)propionic acid, 3-[3-[3-(pyridin-2-ylamino)propyl]indazol-6-ylcarbonylamino]-2-(benzyloxycarbonylamino)propionic acid, 3-[1-methyl-3-[3-(pyridin-2-ylamino)propyl]indazol-6-ylcarbonylamino]-2-(2,4,6-trimethylbenzenesulfonylamino)propionic acid, 3-[3-[3-(pyridin-2-ylamino)propyl]indazol-6-ylcarbonylamino]-2-(benzenesulfonylamino)propionic acid, 3-[1-methyl-3-[3-(pyridin-2-ylamino)propyl]indazol-6-ylcarbonylamino]-2-(2,6-dichlorobenzenesulfonylamino) propionic acid, 3-[3-[3-(pyridin-2-ylamino)propyl]indazol-6-ylcarbonylamino]-2-(3,5-dimethylisoxazol-4-ylsulfonylamino)propionic acid, 3-[1-methyl-3-[3-(pyridin-2-ylamino)propyl]indazol-6-ylcarbonylamino]-2-(2,6-dimethylbenzenesulfonylamino)propionic acid, 3-[3-[3-(pyridin-2-ylamino)propyl]indazol-6-ylcarbonylamino]-2-(2,6-dimethyl-4-phenylbenzenesulfonylamino)propionic acid, 3-[1-methyl-3-[3-(pyridin-2-ylamino)propyl]indazol-6-ylcarbonylamino]-2-(4-phenylbenzenesulfonylamino)propionic acid, 3-[3-[3-(imidazolin-2-ylamino)propyl]indazol-7-ylcarbonylamino]-2-(benzyloxycarbonylamino)propionic acid, 3-[1-methyl-3-[3-(imidazolin-2-ylamino)propyl]indazol-7-ylcarbonylamino]-2-(2,4,6-trimethylbenzenesulfonylamino)propionic acid, 3-[3-[3-(imidazolin-2-ylamino)propyl]indazol-7-ylcarbonylamino]-2-(benzenesulfonylamino)propionic acid, 3-[1-methyl-3-[3-(imidazolin-2-ylamino)propyl]indazol-7-ylcarbonylamino]-2-(2,6-dichlorobenzenesulfonylamino)propionic acid, 3-[3-[3-(imidazolin-2-ylamino)propyl]indazol-7-ylcarbonylamino]-2-(3,5-dimethylisoxazol-4-ylsulfonylamino)propionic acid, 3-[1-methyl-3-[3-(imidazolin-2-ylamino)propyl]indazol-7-ylcarbonylamino]-2-(2,6-dimethylbenzenesulfonylamino)propionic acid, 3-[3-[3-(imidazolin-2-ylamino)propyl]indazol-7-ylcarbonylamino]-2-(2,6-dimethyl-4-phenylbenzenesulfonylamino)propionic acid, 3-[1-methyl-3-[3-(imidazolin-2-ylamino)propyl]indazol-7-ylcarbonylamino]-2-(4-phenylbenzenesulfonylamino)propionic acid, 3-[3-[3-(tetrahydropyrimid-2-ylamino)propyl]indazol-7-ylcarbonylamino]-2-(benzyloxycarbonylamino)propionic acid, 3-[1-methyl-3-[3-(tetrahydropyrimid-2-ylamino)propyl]indazol-7-ylcarbonylamino]-2-(2,4,6-trimethylbenzenesulfonylamino)propionic acid, 3-[3-[3-(tetrahydropyrimid-2-ylamino)propyl]indazol-7-ylcarbonylamino]-2-(benzenesulfonylamino)propionic acid, 3-[1-methyl-3-[3-(tetrahydropyrimid-2-ylamino)propyl]indazol-7-ylcarbonylamino]-2-(2,6-dichlorobenzenesulfonylamino)propionic acid, 3-[3-[3-(tetrahydropyrimid-2-ylamino)propyl]indazol-7-ylcarbonylamino]-2-(3,5-dimethylisoxazol-4-ylsulfonylamino)propionic acid, 3-[1-methyl-3-[3-(tetrahydropyrimid-2-ylamino)propyl]indazol-7-ylcarbonylamino]-2-(2,6-dimethylbenzenesulfonylamino)propionic acid, 3-[3-[3-(tetrahydropyrimid-2-ylamino)propyl]indazol-7-ylcarbonylamino]-2-(2,6-dimethyl-4-phenylbenzenesulfonylamino)propionic acid, 3-[1-methyl-3-[3-(tetrahydropyrimid-2-ylamino)propyl]indazol-7-ylcarbonylamino]-2-(4-phenylbenzenesulfonylamino)propionic acid, 3-[3-[3-(imidazol-2-ylamino)propyl]indazol-7-ylcarbonylamino]-2-(benzyloxycarbonylamino)propionic acid, 3-[1-methyl-3-[3-(imidazol-2-ylamino)propyl]indazol-7-ylcarbonylamino]-2-(2,4,6-trimethylbenzenesulfonylamino)propionic acid, 3-[3-[3-(imidazol-2-ylamino)propyl]indazol-7-ylcarbonylamino]-2-(benzenesulfonylamino)propionic acid, 3-[1-methyl-3-[3-(imidazol-2-ylamino)propyl]indazol-7-ylcarbonylamino]-2-(2,6-dichlorobenzenesulfonylamino) propionic acid, 3-[3-[3-(imidazol-2-ylamino)propyl]indazol-7-ylcarbonylamino]-2-(3,5-dimethylisoxazol-4-ylsulfonylamino)propionic acid, 3-[1-methyl-3-[3-(imidazol-2-ylamino)propyl]indazol-7-ylcarbonylamino]-2-(2,6-dimethylbenzenesulfonylamino)propionic acid, 3-[3-[3-(imidazol-2-ylamino)propyl]indazol-7-ylcarbonylamino]-2-(2,6-dimethyl-4-phenylbenzenesulfonylamino)propionic acid, 3-[1-methyl-3-[3-(imidazol-2-ylamino)propyl]indazol-7-ylcarbonylamino]-2-(4-phenylbenzenesulfonylamino)propionic acid, 3-[3-[3-(pyridin-2-ylamino)propyl]indazol-7-ylcarbonylamino]-2-(benzyloxycarbonylamino)propionic acid, 3-[1-methyl-3-[3-(pyridin-2-ylamino)propyl]indazol-7-ylcarbonylamino]-2-(2,4,6-trimethylbenzenesulfonylamino)propionic acid, 3-[3-[3-(pyridin-2-ylamino)propyl]indazol-7-ylcarbonylamino]-2-(benzenesulfonylamino)propionic acid, 3-[1-methyl-3-[3-(pyridin-2-ylamino)propyl]indazol-7-ylcarbonylamino]-2-(2,6-dichlorobenzenesulfonylamino) propionic acid, 3-[3-[3-(pyridin-2-ylamino)propyl]indazol-7-ylcarbonylamino]-2-(3,5-dimethylisoxazol-4-ylsulfonylamino)propionic acid, 3-[1-methyl-3-[3-(pyridin-2-ylamino)propyl]indazol-7-ylcarbonylamino]-2-(2,6-dimethylbenzenesulfonylamino)propionic acid, 3-[3-[3-(pyridin-2-ylamino)propyl]indazol-7-ylcarbonylamino]-2-(2,6-dimethyl-4-phenylbenzenesulfonylamino)propionic acid, and 3-[1-methyl-3-[3-(pyridin-2-ylamino)propyl]indazol-7-ylcarbonylamino]-2-(4-phenylbenzenesulfonylamino) propionic acid.

[11] Also specifically preferred are ester prodrugs of the specifically preferred compounds of Formula Ib, said esters being chosen from the group consisting of:

methyl, ethyl, isopropyl, n-butyl, isobutyl, benzyl, methylcarbonyloxymethyl, ethylcarbonyloxymethyl, tert-butylcarbonyloxymethyl, cyclohexylcarbonyloxymethyl, tert-butyloxycarbonyloxymethyl, dimethylaminoethyl, and diethylaminoethyl, pyrroldinoethyl, and trimethylanimonioethyl.

[12] Yet another aspect of the present invention comprises compounds of Formula Ic:

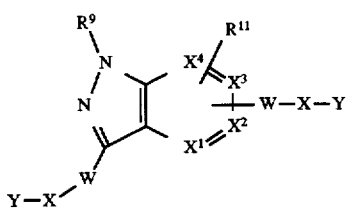

Ic including stereoisomeric forms thereof, or mixtures of stereoisomeric forms thereof, or pharmaceutically acceptable salt or prodrug forms, thereof wherein:

$X^1$, $X^2$, $X^3$, and $X^4$ are independently selected from nitrogen or carbon provided that at least two of $X_1$, $X^2$, $X^3$ and $X^4$ are carbon;

$R^1$ is selected from:

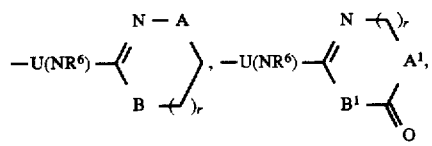

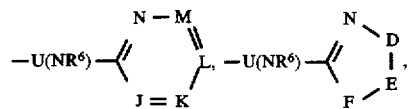

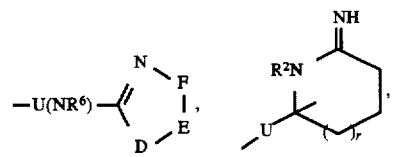

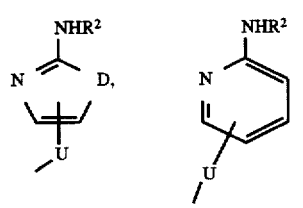

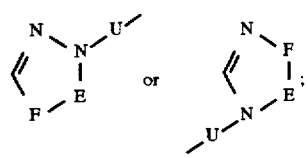

A and B are independently —$CH_2$—, —O—, —$N(R^2)$—, or —C(=O)—;

$A^1$ and $B^1$ are independently —$CH_2$— or —$N(R^3)$—;

D is —$N(R^2)$—, —O—, —S—, —C(=O)— or —$SO_2$—;

E—F is —$C(R^4)$=$C(R^5)$—, —N=$C(R^4)$—, —$C(R^4)$=N—, or —$C(R^4)_2C(R^5)_2$—;

J, K, L and M are independently selected from —$C(R^4)$—, —$C(R^5)$— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl; ($C_1$–$C_6$ alkyl)aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl $C_1$–$C_6$ alkyl, ($C_1$–$C_6$ alkyl)carbonyl, or arylcarbonyl, $C_1$–$C_6$ alkylsulfonyl, arylsulfonyl aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_{3-C7}$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, ($C_1$–$C_6$ alkyl)carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7$=$CR^8)(CH_2)_m$—
—$(CH_2)_n$(C≡C)$(CH_2)_m$—
—$(CH_2)_nQ(CH_2)_m$—
—$(CH_2)_nO(CH_2)_m$—,
—$(CH_2)_nN(R^6)(CH_2)_m$—,
—$(CH_2)_nC$(=O)$(CH_2)_m$—,
—$(CH_2)_n$(C=O)$N(R^6)(CH_2)_m$—
—$(CH_2)_nN(R^6)$(C=O)$(CH_2)_m$—, or
—$(CH_2)_nS(O)_p(CH_2)_m$—;

wherein one of the methylene groups is optionally substituted with $R^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, C(=O)$R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)-substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:
—$(C(R^{12})_2)_qC$(=O)$N(R^{13})$—, or
—C(=O)—$N(R^{13})$—$(C(R^{12})_2)_q$—;

X is —$C(R^{12})(R^{14})$—$C(R^{12})(R^{15})$—; or alternatively, W and X can be taken together to be

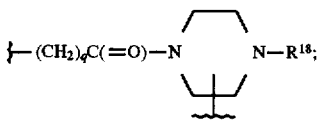

R$^{12}$ is selected from: H, halogen, C$_1$–C$_6$ alkyl, C$_2$–C$_6$ alkenyl, C$_2$–C$_6$ alkynyl, C$_3$–C$_7$ cycloalkyl, C$_4$–C$_{10}$ cycloalkylalkyl, (C$_1$–C$_4$ alkyl)carbonyl, aryl, or aryl (C$_1$–C$_6$ alkyl)–;

R$^{13}$ is selected from: H, C$_1$–C$_6$ alkyl, C$_3$–C$_7$ cycloalkylmethyl, or aryl(C$_1$–C$_6$ alkyl)

R$^{14}$ is selected from:

H, C$_1$–C$_6$ alkylthio(C$_1$–C$_6$ alkyl)–, aryl(C$_1$–C$_{10}$ alkylthioalkyl)–, aryl(C$_1$–C$_{10}$ alkoxyalkyl)–, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl(C$_1$–C$_6$ alkyl)–, heteroaryl(C$_1$–C$_6$ alkyl)–, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be unsubstituted or substituted independently with 0–1 R$^{16}$ or 0–2 R$^{11}$;

R$^{15}$ is selected from:

H, R$^{16}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, (C$_1$–C$_{10}$ alkyl)carbonyl, aryl(C$_0$–C$_6$ alkyl)carbonyl, C$_1$–C$_{10}$ alkenyl, C$_1$–C$_{10}$ alkynyl, C$_3$–C$_{10}$ cycloalkyl, C$_3$–C$_{10}$ cycloalkylalkyl, aryl(C$_1$–C$_6$ alkyl)–, heteroaryl(C$_1$–C$_6$ alkyl)–, aryl, heteroaryl, CO$_2$R$^{17}$, C(=O)R$^{17}$, CONR$^{17}$R$^{20}$, SO$_2$R$^{17}$, or SO$_2$NR$^{17}$R$^{20}$, provided that any of the above alkyl, cycloalkyl, aryl or heteroaryl groups may be unsubstituted or substituted independently with 0–2 R$^{11}$;

Y is selected from:

—COR$^{19}$, —SO$_3$H, —PO$_3$H, tetrazolyl, —CONHNHSO$_2$CF$_3$, —CONHSO$_2$R$^{17}$, —CONHSO$_2$NHR$^{17}$, —NHCOCF$_3$, —NHCONHSO$_2$R$^{17}$, —NHSO$_2$R$^{17}$, —OPO$_3$H$_2$, —OSO$_3$H, —PO$_3$H$_2$, —SO$_3$H, —SO$_2$NHCOR$^{17}$, —SO$_2$NHCO$_2$R$^{17}$,

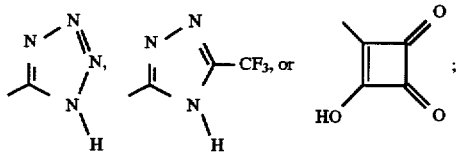

R$^{16}$ is selected from:

—N(R$^{20}$)—C(=O)—O—R$^{17}$,
—N(R$^{20}$)—C(=O)—R$^{17}$,
—N(R$^{20}$)—C(=O)—NH—R$^{17}$,
—N(R$^{20}$)SO$_2$—R$^{17}$, or
—N(R$^{20}$)SO$_2$—NR$^{20}$R$^{17}$;

R$^{17}$ is selected from:

C$_1$–C$_{10}$ alkyl, C$_3$–C$_{11}$ cycloalkyl, aryl(C$_1$–C$_6$ alkyl)–, (C$_1$–C$_6$ alkyl)aryl, heteroaryl(C$_1$–C$_6$ alkyl)–, (C$_1$–C$_6$ alkyl)heteroaryl, biaryl(C$_1$–C$_6$ alkyl)–, heteroaryl, or aryl, wherein said aryl or heteroaryl groups are optionally substituted with 0–3 substituents selected from the group consisting of: C$_1$–C$_4$ alkyl, C$_1$–C$_4$ alkoxy, aryl, heteroaryl, halo, cyano, amino, CF$_3$, and NO$_2$;

R$^{18}$ is selected from:

H,
—C(=O)—O—R$^{17}$,
—C(=O)—R$^{17}$,
—C(=O)—NH—R$^{17}$,
—SO$_2$—R$^{17}$, or
—SO$_2$—NR$^{20}$R$^{17}$;

R$^{19}$ is selected from hydroxy, C$_1$–C$_{10}$ alkyloxy, C$_3$–C$_{11}$ cycloalkyloxy, aryloxy, aryl(C$_1$–C$_6$ alkoxy)–, C$_3$–C$_{10}$ alkylcarbonyloxyalkyloxy, C$_3$–C$_{10}$ alkoxycarbonyloxyalkyloxy, C$_2$–C$_{10}$ alkoxycarbonylalkyloxy, C$_5$–C$_{10}$ cycloalkylcarbonyloxyalkyloxy, C$_5$–C$_{10}$ cycloalkoxycarbonyloxyalkyloxy, C$_5$–C$_{10}$ cycloalkoxycarbonylalkyloxy, C$_7$–C$_{11}$ aryloxycarbonylalkyloxy, C$_8$–C$_{12}$ aryloxycarbonyloxyalkyloxy, C$_8$–C$_{12}$ arylcarbonyloxyalkyloxy, C$_5$–C$_{10}$ alkoxyalkylcarbonyloxyalkyloxy, C$_5$–C$_{10}$ (5-alkyl-1,3-dioxa-cyclopenten-2-one-yl)methyloxy, C$_{10}$–C$_{14}$ (5-aryl-1,3-dioxa-cyclopenten-2-one-yl)methyloxy, or (R$^{11}$)(R$^{12}$)N—(C$_1$–C$_{10}$ alkoxy)–;

R$^{20}$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)–, or heteroaryl(C$_1$–C$_6$ alkyl)–;

R$^{21}$ is selected from COOH or NR$^6{}_2$;

m is 0–4;

n is 0–4;

p is 0–2;

q is 0–2; and r is 0–2;

with the following provisos:

(1) t, n, m and q are chosen such that the number of atoms connecting R$^1$ and Y is in the range of 10–14; and (2) n and m are chosen such that the value of n plus m is greater than one unless U is —(CH$_2$)$_r$Q(CH$_2$)$_m$—.

[13] Preferred compounds of the invention as described above are compounds of the Formula Ic:

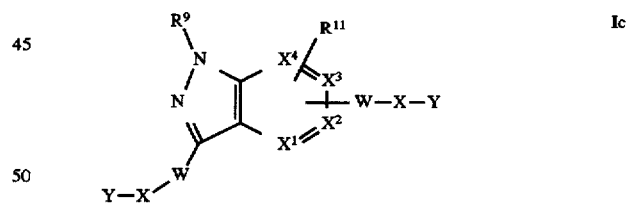

including stereoisomeric forms thereof, or mixtures of stereoisomeric forms thereof, or pharmaceutically acceptable salt or prodrug forms thereof wherein:

X$^1$, X$^2$, X$^3$, and X$^4$ are independently selected from nitrogen or carbon provided that at least two of X$^1$, X$^2$, X$^3$ and X$^4$ are carbon;

R$^1$ is selected from:

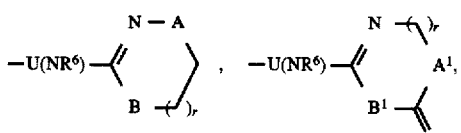

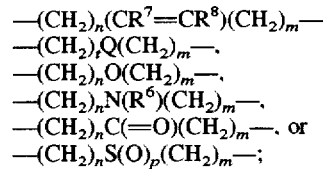

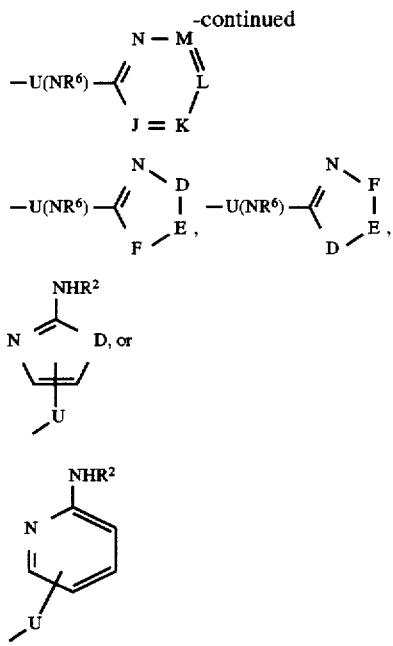

A and B are independently —CH$_2$—, —O—, —N(R$^2$)—, or —C(=O)—;

A$^1$ and B$^1$ are independently —CH$_2$— or —N(R$^3$)—;

D is —N(R$^2$)—, —O—, —S—, —C(=O)— or —SO$_2$—;

E-F is —C(R$^4$)=C(R$^5$)—, —N=C(R$^4$)—, —C(R$^4$)=N—, or —C(R$^4$)$_2$C(R$^5$)$_2$—;

J, K, L and M are independently selected from: —C(R$^4$)—, —C(R$^5$)— or —N—, provided that at least one of J, K, L and M is not —N—;

R$^2$ is selected from: H, C$_1$–C$_6$ alkyl, (C$_1$–C$_6$ alkyl)carbonyl, (C$_1$–C$_6$ alkoxy)carbonyl, C$_1$–C$_6$ alkylaminocarbonyl, C$_3$–C$_6$ alkenyl, C$_3$–C$_7$ cycloalkyl, C$_4$–C$_{11}$ cycloalkylalkyl, aryl, heteroaryl(C$_1$–C$_6$ alkyl)carbonyl, heteroarylcarbonyl, aryl(C$_1$–C$_6$ alkyl)-, (C$_1$–C$_6$ alkyl)carbonyl, arylcarbonyl, alkylsulfonyl, arylsulfonyl, aryl(C$_1$–C$_6$ alkyl)sulfonyl, heteroarylsulfonyl, heteroaryl(C$_1$–C$_6$ alkyl)sulfonyl, aryloxycarbonyl, aryl(C$_1$–C$_6$ alkoxy)carbonyl, wherein said aryl groups are substituted with 0–2 substituents selected from the group consisting of C$_1$–C$_4$ alkyl, C$_1$–C$_4$ alkoxy, halo, CF$_3$, and nitro;

R$^3$ is selected from: H, C$_1$–C$_6$ alkyl, C$_3$–C$_7$ cycloalkyl, C$_4$–C$_{11}$ cycloalkylalkyl, aryl, aryl(C$_1$–C$_6$ alkyl)-, or heteroaryl(C$_1$–C$_6$ alkyl)-;

R$^4$ and R$^5$ are independently selected from: H, C$_1$–C$_4$ alkoxy, NR$^2$R$^3$, halogen, NO$_2$, CN, CF$_3$, C$_1$–C$_6$ alkyl, C$_3$–C$_6$ alkenyl, C$_3$–C$_7$ cycloalkyl, C$_4$–C$_{11}$ cycloalkylalkyl, aryl, aryl(C$_1$–C$_6$ alkyl)-, C$_2$–C$_7$ alkylcarbonyl, arylcarbonyl or alternatively, when substituents on adjacent atoms, R$^4$ and R$^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: C$_1$–C$_4$ alkyl, C$_1$–C$_4$ alkoxy, halo, cyano, amino, CF$_3$, or NO$_2$;

U is selected from:
—(CH$_2$)$_n$—,

—(CH$_2$)$_n$(CR$^7$=CR$^8$)(CH$_2$)$_m$—
—(CH$_2$)$_n$Q(CH$_2$)$_m$—,
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—, or
—(CH$_2$)$_n$S(O)$_p$(CH$_2$)$_m$—;

wherein one of the methylene groups is optionally substituted with R$^7$;

Q is selected from 1,2-phenylene, 1,3-phenylene, 2,3-pyridinylene, 3,4-pyridinylene, or 2,4-pyridinylene;

R$^6$ is selected from: H, C$_1$–C$_4$ alkyl, or benzyl;

R$^7$ and R$^8$ are independently selected from: H, C$_1$–C$_6$ alkyl, C$_3$–C$_7$ cylcloalkyl, C$_4$–C$_{11}$ cycloalkylalkyl, aryl, aryl(C$_1$–C$_6$ alkyl)-, or heteroaryl(C$_0$–C$_6$ alkyl)-;

R$^9$ is selected from: H, CO$_2$R$^{17}$, C(=O)R$^{17}$, CONR$^{17}$R$^{20}$, —SO$_2$R$^{17}$, —SO$_2$NR$^{17}$R$^{20}$, C$_1$–C$_6$ alkyl substituted with 0–1 R$^{15}$ or 0–1 R$^{21}$, C$_3$–C$_6$ alkenyl substituted with 0–1 R$^{15}$ or 0–1 R$^{21}$, C$_3$–C$_7$ cycloalkyl substituted with 0–1 R$^{15}$ or 0–1 R$^{21}$, C$_4$–C$_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl(C$_1$–C$_6$ alkyl)- substituted with 0–1 R$^{15}$ or 0–2 R$^{11}$ or 0–1 R$^{21}$;

R$^{11}$ is selected from: H, halogen, CF$_3$, CN, NO$_2$, hydroxy, NR$^2$R$^3$, C$_1$–C$_4$ alkyl substituted with 0–1 R$^{21}$, C$_1$–C$_4$ alkoxy substituted with 0–1 R$^{21}$, aryl substituted with 0–1 R$^{21}$, aryl(C$_1$–C$_6$ alkyl)- substituted with 0–1 R$^{21}$, (C$_1$–C$_4$ alkoxy)carbonyl substituted with 0–1 R$^{21}$, (C$_1$–C$_4$ alkyl)carbonyl substituted with 0–1 R$^{21}$, C$_1$–C$_4$ alkylsulfonyl substituted with 0–1 R$^{21}$, or C$_1$–C$_4$ alkylaminosulfonyl substituted with 0–1 R$^{21}$;

W is —C(=O)—N(R$^{13}$)—(C(R$^{12}$)$_2$)$_q$—;

X is —C(R$^{12}$)(R$^{14}$)—C(R$^{12}$)(R$^{15}$)—; alternatively, W and X can be taken together to be

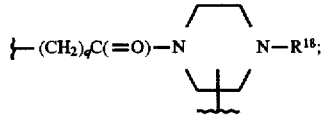

R$^{12}$ is H or C$_1$–C$_6$ alkyl;

R$^{13}$ is selected from: H, C$_1$–C$_6$ alkyl, C$_3$–C$_7$ cycloalkylmethyl, or aryl(C$_1$–C$_6$ alkyl)-;

R$^{14}$ is selected from:
H, C$_1$–C$_6$ alkylthioalkyl, aryl(C$_1$–C$_{10}$ alkylthioalkyl)-, aryl(C$_1$–C$_{10}$ alkoxyalkyl)-, C$_1$–C$_{10}$ alkyl, C$_1$–C$_{10}$ alkoxyalkyl, C$_1$–C$_6$ hydroxyalkyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl(C$_1$–C$_6$ alkyl)-, heteroaryl (C$_1$–C$_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be unsubstituted or substituted independently with 0–1 R$^{16}$ or 0–2 R$^{11}$;

R$^{15}$ is selected from:
H, R$^{16}$, C$_1$–C$_{10}$ alkyl, C$_1$–C$_{10}$ alkoxyalkyl, C$_1$–C$_{10}$ alkylaminoalkyl, C$_1$–C$_{10}$ dialkylaminoalkyl, C$_1$–C$_{10}$ alkylcarbonyl, aryl(C$_1$–C$_6$ alkyl)carbonyl, C$_2$–C$_{10}$ alkenyl, C$_2$–C$_{10}$ alkynyl, C$_3$–C$_{10}$ cycloalkyl, C$_3$–C$_{10}$ cycloalkylalkyl, aryl(C$_1$–C$_6$ alkyl)-, heteroaryl (C$_1$–C$_6$ alkyl)-, aryl, heteroaryl, CO$_2$R$^{17}$, C(=O)R$^{17}$, CONR$^{17}$R$^{20}$, SO$_2$R$^{17}$, or SO$_2$NR$^{17}$R$^{20}$, provided that any of the above alkyl, cycloalkyl, aryl or heteroaryl groups may be unsubstituted or substituted independently with 0–2 R$^{11}$;

Y is selected from:

—COR¹⁹, —SO₃H,

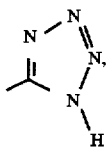

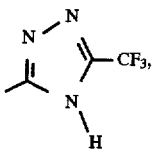

or

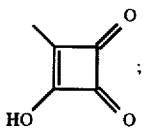

;

R¹⁶ is selected from:
—N(R²⁰)—C(=O)—O—R¹⁷,
—N(R²⁰)—C(=O)—R¹⁷,
—N(R²⁰)—C(=O)—NH—R¹⁷,
—N(R²⁰)SO₂—R¹⁷, or
—N(R²⁰)SO₂—NR²⁰R¹⁷;

R¹⁷ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, CF₃, and NO₂;

R¹⁸ is selected from:
H,
—C(=O)—O—R¹⁷,
—C(=O)—R¹⁷,
—C(=O)—NH—R¹⁷,
—SO₂—R¹⁷, or
—SO₂—NR²⁰R¹⁷;

R¹⁹ is selected from: hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or (R¹¹)(R¹²)N—($C_1$–$C_{10}$ alkoxy)-;

R²⁰ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

R²¹ is selected from COOH or NR⁶₂;
m is 0–4;

n is 0–4;
t is 0–4;
p is 0–2;
q is 0–2; and
r is 0–2.

[14] Further preferred compounds of the invention as described above are compounds of the Formula IIe or IIf:

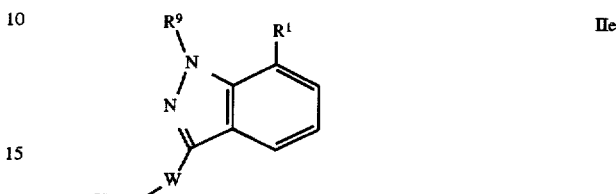

IIe

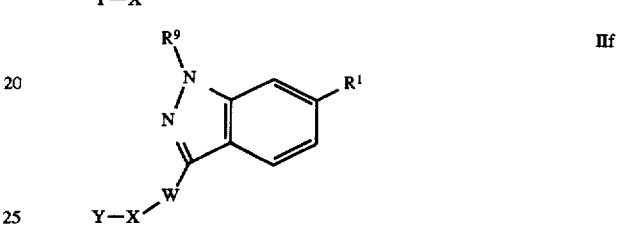

IIf including stereoisomeric forms thereof, or mixtures of stereoisomeric forms thereof, or pharmaceutically acceptable salt or prodrug forms thereof, wherein:

R¹ is selected from:

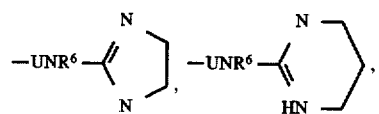

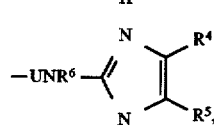

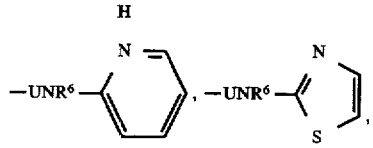

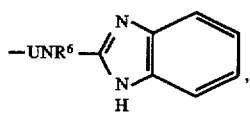

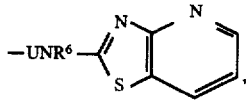

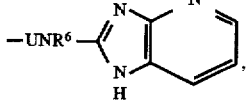

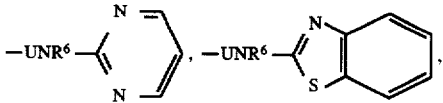

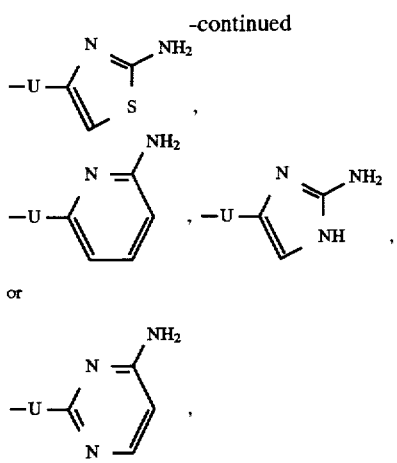

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is $-(CH_2)_n-$, $-(CH_2)_tQ(CH_2)_m-$ or $-C(=O)(CH_2)_{n-1}-$, wherein one of the methylene groups is optionally substituted with $R^7$;

Q is selected from 1,2-phenylene, 1,3-phenylene, 2,3-pyridinylene, 3,4-pyrdinylene, or 2,4-pyridinylene;

$R^6$ is selected from: H, $C_1$–$C_4$ alkyl, or benzyl;

R7 is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, $-SO_2R^{17}$, $-SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$ aryl substituted with 0–1 $R^{15}$ or 0–2 $R^{11}$ or 0–1 $R^{21}$, or aryl($C_1$–$C_6$ alkyl)-substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}_1$ aryl($C_1$–$C_6$ alkyl)-substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is $-C(=O)-N(R^{13})-$;

X is $-CH(R^{14})-CH(R^{15})-$;

$R^{13}$ is H or $CH_3$;

$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is $-COR^{19}$;

$R^{16}$ is selected from:
$-NH(R^{20})-C(=O)-O-R^{17}$,
$-N(R^{20})-C(=O)-R^{17}$,
$-N(R^{20})-C(=O)-NH-R^{17}$,
$-N(R^{20})SO_2-R^{17}$, or
$-N(R^{20})SO_2-N(R^{20})R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
or
1-(2-(2-methoxypropyl)carbonyloxy)ethoxy-;

$R^{20}$ is H or $CH_3$;

$R^{21}$ is selected from COOH or $NR^6_2$; and m is 0 or 1;

n is 1–4; and t is 0 or 1.

[15] Still further preferred compounds of the above described are compounds of the Formula IIe or IIf:

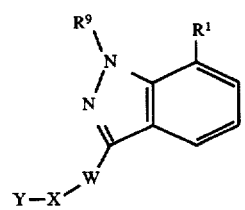

IIe

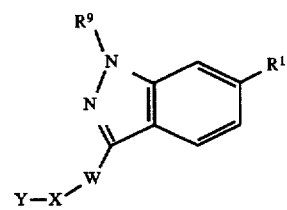

IIf including stereoisomeric forms thereof, or mixtures of stereoisomeric forms thereof, or pharmaceutically acceptable salt or prodrug forms thereof, wherein: $R^1$ is selected from:

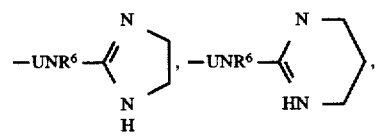

-continued

[chemical structures shown]

wherein the above heterocycles are optionally substituted with 0-2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_tQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ selected from: H, $C_1$–$C_4$ alkyl, or benzyl;

R7 is selected from $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)-substituted with 0–1 $R^{15}$ or 0–2 $R^{11}$ or 0–1 $R^{21}$;

$R^{11}$ is selected from H, halogen, $CF_3CN$, $NO_2$, hydroxy, $NR^2R^3C_1$–$C_4$ alkyl substituted with 0–1 $R^{21}C_1$–$C_4$ alkoxy substituted with 0–1 $R^{21}$, aryl substituted with 0–1 $R^{21}$, aryl($C_1$–$C_6$ alkyl)-substituted with 0–1 $R^{21}$ ($C_1$–$C_4$ alkoxy)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;W is —C(=O)—N($R^{13}$)—;

W is —C(=O)—N($R^{13}$)—;

X is —CH($R^{14}$)—CH($R^{15}$)

$R^{13}$ is H or $CH_3$;

$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6_2$; and m is 0 or 1;

n is 1–4; and t is 0 or 1.

In the present invention it has been discovered that the compounds of Formula Ia, Ib or Ic above are useful as inhibitors of cell-matrix and cell-cell adhesion processes. The present invention includes novel compounds of Formula Ia, Ib or Ic and methods for using such compounds for the prevention or treatment of diseases resulting from abnormal cell adhesion to the extracellular matrix which comprises administering to a host in need of such treatment a therapeutically effective amount of such compound of Formula Ia, Ib or Ic.

In the present invention it has also been discovered that the compounds of Formula Ia, Ib or Ic above are useful as inhibitors of $\alpha_v\beta_3$. The compounds of the present invention inhibit the binding of vitronectin to $\alpha_v\beta_3$ and inhibit cell adhesion.

The present invention also provides pharmaceutical compositions comprising a compound of Formula Ia, Ib or Ic and a pharmaceutically acceptable carrier.

The compounds of Formula Ia, Ib or Ic of the present invention are useful for the treatment (including prevention) of angiogenic disorders, comprising administering to a mammal in need of such treatment a therapeutically effective amount of a compound of Formula Ia, Ib or Ic described above. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion.

The compounds of Formula Ia, Ib or Ic of the present invention are also useful for the treatment (including prevention) of thromboembolic disorders, comprising administering to a mammal in need of such treatment a therapeutically effective amount of a compound of Formula Ia, Ib or Ic described above. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolisms, kidney embolisms, pulmonary embolisms, or such disorders associated with diabetes.

The compounds of Formula Ia, Ib or Ic of the present invention may also be useful for the treatment or prevention of other diseases which involve cell adhesion processes, including, but not limited to, inflammation, bone degradation, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formula Ia, Ib or Ic of the present invention may also be useful for wound healing.

The compounds of the present invention may be used for other ex vivo applications to prevent cellular adhesion in biological samples.

The compounds of the present invention can also be administered in combination with one or more additional therapeutic agents selected from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula Ia, Ib or Ic of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic or other disorders.

By "therapeutically effective amount" is meant an amount of a compound of Formula Ia, Ib or Ic that when administered alone or in combination with an additional therapeutic agent to a cell or mammal is effective to prevent or ameliorate the disease condition or the progression of the disease.

By "administered in combination" or "combination therapy" it is meant that the compound of Formula Ia, Ib or Ic and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin sodium crystalline clathrate and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Other suitable anti-platelet agents include ticlopidine, including pharmaceutically acceptable salts or prodrugs thereof. Ticlopidine is also a preferred compound since it is known to be gentle on the gastrointestinal tract in use. Still other suitable platelet inhibitory agents include thromboxane-$A_2$-receptor antagonists and thromboxane-$A_2$-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase, retivase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. The term urokinase, as used herein, is intended to denote both dual and single chain urokinase, the latter also being referred to herein as prourokinase.

The compounds of the present invention are also useful as standard or reference compounds, for example as a quality standard or control, in tests or assays involving the binding of vitronectin or fibrinogen to $\alpha_v\beta_3$. Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^4$, $R^6$, $R^7$, $R^8$, $R^{12}$, and $R^{14}$, n, etc.) occurs more than one time in any constituent or in any formula, its definition on each occurrence is independent of its definition at every other occurrence. Thus, for example, if a group is shown to be substituted with 0–3 $R^4$, then said group may optionally be substituted with up to three $R^4$ and $R^4$ at each occurrence is selected independently from the defined list of possible $R^4$. Also, by way of example, for the group —N($R^{5a}$)$_2$, each of the two $R^{5a}$ substituents on N is independently selected from the defined list of possible $R^{5a}$. Similarly, by way of example, for the group —C($R^7$)$_2$—, each of the two $R^7$ substituents on C is independently selected from the defined list of possible $R^7$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula Ia, Ib or Ic, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula Ia, Ib or Ic via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_0$–$C_{10}$" denotes alkyl having 0 to 10 carbon atoms; $C_0$ denotes a direct bond between the groups linked by the $C_0$ group; also by way of example, "$C_1$ to $C_4$" denotes methyl, ethyl, n-propyl, isopropyl, n-butyl, 2-methylpropyl, 1-methylpropyl, 1,1-dimethyl ethyl); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0] bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula Ia, Ib or Ic. Such "alkylene", "alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocyclic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

As used herein, "pharmaceutically acceptable salts" refer to derivatives of the disclosed compounds wherein the parent compound of Formula Ia, Ib or Ic is modified by making acid or base salts of the compound of Formula Ia, Ib or Ic. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula Ia, Ib or Ic in vivo when such prodrug is administered to a mammalian subject. Prodrugs of the compounds of Formula Ia, Ib or Ic are prepared by modifying functional groups present in the compounds in such a way that the modifications are cleaved, either in routine manipulation or in vivo, to the parent compounds. Prodrugs include compounds of Formula Ia, Ib or Ic wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula Ia, Ib or Ic, and the like. Examples of representative carboxyl and amino prodrugs are included under the definition of $R^2$, $R^3$, and Y.

The pharmaceutically acceptable salts of the compounds of Formula Ia, Ib or Ic include the conventional non-toxic salts or the quaternary ammonium salts of the compounds of Formula Ia, Ib or Ic formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethanesulfonic, ethanedisulfonic, oxalic, isethionic, and the like.

The pharmaceutically acceptable salts of the present invention can be synthesized from the compounds of Formula Ia, Ib or Ic which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula Ia, Ib or Ic may be prepared by reacting the acid with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, methanol, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

Compounds of Formula Ia, Ib or Ic wherein $X^1$, $X^2$, $X^3$ and $X^4$ are all carbon and W is C(=O)NH can be prepared from appropriately substituted 4-, 5-, 6-, or 7-alkoxycarbonyl indazoles, IIIa, wherein R is an alkyl group such as methyl, ethyl or tert-butyl.

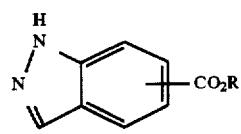

IIIa

The requisite indazoles can be conveniently prepared from the commercially available nitrotoluic acids according to the example shown in Scheme 1. Conversion of the acid 1a to a suitable ester, such as the ethyl ester 1b, may be carried out by one of many methods well-known to one skilled in the art of organic synthesis, for example treatment with a suitable base, such as sodium bicarbonate, in a suitable solvent, such as N,N-dimethylformamide, followed by treatment with an alkyl halide, such as iodoethane. Reduction of the nitro group of 1b can be effected in a number of ways known to one skilled in the art of organic synthesis, including treatment with tin(II) chloride in ethanol. The resulting aniline derivative can be converted to the desired substituted indazole IIIa according to the method of Bartsch and Yang (*J. Heterocycl. Chem.* 1984, 21(4): 1063–1064). A variation of the conversion of the aniline 1c to the indazole IIIa proceeds through an N-acylated intermediate 1d followed by cyclization and deacetylation, according to the method reported by Rüchardt and Hassmann (*Liebigs Ann. Chem.* 1980, 908–927).

The order of the esterification and reduction steps may be reversed, such that the nitrotoluic acid is first converted to an aminotoluic acid, which is then esterified. In some cases other intermediates related to those shown in Scheme 1 are commercially available or may be prepared using methods described in the literature of organic chemistry; in these cases transformations similar to those shown in Scheme 1 may be used to prepare the desired compounds IIIa. For example, commercially available methyl 3-amino-4-methylbenzoate may be directly transformed into 6-methoxycarbonylindazole.

dard functional group transformations well known to one skilled in the art.

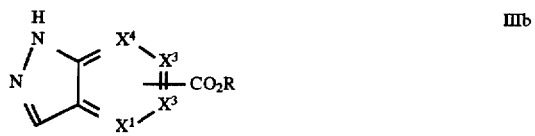

Functionalized pyrazines could be prepared according to procedures outlined in *The Chemistry of Heterocyclic Compounds: The Pyrazines*, Vol. 41 (Arnold Weissberger and Edward C. Taylor, Eds.),. John Wiley and Sons (New York: 1982). Preparation of appropriately functionalized pyridazines could be achieved using the methods described in *The Chemistry of Heterocyclic Compounds: Condensed Pyridazines Including Cinnolines and Phthalazines*, Vol. 27 (Arnold Weissberger and Edward C. Taylor, Eds.), John Wiley and Sons (New York: 1973) and *The Chemistry of Heterocyclic Compounds: Pyridazines*, Vol. 28 (Arnold Weissberger and Edward C. Taylor, Eds.), John Wiley and Sons (New York: 1973). For the synthesis of functionalized pyrimidines one could follow procedures in *The Chemistry of Heterocyclic Compounds: The Pyrimidines*, (Arnold Weissberger, Consulting Ed.) John Wiley and Sons (New York: 1962), *The Chemistry of Heterocyclic Compounds: The Pyrimidines*, Supplement I, (Arnold Weissberger and Edward C. Taylor, Consulting Eds.) John Wiley and Sons (New York: 1970), and *The Chemistry of Heterocyclic Compounds: The Pyrimidines*, Supplement II, Vol. 16

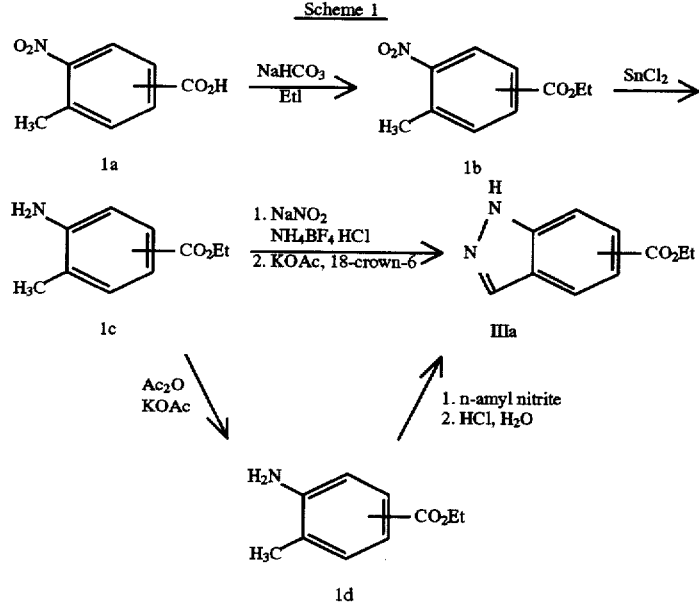

Scheme 1

Compounds of Formula Ia or Ib wherein one or more of $X^1$, $X^2$, $X^3$ or $X^4$ are nitrogen may be prepared from the corresponding alkoxycarbonylindazoles IIIb in which the appropriate carbon atom or atoms have been replaced by nitrogen. These may in turn be prepared by substitution of the appropriately substituted heterocycle for the nitrotoluic acids, nitrotoluic acid esters, or aminotoluic acid esters in Scheme 1 above. The starting heterocycles could be obtained by following the procedures and methods in references outlined below, along with implementation of stan- (Arnold Weissberger and Edward C. Taylor, Consulting Eds.) John Wiley and Sons (New York: 1985). Functionalized pyridines which can serve as starting materials in Scheme 1 could be made by the methods described in *The Chemistry of Heterocyclic Compounds: Pyridine and Its Derivatives*, Part Four, (Arnold Weissberger, Consulting Ed.) John Wiley and Sons (New York: 1964), *The Chemistry of Heterocyclic Compounds: Pyridine and Its Derivatives*, Supplement Part Two, (Arnold Weissberger and Edward C. Taylor, Consulting Eds.) John Wiley and Sons (New York: 1974), *The Chemistry of Heterocyclic Compounds: pyridine* and Its Derivatives, Supplement Part Three, Vol. 14 (Arnold Weissberger and Edward C. Taylor, Consulting Eds.) John Wiley and Sons (New York: 1974), The Chemistry of Heterocyclic Compounds: Pyridine and Its Derivatives, Supplement Part Four, Vol. 14 (Arnold Weissberger and Edward C. Taylor, Consulting Eds.) John Wiley and Sons (New York: 1975), and The Chemistry of Heterocyclic Compounds: Pyridine and Its Derivatives, Part Five, Vol. 14 (Arnold Weissberger and Edward C. Taylor, Consulting Eds.) John Wiley and Sons (New York: 1984). One example of the preparation of an appropriately substituted pyridine starting material is the preparation of 2-methyl-3-aminopyridine-5-carboxylic acid half-sulfate salt, as described by Argoudelis and Kummerow (J. Org. Chem. 1961, 26: 3420–3422).

Compounds of Formula Ia wherein $R^{10}$ is not hydrogen may be prepared from appropriately substituted alkoxycarbonylindazoles. Some such substituted alkoxycarbonylindazoles may be prepared using the method outlined in Scheme 1. For example, methyl 4-amino-3-ethylbenzoate may be prepared as described by Witte and BoekeOheide (J. Org. Chem. 1972, 37 (18): 2849–2853) This compound may be converted to the diazonium fluoroborate and cyclized to 3-methyl-2-methoxycarbonylindazole using the method outlined in Scheme 1. This compound may be used as a starting material for preparation of the corresponding compounds of Formula Ia wherein $R^{10}$ is methyl.

Other substituted alkoxycarbonylindazoles may be prepared from unsubstituted alkoxycarbonylindazoles using the methods outlined in Scheme 2. For example, an ethoxycarbonylindazole may be brominated by treatment with bromine in a suitable solvent, such as acetic acid, to provide the corresponding 3-bromo-ethoxycarbonyl-indazole IIIc. This compound may be coupled with a suitable reagent, alternatively followed by additional synthetic manipulations, to provide the desired 3-substituted-ethoxycarbonylindazole. For example, coupling with phenylboronic acid in the presence of tetrakis-(triphenylphosphine)palladium and triethylamine in N,N-dimethylformamide, using the method of Miyaura, Suginome and Suzuki (Tetrahedron 1983, 2: 3271) provides the corresponding 3-phenyl-ethoxycarbonylindazole IIId. Similar methods, starting from compounds of Formula IIIb, may be used to prepare the corresponding compounds wherein one or more of the ring carbons (corresponding to those designated $X^1$, $X^2$, $X^3$ and $X^4$ in Formula Ia) are replaced by nitrogen.

Scheme 2

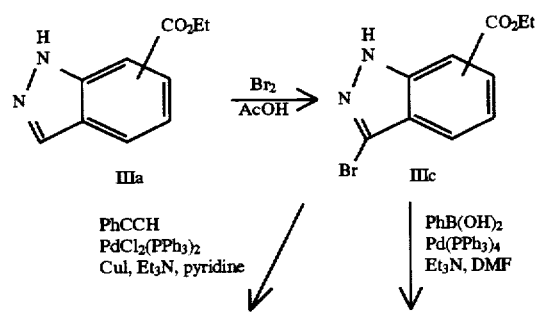

As another example, also shown in Scheme 2, coupling of IIIc with phenylacetylene in the presence of bis-(triphenylphosphine)palladium(II) chloride, copper(I) chloride, and triethylamine in pyridine according to the method of Melissaris and Litt (J. Org. Chem. 1992, 57: 6998–6999) provides the corresponding 3-(2-phenylethynyl)-ethoxycarbonylindazole IIIe, which may be reduced using hydrogen in the presence of palladium on charcoal to provide the corresponding 3-(2-phenyl-ethyl) ethoxycarbonylindazole IIIf. Similar methods, starting from compounds of Formula IIIb, may be used to prepare the corresponding compounds wherein one or more of the ring carbons (corresponding to those designated $X^1$, $X^2$, $X^3$ and $X^4$ in Formula Ia) are replaced by nitrogen.

Compounds IIIc, IIId, IIIe and IIIf may be used in the preparation of compounds of Formula Ia in which $R^{10}$ is phenyl, 2-phenylethynyl, or 2-phenylethyl, respectively. Alternatively, further manipulations of the substituent may be accomplished at a later stage in the synthesis of the compound of Formula Ia. For example, the 2-phenylethynyl indazoles IIIe may be used in a synthetic sequence during the course of which the acetylene will be reduced, providing ultimately compounds of Formula Ia in which $R^{10}$ is 2-phenylethyl.

Other appropriately substituted alkoxycarbonylindazoles, for use in the preparation of compounds of Formula Ia wherein $R^{10}$ is not hydrogen, may be prepared using other methods known in the art of organic synthesis, such as those outlined in The Chemistry of Heterocyclic Compounds: Pyrazoles, Pyrazolines, Pyrazolidines, Indazoles and Condensed Rings, Vol. 22 (Arnold Weissberger, Ed.), John Wiley and Sons (New York: 1967), Chapter 10.

Hereinafter, unless otherwise specified, phrases such as "indazoles III" and "indazoles of Formula III" are meant to

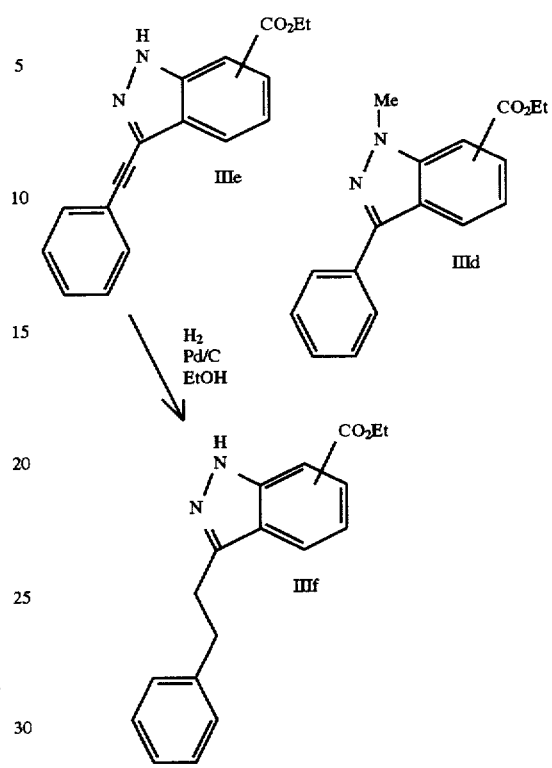

include simple indazoles IIIa, mono- or diazaindazoles IIIb, and substituted indazoles such as but not restricted to IIIc, IIId, IIIe and IIIf. Substituted mono- and diazaindazoles such as but not restricted to mono- and diaza analogs of IIIc, IIId, IIIe and IIIf are also included.

Compounds of Formula Ia may be prepared from indazoles III as outlined in Scheme 3. Alkylation of the indazoles of Formula III with a suitably functionalized alkyl halide can be effected in a variety of ways known to one skilled in the art. For example, using a method similar to that described by Granger et al. (*Chim. Ther.* 1970, 5: 24), an indazole of Formula III is treated with a suitable base, such as potassium bis(trimethylsilyl) amide, followed by addition of the alkyl halide, for example, 3-bromopropylphthalimide. Alternately, the alkylation can be carried out utilizing Mitsunobu conditions (Mitsunobu, *Synthesis*, 1981, 1–28) by addition of the corresponding alcohol, 3-hydroxypropylphthalimide, to a mixture of diethyl azodicarboxylate and triphenylphosphine in a suitable solvent, usually dry tetrahydrofuran, followed by addition of the indazole III. Separation, if necessary, of the mixture of 1- and 2-substituted isomers by chromatography provides the desired 1-alkylated product 3a. Removal of the phthalimide may be achieved by treatment with anhydrous hydrazine to give the primary amine 3b.

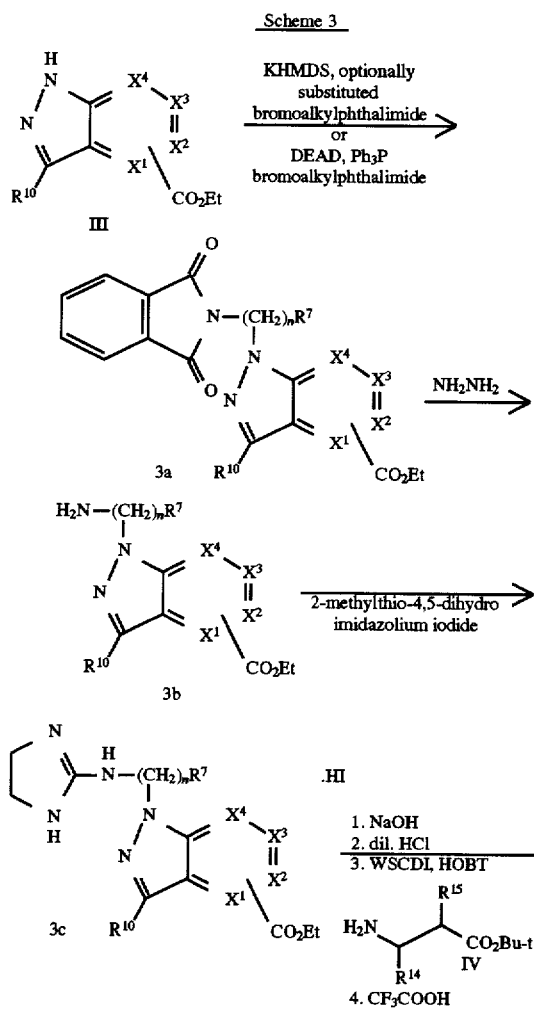

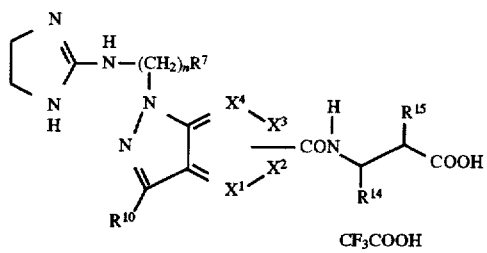

As further shown in Scheme 3,2-imidazolinyl-aminoalkylindazoles may be prepared by treatment of the amine 3b with a suitable reagent such as 2-methylthio-4,5-dihydroimidazolium iodide. Hydrolysis of the ester, using conventional methods known to one skilled in the art of organic synthesis, may be followed by coupling of the resulting acid to an appropriately substituted α- or β-amino ester such as a compound of Formula IV, to provide an intermediate which, after deprotection, affords compounds of Formula Ia wherein $R^1$ is 2-imidazolinylaminoalkyl. The coupling may be carried out using any of the many methods for the formation of amide bonds known to one skilled in the art of organic synthesis. Those methods include, but are not limited to, use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides (WSCDI)) method, active ester (p-nitrophenyl ester, N-hydroxysuccinic imido ester) method, or by the use of one of many other known coupling reagent such as BOP-Cl. Some of these methods (especially the carbodiimide method) can be enhanced by the addition of 1-hydroxybenzotriazole to the reaction mixture.

An alternative method for preparing amines 3b wherein n=3 is outlined in Scheme 4. Alkylation of the indazole III may be achieved by treatment with an optionally substituted acrylonitrile in the presence of a catalytic amount of a base such as sodium ethoxide or sodium bis(trimethylsilyl)amide, in a suitable solvent such as ethanol, to provide the intermediate nitrile 4a. This may be converted to the amine 3b by reduction using any of a number of methods known to one skilled in the art of organic synthesis, such as by treatment with hydrogen in the presence of a catalyst such as palladium on charcoal. An acid such as aqueous hydrochloric acid may be added to the reaction mixture to minimize side reactions during the reduction.

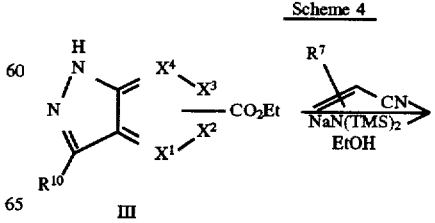

-continued
Scheme 4

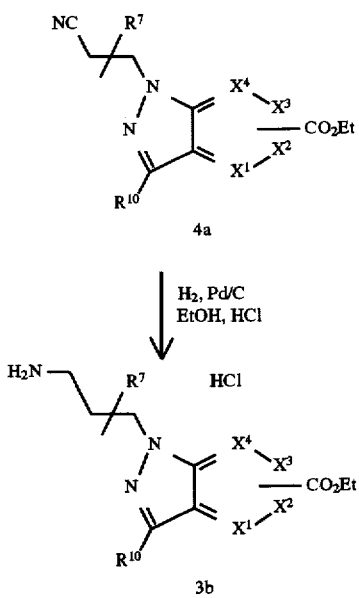

Scheme 5

Method 2

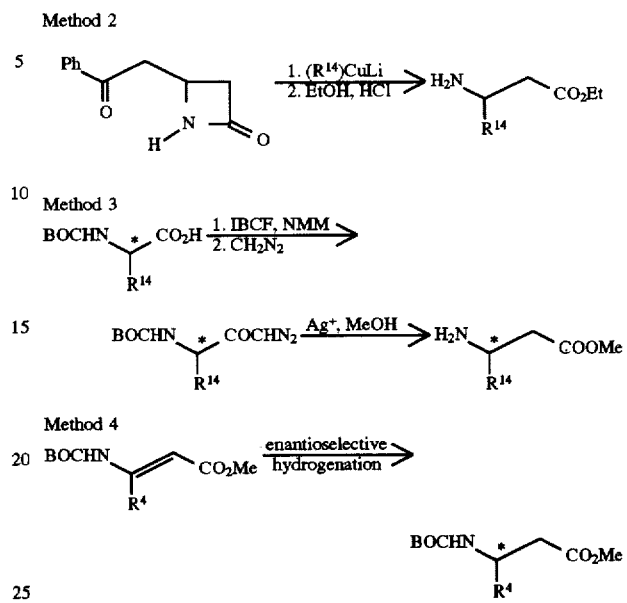

Appropriately substituted racemic β-amino acids IV (used in Scheme 3) may be purchased commercially or, as is shown in Scheme 5, Method 1, prepared from the appropiate aldehyde, malonic acid and ammonium acetate according to the procedure of Johnson and Livak (*J. Am. Chem. Soc.*, 1936, 58, 299). Racemic β-substituted-β-amino esters may be prepared through the reaction of dialkylcuprates or alkyllithiums with 4-benzoyloxy-2-azetidinone followed by treatment with anhydrous ethanol (Scheme 5, Method 2) or by reductive amination of β-keto esters as is described in WO93/16038 (also see Rico et al., *J. Org. Chem.*, 1993, 58, 7948–51). Enantiomerically pure β-substituted-β-amino acids can be obtained through the optical resolution of the racemic mixture or can be prepared using numerous methods, including: Arndt-Eistert homologation of the corresponding β-amino acids as shown in Scheme 5, Method 3 (see Meier and Zeller, *Angew. Chem. Int. Ed. Engl.*, 1975 14, 32; Rodriguez et al., *Tetrahedron Lett.*, 1990, (31), 5153; Greenlee, *J. Med. Chem.* 1985, 28, 434 and references cited within); and through an enantioselective hydrogenation of a dehydroamino acid as is shown in Scheme 5, Method 4 (see *Asymmetric Synthesis*, Vol. 5, (Morrison, ed.) Academic Press, New York: 1985). A comprehensive treatise on the preparation of β-amino acid derivatives may be found in patent application WO 93/07867, the disclosure of which is hereby incorporated by reference.

Scheme 5

Method 1

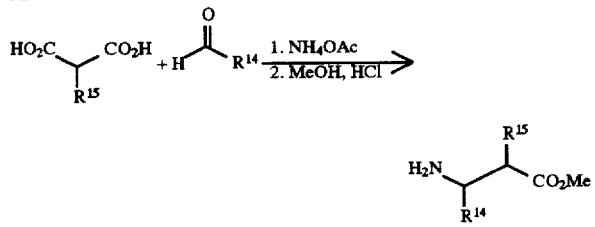

The synthesis of $N^2$-substituted diaminopropionic acid derivatives IV can be carried out via Hoffmann rearrangement of a wide variety of asparagine derivatives as described, for example, by Waki et al. (*Synthesis* 1981, 266–267) or by Moore et al. (*J. Med. Chem.* 1976, 19(6), 766–772). An example is shown in Scheme 6, Method 1. They may also be prepared by manipulations, which will be familiar to one skilled in the art of organic synthesis, of the commercially available 3-amino-2-benzyloxycarbonylaminopropionic acid. An example is shown in Scheme 6, Method 2.

Scheme 6

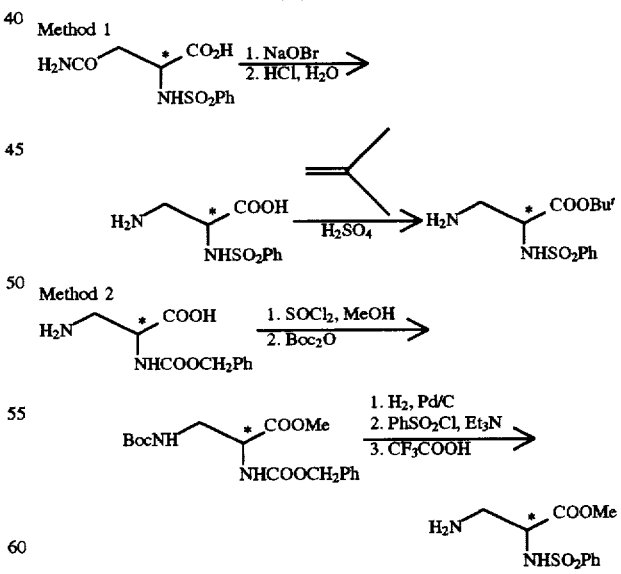

Compounds of Formula Ia above wherein $R^1$ is 2-pyridinylaminoalkyl may be prepared by the method outlined in Scheme 7. Treatment of the intermediate aminoalkylindazole 3b from Scheme 3 (or the corresponding salt from Scheme 4) with 2-chloropyridine N-oxide hydrochloride, using a modification of the method described by Misra, et al. (*Bioorg. and Med. Chem. Letters*, 1994, 4, 2165–2170), and subsequent reduction of the resulting N-oxide derivative 7a provides a 2-pyridinylaminoalkyl intermediate 7b. This reduction may be performed using a number of methods known to one skilled in the art of organic synthesis, such as that using ammonium formate in the presence of 10% palladium on charcoal in refluxing ethanol, as described by Balicki (*Synthesis*, 1989, 645–646), or by reduction with hydrogen in the presence of a catalyst such as palladium on charcoal or Raney nickel, or by treatment with triphenylphosphine. The resulting 2-aminopyridine moiety of 7b may be optionally protected, for example by treatment with di-t-butyldicarbonate in dry tetrahydrofuran in the presence of a suitable base, such as triethylamine or N,N-dimethylaminopyridine, using the method of Iwanowicz (*Synth. Commun.*, 1993, 23(10), 1443–1445), to provide intermediate 7c. Ester hydrolysis, coupling and deprotection as outlined in Scheme 3 can then provide the desired compounds of Formula Ia.

described above (see Scheme 3) to provide 8a. Deprotection to the aldehyde 8b, for example by treatment with aqueous acid, may be followed by reductive amination with a heteroarylamine such as 2-aminopyridine or a suitably protected 2-aminoimidazole, such as 1-triphenylmethyl-2-aminoimidazole, in the presence of a reducing agent such as sodium triacetoxyborohydride or sodium cyanoborohydride, to provide the 1-(heteroarylaminoalkyl)indazole 8c. The intermediates 8c can then be elaborated to the corresponding compounds of Formula Ia, for example as described in Scheme 3.

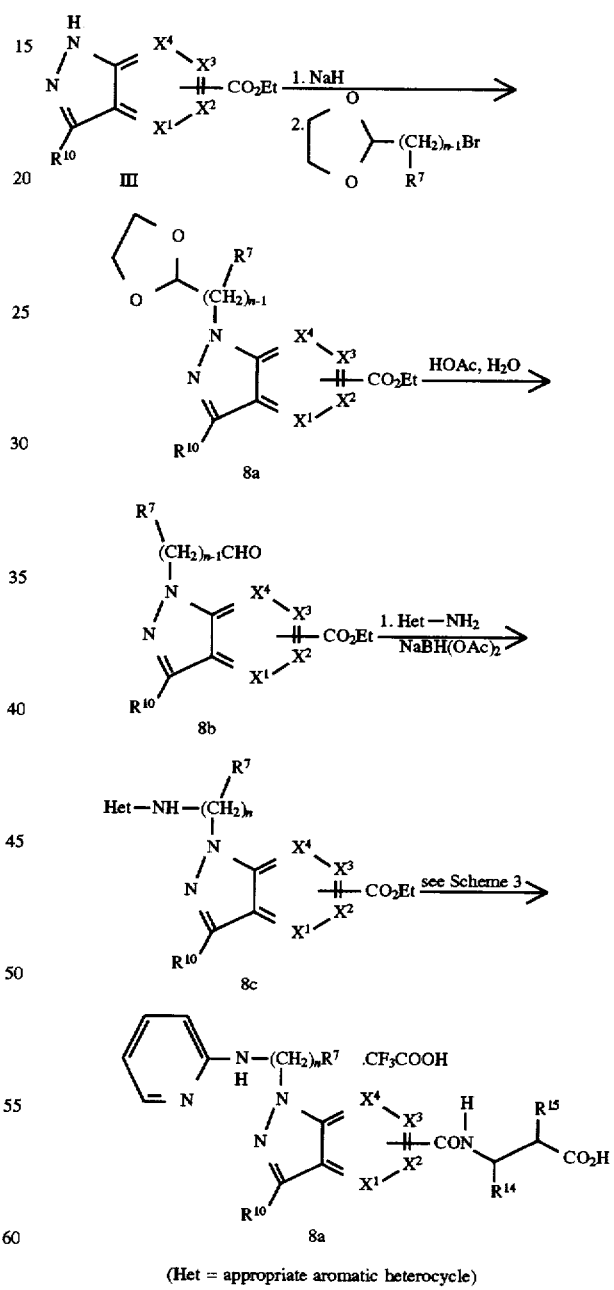

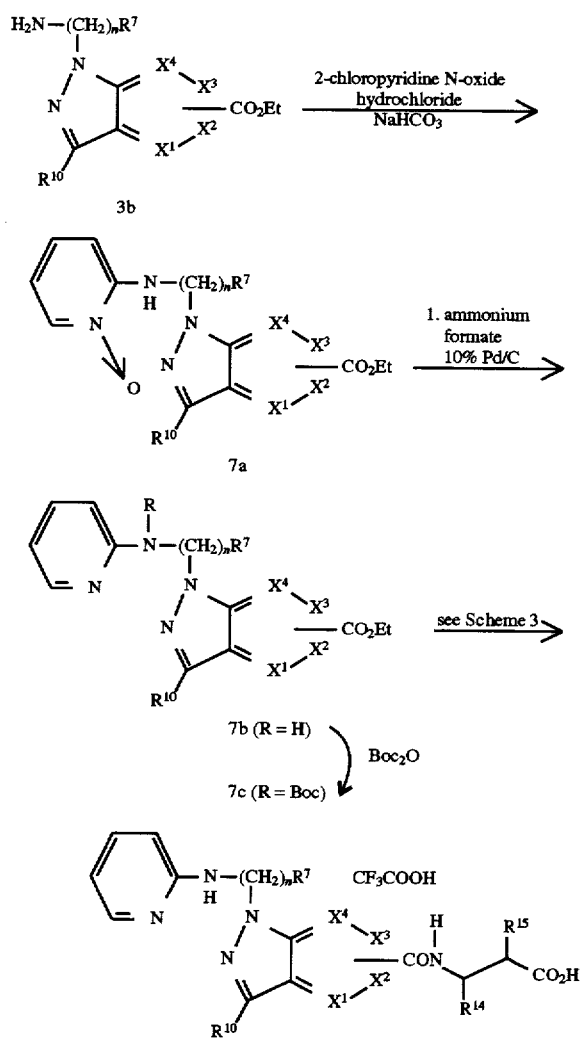

An alternative route to 1-(heteroarylaminoalkyl)indazoles of Formula Ia is outlined in Scheme 8. A suitable indazole III can be alkylated with an alkyl halide bearing a protected aldehyde, such as a 1,3-dioxolane, using conditions A route to 1-(heteroarylaminocarbonylethyl) 10 indazoles of Formula Ia is outlined in Scheme 9. A suitable indazole III can be alkylated by treatment with an acrylic acid ester such as tert-butyl acrylate, using a method such as that described in Scheme 4. Removal of the ester of 9a may be followed by conversion to a heteroaryl amide by treatment with a heteroaryl amine using any of a number of methods well known to one skilled in the art of organic synthesis. The resulting 1-(heteroarylaminocarbonylethyl)indazole 9b can then be elaborated to the corresponding compounds of Formula Ia, for example as described in Scheme 3.

Formula Ib, for example using methods described in Scheme 3.

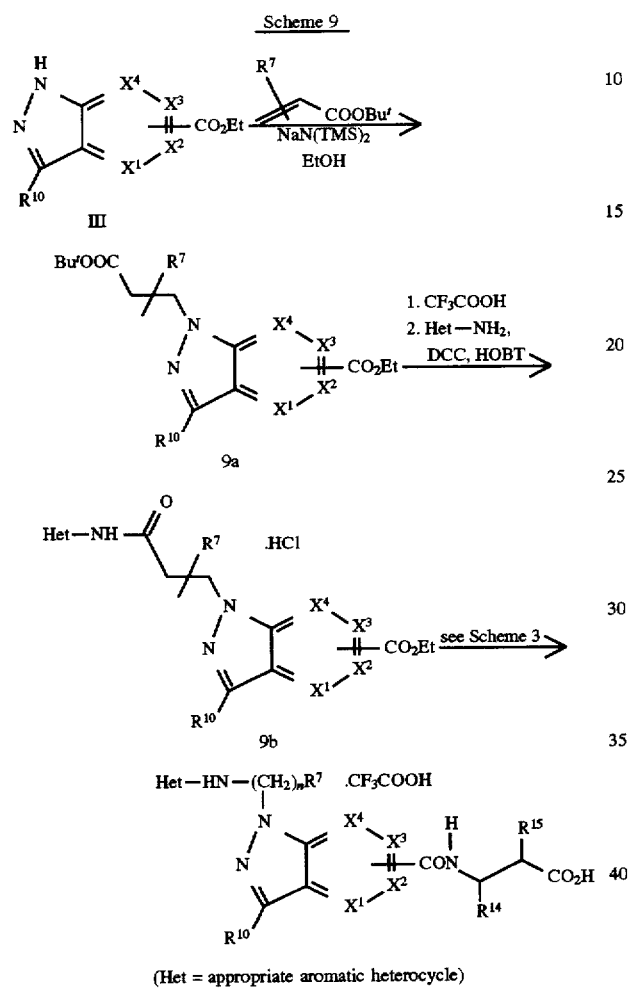

(Het = appropriate aromatic heterocycle)

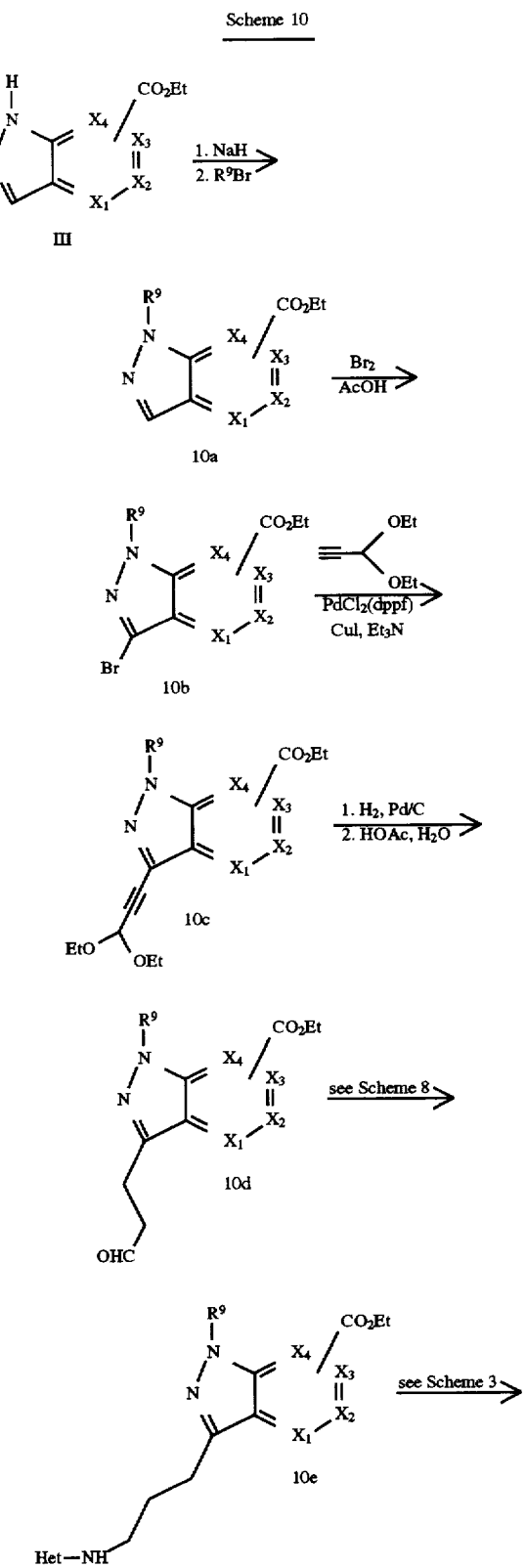

Compounds of Formula Ib may be prepared according to the method outlined in Scheme 10. Thus, the appropriate indazole III may be alkylated by treatment with a suitable base, for example sodium hydride, followed by addition of a suitable alkylating agent such as an alkyl halide $R^9$-Br or $R^9$-I. Bromination of the intermediate 10a using, for example, bromine in acetic acid, provides the corresponding 3-bromo derivative 10b. (The order of these two synthetic steps may also be reversed. That is, the indazole III may be brominated, and resulting bromoindazole may be alkylated, to provide similar products 10b.) Coupling of 10b with, for example, 3,3-diethoxy-1-propyne, under conditions similar to those described by Sakamoto et al. (*Synthesis* 1992, 746–748) provides a functionallzed alkynyl derivative 10c. Reduction of the acetylenic bond of 10c using, for example, hydrogen in the presence of a catalyst such as palladium on charcoal, followed by hydrolysis of the acetal with aqueous acid provides an aldehyde intermediate 10d which, using methods analogous to those outlined in Scheme 8, may be elaborated to an intermediate 10e containing a heteroarylaminoalkyl substituent at the 3-position. This intermediate may then in turn be elaborated to the desired compounds of -continued
Scheme 10

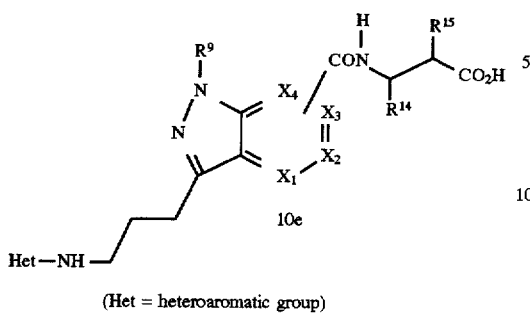

10e (Het = heteroaromatic group)

Compounds of Formula Ib may alternatively be prepared from the intermediate 10b to the method described in Scheme 11. Thus, coupling of 10b under conditions similar to those described by Murakami et al. (*Heterocycles*, 1990, 31(8), 1505–11) can provide a 3-allyl derivative 11a. Hydroboration as described by Brown and Subba Rao (*J. Am. Chem. Soc.* 81, 6428–6433) can provide the alcohol 11b, which may be subjected to the Mitsunobu reaction (vide supra) with phthalimide followed by deprotection to provide an amine intermediate 11c which, analogously to the method shown in Schemes 10 and 3, can be elaborated to the desired compounds of Formula Ib. Alternatively, the intermediate 11b may be prepared by reduction of the aldehyde 10d shown in Scheme 10. Other methods can be used for the conversion of intermediates 10d and 11b to the primary amine 10c which are known to those skilled in the art of organic synthesis.

Scheme 11

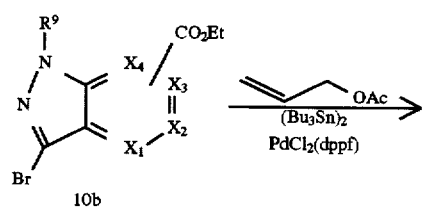

10b

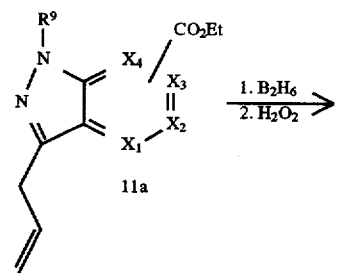

11a

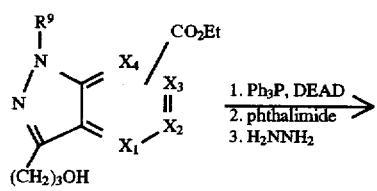

11b

-continued
Scheme 11

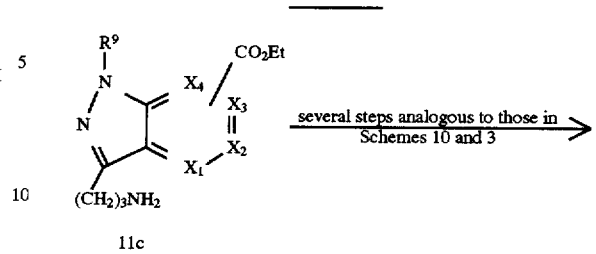

11c

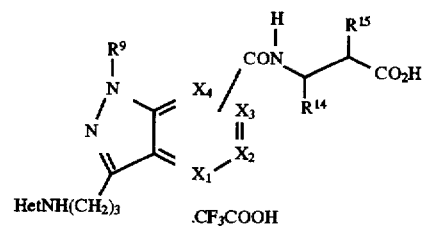

(Het = heterocyclic group)

Compounds of Formula Ic may be prepared according to methods outlined in Scheme 12. Treatment of the appropriate indazole starting material 12a with zinc bromide and vinylmagnesium bromide followed by dichloro[1,1'-bis(diphenylphosphino)ferrocene] palladium (II), using a procedure similar to that described by Brown, et al. (U.S. Pat. No. 4,898,863), can provide the desired 3-vinyl derivative 12b. Treatment of this compound with ozone (F. J. Brown, et al. Ibid.), can provide an aldehyde 12c. Oxidation using silver(I) oxide, as described by Campaigne and LeSuer (*Organic Syntheses*, 1963, Coll. Vol. 4, 919), can provide the desired carboxylic acid 12d. Esterification and deprotection of the ether oxygen of 12e using boron tribromide, by a method analogous to that detailed by Manson and Musgrave (*J. Chem. Soc.* 1011 (1963)), can provide the hydroxy intermediate 12f. Mitsunobu coupling, (vide supra), followed by further transformations of 12g similar to those shown in Scheme 3, can provide compounds of Formula Ic.

Scheme 12

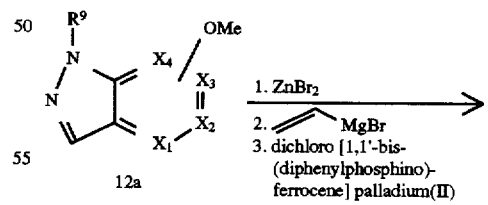

12a

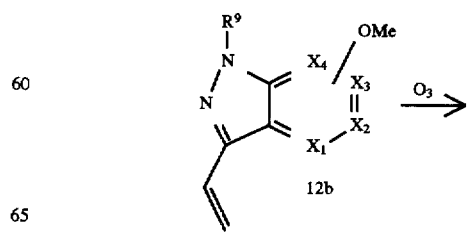

12b

Scheme 12
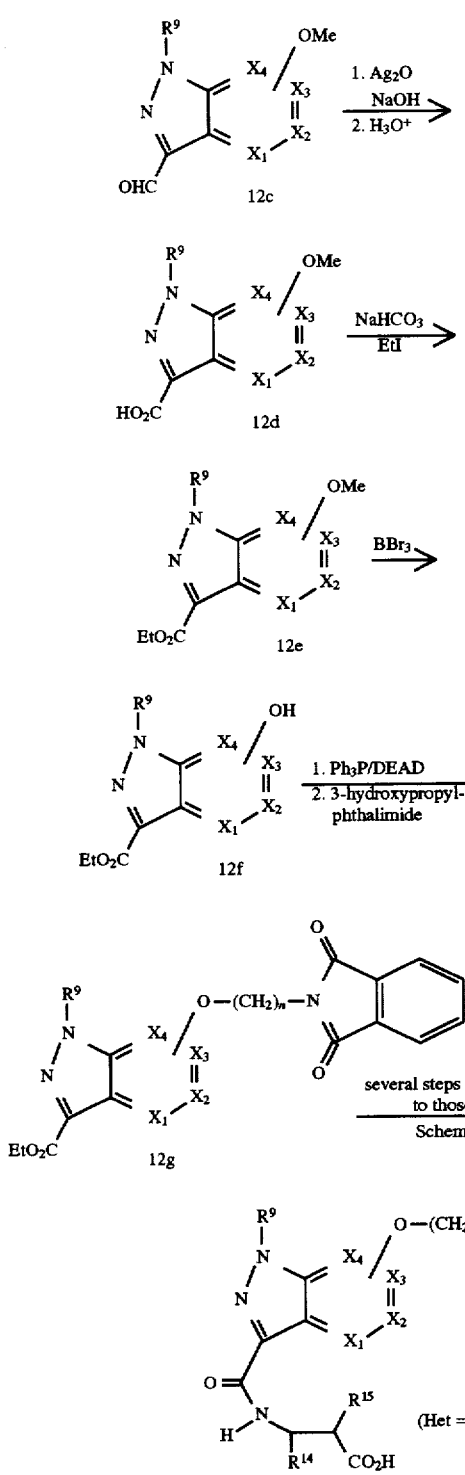
Additional alcohols useful for the preparation of compounds of Formula Ia, Ib and Ic through the Mitsunobu reaction described in the above schemes may be prepared as described in Scheme 13.
Scheme 13
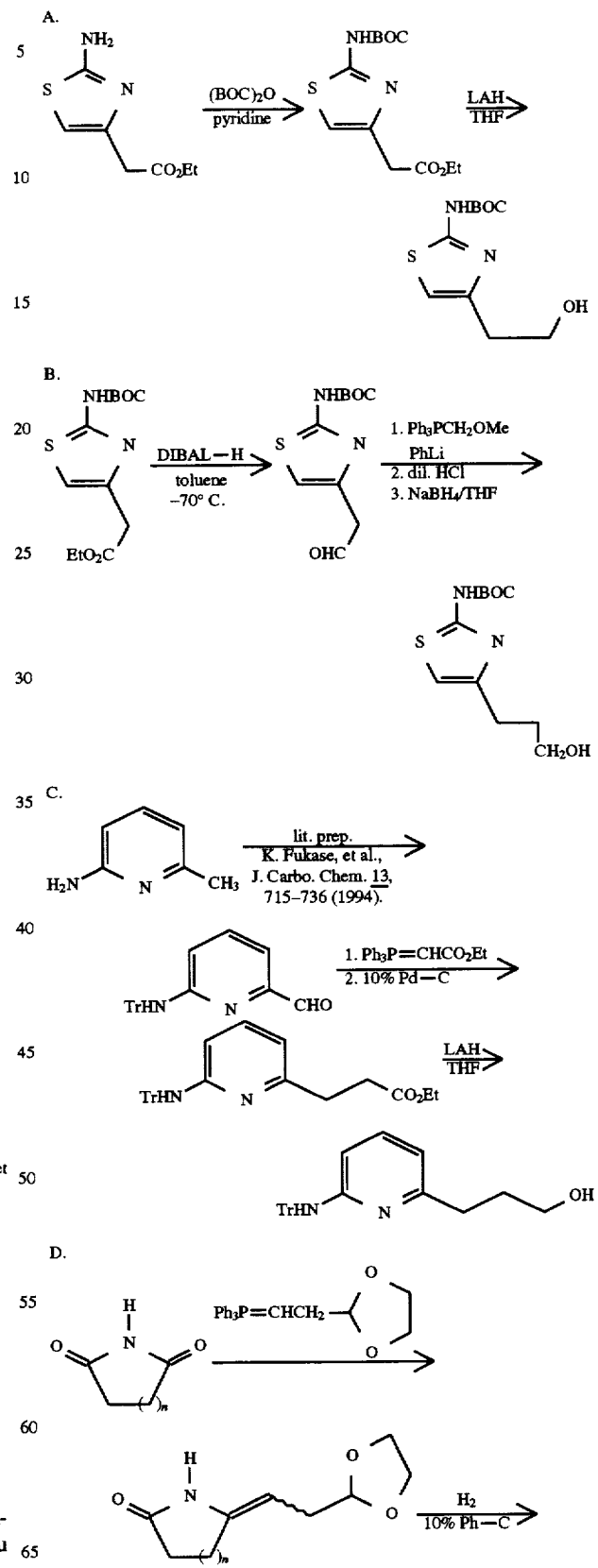

69

-continued
Scheme 13

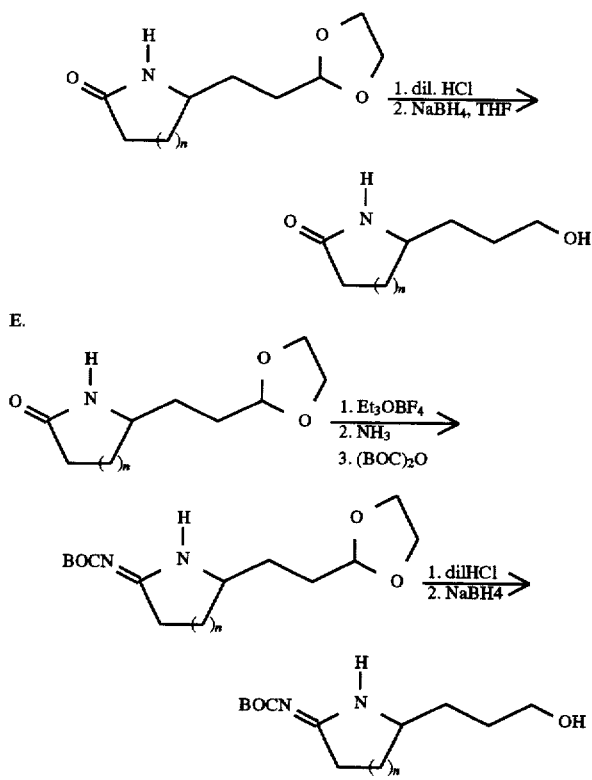

E.

Various compounds of Formula Ia, Ib or Ic may be prepared from a common derivative of the corresponding compounds of Formula Ia, Ib or Ic by functional group manipulations familiar to one skilled in the art of organic synthesis. As one example, preparation of compounds of Formula Ia having different sulfonamide substituents at $R^{16}$ may be achieved as outlined in Scheme 14. Thus, the compound of Formula Ia having a benzyloxycarbonylamino group at $R^{16}$ (14a) may be hydrogenolyzed using, for example, hydrogen in the presence of a catalyst such as palladium on charcoal to provide the primary amine derivative 14b. This may be reacted with a sulfonylating agent such as $R^{17}SO_2Cl$ in the presence of an amine such as triethylamine to provide, after deprotection of the ester, the desired compound of Formula Ia. In place of the sulfonyl chloride, use of a carboxylic acid, acid chloride or acid anhydride can provide the corresponding amide derivative, use of a chloroformate can provide the corresponding carbamate derivative, use of a sulfamoyl chloride can provide the corresponding sulfamide derivative, and use of an isocyanate can provide the corresponding urea derivative.

Scheme 14

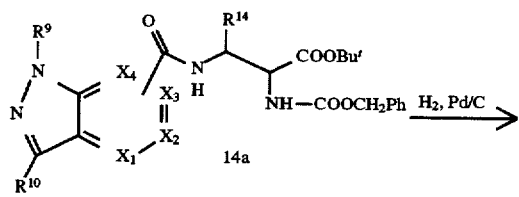

70

-continued
Scheme 14

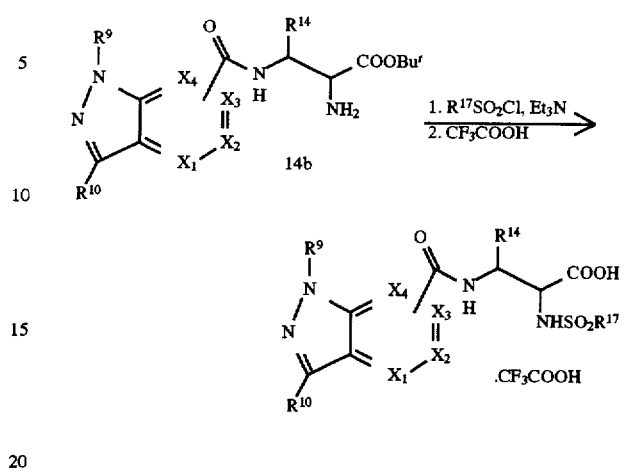

As another example, compounds of Formula Ia with different variations in $R^1$ may be prepared from a common precursor as outlined in Scheme 15. Thus, the amine intermediate 3b may be reacted, for example, with benzyl chloroformate to provide the benzyl carbamate. Hydrolysis of the ester, for example with lithium hydroxide, can provide the acid intermediate 15a. Using methods described earlier, 15a may be reacted with, for example, a suitable beta-amino ester, followed by removal of the benzyl carbamate, for example by hydrogenolysis, to provide the amine intermediate 15b. Using, for example, steps analogous to those shown in Schemes 3 or 7, the amine may be converted to an aminoheterocyclic group. After deprotection of the ester, the desired compound of Formula Ia may be obtained.

Scheme 15

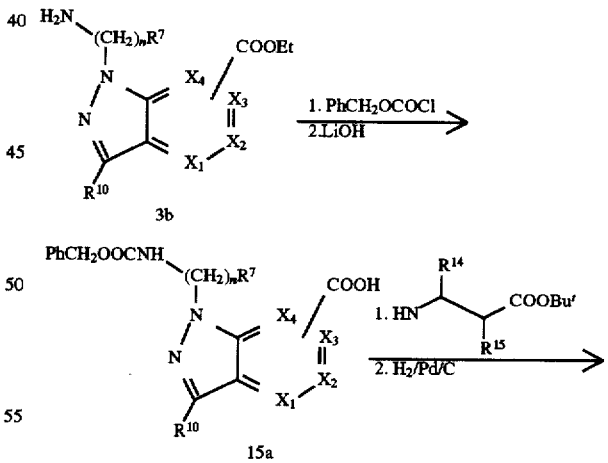

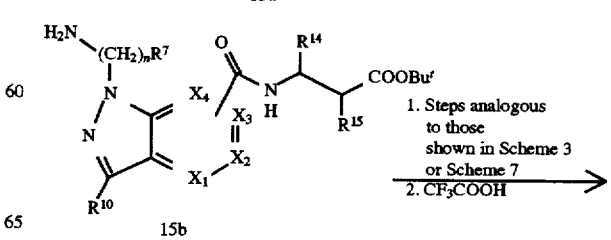

-continued
Scheme 15

.CF₃COOH

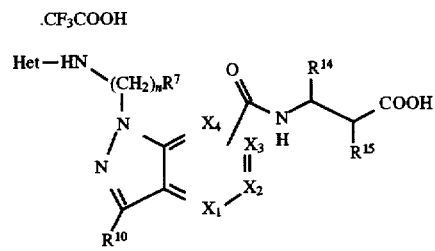

The example outlined in Scheme 15 will also serve to demonstrate that the order in which the different substituents are elaborated to give the compounds of Formula Ia, Ib and Ic may be varied from that in the examples shown in Schemes 1 through 14. This example will also serve to demonstrate the use of protecting groups to temporarily protect a functional group in the course of a synthetic sequence when that functional group is not compatible with one or more of the synthetic transformations that are to be accomplished. Such use of protecting groups, while not always explicitly shown in Schemes 1 through 15, is well known to one skilled in the art of organic synthesis. Many examples of protecting groups may be found, for example, in Greene, "Protective Groups in Organic Syntheses", Wiley (New York), 1981.

The detailed processes for preparing the compounds of Formula Ia, Ib or Ic are illustrated by the following Examples. It is, however, understood that this invention is not limited to the specific details of these examples. Reactions were run under an atmosphere of nitrogen unless otherwise indicated. Solvent removal from reaction mixtures, extracts, and the like was performed under vacuum on a rotary evaporator. Flash chromatography refers to the medium-pressure column chromatography method described by Still et al. (J. Org. Chem. 1978, 43(14), 2923–2925). Melting points (mp) are uncorrected. Proton nuclear magnetic resonance spectra (NMR) were measured in chloroform-d (CDCl₃), dimethyl sulfoxide-d₆ (DMSO-d₆) or methanol-d₄ (MeOH-d₄) and the peaks are reported in parts per million downfield from tetramethylsilane (δ). The coupling patterns are reported as follows: s, singlet; d, doublet; t, triplet; q, quartet; m, multiplet; b, broad. Mass spectra were measured using electrospray ionization (ESI), ammonia chemical ionization (NH₃—CI), fast-atom bombardment from a glycol matrix (FAB), or electron impact ionization (EI).

EXAMPLE 1035b

3-[1-[3-(N-imidazol-2-ylamino)propyl]-indazol-5-ylcarbonyl-amino]-2(S)-(2 6-dimethyl-4-phenylbenzene-sulfonylamino)-propionic acid trifluoroacetate A. tert-Butyl 3-[1-[3-(N-(1-triphenylmethylimidazol-2-yl)-amino)propyl]-indazol-5-ylcarbonylamino]-2(S)-(2,4,6-trimethylbenzenesulfonylamino)propionate A mixture of the product prepared according to Example 1050e Part K (215 mg, 407 µmol, the product prepared according to Example 1178b Part E (140 mg, 407 µmol), 1-hydroxybenzotriazole hydrate (57 mg, 407 µmol) and N,N-dimethylformamide (5 µL) was treated with dicyclohexylcarbodiimide (870 mg, 407 µmol) and stirred at room temperature for 24 h. The mixture was poured into water (75 mL) and extracted with ethyl acetate (3×50 mL) The organic phase was dried (MgSO₄) and concentrated under vacum. The residue was flash chromatographed (toluene:ethyl acetate, step gradient from 50:50 to 10:90) to provide the title product (262 mg, 75%) as a colorless glassy foam: ¹H NMR (CDCl₃)δ8.17 (s, 1H), 7.97 (d, 1H), 7.73 (dd, 1H), 7.4–7.1 (15H), 6.99 (d, 1H), 6.94 (s, 2H), 6.85 (bt, 1H), 6.68 (d, 1H), 6.42 (d, 1H) 5.82 (bd, 1H), 4.07 (t, 2H), 3.93 (m, 1H), 3.83 (m, 1H), 3.62 (m, 1H), 3.04 (m, 1H), 2.97 (m, 2H), 2.65 (s, 6H), 2.26 (s, 3H) 1.82 (m, 2H), 1.32 (s, 9H); Mass spectrum (ESI) m/z 852.4 (100%, M+H⁺).

Alternatively, a solution of the product prepared according to Example 1050e Part K (1.108 g, 2.1 mmol) in N,N-dimethylformamide (15 mL) was treated with the product prepared according to Example 1178b Part E (719 mg, 2.1 mmol), BOP reagent (975 mg, 2.2 mmol and diisopropylethyl-amine (543 mg, 4.2 mmol) and the mixture was stirred at room temperature overnight. The mixture was concentrated under vacuum and the residue was partitioned between ethyl acetate (100 mL) and water (25 mL). The aqueous phase was extracted with additional ethyl acetate (3×25 mL) and the combined organic phases were washed with hydrochloric acid (1.0N; 10 mL), water (2×10 mL), saturated aqueous sodium bicarbonate (10 mL) and brine (2×10 mL) then were dried (MgSO₄) and concentrated wider vacuum. This material was combined with the crude product from another run, starting from 10.8 g of the product prepared according to Example 1050e Part K (20.5 mmol), to provide the title product as a crude material; (23.0 g) which was used in the next step without purification.

B. tert-Butyl 3-[1-[3-(N-imidazol-2-ylamino)propyl]-indazol-5-ylcarbonylamino]-2(S)-(2,6-dimethyl-4-phenylbenzene-sulfonylamino)propionate The product prepared according to Example 1035b Part A (3.3 g, 3.9 mmol) was combined with methanol (100 mL) and acetic acid (10 mL) and the mixture was heated at reflux overnight. The mixture was concentrated under vacuum, and the residue was flash chromatographed (chloroform: methanol:aqueous ammonia 100:10:1) to provide the product as a glassy foam. This was combined with the product from another run, starting from 19.0 g of the product prepared according to Example 1035b Part A (22.3 mmol), to provide the title product (4.5 g). Impure material from the column was re-chromatographed (chloroform: methanol:aqueous ammonia 100:5:0.5) to provide additional pure title product (6.5 g; total combined yield 81%): ¹H NMR (MeOH-d₄) δ 8.17 (d, 1H), 8.13 (d, 1H), 7.76 (dd, 1H), 7.57 (d, 1H), 6.85 (s, 2H), 6.51 (s, 2H), 4.53 (t, 2H), 4.06 (dd, 1H), 3.70 (dd, 1H), 3.50 (dd, 1H), 3.17 (t, 2H), 2.59 (S, 6H), 2.16 (m, 2H), 2.10 (s, 3H), 1.22 (s, 9H).

C. 3-[1-[3-(N-imidazol-2-ylamino)propyl]-indazol-5-ylcarbonylamino]-2(S)-(2,6-dimethyl-4-phenylbenzenesulfonyl-amino)propionic acid trifluoroacetate A solution of the product prepared according to Example 1035b Part B (480 mg, 788 µmol) in dichloromethane (30 mL) was treated with trifluoroacetic acid (5 mL) and stirred for 1 h at room temperature. The solution was concentrated under vacuum, and the residue was dissolved in methanol (3 mL) and purified by preparative reverse-phase HPLC to provide, after lyophilization, the title product (432 mg, 82%) as an amorphous white solid: HPLC T$_R$ 12.33 min (95%); ¹H NMR (MeOH-d₄) δ 8.12 (s, 2H), 7.72 (dd, 1H), 7.54 (d, 1H), 6.76 (s, 2H), 6.73 (s, 2H), 4.53 (t, 2H), 4.16 (dd, 1H), 3.76 (dd, 1H), 3.49 (dd, 1H), 3.23 (t, 2H), 2.56 (s, 6H), 2.22 (m, 2H), 1.98 (s, 3H); High resolution mass spectrum (FAB) calculated (M+H⁺) 554.2186, found 554.2196.

Alternatively, a solution of the product prepared according to Example 1035b Part A (249 mg, 292 µmol) in trifluoroacetic acid (2.5 mL) was heated at reflux for 60 min. The mixture was as cooled and concentrated, and the residue was purified by preparative reverse-phase HPLC to provide, after lyophilization, the title product (153 mg, 78%) as a white powder.

EXAMPLE 1050e

3-[1-[3-(N-imidazol-2-ylamino)propyl]indazol-5-ylcarbonylamino]-2(S)-(2,6-dimethyl-4-phenylbenzenesulfonylamino)propionic acid trifluoroacetate A. Ethyl 3-methyl-4-nitrobenzoate A mixture of 3-methyl-4-nitrobenzoic acid (1) (362.3 g, 2.0 mol), N,N-dimethylformamide (2000 mL), sodium bicarbonate (200 g, 2.38 mol) and iodoethane (623.9 g, 4.0 mol) was stirred at 70° C. for 18 h. The mixture was allowed to cool to room temperature and poured into water (2000 mL. The resulting solid was collected by filtration, washed with water and dried. The solid was washed further with hexane and dried to provide the title product (382.1 g, 91%) as an off-white solid: mp 51°-52.5° C.; $^1$H NMR (CDCl$_3$) δ 8.04–7.98 (m, 3H), 4.42 (q, 2H), 2.63 (s, 3H), 1.42 (t, 3H); Mass spectrum (NH$_3$—CI) m/z 210 (100%, M+H$^+$).

B. Ethyl 3-methyl-4-aminobenzoate

A mixture of the product prepared according to Example 1050e Part A (183.96 g, 880 mol), tin (II) chloride hydrate (1025 g, 4.54 mol) and ethanol (3500 mL) was heated at reflux for 2 h. The mixture was cooled and diluted with water (3500 mL) and the pH was adjusted to 8.5. The mixture was diluted further with additional water, and extracted with ethyl acetate. The organic extracts were dried (MgSO$_4$), filtered and concentrated to provide the title product (136.62 g, 87%) as an off-white solid: mp 76°-78° C.; $^1$H NMR (CDCl$_3$) δ 7.78 (s, 1H), 7.76 (d, 1H), 6.63 (d, 1H), 4.31 (q, 2H), 3.99 (bs, 2H), 2.19 (s, 3H), 1.38 (t, 3H); High resolution mass spectrum (NH$_3$—CI) calculated (M+H$^+$) 180.1025, found 180.1023.

C. 5-Ethoxycarbonylindazole

A mixture of the product prepared according to Example 1050e Part B (250.55 g, 1.4 mol, potassium acetate (143.3 g, 1.46 mol), acetic anhydride 285.9 g, 2.8 mol) and chloroform (ethanol free; 2700 mL) was stirred at room temperature. The temperature rose to 40° C., then started to decline, at which time no starting material was detected by TLC. A mixture of 18-crown-6(75 g, 280 mmol) and n-amyl nitrite (364.5 g, 3.1 mol) was added and the mixture was heated at reflux overnight. The cooled mixture was washed with saturated aqueous sodium bicarbonate, then with water, and was dried (MgSO$_4$), filtered and concentrated under vacuum. The residue was combined with that from another batch (711.3 g) and distilled through a 10 cm vigreax column under vacuum to provide 1-Acetyl-5-ethoxcarbonyl-indazole (576 g, 82%), bp 115°–165° C. (1.0 Torr). This intermediate was combined with hydrochloric acid (6N; 2000 mL) and ethanol (2000 mL), and the mixture was stirred overnight at room temperature. The mixture was concentrated under vacuum and the solid was combined with water. The PH of the mixture was adjusted to 8 with aqueous ammonia, and the mixture was extracted with dichloromethane. The organic phase was concentrated to provide a solid (460 g). This was recrystallized from acetonitrile (1000 mL), and the crystals were washed with ethanol, then hexane, and dried to provide 5 (281 g, 60%) as a tan solid: mp 122°–124° C.; $^1$H NMR (CDCl$_3$) δ 10.23 (bs, 1H), 8.57 (s, 1H), 8.20 (s, 1H), 8.10 (d, 1H), 7.53 (d, 1H), 4.42 (q, 2H), 1.42 (t, 3H); High resolution mass spectrum (NH$_3$—CI) calculated (M+H$^+$); 191.0821, found 191.0838.

D. 1-(2-(1,3dioxolan-2-yl)ethyl)-5-ethoxycarbonylindazole

A solution of the product prepared according to Example 1050e Part C (74.5 g, 397 mol: in anhydrous tetrahydrofuran (1000 mL) was treated sequentially with sodium bis (trimethylsilyl)amide (1.0M in tetrahydrofuran; 430 mL, 430 mmol), 18-crown-6 (1.5 g) and 2(2bromoethyl)-1,3-dioxolane (90 g, 496 mmol). The solution was heated at reflux for 20 h, then was cooled to room temperature. The solvent was removed under vacuum, and the residue partitioned between toluene (2000 mL) and water (1000 mL). The aqueous phase was further extracted with toluene (3×200 mL), and the combined organic phases were washed with water (3×200 mL) and brine (2×200 mL). The organic phase was dried (MgSO$_4$) and concentrated under vacuum. The resulting oil was chromatographed with toluene, then with 185:15 toluene-ethyl acetate, to provide the title product (71.0 g, 55%): $^1$H NMR (CDCl$_3$) δ 8.49 (s, 1H), 8.10 (s, 1H), 8.06 (d, 1H), 7.46 (d, 1H), 4.84 (t, 1H), 4.55 (t, 2H), 4.41 (q, 2H), 3.90 (m, 4H), 2.31 (m, 2H), 1.42 (t, 3H); High resolution mass spectrum (NH$_3$—CI) calculated (M+H$^+$) 291.1345, found 291.1328.

E. 1-(3-oxopropyl) -5-ethoxycarbonylindazole

A mixture of the product prepared according to Example 1050e Part D (73.0 g, 256 mmol), acetic acid (365 g) and water (1020 mL) was heated at 70° C. for 20 h. The mixture was cooled to room temperature, extracted with dichloromethane (5×550 mL), and the combined organic layers were washed cautiously with saturated aqueous sodium bicarbonate (until no more gases were evolved), then with water (2×250 mL) and brine (2×250 mL). The organic layer was dried (MgSO$_4$), filtered and concentrated under vacuum to provide the title product (60.9 g, 98%) as a light yellow solid: $^1$H NMR (CDCl$_3$) δ 9.87 (s, 1H), 8.50 (s, 1H), 8.10 (s+d, 2H), 7.51 (d, 1H), 4.70 (t, 2H), 4.41 (q, 2H), 3.19 (t, 2H), 1.42 (t, 3H); High resolution mass spectrum (NH$_3$—CI) calculated (M+H$^+$) 247.1083, found 247.1068.

F. 2-Aminoimidazole

2Aminoimidazole sulfate (50 g, 378 mmol) was dissolved in methanol (1500 mL) and cooled to −78° C. Sodium methoxide (20.44 g, 378 mmol) was added portionwise over 60 min. The mixture stirred at −78° C. for 30 min, then at room temperature for 2.5 h. The solution was filtered through Celite® and concentrated under vacuum to provide 2-aminoimidazole as a semi-solid (32.5 g) which was used directly without further purification: $^1$H NMR (DMSO-d$_6$) δ 6.32 (s, 2H), 5.0 (bs, 2H).

G. 2-Phthalimidoimidazole

A mixture of phthalic anhydride (57.3 g, 387.mmol) and the product prepared according to Example 1050e Part F (32.5 g, 387 mmol) was heated with mechanical stirring to 190°–200° C. for 20 min, then was placed under vacuum for 10 min. The mixture was cooled to room temperature and dried under vacuum for 24 h. This material (80 g, 99%) was used without further purification. It could be purified by flash chromatography (chloroform:methanol gradient from 95:5 to 80:20): $^1$H NMR (DMSO-d$_6$) δ 12.35 (bs, 1H), 7.94–8.06 (m, 4H), 7.16 (bs, 2H); Mass spectrum (ESI) m/z 214.2 (100%, M+H$^+$).

H. 1Triphenylmethyl-2-phthalimidoimidazole

A solution of the product prepared according to Example 1050e Part G (80 g, 375 mmol) in dichloromethane (200 mL) was treated with triphenylmethyl chloride (314 g, 1.126 mol) and triethylamine (151.8 g, 1.5 mol). The mixture was heated at reflux for 5.5 h, then cooled to room temperature and concentrated under vacuum. The residue was extracted several times with hexane/ethyl acetate (70:30). The residual solid was dissolved in dichloromethane and washed several times with water, dried (MgSO₄) and concentrated. The residual solid was boiled in hexane, filtered, and the solid was washed several times with hot hexane until no trityl chloride was present by TLC. This provided the title product (119 g, 70%): $^1$H NMR (CDCl₃) δ 7.64 (s, 4H), 7.28 (d, 6H), 7.17 (m, 7H), 7.06 (t, 3H), 6.80 (d, 1H); Mass spectrum (NH₃—CI) m/z 456 (100%, M+H⁺).

I. 1-Triphenylmethyl-2aminoimidazole

A mixture of the product prepared according to Example 1050e Part H (114 g, 250 mmol), hydrazine (78. mL, 2.50 mol) and ethanol (3500 mL) was heated at reflux for 2 h. The mixture was cooled and the solvent was removed under vacuum. The solid residue was partitioned between water (500 mL) and chloroform (500 mL and the aqueous phase was extracted further with chloroform (3×200 mL). The combined organic layers were washed with water (2×200 mL), dried (MgSO₄) and concentrated to provide a sticky solid. This was heated with hexane and filtered to provide the title product (65 g, 80%) as a granular solid: $^1$H NMR (DMSO-d₆) δ 7.33–7.44 (m, 9H), 7.13 (d, 6H), 6.51 (d, 1H), 6.26 (d, 1H); Mass spectrum (NH₃—CI) 326 (100%, M+H⁺).

J. 1-[3-[N-(1-Triphenylmethylimidazol-2yl)amino]-propyl]-5-ethoxycarbonylindazole A mixture of the product prepared according to Example 1050e Part E (10.0 g, 40.6 mmol), the product prepared according to Example 1050e Part I (13.2 g, 40.6 mmol) and toluene (500 mL) was heated at reflux under a Dean-Stark trap. Toluene (3×100 mL) was removed while adding fresh dry toluene. The mixture fleas then heated further for 20 h, when NMR analysis of an aliquot showed the absence of aldehyde. The mixture was cooled to room temperature and sodium triacetoxyborohydride (34.42 g, 162.4 mmol) was added. The mixture was stirred at room temperature for 20 h, then was poured into water (500 mL). The layers were separated and the aqueous phase was extracted with ethyl acetate (3×100 mL). The combined organics were washed with saturated aqueous sodium bicarbonate (2×100 mL), water (2×100 mL) and brine (2×100 mL), then were dried (MgSO₄), filtered and concentrated under vacuum to provide a crude product (25.0 g). This was combined with the crude product from another run (starting from 7.77 g of the product prepared according to Example 1050e Part E and 10.28 g of the product prepared according to Example 1050e Part I) and was purified by flash chromatography (toluene:ethyl acetate step gradient from 90:10 to 50:50) to provide the title product (21.0 g, 52%) as an oil which slowly solidified: $^1$H NMR (CDCl₃) δ 8.45 (s, 1H), 7.97 (s, 1H), 7.93 (d, 1H), 7.33 (m, 9H), 7.21 (m, 6H), 6.99 (d, 1H), 6.67 (d, 1H), 6.41 (d, 1H), 4.41 (q, 2H), 4.06 (t, 2H), 2.98 (m, 3H), 1.81 (m, 2H), 1.42 (t, 3H); High resolution mass spectrum (FAB) calculated (M+H⁺) 556.2713, found 556.2725.

K. 1-[3-[N-(1Triphenylmethylimidazol-2yl)amino]propylyl]-5-carboxyindazole

A mixture of the product prepared according to Example 1050e Part J (21.0 g, 37.8 mmol), ethanol (600 mL) and aqueous sodium hydroxide (1.0M; 209 mL, 209 mmol) was heated at reflux for 4 h. The mixture was cooled to room temperature and concentrated under vacuum to remove the ethanol. The pH of the residue was adjusted to 4, and the mixture was extracted with dichloromethane and the combined organic phases were dried (Na₂SO₄). The mixture was filtered and the solids were washed with N,N-dimethylformamide to recover precipitated product. The combined filtrates were concentrated under vacuum and the residue was washed with ethanol and dried to provide the title product (16.9 g, 85%, as a white solid: $^1$H NMR (DMSO-d₆) δ 8.39 (s, 1H), 8.13 (s, 1H), 7.87 (d, 1H), 7.36 (m, 10H), 7.12 (d, 6H), 6.51 (d, 1H), 6.28 (d, 1H), 4.05 (t, 2H), 2.84 (m, 2H), 1.63 (m, 2H); High resolution mass spectrum (FAB) calculated (M+H⁺) 528.2400, found 528.2418.

L. Methyl 3-[1-[3(N-(1-triphenylmethylimidazol-2-yl)amino)propyl]indazol-5-ylcarbonylamino]-2(S)-(2,6-dimethyl-4-phenylbenzenesulfonylamino)propionate A mixture of the product prepared according to Example 1050e Part K (293 mg, 566 μmol), methyl 3amino-2(S)-(2,6-dimethyl-4-phenylbenzenesulfonyl)aminopropionate hydrochloride (prepared according to the method of Example 3093 Parts J and K described below; 290 mg, 727 μmol), N,N-dimethylformamide (7 mL), dicyclohexylcarbodiimide (115 mg, 557 μmol), 1-hydroxybenzotriazole hydrate (76 mg, 562 μmol) and triethylamine (230 μL, 1.65 mmol) was stirred at room temperature for 42 h. The mixture was concentrated under vacuum and the residue was purified by flash chromatography (ethyl acetate) to provide the title product (507 mg) contaminated with dicyclohexylurea, which was used in the subsequent reaction without further purification: $^1$H NMR (CDCl₃) δ 8.13 (s, 1H), 8.02 (s, 1H), 7.70 (d, 1H), 7.60–7.15 (22H), 6.98 (d, 1H), 6.87 (t, 1H), 6.67 (d, 1H), 6.41 (d, 1H), 6.08 (bs, 1H), 4.05 (t, 2H), 3.95 (m, 1H), 3.75 (m, 1H), 3.65 (s, 3H), 3.47 (m, 1H), 2.95 (m, 2H), 2.75 (s, 6H), 1.79 (m, 2H); High resolution mass spectrum (FAB) calculated (M+H⁺) 872.3594, found 872.3593.

M. 3-[1-[3-(N-imidazol-2-ylamino)propyl]-indazol-5-ylcarbonylamino]-2(S)-(2,6-dimethyl-4-phenylbenzenesulfonylamino) propionic acid trifluoroacetate A mixture of the product prepared according to Example 1050e Part L (469 mg, 540 μmol), ethanol (13 mL) and aqueous sodium hydroxide (1.0M; 2.7 mL, 2.7 mmol) was heated at reflux for 90 min. The mixture was cooled to room temperature and concentrated, and the residue was taken up in trifluoroacetic acid (6 mL) and heated at reflux for 90 min. The mixture was cooled to room temperature and concentrated. The residue was purified by preparative reverse phase high pressure liquid chromatography (acetonitrile:water containing 0.05% trifluoroacetic acid; gradient from 10:90 to 90:10) to provide the title product (218 mg, 55%) as a white solid: $^1$H NMR (MeOH-d₄) δ 8.06 (s, 1H), 7.95 (s, 1H), 7.63 (d, 1H), 7.34 (d, 1H), 7.28 (m, 5H), 7.09 (s, 2H), 6.75 (s, 2H), 4.34 (t, 2H), 4.27 (dd, 2H), 3.77 (dd, 1H), 3.47 (dd, 1H), 3.17 (t, 2H), 2.66 (s, 6H), 2.12 (m, 2H); High resolution mass spectrum (FAB) calculated (M+H⁺) 616.2342, found 616.2324.

EXAMPLE 1081

3-[1-[3-(N-pyridin-2-ylamino)propyl]indazol-5-ylcarbonylamino]-2(S)-(benzyloxycarbonylamino) propionic acid trifluoroacetate A. 1-[3-(N-phthalimido)-propyl]-5-ethoxycarbonylindazole A mixture of tetrahydrofuran (50 mL) and 18-crown-6 (100 mg) was stirred at room temperature. Potassium bis(trimethylsilyl)amide (0.5M in toluene; 46.6 mL, 23.3 mmol) was added, followed by the product prepared according to Example 1050e Part C (4.43 g, 23.3 mmol) dissolved in dry tetrahydrofuran (50 mL). Then N-(3-bromopropyl) phthalimide (6.24 g, 23.3 mmol) dissolved in dry tetrahydrofuran (50 mL) was added. The mixture was heated at reflux for 16 h. The mixture was allowed to cool to room temperature and poured into water (200 mL). The layers were separated and the aqueous layer was extracted with ethyl acetate. The organic layers were combined, dried over anhydrous magnesium sulfate, filtered and concentrated under vacuum. The residue was purified by flash chromatography (hexanes:ethyl acetate 50:50) to provide the title product (4.25 g, 48%) as a yellow solid: mp 122°–124° C.; $^1$H NMR (CDCl$_3$) δ 8.48 (s, 1H), 8.06 (s, 1H), 8.04 (d, 1H), 7.82 (m, 2H), 7.71 (m, 2H), 7.42 (d, 1H), 4.44 (t, 2H), 4.40 (q, 2H), 3.80 (t, 2H), 2.40 (m, 2H), 1.42 (t, 3H); High resolution mass spectrum (NH$_3$—CI) calculated (M+H$^+$) 378.1454, found 378.1430. Also obtained (as a more polar fraction) was 2-[3-(N-phthalimido)propyl]-5-ethoxycarbonylindazole (2.75 g, 31%) as a yellow solid: mp 133°–135° C.; $^1$H NMR (CDCl$_3$) δ 8.48 (s, 1H), 8.25 (s, 1H), 7.85 (d, 1H), 7.81 (m, 2H), 7.70 (m, 2H), 7.61 (d, 1H), 4.50 (t, 2H), 4.40 (q, 2H), 3.78 (t, 2H), 2.47 (m, 2H), 1.43 (t, 3H); High resolution mass spectrum (NH$_3$—CI) calculated (M+H$^+$) 378.1454, found 378.1430.

B. 1-(3-aminopropyl)-5-ethoxycarbonylindazole

A mixture of the product prepared according to Example 1081 Part A (2.10 g, 5.6 mmol), ethanol (35 mL), anhydrous tetrahydrofuran (35 mL) and anhydrous hydrazine (0.75 mL) was stirred at room temperature for 16 h. Dry tetrahydrofuran (100 mL) was added and the mixture was filtered. The filtrate was concentrated under vacuum. The residue was purified by flash chromatography (dichloromethane:methanol 90:10 containing 1% triethylamine) to provide the title product (1.25 g, 91%) as an orange syrup: $^1$H NMR (CDCl$_3$) δ 8.51 (s, 1H), 8.10 (s, 1H), 8.06 (d, 1H), 7.46 (d, 1H), 4.52 (t, 2H), 4.41 (q, 2H), 2.68 (t, 2H), 2.06 (m, 2H), 1.47 (bs, 2H), 1.43 (t, 3H); High resolution mass spectrum (NH$_3$—CI) calculated (M+H$^+$) 248.1399, found 248.1392.

C. 1-[3-[N-(1-oxido)pyridin-2-ylamino]propyl]-5-ethoxycarbonylindazole

A mixture of the product prepared according to Example 1081 Part B (600 mg, 2.4 mmol), 2-chloropyridine-N-oxide hydrochloride (806 mg, 4.9 mmol), sodium bicarbonate (816 mg, 9.7 mmol) and n-butanol (7 mL) was stirred at 100° C. for 21 h. The mixture was allowed to cool to room temperature and was filtered. The filtrate was concentrated under vacuum. The residue was purified by flash chromatography (dichloromethane:methanol 95:5) to provide the title product (675 mg, 81%) as a pale yellow solid, mp 87°–89° C.: $^1$H NMR (CDCl$_3$) δ 8.52 (s, 1H), 8.15 (s, 1H), 8.13 (d, 1H), 8.03 (d, 1H), 7.39 (d, 1H), 7.10 (t, 1H), 6.93 (bt, 1H), 6.56 (t, 1H), 6.41 (d, 1H), 4.57 (t, 2H), 4.40 (q, 2H), 3.24 (q, 2H), 2.38 (m, 2H), 1.40 (t, 3H); High resolution mass spectrum (NH$_3$—CI) calculated (M+H$^+$) 341.1614, found 341.1622.

D. 1-[3-(N-pyridin-2-ylamino)propyl]-5-ethoxycarbonylindazole

A mixture of the product prepared according to Example 1081 Part C (62 mg, 182 μmol), 10% palladium on charcoal (8 mg) and ethanol (0.5 mL) was stirred at room temperature. Ammonium formate (63 mg, 1.0 mmol) was added and the mixture heated to reflux for 30 min. Additional 10% palladium on charcoal (8 mg) and 6ammonium formate (63 mg, 1.0 mmol) were added and the reaction was continued at reflux for 4 h. The mixture was allowed to cool to room temperature, filtered through Celite® and the solids were rinsed with ethanol. The solvent was evaporated from the filtrate under vacuum. The residue was purified by flash chromatography (dichloromethane:methanol 95:5) to provide the title product (31 mg, 52%) as a glass: $^1$H NMR (CDCl$_3$) δ 8.52 (s, 1H), 8.12 (s, 1H), 8.06 (m, 2H), 7.38 (m, 2H), 6.55 (dd, 1H), 6.32 (d, 1H), 4.70 (bm, 1H), 4.53 (t, 2H), 4.40 (q, 2H), 3.30 (q, 2H), 2.24 (m, 2H), 1.42 (t, 3H); High resolution mass spectrum (NH3—CI) calculated (M+H$^+$); 325.1665, found 325.1659.

E. 1-[3-(N-tert-butyloxycarbonyl-N-pyridin-2-ylamino)propyl]-5-ethoxycarbonylindazole A mixture of the product prepared according to Example 1081 Part D (80 mg, 246 mol), dry tetrahydrofuran (4 mL), triethylamine (0.3 mL) and N,N-dimethylaminopyridine (5 mg) was stirred at 0° C. Di-tert-butyldicarbonate (130 mg, 2.4 equiv.) was added and the mixture was stirred for 30 min. The ice bath was removed and the mixture was stirred at room temperature for 16 h. Additional di-tert-butyldicarbonate (130 mg, 2.4 equiv.) and N,N-dimethylaminopyridine (5 mg) were added and the mixture was stirred at room temperature for 72 h. The solvent was evaporated under vacuum and the residue was purified by flash chromatography (hexanes:ethyl acetate 65:35) to provide the title product (70 mg, 66%) as a clear oil: $^1$H NMR (CDCl$_3$) δ 8.50 (s, 1H), 8.28 (m, 1H), 8.08 (s, 1H), 8.04 (d, 1H), 7.60 (m, 2H), 7.37 (d, 1H), 6.99 (m, 1H), 4.46 (t, 2H), 4.41 (q, 2H), 4.02 (t, 2H), 2.34 (m, 2H), 1.42 (t+s, 12H); High resolution mass spectrum (NH$_3$—CI) calculated (M+H$^+$); 425.2189, found 425.2193.

F. 1-[3-(N-tert-butyloxycarbonyl-N-pyridin-2-ylamino)propyl]-5-carboxyindazole

A mixture of the product prepared according to Example 1081 Part E (7.9 g, 18.6 mmol), water (100 mL), ethanol (100 mL) and aqueous sodium hydroxide (1.0M; 40 ml, 40 mmol) was stirred at reflux for 16 h. The mixture was allowed to cool to room temperature and aqueous hydrochloric acid (1.0M; 43 mL, 43 mmol) was added. The solvent was decanted and the resulting gum was triturated several times with hexane to provide the title product (5.56 g, 75%) as a solid: mp 129°–131° C.; $^1$H NMR (CDCl$_3$) δ 8.59 (s, 1H), 8.30 (m, 1H), 8.12 (s, 1H), 8.07 (d, 1H), 7.61 (m, 2H), 7.41 (d, 1H), 7.00 (m, 1H), 4.46 (t, 2H), 4.01 (t, 2H), 2.34 (m, 2H), 1.42 (s, 9H); High resolution mass spectrum (NH$_3$—CI) calculated (M+H$^+$); 397.1876, found 397.1878.

G. tert-Butyl 3-[1-[3-(N-(tert-butyloxycarbonyl-N-pyridin-2-ylamino)propyl]indazol-5-ylcarbonylamino]-2(S)-(benzyloxycarbonylamino)propionate A mixture of the product prepared according to the procedure of Example 1081 Part F (1.19 g, 3.0 mmol), tert-butyl 3-amino-2(S)-(benzyloxycarbonylamino) propionate (prepared according to Mokotoff and Logue, J. Med. Chem. 1981, 24, 554; 880 mg, 3.0 mmol), 1-hydroxybenzotriazole hydrate (410 mg, 3.0 mmol), and anhydrous tetrahydrofuran (20 mL) was stirred at room temperature. The mixture was treated with dicyclohexylcarbodiimide (660 mg, 3.2 mmol) and stirred for 24 h. The mixture was filtered and solvent was removed under vacuum. The residue was purified by flash chromatography (hexanes:ethyl acetate 50:50) to provide the title product (1.81 g, 89%) as a glass: $^1$H NMR (CDCl$_3$) δ 8.28 (d, 1H), 8.17 (s, 1H), 8.04 (s, 1H), 7.77 (d, 1H), 7.60 (d, 2H), 7.4–7.25 (m, 6H), 6.98 (m, 2H), 5.88 (bd, 1H), 5.13 (s, 2H), 4.47 (bm, 1H), 4.46 (t, 2H), 4.01 (t, 2H), 3.87 (m, 2H), 2.31 (m, 2H), 1.48 (s, 9H), 1.43 (s, 9H); High resolution mass spectrum (NH$_3$—CI) calculated (M+H$^+$) 673.3350, found 673.3324.

H. 3-[1-[3-(N-pyridin-2ylamino)propyl]indazol-5-ylcarbonylamino]-2(S)-(benzyloxycarbonylamino) propionic acid trifluoroacetate A mixture of the product prepared according to Example 1081 Part G (32 mg, 47 μmol), dichloromethane (5 mL) and trifluoroacetic acid (300 μL) was stirred at room temperature for 16 h. The mixture was concentrated under vacuum and toluene was added. The solvent was evaporated and the residue was triturated with ether. The solvent was removed by decantation, and the residue was dried to constant weight under vacuum to provide the desired product (25 mg, 83%) as a hygroscopic white solid: $^1$H NMR (DMSO-d$_6$) δ 8.57 (bm, 1H), 8.53 (bt, 1H), 8.26 (s, 1H), 8.21 (s, 1H), 7.82 (m, 3H), 7.69 (d, 1H), 7.59 (d, 1H), 7.28 (m, 5H), 6.93 (d, 1H), 6.78 (t, 1H), 4.99 (s, 2H), 4.52 (t, 2H), 4.23 (m, 1H), 3.60 (m, 2H), 3.24 (m, 2H), 2.15 (m, 2H); High resolution mass spectrum (FAB) calculated (M+H$^+$) 517.2199, found 517.2213.

EXAMPLE 1094

3-[1-[3-(N-pyridin-2ylamino)propyl]indazol-5-yl-carbonylamino]-2(S)-(isobutyloxycarbonylamino) propionic acid trifluoroacetate A. tert-Butyl 3-[1-[3-(N-tert-butyloxycarbonyl-N-pyridin-2-ylamino)-propyl]indazol-5-ylcarbonylamino]-2(S)-aminopropionate A mixture of the product prepared according to the procedure of Example 1081 Part G (1.60 g, 2.33 mmol), 10% palladium on charcoal (160 mg) and ethanol (30 mL) was placed in a pressure bottle and stirred at room temperature under an atmosphere of hydrogen (1 atmosphere pressure). After 5 h, the mixture was filtered through Celite®, the solids were rinsed with ethanol, and the filtrate was concentrated under vacuum to provide the title product (1.24 g, 97%) as a glass: $^1$H NMR (CDCl$_3$) δ 8.28 (d, 1H), 8.20 (s, 1H), 7.82 (d, 1H), 7.60 (m, 2H), 7.38 (d, 1H), 6.98 (m, 1H), 6.93 (bt, 1H), 4.45 (t, 2H), 4.00 (t, 2H), 3.88 (m, 1H), 3.66 (m, 1H), 3.56 (m, 1H), 2.51 (m, 2H), 2.05 (bs, ca. 2H), 1.48 (s, 9H), 1.42 (s, 9H); High resolution mass spectrum (NH$_3$—CI) calculated (M+H$^+$) 539.2982, found 539.2998.

B. tert-Butyl 3-[1-[3-(N-tert-butyloxycarbonyl-N-pyridin-2ylamino)-propyl]indazol-5-ylcarbonylamino-]2(S)-(isobutyloxycarbonylamino)propionate A solution of the product prepared according to Example 1094 Part A (100 mg, 186 μmol) in N,N-dimethylformamide (5 mL) was treated with isobutyl chloroformate (27 μL, 205 μmol), 4-(N,N-dimethylamino)pyridine (10 mg) and pyridine (15 μL, 205 μmol). The solution was stirred at room temperature for 16 h, then was concentrated under vacuum. The residue was purified by flash chromatography (dichloromethane:ethyl acetate 97:3) to provide the title product (106 mg, 89%) as a gum: $^1$H NMR (DMSO-d$_6$) δ 8.51 (m, 1H), 8.28 (m, 2H), 8.22 (s, 1H), 7.96 (s, 1H), 7.9–7.50 (m, 3H), 7.53 (d, 1H), 7.11 (m, 1H), 4.46 (t, 2H), 4.21 (m, 1H), 3.84 (m, 2H), 3.75 (d, 2H), 3.69 (m, 1H), 3.56 (m, 1H), 2.13 (m, 2H), 1.83 (m, 1H), 1.33 (s, 9H), 1.30 (s, 9H), 0.88 (d, 6H); High resolution mass spectrum (FAB) calculated (M+H$^+$) calculated 639.3480, found 639.3506.

C. 3-[1-[3(N-pyridin-2ylamino)propyl]indazol-5-yl-carbonylamino]-2(S)-(isobutyloxycarbonylamino)propionic acid trifluoroacetate Using the procedure of Example 1081 Part H, the product prepared according to Example 1094 Part B (106 mg, 166 μmol) was converted to the title product (76 mg, 76%) as a solid: $^1$H NMR (DMSO-d$_6$) δ 8.56 (m, 2H), 8.30 (s, 1H), 8.25 (s, 1H), 7.90–7.75 (m, 3H), 7.72 (d, 1H), 7.44 (d, 1H), 6.96 (d, 1H), 6.80 (t, 1H), 4.56 (t, 2H), 4.24 (m, 1H), 3.73 (d, 2H), 3.62 (m, 2H), 3.28 (m, 2H), 2.17 (m, 2H), 1.82 (m, 1H), 0.85 (d, 6H); High resolution mass spectrum (NH$_3$—CI) calculated (M+H$^+$) calculated 483.2348, found 483.2356.

EXAMPLE 1099b

3-[1-[3(N-pyridin-2ylamino)propyl]indazol-5-yl-carbonylamino]-2-(S)-(E-[phenylethenyl]carbonylamino)-propionic acid trifluoroacetate A. tert-Butyl 3-[1-[3-(N-tert-butyloxycarbonyl-N-pyridin-2-ylamino)propyl]indazol-5-ylcarbonylamino-2(S)-(E-[phenylethenyl]carbonylamino)propionate A solution of the product prepared according to Example 1094 Part A (100 mg, 186 μmol) in tetrahydrofuran (3 mL) was treated with trans-cinnamic acid (28 mg, 186 μmol), 1-hydroxybenzotriazole hydrate (25 mg, 186 μmol) and dicyclohexylcarbodiimide (39 mg, 186 μmol). The mixture was stirred at room temperature for 18 h, then was concentrated under vacuum. The residue was purified by flash chromatography (hexanes:ethyl acetate 70:30) to provide the title product (108 mg, 87%) as a gummy white solid: $^1$H NMR (CDCl$_3$) δ 8.27 (d, 1H), 8.24 (s, 1H), 8.06 (s, 1H), 7.83 (d, 1H), 7.67 (d, J=17 Hz, 1H), 7.59 (m, 1H), 7.55–7.35 (m, 6H), 6.97 (m, 1H), 6.88 (d, 1H), 6.70 (d, J=17 Hz, 1H), 4.85 (m, 1H), 4.44 (t, 2H), 4.02 (m, 3H), 3.47 (m, 2H), 2.31 (m, 2H), 1.52 (s, 9H), 1.40 (s, 9H); High resolution mass spectrum (FAB) calculated (M+H$^+$) 669.3401, found 669.3389.

B. 3-[1-[3-(N-pyridin-2-ylamino)propyl]indazol-5-yl-carbonylamino]-2(S)-(E-[phenylethenyl]carbonylamino) propionate acid trifluoroacetate Using the procedure of Example 1081 Part H, the product prepared according to Example 1099b Part A (100 mg, 150 μmol) was converted to the title product (90 mg, 96%) as a white solid: $^1$H NMR (DMSO-d$_6$) δ 8.64 (t, 1H), 8.47 (d, 1H), 8.31 (s, 1H), 8.04 (s, 1H), 7.90–7.80 (m, 3H), 7.73 (d, 1H), 7.58 (d, 1H), 7.50–7.35 (m, 6H), 6.98 (d, 1H), 6.82 (t, 1H), 6.74 (d, J=17 Hz, 1H), 4.63 (m, 1H), 4.55 (t, 2H), 3.75–3.55 (m, 2H), 3.27 (m, 2H), 2.18 (m, 2H); High resolution mass spectrum (FAB) calculated (M+H$^+$) 513.2250, found 513.2239.

EXAMPLE 1108b 3-1-[3-(N-pyridin-2-ylamino)propyl]indazol-5-yl-carbonylamino]-2(S)-(cyclohexylcarbonylamino) propionic acid trifluoroacetate A. 1-[3(pyridin-2-ylamino)propyl]-5-carboxyindazole A mixture of the product prepared according to Example 1081 Part D (1.04 g, 3.19 mmol), ethanol (16 mL) and aqueous sodium hydroxide (1.0M; 16 ml, 16 mmol) was stirred at reflux for 20 h. The mixture was allowed to cool to room temperature and aqueous hydrochloric acid (1.0M; 16 mL, 16 mmol) was added. The resulting solid was collected by filtration, washed with water and dried to provide the title product: $^1$H NMR (DMSO-d$_6$) δ 8.42 (s, 1H), 8.22 (s, 1H), 7.90 (m, 2H), 7.76 (d, 1H), 7.38 (m, 1H), 6.58 (t, 1H), 6.42 (m, 2H), 4.52 (t, 2H), 3.20 (q, 2H), 2.08 (m, 2H); Mass spectrum (ESI) m/z 297.3 (100%, M+H$^+$).

B. tert-Butyl 3-[1-[3-(pyridin-2-ylamino)propyl]indazol-5-ylcarbonylamino]-2(S)-(benzyloxycarbonylamino) propionate Using the procedure of 1081 Part G, the product prepared according to the procedure of Example 1108b Part A (740 mg, 2.5 μmmol) was converted to the title product (700 mg, 56%): $^1$H NMR (CDCl$_3$) δ 8.19 (s, 1H), 8.08 (s, 1H), 8.06 (m, 1H), 7.79 (d, 1H), 7.45– 7.25 (m, 7H), 7.02 (bm, 1H), 6.56 (m, 1H), 6.32 (d, 1H), 5.90 (bm, 1H), 5.13 (s, 2H), 4.52 (t, 2H), 4.05 (bm, 1H), 3.87 (m, 2H), 3.47 (m, 1H), 3.28 (m, 2H), 2.26 (m, 2H), 1.48 (s, 9H); Mass spectrum (ESI) m/z 573.4 (22%, M+H$^+$).

C. tert-Butyl 3-1-[3-(pyridin-2-ylamino)propyl]indazol-5-ylcarbonylamino]-2(S)-aminopropionate Using the procedure of 1094 Part A, the product prepared according to the procedure of Example 1108b Part B (700 mg, 1.22 mmol) was converted to the title product (500 mg, 93%) as a gummy solid: $^1$H NMR (CDCl$_3$) δ 8.24 (s, 1H), 8.09 (s, 1H), 8.01 (d, 1H), 7.84 (d, 1H), 7.47 (d, 1H), 7.40 (t, 1H), 7.10 (bm, 1H), 6.56 (t, 1H), 6.33 (d, 1H), 4.54 (t, 2H), 4.11 (m, 1H), 3.86 (m, 1H), 3.59 (m, 1H), 3.25 (m, 2H), 2.27 (m, 2H), 1.49 (s, 9H); Mass spectrum (ESI) m/z 439.3 (100%, M+H$^+$).

D. tert-Butyl 3-[1-[3-(pyridin-2-ylamino)propyl]indazol-5-ylcarbonylamino]-2(S)-(cyclohexylcarbonylamino) propionate Using the procedure of 1094 Part B, the product prepared according to the procedure of Example 1108b Part C (100 mg, 230 μmol) and cyclohexylcarbonyl chloride (31 μL, 230 μmol) were converted to the title product (60 mg, 50%): $^1$H NMR (CDCl$_3$) δ 8.22 (s, 1H), 8.10 (s, 1H), 7.91 (d, 1H), 7.80 (d, 1H), 7.54 (d, 1H), 7.45 (m, 2H), 6.72 (d, 1H), 6.57 (t, 1H), 6.32 (d, 1H), 4.72 (m, 1H), 4.58 (t, 2H), 3.89 (m, 1H), 3.76 (m, 1H), 3.19 (t, 2H), 2.30 (m, 3H), 2.19 (m, 1H), 2.0–1.2 (m, 10H); Mass spectrum (ESI) m/z 549.5 (100%, M+H$^+$).

E. 3-[1-[3-(N-pyridin-2-ylamino)propyl]indazol-5-ylcarbonylamino]-2(S)-(cyclohexylcarbonylamino)propionic acid trifluoroacetate Using the procedure of Example 1081 Part H, the product prepared according to Example title product: $^1$H NMR (DMSO-d$_6$) δ 8.54 (m, 1H), 8.28 (s, 1H), 8.25 (s, 1H), 8.02 (d, 1H), 7.9–7.7 (m, 4H), 6.90 (m, 1H), 6.77 (m, 1H), 4.55 (t, 2H), 4.44 (m, 1H), 3.61 (m, 2H), 3.26 (m, 2H), 2.16 (m, 3H), 2.0–1.0 (m, 10H); High resolution mass spectrum (NH$_3$—CI) calculated (M+H$^+$) 493.2563, found 493.2559.

EXAMPLE 1110a

3-[1-[3-(N-pyridin-2-ylamino)propyl]indazol-5-ylcarbonylamino]-2(S)-(phenylaminocarbonylamino)propionic acid trifluoroacetate A. tert-Butyl 3-[1-[3-(N-tert-butyloxycarbonyl-N-pyridin-2-ylamino)propyl]indazol-5-ylcarbonylamino]-2(S)-(phenylaminocarbonylamino)propionate A solution of the product prepared according to Example 1094 Part A (105 mg, 195 μmol) in dichloromethane (5 mL) was treated sequentially with diisopropylethylamine (69 μL, 385 μmol) and phenyl isocyanate (49 μl, 448 μmol). The solution was stirred at room temperature for 1 h, then was concentrated under vacuum. The residue was purified by flash chromatography (hexanes:ethyl acetate, 50:50) to provide the title product (72 mg, 56%): $^1$H NMR (CDCl$_3$) δ 8.25 (d, 1H), 8.18 (s, 1H), 7.95 (m, 1H), 7.86 (s, 1H), 7.75 (d, 1H), 7.70 (bm, 1H), 7.57 (m, 2H), 7.17 (m, 3H), 7.10 (m, 2H), 6.95 (m, 1H), 6.92 (m, 1H), 6.63 (m, 1H), 4.79 (m, 1H), 4.34 (t, 2H), 3.96 (m, 2H), 3.86 (m, 2H), 2.25 (m, 2H), 1.46 (s, 9H), 1.41 (s, 9H); High resolution mass spectrum (FAB) calculated (M+H$^+$) 658.3353, found 658.3342.

B. 3-[1-[3-(N-pyridin-2-ylamino)propyl]indazol-5-ylcarbonylamino]-2(S)-(phenylaminocarbonylamino) propionic acid trifluoroacetate Using the procedure of Example 1081 Part H, the product prepared according to Example 1110a Part A (68 mg, 104 μmol) was converted to the title product (44 mg, 68%) as a white solid after preparative reverse phase high pressure liquid chromatography (acetonitrile:water containing 0.05% trifluoroacetic acid, gradient from 1:9 to 9:1): $^1$H NMR (MeOH-d$_4$) δ 8.24 (s, 1H), 8.09 (s, 1H), 7.85–7.70 (m, 2H), 7.68 (d, 1H), 7.55 (d, 1H), 7.29 (m, 2H), 7.17 (t, 2H), 6.91 (m, 2H), 6.79 (t, 1H), 4.66 (m, 1H), 4.54 (t, 2H), 3.88 (dd, 1H), 3.77 (dd, 1H), 3.27 (m, 2H), 2.28 (m, 2H); High resolution mass spectrum (FAB) calculated (M+H$^+$) 502.2203, found 502.2196.

EXAMPLE 1129

3-[1-[3-(N-pyridin-2-ylamino)propyl]indazol-5-ylcarbonylamino]-2(S)-(1-naphthalene-sulfonylamino)-propionic acid trifluoroacetate A. 1-(2-cyanoethyl)-5-ethoxycarbonylindazole A mixture of the product prepared according to Example 1050e Part C (3.80 g, 20 mmol), acrylonitrile (7.9 mL, 120 mmol), sodium bis-(trimethylsilyl)amide (1.0M in tetrahydrofuran; 1.0 mL, 1.0 mmol) and ethanol (40 mL) was heated to reflux. After 2 h, the solution was cooled to room temperature and treated with aqueous hydrochloric acid (1.0M; 1.5 mL, 1.5 mmol). After the mixture was partially concentrated under vacuum, a solid formed. Water (100 mL) was added and the mixture was stirred briefly. The resulting solid was collected by filtration, rinsed with water and dried to provide the title product (4.38 g, 90%) as a pale yellow fluffy solid: mp 106°–109° C.; $^1$H NMR (CDCl$_3$) δ 8.54 (s, 1H), 8.16 (s, 1H), 8.13 (d, 1H), 7.48 (d, 1H), 4.70 (t, 2H), 4.42 (q, 2H), 3.03 (t, 2H), 1.43 (t, 3H); High resolution mass spectrum (NH$_3$—CI) calculated (M+H$^+$) 244.1086, found 244.1070.

B. 1-(3-aminopropyl)-5-ethoxycarbonylindazole hydrochloride

A mixture of the product prepared according to Example 1129 Part A (60 g, 260 mmol), platinum oxide (6.0 g), ethanol (1600 mL) and chloroform (200 mL) was placed in a pressure bottle and agitated under an atmosphere of hydrogen (40 psig) for 19 h. The mixture was filtered through Celite® and the solids were washed with ethanol. The filtrate was concentrated under vacuum and the residue was dissolved in aqueous sodium bicarbonate and washed with ethyl acetate. The aqueous phase was acidified with hydrochloric acid and concentrated to a solid. This was dissolved in hot ethanol, filtered, and the filtrate cooled. The resulting crystals were collected by filtration to provide the title product. Repeating the reaction twice more starting with 57 g of the nitrile provided a total of 115 g (57%) of the title product as a white solid: mp 198°–200° C.; $^1$H NMR (DMSO-d$_6$) δ 8.49 (s, 1H), 8.32 (s, 1H), 8.07 (bs, 3H), 7.98 (d, 1H), 7.85 (d, 1H), 4.58 (t, 2H), 4.34 (q, 2H), 2.80 (bm, 2H), 2.14 (m, 2H), 1.34 (t, 3H); High resolution mass spectrum (NH$_3$—CI) calculated (M+H$^+$) 248.1399, found 248.1396.

C. 1-[3-[N-(1-oxido)pyridin-2-ylamino]propyl]-5-ethoxycarbonylindazole

Using the procedure of Example 1081 Part C, the product prepared according to Example 1129 Part B (566 mg, 2.0 mmol) was converted to the title product (470 mg, 69%). This product is the same as the product of Example 1081 Part C.

D. 1-[3-[N-(1-oxido)pyridin-2-ylamino]propyl]-5-carboxyindazole

A mixture of the product prepared according to Example 1129 Part C (470 mg, 1.3 mmol), aqueous sodium hydroxide (1.0M; 4.0 moL, 4.0 mmol), water (10 mL) and ethanol (10 mL) was heated to reflux. After 30 h, additional aqueous sodium hydroxide (1.0M; 2.0 mL) was added and heating was continued. After 48 h more, the mixture was cooled to room temperature and treated with aqueous hydrochloric acid (1.0M; 6.0 mL) to give a precipitate. The solid was collected by filtration, rinsed with water and dried to provide the title product (369 mg, 91%) as a white solid: $^1$H NMR (DMSO-d$_6$) δ 12.70 (bs, 1H), 8.45 (s, 1H), 8.27 (s, 1H), 8.11 (d, 1H), 7.92 (d, 1H), 7.73 (d, 1H), 7.32 (bt, 1H), 7.16 (t, 1H), 6.70 (d, 1H), 6.59 (t, 1H), 4.53 (t, 2H), 3.24 (q, 2H), 2.14 (m, 2H); High resolution mass spectrum (NH$_3$—CI) calculated (M+H$^+$) 313.1301, found 313.1299.

E. tert-Butyl 3-[1-[3-(N-(1-oxido)pyridin-2-ylamino)-propyl]indazol-5-ylcarbonylamino]-2-(S)-(benzyloxycarbonylamino)propionate A mixture of the product prepared according to Example 1129 Part D (312 mg, 1.0 mmol), tert-butyl 3-amino-2(S)-benzyloxycarbonylaminopropionate (prepared according to Mokitoff and Logue, *J. Med. Chem.* 1981, 24, 554; 294 mg, 1.0 mmol), 1-hydroxybenzotriazole hydrate (135 mg, 1.0 mmol), tetrahydrofuran (4 mL) and dry N,N-dimethylformamide (1 mL) was stirred on an ice bath. Dicyclohexylcarbodiimide (227 mg, 1.1 mmol) was added, and the mixture was stirred for 1 h. The ice bath was removed and stirring was continued for 3.5 h more. The mixture was filtered, and the solid was rinsed with tetrahydrofuran. The filtrate was concentrated under vacuum, and the residue was taken up in ethyl acetate. The solution was washed with water, dried over anhydrous sodium sulfate, filtered and concentrated under vacuum. The residue was purified by flash chromatography (dichloromethane/methanol; 96:4, then 94:6) to provide the title product (304 mg, 52%) as an off-white glass: $^1$H NMR (CDCl$_3$) δ 8.00 (s, 1H), 8.11 (d, 1H), 8.07 (s, 1H), 7.76 (d, 1H), 7.4–7.2 (m, 6H), 7.18 (bt, 1H), 7.12 (t, 1H), 6.95 (bt, 1H), 6.53 (t, 1H), 6.39 (d, 1H), 6.10 (d, 1H), 5.11 (s, 2H), 4.50 (t, 3H),3.88 (m, 2H), 3.21 (q, 2H), 2.31 (m, 2H), 1.48 (s, 9H); High resolution mass spectrum (FAB) calculated (M+H$^+$) 589.2775, found 589.2804.

F. tert-Butyl 3-[1-[3-(N-pyridin-2ylamino)-propyl]-indazol-5-ylcarbonylamino]-2-(S)-aminopropionate A mixture of the product prepared according to Example 1129 Part E (266 mg, 452 mol) and 10% palladium on charcoal (65 mg) in ethanol (20 mL) was placed in a pressure bottle and agitated under an atmosphere of hydrogen (55 psig) for 100 h. The mixture was filtered through Celite® and the solids were rinsed with ethanol. The filtrate was concentrated under vacuum, and the residue was purified by flash chromatography (dichloromethane:methanol, step gradient from 96:4, to 92.5:7.5) to provide the title product (100 mg, 50%) as a colorless glass: $^1$H NMR (CDCl$_3$) δ 8.21 (s, 1H), 8.10 (s, 1H), 8.07 (d, 1H), 7.80 (d, 1H), 7.42 (d, 1H), 7.39 (t, 1H), 6.88 (bt, 1H), 6.56 (t, 1H), 6.33 (d, 1H), 4.90 (bt, 1H), 4.53 (t, 2H), 3.86 (m, 1H), 3.63 (m,1H), 3.52 (m, 1H), 3.28 (q, 2H), 2.26 (m, 2H), 1.90 (b, 2H), 1.48 (s, 9H); High resolution mass spectrum (NH$_3$—Cl) calculated (M+H$^+$) 439.2458, found 439.2457.

G. tert-Butyl 3-[1-[3-(N-pyridin-2-ylamino)-propyl]-indazol-5-ylcarbonylamino]-2-(S)-(1-naphthalenesulfonylamino)propionate A solution of the product prepared according to Example 1129 Part F (77 mg, 176 µmol) in dry tetrahydrofuran (2 mL) was treated with 4-(N,N- dimethylamino)pyridine (24 mg, 193 µmol), 1-naphthalenesulfonyl chloride (44 mg, 193 µmol) and pyridine (16 µL, 193 µmol). The mixture was stirred at room temperature for 20 h, then was concentrated under vacuum. The residue was purified by flash chromatography (dichloromethane-methanol, 96:4) and rotary thin-layer chromatography (dichloromethane-methanol, 96:4) to provide the title product (90 mg, 82%) as a colorless glass: $^1$H NMR (CDCl$_3$) δ 8.67 (d, 1H), 8.26 (d, 1H), 8.1–8.0 (m, 4H), 7.88 (d, 1H), 7.70 (m, 2H), 7.56 (m, 2H), 7.20 (m, 2H), 6.60 (m, 2H), 6.34 (d, 1H), 6.10 (bs, 1H), 5.35 (bs, 1H), 4.53 (t, 2H), 3.95 (b, 1H), 3.80 (m, 1H), 3.63 (m, 1H), 3.28 (q, 2H), 2.28 (m, 2H), 1.12 (s, 9H); High resolution mass spectrum (FAB) calculated (M+H$^+$) 629.2546, found 629.2526.

H. 3-[1-[3-(N-pyridin-2-ylamino)-propyl]indazol-5-ylcarbonylamino]-2-(S)-(1-naphthalenesulfonylamino) propionic acid trifluoroacetate A solution of the product prepared according to Example 1129 Part G (77 mg, 122 µmol) in dichloromethane (2 mL) was treated with trifluoroacetic acid (1 mL) and stirred at room temperature for 3 h. The solution was concentrated under vacuum, toluene was added, and the solvent was again removed under vacuum. The residue was triturated in ether, and the resulting solid was collected by filtration to provide the title product (81 mg, 96%) as a white powder: $^1$H NMR (DMSO-d$_6$) δ 8.60 (m, 3H), 8.39 (bt, 1H), 8.21 (s, 1H), 8.09 (d, 2H), 8.05 (s, 1H), 7.90 (t, 2H), 7.83 (t, 1H), 7.67 (m, 3H), 7.55 (m, 2H), 6.97 (d, 1H), 6.81 (t, 1H), 4.56 (t, 2H), 4.08 (q, 1H), 3.53 (m, 1H), 3.30 (m, 3H), 2.18 (m, 2H); High resolution mass spectrum (FAB) calculated (M+H$^+$) 573.1947, found 573.1928.

EXAMPLE 1129a

3-[1-[3-(N-pyridin-2ylamino)propyl]indazol-5-ylcarbonylamino]-2(S)-(4-phenylbenzenesulfonylamino)propionic acid trifluoroacetate A. tert-Butyl 3-[1-[3-(N-tert-butyloxycarbonyl-N-pyridin-2ylamino)propyl]indazol-5-ylcarbonylamino]-2(S)-(4-phenylbenzenesulfonylamino)propionate Using the procedure of Example 1129 Part G, the product prepared according to Example 1094 Part A (86 mg, 159 µmol) and 4-phenylbenzenesulfonyl chloride were converted to the title product (116 mg, 97%): $^1$H NMR (CDCl$_3$) δ 8.28 (m, 1H), 8.23 (2, 1H), 8.06 (s, 1H), 7.92 (d, 2H), 7.81 (d, 1H), 7.68 (d, 2H), 7.60 (m, 2H), 7.53 (m, 2H), 7.45 (m, 3H), 7.37 (d, 1H), 6.99 (m, 1H), 6.88 (bt, 1H), 5.75 (d, 1H), 4.45 (t, 2H), 4.01 (m, 4H), 3.62 (m, 1H), 2.31 (m, 2H), 1.43 (s, 9H), 1.30 (s, 9H); High resolution mass spectrum (FAB) calculated (M+H$^+$) 755.3227, found 755.3200.

B. 3-[1-[3-(N-pyridin-2ylamino)propyl]indazol-5-ylcarbonylamino]-2(S)-(4-phenylbenzenesulfonylamino) propionic acid trifluoroacetate Using the procedure of Example 1129 Part H, the product prepared according to Example 1129 a Part A (108 mg, 143 µmol) was converted to the title product: $^1$H NMR (MeOH-d$_4$) δ 8.16 (s, 1H), 8.08 (s, 1H), 7.85 (d, 2H), 7.8–7.7 (m, 4H), 7.58 (d, 2H), 7.5–7.3 (m, 6H), 6.9–6.75 (m, 2H), 4.48 (t, 2H), 4.23 (m, 1H), 3.78 (dd, 1H), 3.50 (dd, 1H), 3.26 (m, 2H), 2.26 (m, 2H); High resolution mass spectrum (FAB) calculated (M+H$^+$) 599.2077, found 599.2062.

EXAMPLE 1155

3-[1-[3-(N-pyridin-2-ylamino)propyl]indazol-5-ylcarbonylamino]-2(S)-(benzylaminiosulfonylamino) propionic acid trifluoroacetate A. tert-Butyl 3-[1-[3-(N-(tert-butyloxycarbonyl-N-pyridin-2-ylamino)propyl]indazol-5-ylcarbonylamino]-2(S)-(benzylaminosulfonylamino)propionate A solution of the product prepared according to Example 1094 Part A (101 mg, 188 µmol) in anhydrous tetrahydrofuran (5 mL) was treated with N-benzylsulfamoyl chloride (prepared according to the procedures of Audrieth and Sveda, *J. Org. Chem.* 1944, 9, 89–101, and Kloeck and Leschinsky, *J. Org. Chem.* 1976, 41, 4028–4029; 51 mg, 248 µmol), then with 4-(N,N-dimethylamino)pyridine (37 mg, 193 µmol) and pyridine (19 µL, 252 µmol). The resulting mixture was stirred at room temperature for 24 h, then was concentrated under vacuum. The residue was purified by flash chromatography (hexanes:ethyl acetate 45:55) to provide the title product (92 mg, 70%) as a white solid: $^1$H NMR (CDCl$_3$) δ 8.27 (m, 1H), 8.18 (s, 1H), 8.04 (s, 1H), 7.78 (d, 1H), 7.60 (m, 2H), 7.36 (d, 1H), 7.29 (m, 5H), 6.99 (m, 1H), 6.79 (bt, 1H), 5.62 (d, 1H), 4.75 (t, 1H), 4.44 (t, 2H), 4.23 (t, 2H), 4.15 (m, 1H), 4.00 (m, 2H), 3.95 (m, 1H), 3.76 (m, 1H), 2.31 (m, 2H), 1.48 (s, 9H), 1.43 (s, 9H); High resolution mass spectrum (FAB) calculated (M+H$^+$) 708.3179, found 708.3205

B. 3-[1-[3-(N-pyridin-2yl)aminoproply]indazol-5-yl]-carbonylamino-2(S)-benzylaminosulfonylaminopropionic acid trifluoroacetate Using the procedure of Example 1129 Part H, the product prepared according to Example 1155 Part A (21 mg, 30 μmol) was converted to the title product (19 mg, 96%): $^1$H NMR (DMSO-d$_6$) δ 8.56 (m, 2H), 8.33 (s, 1H), 8.24 (s, 1H), 7.90–7.70 (m, 4H), 7.49 (d, 1H), 7.43 (t, 1H), 7.23 (m, 5H), 6.96 (d, 1H), 6.80 (t, 1H), 4.56 (t, 2H), 4.20–3.60 (m, 5H), 3.59 (m, 2H), 2.18 (t, 2H); High resolution mass spectrum (FAB) calculated (M+H$^+$) 552.2029, found 552.2042.

EXAMPLE 1178b

3-[1-[3-(N-3 4,5,6-Tetrahydropyrimidin-2-ylamino)propyl]indazol-5-ylcarbonylamino]-2(S)-(2,4,6-trimethylbenzenesulfonylamino)propionic acid trifluoroacetate A. 1-(3-Benzyloxycarbonylaminopropyl)-5-ethoxycarbonylindazole A mixture of the product prepared according to Example 1129 Part B (5.0 g, 18 mmol) and triethylamine (7.5 mL, 19 mmol) in dichloromethane (100 mL) was cooled on an ice bath and treated with benzyl chloroformate (2.7 mL, 19 mmol). The mixture was stirred at room temperature for 16 h, then was concentrated under vacuum. The residue was dissolved in dichloromethane and washed with water several times, then was dried over anhydrous magnesium sulfate, filtered and concentrated to provide the title product (3.4 g, 49%) as a white solid. While this material was suitable for further use, it could be purified by flash chromatography (dichloromethane:methanol 95:5): $^1$H NMR (CDCl$_3$) δ 8.50 (s, 1H), 8.06 (m, 2H), 7.38 (m, 6H), 5.20 (bm, 1H), 5.02 (s, 2H), 4.42 (m, 4H), 3.18 (m, 2H), 2.18 (m, 2H), 1.40 (m, 3H); Mass spectrum (ESI) m/z 382.5 (100%, M+H$^+$).

B. 1-(3-Benzyloxycarbonylaminopropyl)-5-carboxyindazole

A mixture of the product prepared according to Example 1178b Part A (3.08 g, 8.07 mmol), lithium hydroxide hydrate (678 mg, 16.2 mmol), ethanol (160 mL) and water (40 mL) was stirred at room temperature. Tetrahydrofuran was added until the mixture was homogeneous, then stirring was continued for 5 days. The solution was concentrated, and the residue was taken up in water. The mixture was washed with ethyl acetate, and the aqueous phase was acidified to pH 4–5 with aqueous hydrochloric acid (1.0M). This mixture was then extracted with ethyl acetate. The extract was dried over anhydrous magnesium sulfate, filtered and concentrated to provide the title product (1.6 g, 56%) as a sticky solid: $^1$H NMR (DMSO-d$_6$) δ 8.44 (s, 1H), 8.26 (s, 1H), 7.93 (d, 1H), 7.72 (d, 1H), 7.35 (m, 5H), 5.00 (s, 2H), 4.46 (t, 2H), 3.01 (m, 2H), 1.98 (m, 2H).

C. N$^2$-(2,4,6 trimethylbenzenesulfonyl)-L-asparagine

L- Asparagine (20.0 g, 0.15 mol) was suspended in a mixture of tetrahydrofuran (130 mL) and water (250 mL). Triethylamine (68 mL, 0.48 mol) was added, followed by mesitylenesulfonyl chloride (49.7 g, 0.23 mol) added over 20 min. The reaction mixture became slightly warmer and the solids dissolved to yield a yellow solution. The reaction mixture was stirred for 3 h at room temperature, then washed twice with ether, and twice with dichloromethane. The aqueous layer was acidified to pH 1.5 with concentrated aqueous HCl, during which time a thick precipitate formed. After being stirred for 30 min the solid was collected by filtration, washed with water and dried to yield the title product (34.1 g, 72%) as a white solid: m.p. 193.5°–195° C.; $^1$H NMR (DMSO-d$_6$) δ12.58 (bs, 1H), 7.82 (d, 1H), 7.32 (bs, 1H), 6.99 (s, 2H), 6.88 (bs, 1H) 3.98 (m, 1H), 2.55 (s, 6H), 2.45 (dd, 1H), 2.28 (dd, 1H), 2.24 (s, 3H); Mass spectrum (ESI) m/z 315.2, (100%, M+H$^+$).

D. 3-Amino-2-(S)-(2,4,6-trimethylbenzenesulfonylamino) propionic acid

Sodium hydroxide (32 g, 0.80 mol), was dissolved in water (200 mL) and cooled in an ice bath.

Bromine (6.2 mL, 0.12 mol) was added dropwise over 5 min and the mixture was allowed to stir for 15 min. The product prepared according to Example 1178b Part C (31.44 g, 0.10 mol) was added in several portions over a period of ca. 10 min, during which time the yellow color faded. After stirring for 15 min more, the reaction mixture was heated rapidly to an internal temperature of ca. 85° C. After 1 h, the reaction mixture was allowed to cool to room temperature, then cooled in an ice bath. The reaction mixture was cautiously acidified to pH 6 with concentrated aqueous HCl, during which time a solid formed and gas was evolved. The solid was collected by filtration, washed with cold water, and allowed to dry overnight to provide the title product (23.9 g, 83%) as a white solid: $^1$H NMR (DMSO-d$_6$) δ 7.06 (s, 2H), 3.07 (dd, 1H), 3.35 (broad), 2.94 (dd, 1H), 2.80 (dd, 1H), 2.59 (s, 6H), 2.26 (s, 3H); Mass spectrum (ESI) m/z 287.2 (100%, M+H$^+$).

E. tert-Butyl 3-amino-2-(S)-(2,4,6-trimethylbenzenesulfonylamino)propionate

The product prepared according to Example 1178b Part D (11.45 g, 0.04 mol) was placed in a pressure bottle and dissolved in dioxane (170 mL). Concentrated sulfuric acid (11 mL) was added and the reaction mixture was cooled in a dry ice-acetone bath. Liquid isobutylene (ca. 185 mL) was added, and the bottle was sealed and agitated for 114 h. The bottle was de-pressurized, then purged with nitrogen for a brief time. The reaction mixture was poured into a rapidly stirred mixture of water (225 mL) containing sodium hydroxide (17 g) and ether (600 mL) which had been pre-cooled in an ice bath. The layers were separated, and the aqueous layer was extracted with additional ether. These organic extracts were discarded. The pH of the aqueous layer was carefully adjusted with concentrated aqueous HCl to pH 11.0 and extracted four times with ether. The organic layers from the pH 11 extraction were combined, dried with anhydrous sodium sulfate, filtered and concentrated to yield the title product (8.64 g, 63%) as a viscous oil which gradually solidified: $^1$H NMR (CDCl$_3$) δ 6.95 (s, 2H), 3.69 (m, 1H), 2.93 (m, 2H), 2.67 (s, 6H), 2.28 (s, 3H), 1.28 (s, 9H); Mass spectrum (ESI) m/z 343.3 (100%, M+H$^+$).

F. tert-Butyl 3-[1-(3-benzyloxycarbonylaminopropyl)indazol-5-ylcarbonylamino]-2(S)-(2,4,6-trimethylbenzenesulfonylamino)propionate Using the procedure of Example 1129 Part E, the product prepared according to Example 1178b Part B (100 mg, 283 μmol) and the product prepared according to Example 1178b Part E (107 mg, 283 μmol) were converted to the title product (130 mg, 68%) as a yellowish solid: $^1$H NMR (CDCl$_3$) δ 8.24 (s, 1H), 8.09 (s, 1H), 7.85 (d, 1H), 7.42 (d, 1H), 7.36 (m, 5H), 6.93 (s, 2H), 6.83 (m, 1H), 5.78 (d, 1H), 5.09 (s, 2H), 4.47 (t, 2H), 4.02 (m, 1H), 3.84 (m, 1H), 3.7–3.4 (m, 2H), 3.18 (m, 2H), 2.66 (s, 6H), 2.26 (s, 3H), 2.15 (m, 2H), 1.21 (s, 9H); Mass spectrum (ESI) m/z 678.4 (41%, M+H$^+$).

G. tert-Butyl 3-[1-(3-aminopropyl)-indazol-5-ylcarbonylamino]-2(S)-(2,4,6-trimethylbenzenesulfonylamino)propionate A mixture of the product prepared according to Example 1178b Part F (50 mg, 74 μmol), palladium hydroxide on charcoal (Pearlman's catalyst; 15 mg), 1,4-cyclohexa-diene (1 mL) and methanol (2 mL) was heated at reflux. After 4 h, the mixture was cooled and filtered through Celite®, and the solids were rinsed with methanol. The filtrate was concentrated under vacuum to provide the title product (34 mg, 85%) as a solid which was used in subsequent reactions without further purification: $^1$H NMR (CDCl$_3$) δ 8.03 (s, 1H), 7.80–7.65 (m, 3H), 7.31 (d, 1H), 6.84 (s,H), 4.40 (m, 2H), 4.02 (m, 1H), 3.78 (m, 2H), 3.06 (m, 2H), 2.63 (m, 1H), 2.59 (s, 6H), 2.27 (m, 2H), 2.19 (s, 3H), 1.23 (s, 9H); Mass spectrum (ESI) m/z 544.5 (100%, M+H$^+$).

H. tert-Butyl 3-[1-[3-(N-3,4,5,6-tetrahydropyrimidin-2-ylamino)propyl]-indazol-5-ylcarbonylamino]-2(S)-(2,4,6-trimethylbenzenesulfonylamino)propionate hydriodide A mixture of the product prepared according to Example 1178b Part G (100 mg, 184 μmol) and 2methylthio-3,4,5,6-tetrahydropyrimidine hydriodide (57 mg, 221 μmol) in pyridine (5 mL) was heated at 120° C. After 16 h, the mixture was cooled to room temperature and concentrated under vacuum. The residue was purified by flash chromatography (dichloromethane:methanol, step gradient from 95:5 to 90:10) to provide the title product (37 mg, 27%): $^1$H NMR (CDCl$_3$) δ 8.30 (s, 1H), 8.10 (bm, 1H), 8.08 (s, 1H), 7.92 (d, 1H), 7.85 (t, 1H), 7.51 (d, 1H), 7.10 (bt, 1H), 6.95 (s, 2H), 4.47 (m, 2H), 3.95 (m, 1H), 3.85 (m, 1H), 3.61 (m, 1H), 3.44 (m, 4H), 3.27 (m, 2H), 2.64 (s, 6H), 2.28 (s, 3H), 2.15 (m, 2H), 2.00 (m, 2H), 1.30 (s, 9H); Mass spectrum (ESI) m/z 626.5 (100%, M+H$^+$).

I. 3-[1-[3-(N-3,4,5,6-Tetrahydropyrimidin-2ylamino) propyl]indazol-5-ylcarbonylamino]-2(S)-(2,4,6-trimethylbenzenesulfonylamino)propionic acid trifluoroacetate Using the procedure of Example 1129 Part H, the product prepared according to Example 1178b Part H was converted to the title product: $^1$H NMR (DMSO-d$_6$) δ 8.46 (bt, 1H), 8.24 (s, 1H), 8.19 (s, 1H), 8.07 (d, 1H), 7.79 (d, 1H), 7.32 (bt, 1H), 6.84 (s, 2H), 4.47 (t, 2H), 4.02 (m, 1H), 3.6–3.4 (m, 2H), 3.21 (m, 4H), 3.03 (m, 2H), 2.52 (s, 6H), 2.07 (s, 3H), 2.05 (m, 2H), 1.78 (m, 2H); Mass spectrum (ESI) m/z 570.5 (100%, M+H$^+$).

EXAMPLE 1198

3-[1-[3-(N-4,5-Dihydroimidazol-2-ylamino)propyl] indazol-5-ylcarbonylamino]-2(S)-(benzyloxycarbonylamino)propionic acid trifluoroacetate A. 1-(3-aminoproply)-5-ethoxycarbonylindazole A mixture of the product prepared according to Example 1081 Part A (4.20 g, 11.1 mmol), ethanol (75 mL), dry tetrahydrofuran (75 mL) and anhydrous hydrazine (1.5 mL) was stirred at room temperature for 16 h. Dry tetrahydrofuran (100 mL) was added, the mixture was filtered and the filtrate was concentrated to provide the title product, which was used directly in the subsequent reaction without purification: $^1$H NMR (CDCl$_3$) δ 8.51 (s, 1H), 8.10 (s, 1H), 8.06 (d, 1H), 7.46 (d, 1H), 4.52 (t, 2H), 4.41 (q, 2H), 2.68 (t, 2H), 2.06 (m, 2H), 1.72 (bs, 2H), 1.43 (t, 3H).

B. 1-[3-(N-4,5-Dihydroimidazol-2-ylamino)propyl]-5-ethoxycarbonylindazole hydriodide The crude product of Example 1198 Part A was combined with 2-methylthio-4,5-dihydroimidazole hydriodide (2.71 g, 11.1 mmol) and pyridine (125 mL), and the mixture was heated at 80° C. for 5 h. The mixture was allowed to cool to room temperature and concentrated under vacuum. The residue was purified by flash chromatography (dichloromethane:methanol 80:20) to provide the title product (3.73 g, 75%) as a gum: $^1$H NMR (DMSO-d$_6$) δ 8.50 (s, 1H), 8.30 (s, 1H), 8.24 (bs, 1H), 7.98 (d, 1H), 7.75 (d, 1H), 4.49 (t, 2H), 4.34 (q, 2H), 3.57 (s, 4H), 3.13 (m, 2H), 2.05 (m, 2H), 1.35 (t, 3H); High resolution mass spectrum (NH$_3$—CI) calculated (M+H$^+$) 316.1774, found 316.1765.

C. tert-Butyl 3-[1-[3-(N-4,5-Dihydroimidazol-2yl-amino)-propyl]indazol-5-ylcarbonylamino]-2(S)-(benzyloxycarbonylamino)propionate hydrochloride A mixture of the product prepared according to Example 1198 Part B (3.39 g, 7.64 mmol), aqueous sodium hydroxide (1.0M; 16 mL, 16 mmol) and ethanol (35 mL) was stirred at reflux for 16 h. The mixture was allowed to cool to room temperature and was treated with aqueous hydrochloric acid (1.0M; 16 mL, 16 mmol). The solvent was evaporated under vacuum, benzene was added and solvent was again evaporated. A portion of the resulting residue (77 mg, 240 μmol) was combined with tert-butyl 3-amino-2(S)-benzyloxycarbonylamino)propionate (prepared according to Mokotoff and Logue, *J. Med. Chem.* 1981, 24, 554; 70 mg, 240 μmol), 1-ethyl-3-(3-dimethylaminopropyl)carbodiimide hydrochloride (60 mg, 313 μmol), 1-hydroxybenzotriazole hydrate (10 mg), dry N,N-dimethylformamide (5 mL) and triethylamine (0.1 mL), and the resulting mixture was stirred at room temperature for 16 h. The mixture was concentrated under vacuum and benzene (20 mL) was added. The solvent was evaporated and the residue was purified by flash chromatography (dichloromethane:methanol 90:10) to provide the title product (122 mg, 85%) as a yellow gum: $^1$H NMR (DMSO-d$_6$) δ 8.53 (bt, 1H), 8.30 (s, 1H), 8.24 (s+m, 2H), 7.88 (d, 1H), 7.71 (d, 1H), 7.70 (m, 1H), 7.34 (m, 5H), 5.04 (s, 2H), 4.47 (t, 2H), 4.23 (m, 1H), 3.75–3.50 (m, 2H), 3.55 (s, 4H), 3.12 (q, 2H), 2.06 (m, 2H), 1.33 (s, 9H); High resolution mass spectrum (NH$_3$—CI) calculated (M+H$^+$) 564.2934, found 564.2959.

D. 3-[1-[3-(N-4,5-Dihydroimidazol-2-ylamino)propyl] indazol-5-ylcarbonylamino)-2(S)-(benzyloxycarbonylamino)propionic acid trifluoroacetate Using the procedure of Example 1081 Part H, the product prepared according to Example 1198 Part C (108 mg, 180 μmol) was converted to the title product (74 mg, 75%) as a hygroscopic, off-white solid: $^1$H NMR (DMSO-d$_6$) δ 8.57 (bt, 1H), 8.31 (s, 1H), 8.28 (m, 1H), 8.24 (s, 1H), 7.88 (d, 1H), 7.72 (d, 1H), 7.62 (m, 1H), 7.32 (m, 5H), 5.02 (s, 2H), 4.47 (t, 2H), 4.29 (m, 1H), 3.65 (m, 2H), 3.55 (s, 4H), 3.11 (q, 2H), 2.06 (m, 2H); High resolution mass spectrum (FAB) calculated (M+H$^+$) 508.2308, found 508.2323.

EXAMPLE 1213

3-[1-[3-(N-4,5-Dihydroimidazol-2-ylamino)-propyl] indazol-5-ylcarbonylamino]-2(S)-(benzenesulfonylamino)propionic acid trifluoroacetate A. tert-Butyl 3-[1-[3-(N-4,5-dihydroimidazol-2yl-amino) propyl]indazol-5-ylcarbonylamino]-2(S)-(benzenesulfonylamino)propionate hydrochloride A mixture of tert-butyl 3-benzyloxycarbonylamino-2-(S)-benzenesulfonylamino)propionate (200 mg, 460 μmol), methanol (15 mL) and 10% palladium on charcoal (25 mg) was stirred at room temperature. Hydrogen gas was bubbled through the solution for 5 minutes, and a hydrogen-filled balloon was then placed on the reaction flask. The mixture was stirred at room temperature for 3 h, then was filtered through Celite®. The solids were washed with methanol and the filtrate was concentrated. The residue was mixed with a portion of the intermediate residue obtained in Example 1198 Part C (149 mg, 460 μmol), 1-ethyl-3-(3-dimethylaminopropyl)carbodiimide hydrochloride (120 mg, 626 μmol), 1-hydroxybenzotriazole hydrate (20 mg), dry N,N-dimethylformamide (10 mL) and triethylamine (0.2 mL). The mixture was stirred at room temperature for 16 h.

The solvent was removed under vacuum and the residue was purified by flash chromatography (dichloromethane:ethanol 75:25) to provide the title product (220 mg, 78%) as a gum: $^1$H NMR (CDCl$_3$) δ 8.66–7.04 (m, 13H), 5.99 (bs, 1H), 4.52–1.98 (m, 15H), 1.30 (s, 9H); High resolution mass spectrum calculated (M+H$^+$) 570.2499, found 570.2503.

B. 3-[1-[3-(N-4,5-Dihydroimidazol-2-ylamino)propyl]-indazol-5-ylcarbonylamino]-2(S)-(benzenesulfonylamino) propionic acid trifluoroacetate Using the procedure of Example 1081 Part H, the product prepared according to Example 1213 Part A (202 mg, 333 μmol) was converted to the title product (151 mg, 82%) as a hygroscopic solid: $^1$H NMR (DMSO-d$_6$) δ 8.56–7.08 (m, 15H), 4.54–2.01 (m, 13H); High resolution mass spectrum calculated (M+H$^+$) 514.1873, found 514.1879.

EXAMPLE 1216b

3-[1-[3-(N-4,5-Dihydroimidazol-2-ylamino)propyl] indazol-5-ylcarbonylamino]-2(S)-(2,4,6-trimethylbenzenesulfonylamino)propionic acid trifluoroacetate A. tert-Butyl 3-[1-[3-(N-4,5-dihydroimidazol-2-yl-amino) propyl]indazol-5-ylcarbonylamino-2(S)-(2,4,6-trimethylbenzenesulfonylamino)propionate hydriodide A mixture of the product prepared according to Example 1178b Part G (60 mg, 110 μmol), 2-methylthioimidazoline hydriodide (32 mg, 130 μmol) and pyridine (5 mL) was heated on an oil bath at 120° C. After 16 h, the mixture was cooled to room temperature and concentrated under vacuum. The residue was purified by flash chromatography (dichloromethane:methanol, step gradient from 98:2 to 90:10) to provide the title product (30 mg, 37%): $^1$H NMR (CDCl$_3$) δ 8.03 (s, 1H), 7.82 (s, 1H), 7.73 (d, 1H), 7.70 (bm, 1H), 7.31 (d, 1H), 6.84 (s, 1H), 4.39 (m, 2H), 3.99 (m, 1H), 3.78 (m, 2H), 3.48 (s, 4H), 3.01 (m, 2H), 2.60 (s, 6H), 2.21 (m, 2H), 2.17 (s, 3H), 1.24 (s, 9H); High resolution mass spectrum (FAB) calculated (M+H$^+$) 612.2968, found 612.2975.

B. 3-[1-[3-(N-4,5-Dihydroimidazol-2-ylamino)propyl] indazol-5-ylcarbonylamino]-2(S)-(2,4,6-trimethylbenzenesulfonylamino)propionic acid trifluoroacetate Using the procedure of Example 1129 Part H, followed by purification by preparative reverse phase high pressure liquid chromatography (acetonitrile:water containing 0.05% trifluoroacetic acid; gradient from 10:90 to 90:10), the product prepared according to Example 1216b Part A was converted to the title product (15 mg, 48%): $^1$H NMR (MeOH-d$_4$) δ 8.16 (s, 2H), 7.79 (d, 1H), 7.59 (d, 1H), 6.76 (s, 2H), 4.52 (t, 2H), 4.16 (dd, 1H), 3.77 (dd, 1H), 3.59 (s, 4H), 3.47 (dd, 1H), 3.16 (m, 2H), 2.57 (s, 6H), 2.18 (m, 2H), 2.02 (s, 3H); High resolution mass spectrum (FAB) calculated (M+H$^+$) 556.2372, found 556.2342.

EXAMPLE 1326b

3-[1-[1-(RS)-Methyl-3-(N-pyridin-2ylamino)propyl] indazol-5-ylcarbonylamino]-2(S)-(2,4,6-trimethylbenzenesulfonylamino)propionic acid trifluoroacetate A. 1-(1-(RS)-methyl-2-cyanoethyl)-5-ethoxycarbonylindazole A mixture of the product prepared according to Example 1050e Part C (1.90 g, 10 mmol), crotononitrile (4.9 mL, 60 mmol), sodium bis(trimethylsilyl)amide (1.0M in tetrahydrofuran; 0.5 mL, 0.5 mmol) and ethanol (20 mL) was heated at reflux for 18 h. The solution was cooled to room temperature and treated with aqueous hydrochloric acid (1.0M; 0.5 mL). The solvent was removed under vacuum, and the residue was taken up in dichloromethane and washed with water. The organic phase was dried over anhydrous magnesium sulfate, filtered, and concentrated under vacuum. The residue was purified by flash chromatography (hexanes:ethyl acetate 60:40) to provide the title product (2.49 g, 96%) as a viscous syrup which gradually solidified on standing: $^1$H NMR (CDCl$_3$) δ 8.53 (s, 1H), 8.17 (s, 1H), 8.11 (d, 1H), 7.45 (d, 1H), 5.03 (m, 1H), 4.41 (q, 2H), 3.05 (m, 2H), 1.74 (d, 3H), 1.43 (t, 3H); High resolution mass spectrum (NH$_3$—CI) calculated (M+H$^+$) 258.1243, found 258.1248.

B. 1-(1-(RS)-methyl-3-aminopropyl)-5-ethoxycarbonylindazole hydrochloride

Using the procedure of Example 1129 Part B, the product prepared according to Example 1326b Part A (2.0 g, 7.8 mmol) was converted into the title product (2.22 g, 96%) as a pale yellow, hygroscopic glass: $^1$H NMR (DMSO-d$_6$) δ 8.48 (s, 1H), 8.33 (s, 1H), 8.10 (bs, 3H), 7.96 (d, 1H), 7.88 (d, 1H), 5.11 (m, 1H), 4.34 (q, 2H), 2.75 (bm, 1H), 2.45 (bm, 1H), 2.30 (bm, 1H), 2.15 (bm, 1H), 1.49 (d, 3H), 1.35 (t, 3H); high resolution mass spectrum (NH$_3$—CI) calculated (M+H$^+$) 262.1556, found 262.1561.

C. 1-(1-(RS)-methyl-3-[N-(1-oxido)pyridin-2-ylamino] propyl)-5-ethoxycarbonylindazole. Using the procedure of Example 1081 Part C, the product prepared according to Example 1326b Part B (596 mg, 2.0 mmol) was converted into the title product (312 mg, 44%) as a tan glass: $^1$H NMR (CDCl$_3$) δ 8.52 (s, 1H), 8.18 (s, 1H), 8.09 (d, 1H), 7.98 (d, 1H), 7.38 (d, 1H), 6.99 (t, 1H), 6.82 (bt, 1H), 6.51 (d, 1H), 4.90 (m, 1H), 4.41 (q, 2H), 3.12 (m, 1H), 2.95 (m, 1H), 2.61 (m, 1H), 2.22 (m, 1H), 1.62 (d, 3H), 1.42 (t, 3H); High resolution mass spectrum (NH$_3$—CI) calculated (M+H$^+$) 355.1770, found 355.1771.

D. 1-(1-(RS)-methyl-3-[N-pyridin-2-ylamino]propyl)-5-ethoxycarbonylindazole

A mixture of the product prepared according to Example 1326b Part C (292 mg, 824 μmol), polymer-supported triphenylphosphine (550 mg, ca. 1.65 mmol) and N,N-dimethylformamide (5 mL) was heated on an oil bath at 160° C. After 18.5 h, an additional aliquot of polymer-supported triphenylphosphine (550 mg) was added, and the reaction was heated for 24 h more. The mixture was cooled to room temperature and filtered. The solid was washed with N,N-dimethylformamide, and the filtrate was concentrated under vacuum. The residue was purified by flash chromatography (dichloromethane:methanol 96:4) and rotary thin-layer chromatography (dichloromethane:methanol 97:3) to provide the title product (189 mg, 67%) as a pale yellow gum which gradually solidified on standing: $^1$H NMR (CDCl$_3$) δ 8.52 (s, 1H), 8.16 (s, 1H), 8.05–8.00 (m, 2H), 7.41 (d, 1H), 7.33 (t, 1H), 6.54 (t, 1H), 6.19 (d, 1H), 4.87 (m, 1H), 4.50–4.30 (m, 3H), 3.16 (m, 1H), 3.05 (m, 1H), 2.45 (m, 1H), 2.23 (m, 1H), 1.61 (d, 3H), 1.42 (t, 3H); High resolution mass spectrum (NH$_3$—CI) calculated (M+H$^+$) 339.1821, found 339.1832.

E. 1-(1-(RS)-methyl-3-[N-pyridin-2-ylamino]propyl)-5-carboxyindazole

A mixture of the product prepared according to Example 1326b Part D (180 mg, 532 μmol), aqueous sodium hydroxide (1.0M; 2.13 mL, 2.13 mmol) and ethanol (4 mL) was heated to reflux. After 4.25 h, the solution was cooled to room temperature and concentrated under vacuum. The residue was used directly in the next reaction without purification or characterization.

F. tert-Butyl 3-[1-[1-(RS)-methyl-3-(N-pyridin-2-ylamino) propyl]indazol-5-ylcarbonylamino]-2-(S)-(2,4,6-trimethylbenzenesulfonylamino)propionate The product of Example 1326b Part E was combined with the product prepared according to Example 1178b Part E (183 mg, 535 µmol), 1-hydroxybenzotriazole hydrate (72 mg, 535 µmol), N,N-dimethylformamide (8 mL), and triethylamine (1 drop), and the mixture was treated with dicyclohexylcarbodiimide (121 mg, 589 µmol) and stirred at room temperature. After 21.75 h, the mixture was diluted with ethyl acetate and filtered. The filtrate was concentrated under vacuum, and the residue was purified by flash chromatography (dichloromethane:methanol 97:3) to provide the title product (286 mg, 85%) as a colorless glass: $^1$H NMR (CDCl$_3$) δ 8.21 (s, 1H), 8.12 (s, 1H), 8.04 (dd, 1H), 7.77 (dt, 1H), 7.40 (d, 1H), 7.33 (t, 1H), 6.93 (s, 2H), 6.87 (bt, 1H), 6.53 (dd, 1H), 6.18 (d, 1H), 6.01 (bs, 1H), 4.86 (bm, 1H), 4.51 (m, 1H), 4.0–3.8 (m, 2H), 3.65 (m, 1H), 3.15 (m, 1H), 3.03 (m, 1H), 2.66 (s, 6H), 2.44 (m, 1H), 2.26 (s, 3H), 2.22 (m, 1H) 1.61 (d, 3H), 1.30 (s, 9H); High resolution mass spectrum (FAB) calculated (M+H$^+$) 635.3016, found 635.3019.

G. 3-[1-[1-(RS)-Methyl-3-(N-pyridin-2-ylamino)propyl]indazol-5-ylcarbonylamino]-2(S)-(2,4,6-trimethylbenzenesulfonyl)aminopropionic acid trifluoroacetate Using the procedure of Example 1129 Part H, the product prepared according to Example 1326b Part F (109 mg, 172 µmol) was converted to the title product (92 mg, 77%) as a white powder: $^1$H NMR (DMSO-d$_6$) δ 8.43 (bt, 2H), 8.27 (s, 1H), 8.17 (s, 1H), 8.06 (d, 1H), 7.8–7.6 (m, 4H), 6.87 (d, 1H), 6.82 (d, 2H), 6.74 (t, 1H), 5.02 (m, 1H), 4.02 (q, 1H), 3.57 (m, 1H), 3.40 (m, 1H), 3.07 (m, 2H), 2.53 (s, 6H), 2.37 (m, 1H), 2.21 (m, 1H), 2.05 (s, 3H), 1.52 (d, 3H); High resolution mass spectrum (FAB) calculated (M+H$^+$) 579.2390, found 579.2405.

EXAMPLE 1326f

3-[1-[3-(N-pyridin-2ylamino)propyl]-3-phenylindazol-5-ylcarbonylamino]-2(S)-(2,4,6-trimethylbenzenesulfonylamino)propionic acid trifluoroacetate A. 3-Bromo-5-ethoxycarbonylindazole A solution of the product prepared according to Example 1050e Part C (3.80 g, 20 mmol) in acetic acid (120 mL) was stirred at room temperature and treated with bromine (1.55 mL, 30 mmol). The mixture was stirred in the dark for 51 h, then was poured into water (600 mL). The resulting slurry was stirred at room temperature and treated with small portions of solid sodium bisulfite, whereupon the original orange color faded to almost white. After stirring 20 min more, the solid was collected by filtration, rinsed with water and dried to provide the title product (5.14 g, 96%) as a white solid. While pure enough for use in subsequent reactions, this material could be purified further by flash chromatography (hexanes:ethyl acetate 70:30): $^1$H NMR (DMSO-d$_6$) δ 13.80 (bs, 1H), 8.20 (d, 1H), 8.01 (dd, 1H), 7.69 (d, 1H), 4.36 (q, 2H), 1.37 (t, 3H); Mass spectrum (NH$_3$—CI) m/z 269 (100%), 271 (95%) (M+H$^+$).

B. 3-Phenyl-5-ethoxycarbonylindazole

A mixture of the product prepared according to Example 1326f Part A (2.69 g, 10.0 mmol), phenylboronic acid (1.71 g, 14.0 mmol), triethylamine (5.6 mL, 40.0 mmol), and N,N-dimethylformamide (20 mL) was purged of oxygen by bubbling with nitrogen for 20 min. Tetrakis (triphenylphosphine)palladium (580 mg, 500 µmol) was added, and the mixture was heated on an oil bath at 110° C. under nitrogen. After 48 h, the mixture was cooled to room temperature and diluted with water. The mixture was extracted with ethyl acetate, and the organic phase was dried over anhydrous magnesium sulfate, filtered and concentrated under vacuum. The residue was purified by flash chromatography (hexanes:ethyl acetate 80:20) to provide the title product (542 mg, 20 %) as a white solid: $^1$H NMR (CDCl$_3$ ) δ 11.44 (bs, 1H), 8.78 (s, 1H), 8.06 (d, 1H), 8.01 (d, 2H), 7.57 (t, 2H), 7.49 (t, 1H), 7.30 (d, 1H), 4.44 (q, 2H), 1.43 (t, 3H); High resolution mass spectrum (NH$_3$—CI) calculated (M+H$^+$) 267.1134, found 267.1132.

C. 1-(2-Cyanoethyl)-3-phenyl-5-ethoxycarbonylindazole

Using the procedure of Example 1129 Part A, followed by purification by flash chromatography (hexanes:ethyl acetate 70:30),the product prepared according to Example 1326f Part B (266 mg, 1.0 mmol) was converted to the title product (263 mg, 82%) as a white solid: mp 99°–102° C.; $^1$H NMR (CDCl$_3$) δ 8.77 (s, 1H), 8.16 (d, 1H), 7.96 (m, 2H), 7.60–7.40 (m, 4H), 4.73 (t, 2H), 4.43 (q, 2H), 3.10 (t, 2H), 1.44 (t, 3H); High resolution mass spectrum (NH$_3$—CI) calculated (M+H$^+$) 320.1399, found 320.1386.

D. 1-(3-aminopropyl)-3-phenyl-5-ethoxycarbonylindazole hydrochloride

Using the procedure of Example 1129 Part B, the product prepared according to Example 1326f Part C (214 mg, 670 µmol) was converted to the title product (260 mg, >100%) as a tan solid which was not purified, but was used directly in subsequent reactions: $^1$H NMR (DMSO-d$_6$) δ 8.64 (s, 1H), 8.05 (d, 1H), 8.0–7.9 (m), 7.60 (t, 2H), 7.49 (m, 1H), 4.63 (t, 2H), 4.37 (q, 2H), 2.90 (m, 2H), 2.18 (m, 2H), 1.36 (t, 3H); High resolution mass spectrum (ESI) calculated (M+H$^+$) 323.1634, found 323.1645.

E. 1-[3-(N-(1-oxido)pyridin-2-ylamino)propyl]-3phenyl-5-ethoxycarbonylindazole

Using the procedure of Example 1081 Part C, the crude product of Example 1326f Part D was converted into the title product (122 mg, 43%) as a tan glass: $^1$H NMR (CDCl$_3$) δ 8.78 (s, 1H), 8.13 (d, 1H), 8.07 (d, 1H), 7.99 (d, 2H), 7.55 (t, 2H), 7.47 (d, 1H), 7.42 (d, 1H), 7.09 (t, 1H), 6.97 (bt, 1H), 6.56 (t, 1H), 6.47 (d, 1H), 4.59 (t, 2H), 4.43 (q, 2H), 3.32 (q, 2H), 2.41 (m, 2H), 1.43 (t, 3H); High resolution mass spectrum (NH$_3$—CI) calculated (M+H$^+$) 417.1927, found 417.1918.

F. 1-[3-(N-pyridin-2-ylamino)propyl]-3-phenyl-5-ethoxycarbonylindazole

Using the procedure of Example 1129 Part F, the product prepared according to Example 1326f Part E (106 mg, 255 µmol) was converted to the title product (39 mg, 38%) as a glass: $^1$HNMR (CDCl$_3$) δ 8.77 (s, 1H), 8.08 (m, 2H), 7.98 (d, 2H), 7.54 (t, 2H), 7.5–7.3 (m, 3H), 6.56 (t, 1H), 6.32 (d, 1H), 4.77 (bt, 1H), 4.55 (t, 2H), 4.42 (q, 2H), 3.35 (q, 2H), 2.30 (m, 2H), 1.43 (t, 3H); High resolution mass spectrum (NH$_3$—CI) calculated (M+H$^+$) 401.1978, found 401.1977.

G. tert-Butyl 3-[1-[3-(N-pyridin-2-ylamino)propyl]-3-phenylindazol-5-ylcarbonylamino]-2(S)-(2,4,6-trimethylbenzenesulfonylamino)propionate Using the procedures of Example 1326b Parts E and F, the product prepared according to Example 1326f Part F (38 mg, 95 µmol) was converted to the title product (59 mg, 89%) as a glass: $^1$H NMR (CDCl$_3$) δ 8.57 (s, 1H), 8.08 (d, 1H), 8.01 (d, 2H), 7.85 (d, 1H), 7.53 (t, 2H), 7.5–7.4 (m, 3H), 6.97 (m, 1H), 6.92 (s, 2H), 6.57 (dd, 1H), 6.33 (d, 1H), 5.86 (d, 1H), 4.57 (t, 2H), 3.98 (m, 1H), 3.83 (m, 1H), 3.53 (m, 1H), 3.35 (q, 2H), 2.65 (s, 6H), 2.31 (m, 2H), 2.24 (s, 3H), 1.31 (s, 9H); High resolution mass spectrum (FAB) calculated (M+H$^+$) 697.3172, found 692.3184.

H. 3-[1-[3-(N-pyridin-2-yl)aminopropyl]3-phenylindazol-5-yl]carbonylamino-2(S)-(2,4,6-trimethylbenzenesulfonyl)aminopropionic acid trifluoroacetate Using the procedure of Example 1129 Part H, the product prepared according to Example 1326f Part G (44 mg, 63 μmol) was converted to the title product (32 mg, 80%) as an off-white powder: $^1$H NMR (DMSO-d$_6$) δ 8.61 (bt, 1H), 8.38 (s, 1H), 8.08 (d, 1H), 8.01 (d, 2H), 7.88 (d, 1H), 7.82 (d, 1H), 7.75 (d, 1H), 7.71 (bm, 1H), 7.57 (t, 2H), 7.47 (t, 1H), 6.86 (bd, 1H), 6.72 (bt, 1H), 6.70 (s, 2H), 4.61 (t, 2H), 4.07 (in, 1H), 3.58 (m, 1H), 3.5–3.3 (m, 3H), 2.51 (s, 6H), 2.23 (in, 2H), 1.92 (s, 3H); High resolution mass spectrum (FAB) calculated (M+H$^+$) 641.2546, found 641.2569.

EXAMPLE 1326g

3-[1-[3-(N-pyridin-2-ylamino)propyl]-3-(2-phenylethyl)indazol-5-ylcarbonylamino]-2(S)-(2,4,6-trimethylbenzenesulfonylamino)propionic acid trifluoroacetate A. 3-Phenylethynyl-5-ethoxycarbonylindazole A mixture of the product prepared according to Example 1326f Part A (269 mg, 1.0 mmol), triphenylphosphine (21 mg, 80 μmol), copper(I) iodide (8 mg, 40 μmol), phenylacetylene (165 μL, 1.5 mmol) and diethylamine (5 mL) was purged of oxygen by bubbling with nitrogen for 35 min. Bis(triphenylphosphine)palladium(II) chloride (14 mg, 20 μmol) was then added, and the mixture was heated to reflux under nitrogen. After 16.5 h, the mixture was cooled to room temperature and concentrated under vacuum. The residue was purified by flash chromatography (hexanes:ethyl acetate 80:20) to provide the title product (227 mg, 78%) as a yellowish solid: $^1$H NMR (CDCl$_3$) δ 8.66 (s, 1H), 8.13 (d, 1H), 7.68 (m, 2H), 7.55 (d, 1H), 7.42 (m, 3H), 4.45 (q, 2H), 1.45 (t, 3H); High resolution mass spectrum (NH$_3$—CI) calculated (M+H$^+$) 291.1134, found 291.1111.

B. 1-(2-Cyanoethyl)-3-(2-phenylethynyl)-5-ethoxycarbonylindazole

Using the procedure of Example 1129 Part A, the product prepared according to Example 1326g Part A (278 mg, 958 μmol) was converted to the title product (254 mg, 77%) as a tan solid: mp 90°–94° C.; $^1$H NMR (CDCl$_3$) δ 8.63 (s, 1H), 8.17 (d, 1H), 7.67 (m, 2H), 7.52 (d, 1H), 7.42 (m, 3H), 4.70 (t, 2H), 4.45 (q, 2H), 3.09 (t, 2H), 1.46 (t, 3H); High resolution mass spectrum (NH$_3$—CI) calculated (M+H$^+$) 344.1399, found 344.1391.

C. 1-(3-Aminopropyl)-3-(2-phenylethyl)-5-ethoxycarbonylindazole hydrochloride

Using the procedure of Example 1129 Part B, the product prepared according to Example 1326g Part B (240 mg, 699 μmol) was converted to the title product (277 mg, >100%) as a pale yellow solid which was not purified, but was used directly in subsequent reactions: $^1$H NMR (DMSO-d$_6$) δ 4.50 (m, 2H), 3.28 (t, 2H), 3.05 (t, 2H), 2.80 (m, 2H), 2.10 (m, 2H).

D. 1-[3-[N-(1-oxido)pyridin-2-ylamino]propyl]-3-(2-phenylethyl)-5-ethoxycarbonylindazole Using the procedure of Example 1081 Part C, the crude product of Example 1326g Part C was converted into the title product (145 mg, 46%) as a pale yellow glass which was not purified but was used in subsequent reactions: Mass spectrum (ESI) m/z 445.4 (100%, M+H$^+$).

E. 1-[3-[N-pyridin-2-ylamino]propyl]-3-(2phenylethyl)-5-ethoxycarbonylindazole

Using the procedure of Example 1326b Part D, the impure product of Example 1326g Part D was converted to the title product (90 mg, 70%) as a yellow gum, which impure but was used in subsequent reactions without further purification.

F. tert-Butyl 3-[1-[3-(N-pyridin-2-ylamino)propyl]-3-(2-phenylethyl)indazol-5-ylcarbonylamino]-2(S)-(2,4,6-trimethylbenzenesulfonylamino)propionate Using the procedures of Example 1326b Parts E and F, the impure product of Example 1326g Part E was converted to the title product (98 mg, 64%) as a glass, which was impure but was used without further purification in the subsequent reaction.

G. 3-[1-[3-(N-pyridin-2-ylamino)propyl]-3-(2phenylethyl)indazol-5-ylcarbonylamino]-2(S)-(2,4,6-trimethylbenzenesulfonylamino)propionic acid trifluoroacetate Using the procedure of Example 1129 Part H, the impure product of Example 1326g Part F was converted to the title product. The crude material was purified by preparative reverse-phase high pressure liquid chromatography (acetonitrile-water containing 0.05% trifluoroacetic acid, gradient from 10:90 to 90:10) to provide the title product (20 mg, 20 %) as an off-white powder: High resolution mass spectrum (FAB) calculated (M+H$^+$) 669.2859, found 669.2881.

EXAMPLE 1327b

3-[1-[2-(N-Imidazol-2-ylaminocarbonyl)ethyl]indazol-5-ylcarbonylamino]-2(S)-(2,4,6-trimethylbenzenesulfonylamino)propionic acid trifluoroacetate A. 1-(2-tert-Butyloxycarbonylethyl)-5-ethoxycarbonylindazole A mixture of the product prepared according to Example 1050e Part C (2.0 g, 10.5 mmol), tert-butyl acrylate (9.3 mL, 63.5 mmol) and ethanol (21 mL) was treated with sodium bis(trimethylsilyl)amide (1.0M in tetrahydrofuran; 530 μL, 530 μmol). The resulting solution was heated at reflux for 3 h, then was cooled to room temperature. Aqueous hydrochloric acid (1.0M; 550 μL, 550 μmol) was added, and the mixture was concentrated. The residue was partitioned between ether and water, and the aqueous phase was extracted further with ether. The combined organic phases were dried over anhydrous sodium sulfate, filtered and concentrated under vacuum. The residue was purified by flash chromatography (hexanes:ethyl acetate 85:15) to provide the title product (830 mg, 25%): $^1$H NMR (CDCl$_3$) δ 8.49 (s, 1H), 8.10 (s, 1H), 8.07 (d, 1H), 7.50 (d, 1H), 4.64 (t, 2H), 4.41 (q, 2H), 2.91 (t, 2H), 1.42 (t, 3H), 1.33 (s, 9H); high resolution mass spectrum (NH$_3$—CI) calculated (M+H$^+$) 319.1658, found 319.1655.

B. 1-(2-Carboxyethyl)-5-ethoxycarbonylindazole

A solution of the product prepared according to Example 1327b Part A (791 mg, 2.49 mmol) in dichloromethane (28 mL) was treated with trifluoroacetic acid (6 mL). The mixture was stirred at room temperature for 16 h, then was concentrated under vacuum. Addition of ether to the residue produced, after filtering and drying, the title product (571 mg, 88%) as a white solid: $^1$H NMR (CDCl$_3$) δ 8.52 (s, 1H), 8.12 (s, 1H), 8.09 (d, 1H), 7.49 (d, 1H), 4.67 (t, 2H), 4.41 (q, 2H), 3.07 (t, 2H), 1.42 (t, 3H); Mass spectrum (ESI) m/z 263.3 (100%, M+H$^+$).

C. 1-(2-(N-imidazol-2-ylaminocarbonyl)ethyl)-5-ethoxycarbonylindazole

A mixture of the product prepared according to Example 1327b Part B (352 mg, 1.34 mmol), 2-aminoimidazole sulfate (0.55 g, 4.15 mmol), diisopropylethylamine (1.17 mL, 6.7 mL) and N,N-dimethylformamide (7 mL) was treated with benzotriazol-1-yloxy-tris(dimethylamino)phosphonium hexafluorophosphonate (BOP Reagent; 891 mg, 2.0 mmol) and warmed to 70° C. on an oil bath. The mixture was stirred at this temperature for 18 h, then was cooled to room temperature and diluted with water (75 mL). The resulting precipitate was collected by filtration to provide the title product (310 mg, 71%) which was used in subsequent reactions without further purification: $^1$H NMR (CDCl$_3$) δ 8.49 (s, 1H), 8.11 (s, 1H), 8.07 (d, 1H), 7.88 (b, 1H), 7.55 (d, 1H), 7.40 (b, 1H), 4.75 (t, 2H), 4.41 (q, 2H), 3.01 (t, 2H), 1.42 (t, 3H); high resolution mass spectrum (NH$_3$—CI) calculated (M+H$^+$) 328.1046, found 328.1031.

D. 1-(2-(N-imidazol-2-ylaminocarbonyl)ethyl)-5-carboxyindazole

A mixture of the product of Example 1327b Part C (145 mg, 443 μmol), tetrahydrofuran (2 mL) and water (2 mL) was treated with aqueous lithium hydroxide (1.0 M; 0.56 mL, 560 μmol) and stirred at room temperature for 21 h. The reaction was incomplete by thin-layer chromatography, so additional lithium hydroxide solution (a total of 1.35 mL) was added in four portions over the next 8 h. After stirring for 16 h more, the reaction was acidified with aqueous hydrochloric acid (1.0M) and concentrated under vacuum. The residue was partitioned between water and dichloromethane, and the organic phase was dried over anhydrous magnesium sulfate, filtered and concentrated to provide the title product (49 mg, 37%): $^1$H NMR (DMSO-d$_6$) δ 8.41 (s, 1H), 8.24 (s, 1H), 7.94 (d, 1H), 7.76 (d, 1H), 6.67 (s, 2H), 4.73 (t, 2H), 3.00 (t, 2H); High resolution mass spectrum (NH$_3$—CI) calculated (M+H$^+$) 300.1097, found 300.1097.

E. tert-Butyl 3-[1-[2-(N-imidazol-2ylaminocarbonyl)ethyl]indazol-5-ylcarbonylamino]-2-(S)-(2,4,6-trimethylbenzenesulfonylamino)propionate Using the procedure of Example 1326b Part F, the product prepared according to Example 1327b Part D (48 mg, 160 μmol) was converted to the title product (32 mg, 32%): Mass spectrum (ESI) m/z 624.4 (100%, M+H$^+$).

F. 3-[1-[2-(N-imidazol-2-ylaminocarbonyl)ethyl]indazol-5-ylcarbonylamino]-2(S)-(2,4,6-trimethylbenzenesulfonylamino)propionic acid trifluoroacetate Using the procedure of Example 1081 Part H followed by purification by preparative reverse phase high pressure liquid chromatography (acetonitrile:water containing 0.05% trifluoroacetic acid, gradient from 10:90 to 90:10), the product prepared according to Example 1327b Part E (32 mg, 52 μmol) was converted to the title product (28 mg, 95%) as a white powder after lyophilization: $^1$H NMR (MeOH-d$_4$) δ 8.11 (s, 1H), 8.09 (s, 1H), 7.77 (d, 1H), 7.68 (d, 1H), 7.10 (s, 2H), 6.73 (s, 2H), 4.81 (t, 2H), 4.14 (dd, 1H), 3.75 (dd, 1H), 3.47 (dd, 1H), 3.19 (t, 1H), 2.56 (s, 6H), 1.97 (s, 3H); high resolution mass spectrum (FAB) calculated (M+H$^+$) 568.1978, found 568.1972.

EXAMPLE 2328

3-[1-[4-(N-4,5-Dihydroimidazol-2-ylamino)butyl]indazol-4-ylcarbonylamino]-2(S)-(benzyloxycarbonylamino)propionic acid trifluoroacetate A. Methyl 2-methyl-3-aminobenzoate A mixture of methyl 2-methyl-3-nitrobenzoate (30 g, 154 mmol), 10% palladium on charcoal (3.0 g) and ethanol (350 mL) was shaken under hydrogen at 50 psig. After 4 h, the mixture was filtered through Celite® and the solids were washed with additional ethanol. The filtrate was concentrated to provide the title product (24.4 g, 96%) as a tan oil: $^1$H NMR (CDCl$_3$) δ 7.18 (m, 1H), 7.06 (m, 1H), 6.78 (m, 1H), 3.85 (s, 3H), 2.34 (s, 3H); high resolution mass spectrum (NH$_3$—CI) calculated (M+H$^+$) 166.0868, found 166.0866.

B. 4-Methoxycarbonylindazole

The product prepared according to Example 2328 Part A (24.25 g, 147 mmol) was combined with concentrated hydrochloric acid (30.1 mL) and water (170 mL). Ammonium tetrafluoroborate (20.62 g, 197 mmol) was added and the mixture was stirred at 0° C. A solution of sodium nitrite (10.14 g, 147 mmol) in water (25 mL) was added dropwise, and the mixture was stirred for 40 min after addition was complete. The white precipitate was collected by filtration and washed with water (3×80 mL), then with methanol (80 mL) and finally with ether (3×60 mL). The resulting solid was added to a stirred mixture of potassium acetate (17.89 g, 182 mmol), 18-crown-6 (1.20 g, 4.5 mmol) and chloroform (360 mL) at room temperature. The resulting mixture was stirred for 50 min, then water (250 mL) was added and the layers were separated. The organic phase was washed with water (250 mL) and brine (300 mL), and dried over anhydrous magnesium sulfate, filtered and concentrated under reduced pressure. The residue was triturated with hexanes and filtered to provide after drying the title product (16.96 g, 62%) as an orange solid: $^1$H NMR (CDCl$_3$) δ 8.60 (s, 1H), 7.98 (d, 1H), 7.74 (d, 1H), 7.42 (t, 1H), 4.01 (s, 3H); High resolution mass spectrum (NH$_3$—CI) calculated (M+H$^+$) 177.0664, found 177.0669.

C. 1-[4-(N-phthalimido)butyl]-4-methoxycarbonylindazole

Following the procedure of Example 1081 Part A, the product prepared according to Example 2328 Part B (2.97 g, 16.9 mmol) and N-(4-bromobutyl)phthalimide (4.99 g, 16.9 mmol) were converted to the title product (1.88 g, 29%) as an orange oil: $^1$H NMR (CDCl$_3$) δ 8.45 (s, 1H), 7.91 (d, 1H), 7.82 (m, 2H), 7.72 (m, 2H), 7.66 (d, 1H), 7.43 (t, 1H), 4.46 (t, 2H), 4.02 (t, 3H), 3.75 (t, 2H), 1.99 (m, 2H), 1.72 (m, 2H); Mass spectrum (NH$_3$—CI) m/z 378.0 (100%, M+H$^+$).

D. 1-[4-(Aminobutyl)-4-methoxycarbonylindazole

Using the procedure of Example 1081 Part B, the product prepared according to Example 2328 Part C (1.81 g, 4.8 mmol) was converted to the title product (0.72 g, 60%) as a yellow oil: $^1$H NMR (CDCl$_3$) δ 8.48 (s, 1H), 7.93 (d, 1H), 7.64 (d, 1H), 7.44 (t, 1H), 4.44 (t, 2H), 4.02 (s, 3H), 2.74 (t, 2H), 2.00 (m, 2H), 1.84 (bs, 2H), 1.47 (m, 2H); High resolution mass spectrum (NH$_3$—CI) calculated (M+H$^+$); 248.1399, found 248.1391.

E. 1-[4-(N-4,5-Dihydroimidazol-2ylamino)butyl]-4-methoxycarbonylindazole hydriodide Using the procedure of Example 1198 Part B, the product prepared according to Example 2328 Part D (247 mg, 1.0 mmol) was converted to the title product (223 mg, 50%) as a gum. $^1$H NMR (DMSO-d$_6$) δ 8.37 (s, 1H), 8.11 (bs, 1H), 8.01 (d, 1H), 7.82 (d, 1H), 7.51 (t, 1H), 4.46 (t, 2H), 3.90 (s, 3H), 3.53 (s, 4H), 3.08 (m, 2H), 1.81 (m, 2H), 1.38 (m, 2H); High resolution mass spectrum (NH$_3$—CI) calculated (M+H$^+$) 316.1774, found 316.1772.

F. tert-Butyl 3-[1-[4-(N-4,5-dihydroimidazol-2-yl-amino)butyl]indazol-4-ylcarbonylamino]-2(S)-(benzyloxycarbonylamino)propionate hydrochloride Using the procedure of Example 1198 Part C, the product prepared according to Example 2328 Part E (215 mg, 485 μmol) was converted to the title product (178 mg, 59%) as a clear gum: $^1$H NMR (DMSO-d$_6$) δ 8.52 (m, 1H), 8.32 (s, 1H), 8.13 (bm, 1H), 7.85 (d, 1H), 7.69 (d, 1H), 7.50 (t, 2H), 7.45 (m, 1H), 7.30 (m, 5H), 5.01 (s, 2H), 4.44 (t, 2H), 4.24 (m, 1H), 3.75–3.50 (m, 2H), 3.50 (s, 4H), 3.19 (m, 2H), 1.80 (m, 2H), 1.37 (m, 2H), 1.31 (s, 9H); High resolution mass spectrum (FAB) calculated (M+H$^+$); 578.3091, found 578.3119.

G. 3-[1-[4-(N-4,5-Dihydroimidazol-2-ylamino)butyl] indazol-4-ylcarbonylamino]-2(S)-(benzyloxycarbonylamino)propionic acid hydrochloride Using the procedure of Example 1081 Part H, the product prepared according to Example 2328 Part F (121 mg, 197 μmol) was converted to the title product (88 mg, 80%) as a hygroscopic white solid: $^1$H NMR (DMSO-$d_6$) δ 8.57 (m, 1H), 8.31 (s, 1H), 8.18 (bm, 1H), 7.86 (d, 1H), 7.63 (d, 1H), 7.50–7.35 (m, 3H), 7.30 (m, 5H), 5.00 (s, 2H), 4.43 (t, 2H), 4.28 (m, 1H), 3.75–3.40 (m, 6H), 3.07 (m, 2H), 1.78 (m, 2H), 1.38 (m, 2H); High resolution mass spectrum (FAB) calculated (M+H$^+$); 522.2465, found 522.2484.

EXAMPLE 3093

3-[1-Methyl-3-[3-(N-imidazol-2-ylamino)propyl] indazol-6-ylcarbonylamino]-2(S)-(2,6-dimethylbenzenesulfonylamino)propionic acid trifluoroacetate A. 6-Methoxycarbonylindazol Using the procedure of Example 2328 Part B, methyl 3amino-4-methylbenzoate (12.39 g, 75 mmol) was converted to the title product (8.85 g, 67%) which could be recrystallized from acetonitrile to give pale orange crystals: mp 142°–144° C.; $^1$H NMR (CDCl$_3$) δ 11.17 (bs, 1H), 8.30 (s, 1H), 8.18 (s, 1H), 7.83 (m, 2H), 3.97 (s, 3H); Mass spectrum (NH$_3$—CI) m/z 177 (100%, M+H$^+$).

B. 3-Bromo-6-methoxycarbonylindazole

Using the procedure of Example 1326f Part A, the product prepared according to Example 3093 Part A (3.52 g, 20 mmol) was converted to the title product (4.46 g, 87%) as a light yellow powder: mp 186°–189° C.; $^1$H NMR (CDCl$_3$) δ 8.24 (s, 1H), 7.91 (d, 1H), 7.70 (d, 1H), 3.92 (s, 3H); Mass spectrum (NH$_3$—CI) m/z 255 (100%), 257 (96%) (M+H$^+$); High resolution mass spectrum (EI) calculated (M$^+$) 253.9691, found 253.9694.

C. 1-Methyl-3-bromo-6-methoxycarbonylindazole

Sodium hydride (60% in mineral oil; 600 mg, 15 mmol) was placed in a dry flask under nitrogen and suspended in dry N,N-dimethylformamide (20 mL). The suspension was stirred on an ice bath and treated with a solution of the product prepared according to Example 3093 Part B (2.55 g, 10 mmol) in dry N,N-dimethylformamide (20 mL) over ca. 3 min. The resulting yellow solution was stirred for 10 min more, then was treated with iodomethane (0.7 mL, 11 mmol). The mixture was stirred at room temperature for 22.5 h, then was poured into water (ca. 600 mL). After being stirred for 10 min, the suspension was filtered, and the solid was washed with water and dried to provide the title product (2.57 g, 95%) as a yellow solid, which could be recrystallized from ethanol: mp 122°–125° C.; $^1$H NMR (CDCl$_3$) δ 8.16 (s, 1H), 7.87 (d, 1H), 7.65 (d, 1H), 4.13 (s, 3H), 3.99 (s, 3H); Mass spectrum (NH$_3$—CI) m/z 269 (100%), 271 (92%) (M+H$^+$); High resolution mass spectrum (NH$_3$—CI) calculated 268.9926, found 268.9914.

D. 1-Methyl-3-(3,3diethylpropyl)-6-methoxycarbonylindazole

A mixture of the product prepared according to Example 3093 Part C (1.93 g, 7.2 mmol), 3,3-diethoxypropyne (1.65 mL, 11.5 mmol), triphenylphosphine (190 mg, 720 μmol), copper(I) iodide (68 mg, 360 μmol) and triethylamine (60 mL) was purged of oxygen by bubbling with nitrogen for 25 min. Bis(triphenylphosphine)palladium(II) chloride (126 mg, 180 μmol) was added, and the mixture was heated at 100° C. After 14 h, the mixture was concentrated under a nitrogen stream and cooled to room temperature. The residue was purified by flash chromatography (hexanes:ethyl acetate 85:15) to provide an orange, sticky solid. This was recrystallized (methanol) to provide the title product (1.26 g, 56%) as light yellow fibrous needles: mp 91°–93° C.; $^1$H NMR (CDCl$_3$) δ 8.18 (s, 1H), 7.88 (d, 1H), 7.83 (d, 1H), 5.59 (s, 1H), 4.14 (s, 3H), 3.98 (s, 3H), 3.89 (m, 2H), 3.72 (m, 2H), 1.30 (t, 6H); Mass spectrum (ESI) m/z 317.4 (100%, M+H$^+$).

E. 1-Methyl-3-(3,3diethoxypropyl)-6-methoxycarbonylindazole

A mixture of the product prepared according to Example 3093 Part D (1.24 g, 3.92 mmol), 10% palladium, on charcoal (130 mg), methanol (40 mL) and tetrahydrofuran (60 mL) was placed in a pressure bottle and shaken under an atmosphere of hydrogen (60 psig). After 60 min, the bottle was vented and the mixture was filtered through Celite.® The solids were rinsed with methanol and tetrahydrofuran, and the filtrate was concentrated under vacuum to provide the title product (1.31 g, >100%) as a slightly cloudy oil which was not purified further: $^1$H NMR (CDCl$_3$) δ 8.11 (s, 1H), 7.77 (d, 1H), 7.72 (d, 1H), 4.57 (t, 1H), 4.08 (s, 3H), 3.97 (s, 3H), 3.69 (m, 2H), 3.52 (m, 2H), 3.06 (t, 2H), 2.13 (m, 2H), 1.22 (t, 6H); High resolution mass spectrum (NH$_3$—CI) calculated (M+H$^+$) 321.1814, found 321.1830.

F. 1-Methyl-3-(3-oxopropyl)-6-methoxycarbonylindazole

A mixture of the product prepared according to Example 3093 Part E (1.29 g, 4.0 mmol), acetic acid (20 mL) and water (30 mL) was heated on an oil bath at 80° C. After 30 min, the solvent was removed under vacuum, and the residue-was dissolved in ethyl acetate. The solution was washed with saturated aqueous sodium bicarbonate, dried over anhydrous magnesium sulfate, filtered and concentrated under vacuum to provide a light brown oil. On further concentration under vacuum, a tan solid slowly formed, which was the title product (982 mg, 98%): mp 80°–83° C.; $^1$H NMR (CDCl$_3$) δ 9.92 (s, 1H), 8.11 (s, 1H), 7.79 (d, 1H), 7.71 (d, 1H), 4.07 (s, 3H), 3.98 (s, 3H), 3.31 (t, 2H), 3.03 (t, 2H); High resolution mass spectrum (NH$_3$—CI) calculated (M+H$^+$) 247.1083, found 247.1077.

G. 1-Methyl-3-[3-[N-(1-triphenylmethylimidazol-2yl-amino)propyl]-6-methoxycarbonylindazole A solution of the product prepared according to Example 3093 Part F (900 mg, 3.65 mmol) and the product prepared according to Example 1050e Part I (1.19 g, 3.65 mmol) in toluene (130 mL) was heated at reflux under an empty Dean-Stark water trap. After 22.5 h, additional toluene (ca. 40 mL) was removed by distillation, and the solution was cooled to room temperature under a nitrogen atmosphere. The solution was then cooled on an ice bath and treated with sodium triacetoxyborohydride (3.09 g, 14.6 mmol) and the mixture was stirred at room temperature for 21.75 h. Water (ca. 4 mL) was added cautiously and the mixture was stirred for 15 min. Additional water (75 mL) was added, and the layers were separated. The aqueous phase was extracted with ethyl acetate, and the combined organic phases were dried over anhydrous magnesium sulfate, filtered and concentrated under vacuum. The residue was purified by flash chromatography (toluene:ethyl acetate 50:50) to provide the title product (1.56 g, 77 %) as a pale tan glass: $^1$H NMR (CDCl$_3$) δ 8.07 (s, 1H), 7.72 (d, 1H), 7.43 (d, 1H), 7.30 (m, 9H), 7.20 (m, 6H), 6.68 (d, 1H), 6.38 (d, 1H), 4.01 (s, 3H), 3.97 (s, 3H), 3.13 (q, 2H), 2.96 (t, 1H), 2.61 (t, 2H), 1.61 (m, 2H); High resolution mass spectrum (NH$_3$—CI) calculated (M+H$^+$) 556.2713, found 556.2732.

H. Methyl 3-amino-2-(S)-benzoyloxycarbonyl) aminopropionate, hydrochloride salt

A suspension of 3-amino-2-(S)-N-benzyloxycarbonyl) aminopropionic acid (11.0 g, 46.2 mmol) in methanol (165 mL) was stirred on an ice/acetone bath until the internal temperature was below 0° C. Thionyl chloride (3.7 mL, 50.8 mmol) was added dropwise over 10 min. The mixture was stirred for an additional 10 min at 0° C., then for 17.25 h at room temperature. The mixture was concentrated under vacuum and the gummy residue was stirred in ether (300 mL) to provide a white solid. This was collected by filtration, rinsed with additional ether and dried to provide the title product (12.9 g, 97%) as a white powder: $^1$H NMR (DMSO-$d_6$) δ 8.32 (bs, 3H), 7.94 (d, 1H), 7.37 (5H), 5.07 (s, 2H), 4.45 (m, 1H), 3.68 (s, 3H), 3.22 (m, 1H), 3.07 (m, 1H).

I. Methyl 3-(tert-butyloxycarbonylamino)-2-(benzyloxycarbonylamino)propionate

A suspension of the product prepared according to Example 3093 Part H (8.00 g, 27.7 mmol) in dichloromethane (140 mL) and saturated aqueous sodium bicarbonate (85 mL) was stirred at room temperature and treated with di-tert-butyldicarbonate (6.11 g, 28 mmol). The mixture was stirred at room temperature for 16.5 h, then filtered and the layers were separated. The aqueous layer was extracted with additional dichloromethane, and the combined organics were washed with brine, dried over magnesium sulfate, and concentrated under vacuum. The resulting viscous oil was stirred in hexane (ca. 200 mL) overnight. The resulting solid was collected by filtration, washed with hexane and dried to provide the title product (7.66 g, 78%) as a white powder: $^1$H NMR (CDCl$_3$) δ 7.36 (5H), 5.80 (bd, 1H), 5.12 (s, 2H), 4.84 (b, 1H), 4.41 (b, 1H), 3.77 (s, 3H), 3.55 (b, 2H), 1.42 (s, 9H).

J. Methyl 3-(tert-butyloxycarbonylamino)-2-aminopropionate.

A solution of the product prepared according to Example 3093 Part I (7.50 g, 21.3 mmol) in ethanol (200 mL) was treated with 10% palladium on charcoal (0.75 g) and stirred under hydrogen (1 atmosphere) for 8.5 h. The mixture was filtered through Celite® and the solids were rinsed with additional ethanol. The filtrate was concentrated to provide the title product (4.65 g, 100%) as a viscous oil: $^1$H NMR (CDCl$_3$) δ 5.02 (bs, 1H), 3.75 (s, 3H), 3.59 (t, 1H), 3.50 (m, 1H), 3.27 (m, 1H), 1.67 (bs, 2H), 1.44 (s, 9H).

K. Methyl 3-(tert-butyloxycarbonylamino)-2-(S)-(2,6-dimethylbenzenesulfonylamino)propionate A solution of the product prepared according to Example 3093 Part J (6.24 g, 24.5 mmol), and diisopropylamine (6.34 g, 49 mmol) in dichloromethane (25 mL) was cooled on an ice bath. A solution of 2,6-dimethylbenzenesulfonyl chloride (prepared according to Wagenaar and Engberts, *J. Royal Neth. Chem. Soc.* 1982, 101(5), 91–94; 5.01 g, 24.5 mmol) in dichloromethane (75 mL) was added over 15 min. The ice bath was removed and the mixture was stirred at room temperature for 18 h. Additional dichloromethane was added and the solution was washed with water. The organic phase was dried over anhydrous magnesium sulfate, filtered and concentrated under vacuum. The residue was purified by flash chromatography (hexanes:ethyl acetate, step gradient from 80:20 to 60:40) to provide the title product (7.25 g, 76%) as a colorless gum: $^1$H NMR (CDCl$_3$) δ 7.29 (t, 1H), 7.14 (d, 2H), 5.78 (bd, 1H), 4.89 (bt, 1H), 3.92 (m, 1H), 3.55 (s, 3H), 3.47 (m, 2H), 2.68 (s, 6H), 1.42 (s, 9H).

L. Methyl 3-amino-2-(S)-(2,6-dimethylbenzenesulfonylamino)propionate (+)-camphorsulfonate The product prepared according to Example 3093, Part K (7.25 g, 18.8 mmol) was dissolved in HCl/dioxane (4.0M; 50 mL) and the solution was stirred at room temperature for 18 h. The mixture was concentrated under vacuum to yield a hygroscopic solid (6.63 g) which was dissolved in tetrahydrofuran and treated with triethylamine (1.0 equiv.). The resulting solid was removed by filtration, and the filtrate was treated with (+)-camphorsulfonic acid (1.0 equiv.). The mixture was stirred at room temperature for 15 min, and the resulting solid was collected by filtration, rinsed with tetrahydrofuran, and dried to provide the title product (6.63 g, 68%) as a white solid: $^1$H NMR (DMSO-$d_6$) δ 8.30 (bs, 1H), 7.94 (bs, 3H), 7.33 (t, 1H), 7.19 (d, 2H), 4.09 (bt, 1H), 3.21 (s, 3H), 3.10 (dd, 1H), 2.93 (dd, 1H), 2.83 (d, 1H), 2.64 (t, 1H), 2.56 (s, 6H), 2.34 (d, 1H), 2.20 (dm, 1H), 1.90 (m, 2H), 1.80 (d, 1H), 1.24 (dd, 2H), 1.01 (s, 3H), 0.70 (s, 3H).

M. Methyl 3-[1-methyl-3-[3-(N-(1-triphenylmethylimidazol-2-ylamino)propyl]indazol-5-ylcarbonylamino]-2(S)-(2,6-dimethylbenzenesulfonylamino)propionate A mixture of the product prepared according to Example 3093 Part G (1.43 g, 2.57 mmol), aqueous sodium hydroxide (1.0M; 13 mL, 13 mmol) and ethanol (32 mL) was heated at reflux. After 80 min, the mixture was cooled to room temperature and aqueous hydrochloric acid (1.0M; 13 mL, 13 mmol) was added. The mixture was concentrated under vacuum and dried. A portion of this material (which contains sodium chloride; 77 mg, 92 μmol) was combined with the product prepared according to Example 3093 Part L (52 mg, 101 μmol), 1-hydroxybenzotriazole hydrate (13 mg, 92 μmol), and triethylamine (25 μL, 184 μmol) in N,N-dimethylformamide (5 mL) and treated with dicyclohexylcarbodiimide (19 mg, 92 μmol). The mixture was stirred at room temperature for 2.5 days, then was concentrated under vacuum. The residue was partially purified by flash chromatography (dichloromethane:methanol 95:5) to provide the title product (75 mg, 100%) which was impure but was used directly in the subsequent reaction.

N. 3-[1-Methyl-3-[3-(N-imidazol-2-ylamino)propyl]indazol-5-ylcarbonylamino]-2(S)-(2,6-dimethylbenzenesulfonylamino)propionic acid trifluoroacetate Using the procedure of Example 1050e Part M, the product prepared according to Example 3093 Part M (75 mg, 92 μmol) was converted to the title product as a white powder (after lyophilization): $^1$H NMR (MeOH-$d_4$) δ 7.90 (s, 1H), 7.76 (d, 1H), 7.47 (d, 1H), 7.09 (m, 1H), 7.01 (m, 2H), 6.81 (s, 2H), 4.16 (m, 1H), 4.04 (s, 3H), 3.78 (dd, 1H), 3.52 (dd, 1H), 3.34 (t, 2H), 3.09 (t, 2H), 2.62 (s, 6H), 2.14 (m, 2H); High resolution mass spectrum (FAB) calculated (M+H$^+$) 554.2186, found 554.2184.

EXAMPLE 3142

3-[1-Methyl-3-[3-(N-pyridin-2-ylamino)propyl]indazol-6-ylcarbonylamino]-2(S)-(2,4,6-trimethylbenzenesulfonylamino)propionic acid trifluoroacetate A. 1-Methyl-3-[3-[N-pyridin-2-ylamino)propyl]-6-methoxycarbonylindazole A solution of the product prepared according to Example 3093 Part F (201 mg, 816 μmol) and 2aminopyridine (154 mg, 1.63 mmol) in dichloroethane (4 mL) was stirred at room temperature and treated with sodium triacetoxyborohydride (346 mg, 1.63 mmol). After 16.5 h, the mixture was diluted with water (ca. 5 mL) and saturated aqueous sodium bicarbonate (ca. 2 mL) and stirred for 15 min. The mixture was extracted three times with dichloromethane, and the combined organic phases were dried over anhydrous magnesium sulfate, filtered and concentrated under vacuum. The residue was purified by flash chromatography (dichloromethane:isopropanol 95:5) to provide the title product (214 mg 81%) as a white solid: mp 101°–104° C.; $^1$H NMR (CDCl$_3$) δ 8.13 (s, 1H), 8.07 (d, 1H), 7.76 (d, 1H), 7.67 (d, 1H), 7.39 (t, 1H), 6.56 (dd, 1H), 6.36 (d, 1H), 4.65 (bt, 1H), 4.08 (s, 3H), 3.98 (s, 3H), 3.38 (q, 2H), 3.10 (t, 3H), 2.16 (m, 2H); High resolution mass spectrum (NH$_3$—CI) calculated (M+H$^+$) 325.1665, found 325.1653.

B. tert-Butyl 3-[1-methyl-3-[3-(N-pyridin-2-ylamino) propyl]indazol-6-ylcarbonylamino]-2(S)-(2,4,6-trimethylbenzenesulfonyl)aminopropionate Using the procedures of Example 1326b Parts E and F, the product prepared according to Example 3142 Part A (59 mg, 182 μmol) was converted to the title product (108 mg, 93%) as a colorless glass: $^1$H NMR (CDCl$_3$) δ 8.08 (d, 1H), 7.95 (s, 1H), 7.70 (d, 1H), 7.46 (d, 1H), 7.40 (m, 1H), 6.94 (s, 2H), 6.92 (m, 1H), 6.56 (m, 1H), 6.37 (d, 1H), 5.79 (d, 1H), 4.67 (m, 1H), 4.08 (s, 3H), 3.95 (m, 1H), 3.83 (m, 1H), 3.61 (m, 1H), 3.38 (q, 2H), 3.10 (t, 2H), 2.66 (s, 6H), 2.27 (s, 3H), 2.16 (m, 2H), 1.32 (s, 9H); High resolution mass spectrum (FAB) calculated (M+H$^+$) 635.3016, found 635.3028.

C. 3-[1-Methyl-3-[3-(N-pyridin-2-ylamino)propyl]-indazol-6-ylcarbonylamino]-2(S)-(2,4,6-trimethylbenzenesulfonylamino)propionic acid trifluoroacetate Using the procedure of Example 1129 Part H, the product prepared according to Example 3142 Part B (100 mg, 158 μmol) was converted to the title product (84 mg, 77%) as a white powder: $^1$H NMR (DMSO-d$_6$) δ 8.52 (m, 2H), 8.08 (d, 1H), 7.95 (s, 1H), 7.90 (d, 1H), 7.82 (t, 1H), 7.77 (d, 1H), 7.46 (d, 1H), 6.97 (d, 1H), 6.79 (s+m, 3H), 4.05 (m, 1H), 4.01 (s, 3H), 3.59 (m, 2H), 3.39 (m, 2H), 3.03 (t, 2H), 2.52 (s, 6H), 2.07 (m, 2H), 2.00 (s, 3H); High resolution mass spectrum (FAB) calculated (M+H$^+$) 579.2390, found 579.2400.

EXAMPLE 3339

3-[1-Benzyl-3-[3-(N-pyridin-2-ylamino)propyl] indazol-6-ylcarbonylamino]-2(S)-(2,4,6-trimethylbenzenesulfonylamino)propionic acid trifluoroacetate A. 3-(3,3-Diethoxypropynyl)-6-methoxycarbonylindazole Using the procedure of Example 3093 Part D, the product prepared according to Example 3093 Part B (2.55 g, 10 mmol) was converted to the title product (1.49 g, 49%) as a brown gum: $^1$H NMR (CDCl$_3$) δ 8.28 (s, 1H), 7.90 (d, 1H), 7.85 (d, 1H), 5.61 (s, 1H), 3.98 (s, 3H), 3.88 (m, 2H), 3.75 (m, 2H), 1.31 (t, 6H); Mass spectrum (NH$_3$—CI) m/z 257 (100%, (M+H-EtOH)$^+$).

B. 3-(3,3-Diethoxypropynyl)-6-methoxycarbonylindazole

Using the procedure of Example 3093 Part E, the product prepared according to Example 3339 Part A (263 mg, 870 μmol) was converted to the title product (106 mg, 40%) as an orange oil, which contained a contaminant but was used directly in the subsequent reaction: $^1$H NMR (CDCl$_3$) δ 8.20 (s, 1H), 7.81 (d, 1H), 7.76 (d, 1H), 4.60 (t, 1H), 3.96 (s, 3H), 3.68 (m, 2H), 3.51 (m, 2H), 3.09 (m, 2H), 2.17 (m, 2H), 1.22 (t, 6H); High resolution mass spectrum (NH$_3$—CI) calculated (M+H$^+$) 307.1658, found 307.1636.

C. 1-Benzyl-3-(3,3-diethoxypropyl)-6-methoxycarbonylindazole

A solution of the product prepared according to Example 3339 Part B (230 mg, 750 μmol) and benzyl chloride (95 μL, 826 μmol) in dry N,N-dimethylformamide (4 mL) was stirred on an ice bath and treated with sodium hydride (60% in mineral oil; 36 mg, 900 μmol).

The mixture was stirred 10 min, then was allowed to warm to room temperature and stirred for 23 h. The mixture was diluted with water and extracted three times with ethyl acetate. The combined organic phases were washed twice with water, then dried over magnesium sulfate, filtered and concentrated under vacuum. The residue was purified by flash chromatography (hexanes:ethyl acetate 85:15) to provide the title product (152 mg, 51%) as an oil, which was impure but was used directly in the subsequent reaction: $^1$H NMR (CDCl$_3$) δ 8.08 (s, 1H), 7.75 (m, 2H), 7.25 (m, 3H), 7.17 (m, 2H), 5.59 (s, 2H), 4.56 (t, 1H), 3.94 (s, 3H), 3.67 (m, 2H), 3.50 (m, 2H), 3.08 (m, 2H), 2.2–2.05 (m, 2H), 1.22 (t, 6H); Mass spectrum (NH$_3$—CI) m/z 397.5 (10%, M+H$^+$), 351 (100%, (M+H-EtOH)$^+$).

D. 1-Benzyl-3-(3-oxopropyl)-6-methoxycarbonylindazole

Using the procedure of Example 3093 Part F, the product of Example 3339 Part C (115 mg, 567 μmol) was converted to the title product (110 mg, 60%) as an oil which solidified on standing: $^1$H NMR (CDCl$_3$) δ 9.91 (s, 1H), 8.08 (s, 1H), 7.78 (d, 1H), 7.72 (d, 1H), 7.27 (m, 3H), 7.16 (m, 2H), 5.57 (s, 2H), 3.93 (s, 3H), 3.33 (t, 2H), 3.05 (t, 2H); Mass spectrum (ESI) m/z 323.4 (24%, M+H$^+$).

E. 1-Benzyl-3-[3-(N-pyridin-2-ylamino)propyl]-6-methoxycarbonylindazole

Using the procedure of Example 3142 Part A, the product prepared according to Example 3339 Part D (91 mg, 282 μmol) was converted to the title product (90 mg, 80%) as a viscous oil which solidified on standing. This material contained a contaminant but was used directly in the subsequent reaction: $^1$H NMR (CDCl$_3$) δ 8.08 (m, 2H), 7.77 (d, 1H), 7.70 (d, 1H), 7.36 (m, 1H), 7.3–7.2 (m, 3H), 7.17 (m, 2H), 6.54 (dd, 1H), 6.30 (d, 1H), 5.60 (s, 2H), 4.65 (bt, 1H), 3.93 (s, 3H), 3.37 (q, 2H), 3.13 (t, 2H), 2.16 (m, 2H); High resolution mass spectrum (FAB) calculated (M+H$^+$) 401.1978, found 401.1982.

F. tert-Butyl 3-[1-benzyl-3-[3-(N-pyridin-2-ylamino) propyl]indazol-6-ylcarbonylamino]-2(S)-(2,4,6-trimethylbenzenesulfonyl)aminopropionate Using the procedure of Example 1326b Parts E and F, the product prepared according to Example 3339 Part E (81 mg, 202 μmol) was converted to the title product (162 mg, >100%) as a colorless glass which contained a contaminant but was used directly in the subsequent reaction: $^1$H NMR (CDCl$_3$) δ 8.07 (m, 1H), 7.94 (s, 1H), 7.71 (d, 1H), 7.47 (d, 1H), 7.38 (m, 1H), 7.26 (m, 5H), 6.92 (s+bm, 3H), 6.55 (m, 1H), 6.33 (d, 1H), 5.81 (d, 1H), 5.59 (s, 2H), 4.69 (bt, 1H), 3.94 (m, 1H), 3.81 (m, 1H), 3.56 (m, 1H), 3.38 (q, 2H), 3.13 (t, 2H), 2.63 (s, 6H), 2.26 (s, 3H), 2.17 (m, 2H), 1.29 (s, 9H); High resolution mass spectrum (FAB) calculated (M+H$^+$) 711.3329, found 711.3341.

G. 3-[1-Benzyl-3-[3-(N-pyridin-2-ylamino)propyl]indazol-6-ylcarbonylamino]-2(S)-(2,4,6-trimethylbenzenesulfonylamino)propionic acid trifluoroacetate Using the procedure of Example 1129 Part H, the product prepared according to Example 3339 Part F (136 mg, 191 μmol) was converted to the title product (110 mg, 75%) as a white powder: $^1$H NMR (DMSO-d$_6$) δ 8.49 (t, 1H), 8.07 (d, 1H), 8.05 (s, 1H), 7.92 (d, 1H), 7.81 (d, 1H), 7.72 (m, 1H), 7.45 (d, 1H), 7.35–17.20 (m, 5H), 6.88 (d, 1H), 6.73 (s+m, 3H), 5.62 (s, 2H), 4.05 (m, 1H), 3.58 (m, 1H), 3.5–3.3 (m, 3H), 3.05 (t, 2H), 2.52 (s, 6H), 2.07 (m, 2H), 1.95 (s, 3H); High resolution mass spectrum (FAB) calculated (M+H$^+$) 655.2703, found 655.2701.

Using the methods described above and modifications thereof known to one skilled in the art of organic synthesis, the following additional examples in Tables 1–8 can be prepared.

UTILITY

The compounds of Formula Ia, Ib or Ic of the present invention possess activity as antagonists of integrins such as, for example, the $\alpha_v\beta_3$ or vitronectin receptor, $\alpha_v\beta_5$ or $\alpha_5\beta_1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their reduced activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula Ia, Ib or Ic of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula Ia, Ib or Ic have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta) —Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an $IC_{50}$ or $K_i$ value of less than about 10 μM for the inhibition of $\alpha_v\beta_3$-Vitronectin Binding Assay, with compounds preferably having $K_i$ values of less than about 0.1 μM. Tested compounds of the present invention are active in the $\alpha_v\beta_3$-Vitronectin Binding Assay.
Purified $\alpha_v\beta_3$ (human placenta)—Vitronectin ELISA The $\alpha_v\beta_3$ receptor was isolated from human placental extracts prepared using octylglucoside. The extracts were passed over an affinity column composed of anti-$\alpha_v\beta_3$ monoclonal antibody (LM609) bound to Affigel. The column was subsequently washed extensively at pH 7 and pH 4.5 followed by elution at pH 3. The resulting sample was concentrated by wheat germ agglutinin chromatography to provide two bands by SDS gel electrophoresis which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel and according to effects of blocking antibodies for the $\alpha_v\beta_3$ or $\alpha_v\beta_5$ integrins in the ELISA.

A submaximal concentration of biotinylated vitronectin was selected based on a concentration response curve with fixed receptor concentration and variable concentrations of biotinylated vitronectin.
$\alpha_v\beta_3$-Vitronectin Binding Assay The purified receptor is diluted with coating buffer (20 mM Tris HCl, 150 mM NaCl, 2.0 mM $CaCl_2$, 1.0 mM $MgCl_2.6H_2O$, 1.0 mM $MnCl_2.4H_2O$) and coated (100 μL/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM $CaCl_2$, 1.0 mM $MgCl_2.6H_2O$, 1.0 mM $MnCl_2.4H_2O$). Receptor is then blocked (200 μL/well) with 3.5% BSA in B/B buffer for 2 hours at room temperature. After washing once with 1.0 % BSA in B/B buffer, biotinylated vitronectin (100 μL) and either inhibitor (11 μL) or B/B buffer w/1.0% BSA (11 μL) is added to each well. The plates are incubated 2 hours at room temperature. The plates are washed twice with B/B buffer and incubated 1 hour at room temperature with anti-biotin alkaline phosphatase (100 μL/well) in B/B buffer containing 1.0 % BSA. The plates are washed twice with B/B buffer and alkaline phosphatase substrate (100 μL) is added. Color is developed at room temperature. Color development is stopped by addition of 2N NaOH (25 μL/well) and absorbance is read at 405 nm. The $IC_{50}$ is the concentration of test substance needed to block 50% of the vitronectin binding to the receptor.
Integrin Cell-Based Adhesion Assays In the adhesion assays, a 96 well plate was coated with the ligand (i.e., fibrinogen) and incubated overnight at 4° C. The following day, the cells were harvested, washed and loaded with a fluorescent dye. Test compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_v\beta_1$ integrin interactions.
Platelet Aggregation Assay Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 µL of PRP (5×10⁸ platelets/mL) were added to each micro test tube, and transmittance was set to 0%. 20 µL of ADP (10 µM) was added to each tube, and the aggregation profiles were plotted (% transmittance versus time). Test agent (20 µL) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., *J. Clin. Invest.* (1995) 95: 713–724).

In Vivo Angiogenesis Model

A quantitative method for assessing angiogenesis and antiangiogenic agents is described in Passaniti et al., *Laboratory Investigation* (1992) 67: 519–528

Pig Restenosis Model

A method for assessing restenosis and agents which inhibit restenosis is described in Schwartz et al., *J. Am. College of Cardiology* (1992) 19: 267–274.

Mouse Retinopathy Model

A method for assessing retinopathy and agents which inhibit retinopathy is described in Smith et al., *Invest. Ophthal. & Visual Science* (1994) 35: 101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered by injection, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/ or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/ or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/ or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an antiplatelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIALTM™ two-part container (available from Abbott Labs, Chicago, Illinois), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art.

Instructions, either as inserts or as labels, indicating quantities of the components to be administered, guidelines for administration, and/or guidelines for mixing the components, may also be included in the kit.

TABLE 1

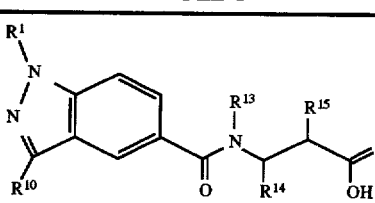

| Ex. No. | $R^1$ | $R^{10}$ | $R^{13}$ | $R^{14}$ | $R^{15}$ | MS |
|---|---|---|---|---|---|---|
| 1001 | imidazol-2-ylamino-$(CH_2)_3$ | H | H | H | H | |
| 1002 | imidazol-2-ylamino-$(CH_2)_3$ | H | H | H | $NHCO_2CH_2Ph$ | |
| 1003 | imidazol-2-ylamino-$(CH_2)_3$ | H | H | H | $NHCO_2CH_2C_6H_4$-(2-$CH_3$) | |
| 1004 | imidazol-2-ylamino-$(CH_2)_3$ | H | H | H | $NHCO_2CH_2C_6H_4$-(3-$CH_3$) | |
| 1005 | imidazol-2-ylamino-$(CH_2)_3$ | H | H | H | $NHCO_2CH_2C_6H_4$-(4-$CH_3$) | |
| 1006 | imidazol-2-ylamino-$(CH_2)_3$ | H | H | H | $NHCO_2CH_2$(2-pyridinyl) | |
| 1007 | imidazol-2-ylamino-$(CH_2)_3$ | H | H | H | $NHCO_2CH_2$(3-pyridinyl) | |
| 1008 | imidazol-2-ylamino-$(CH_2)_3$ | H | H | H | $NHCO_2CH_2$(4-pyridinyl) | |
| 1009 | imidazol-2-ylamino-$(CH_2)_3$ | H | H | H | $NHCO_2CH_2$(2-thiazolyl) | |
| 1010 | imidazol-2-ylamino-$(CH_2)_3$ | H | H | H | $NHCO_2CH_2$(4-thiazolyl) | |
| 1011 | imidazol-2-ylamino-$(CH_2)_3$ | H | H | H | $NHCO_2CH_2$(5-thiazolyl) | |
| 1012 | imidazol-2-ylamino-$(CH_2)_3$ | H | H | H | $NHCO_2CH_2$(4-isoxazolyl) | |
| 1013 | imidazol-2-ylamino-$(CH_2)_3$ | H | H | H | $NHCO_2CH_2$(2-thienyl) | |
| 1014 | imidazol-2-ylamino-$(CH_2)_3$ | H | H | H | $NHCO_2CH_2$(5-isoxazolyl) | |
| 1015 | imidazol-2-ylamino-$(CH_2)_3$ | H | H | H | $NHCO_2$n-Bu | |
| 1016 | imidazol-2-ylamino-$(CH_2)_3$ | H | H | H | $NHCO_2$i-Bu | |
| 1017 | imidazol-2-ylamino-$(CH_2)_3$ | H | H | H | $NHCO_2$t-Bu | |
| 1017a | imidazol-2-ylamino-$(CH_2)_3$ | H | H | H | NHCOPh | |
| 1018 | imidazol-2-ylamino-$(CH_2)_3$ | H | H | H | $NHCOCH_2Ph$ | |
| 1019 | imidazol-2-ylamino-$(CH_2)_3$ | H | H | H | $NHCOCH_2C_6H_4$-(2-$CH_3$) | |
| 1020 | imidazol-2-ylamino-$(CH_2)_3$ | H | H | H | $NHCOCH_2C_6H_4$-(3-$CH_3$) | |
| 1021 | imidazol-2-ylamino-$(CH_2)_3$ | H | H | H | $NHCOCH_2C_6H_4$-(4-$CH_3$) | |
| 1021a | imidazol-2-ylamino-$(CH_2)_3$ | H | H | H | $NHCOCH_2CH_2Ph$ | |
| 1021b | imidazol-2-ylamino-$(CH_2)_3$ | H | H | H | NHCOCH=CHPh | |
| 1022 | imidazol-2-ylamino-$(CH_2)_3$ | H | H | H | $NHCOCH_2$(2-pyridinyl) | |
| 1023 | imidazol-2-ylamino-$(CH_2)_3$ | H | H | H | $NHCOCH_2$(3-pyridinyl) | |
| 1024 | imidazol-2-ylamino-$(CH_2)_3$ | H | H | H | $NHCOCH_2$(4-pyridinyl) | |
| 1025 | imidazol-2-ylamino-$(CH_2)_3$ | H | H | H | $NHCOCH_2$(2-thiazolyl) | |
| 1026 | imidazol-2-ylamino-$(CH_2)_3$ | H | H | H | $NHCOCH_2$(4-thiazolyl) | |
| 1027 | imidazol-2-ylamino-$(CH_2)_3$ | H | H | H | $NHCOCH_2$(5-thiazolyl) | |
| 1028 | imidazol-2-ylamino-$(CH_2)_3$ | H | H | H | $NHCOCH_2$(4-isoxazol) | |
| 1029 | imidazol-2-ylamino-$(CH_2)_3$ | H | H | H | $NHCOCH_2$(2-thienyl) | |
| 1029a | imidazol-2-ylamino-$(CH_2)_3$ | H | H | H | $NHCOCH_2$(cyclohexyl) | |
| 1029b | imidazol-2-ylamino-$(CH_2)_3$ | H | H | H | NHCO-cyclohexyl | |
| 1030 | imidazol-2-ylamino-$(CH_2)_3$ | H | H | H | NHCOn-Bu | |
| 1031 | imidazol-2-ylamino-$(CH_2)_3$ | H | H | H | NHCOt-Bu | |
| 1031a | imidazol-2-ylamino-$(CH_2)_3$ | H | H | H | $NHCONHPh$ | |
| 1031b | imidazol-2-ylamino-$(CH_2)_3$ | H | H | H | $NHCONHCH_2Ph$ | |
| 1032 | imidazol-2-ylamino-$(CH_2)_3$ | H | H | H | $NHSO_2Ph$ | 512.3 |
| 1033 | imidazol-2-ylamino-$(CH_2)_3$ | H | H | H | $NHSO_2C_6H_4$-(2-$CH_3$) | |
| 1034 | imidazol-2-ylamino-$(CH_2)_3$ | H | H | H | $NHSO_2C_6H_4$-(3-$CH_3$) | |
| 1035 | imidazol-2-ylamino-$(CH_2)_3$ | H | H | H | $NHSO_2C_6H_4$-(4-$CH_3$) | |
| 1035a | imidazol-2-ylamino-$(CH_2)_3$ | H | H | H | $NHSO_2C_6H_3$-(2,6-$CH_3$)$_2$ | 540.4 |
| 1035b | imidazol-2-ylamino-$(CH_2)_3$ | H | H | H | $NHSO_2C_6H_2$-(2,4,6-$CH_3$)$_3$ | 554.4 |
| 1036 | imidazol-2-ylamino-$(CH_2)_3$ | H | H | H | $NHSO_2$(2-pyridyl) | |
| 1037 | imidazol-2-ylamino-$(CH_2)_3$ | H | H | H | $NHSO_2$(3-pyridyl) | |
| 1038 | imidazol-2-ylamino-$(CH_2)_3$ | H | H | H | $NHSO_2$(4-pyridyl) | |
| 1038a | imidazol-2-ylamino-$(CH_2)_3$ | H | H | H | $NHSO_2$(2-thienyl) | |
| 1038b | imidazol-2-ylamino-$(CH_2)_3$ | H | H | H | $NHSO_2$-[3-(2,5-dichloro)thienyl] | |
| 1039 | imidazol-2-ylamino-$(CH_2)_3$ | H | H | H | $NHSO_2$(2-thiaz-olyl) | |
| 1040 | imidazol-2-ylamino-$(CH_2)_3$ | H | H | H | $NHSO_2$(3-thiazolyl) | |
| 1040a | imidazol-2-ylamino-$(CH_2)_3$ | H | H | H | $NHSO_2$-[5-(4-methyl-2-amino)thiazolyl] | |
| 1041 | imidazol-2-ylamino-$(CH_2)_3$ | H | H | H | $NHSO_2$(4-isoxazolyl) | |
| 1042 | imidazol-2-ylamino-$(CH_2)_3$ | H | H | H | $NHSO_2$[4-(3,5-dimethyl)isoxazolyl] | |
| 1043 | imidazol-2-ylamino-$(CH_2)_3$ | H | H | H | $NHSO_2C_6H_4$-(2-Br) | |
| 1044 | imidazol-2-ylamino-$(CH_2)_3$ | H | H | H | $NHSO_2C_6H_4$-(3-Br) | |
| 1045 | imidazol-2-ylamino-$(CH_2)_3$ | H | H | H | $NHSO_2C_6H_4$-(4-Br) | |
| 1046 | imidazol-2-ylamino-$(CH_2)_3$ | H | H | H | $NHSO_2C_6H_4$-(2-F) | |
| 1047 | imidazol-2-ylamino-$(CH_2)_3$ | H | H | H | $NHSO_2C_6H_4$-(3-F) | |
| 1048 | imidazol-2-ylamino-$(CH_2)_3$ | H | H | H | $NHSO_2C_6H_4$-(4-F) | |

TABLE 1-continued

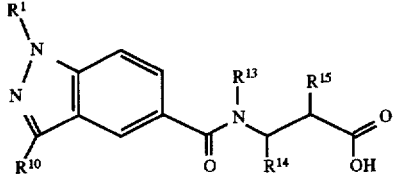

| Ex. No. | $R^1$ | $R^{10}$ | $R^{13}$ | $R^{14}$ | $R^{15}$ | MS |
|---|---|---|---|---|---|---|
| 1048a | imidazol-2-ylamino-$(CH_2)_3$ | H | H | H | $NHSO_2C_6H_3$-(2,6-$Cl_2$) | 580.2 |
| 1049 | imidazol-2-ylamino-$(CH_2)_3$ | H | H | H | $NHSO_2$(2-naphthyl) | |
| 1050 | imidazol-2-ylamino-$(CH_2)_3$ | H | H | H | $NHSO_2$(1-naphthyl) | 562.4 |
| 1050a | imidazol-2-ylamino-$(CH_2)_3$ | H | H | H | $NHSO_2C_6H_4$-(4-Ph) | 588.4 |
| 1050b | imidazol-2-ylamino-$(CH_2)_3$ | H | H | H | $NHSO_2C_6H_4$-4-(4-pyridyl) | |
| 1050c | imidazol-2-ylamino-$(CH_2)_3$ | H | H | H | $NHSO_2C_6H_4$-4-(2-oxazolyl) | |
| 1050d | imidazol-2-ylamino-$(CH_2)_3$ | H | H | H | $NHSO_2C_6H_4$-4-(3-pyrazolyl) | |
| 1050e | imidazol-2-ylamino-$(CH_2)_3$ | H | H | H | $NHSO_2C_6H_2$-4-Ph-2,6-dimethyl | 616.3 |
| 1050f | imidazol-2-ylamino-$(CH_2)_3$ | H | H | H | $NHSO_2C_6H_2$-4-(3-pyridyl)-2,6-dimethyl | |
| 1050g | imidazol-2-ylamino-$(CH_2)_3$ | H | H | H | $NHSO_2C_6H_2$-4-(2-oxazolyl)-2,6-dimethyl | |
| 1050h | imidazol-2-ylamino-$(CH_2)_3$ | H | H | H | $NHSO_2C_6H_2$-4-(3-pyrazolyl)-2,6-dimethyl | |
| 1050i | imidazol-2-ylamino-$(CH_2)_3$ | H | H | H | $NHSO_2C_6H_2$-4-Ph-2,6-dichloro | |
| 1050j | imidazol-2-ylamino-$(CH_2)_3$ | H | H | H | $NHSO_2C_6H_4$-4-(2-furyl) | 578.3 |
| 1050k | imidazol-2-ylamino-$(CH_2)_3$ | H | H | H | $NHSO_2C_6H_2$-4-(3-furyl) | |
| 1050l | imidazol-2-ylamino-$(CH_2)_3$ | H | H | H | $NHSO_2C_6H_2$-4-(3-pyridyl) | |
| 1050m | imidazol-2-ylamino-$(CH_2)_3$ | H | H | H | $NHSO_2C_6H_2$-4-(4-pyridyl)-2,6-dimethyl | |
| 1050n | imidazol-2-ylamino-$(CH_2)_3$ | H | H | H | $NHSO_2C_6H_2$-4-(3-furyl)-2,6-dimethyl | |
| 1050o | imidazol-2-ylamino-$(CH_2)_3$ | H | H | H | $NHSO_2C_6H_2$-4-(2-furyl)-2,6-dichloro | |
| 1051 | imidazol-2-ylamino-$(CH_2)_3$ | H | H | H | $NHSO_2CH=CHPh$ | |
| 1052 | imidazol-2-ylamino-$(CH_2)_3$ | H | H | H | $NHSO_2CH_2Ph$ | |
| 1053 | imidazol-2-ylamino-$(CH_2)_3$ | H | H | H | $NHSO_2CH_2CH=CH-Ph$ | |
| 1054 | imidazol-2-ylamino-$(CH_2)_3$ | H | H | H | $NHSO_2$-n-Bu | |
| 1055 | imidazol-2-ylamino-$(CH_2)_3$ | H | H | H | $NHSO_2$-i-Bu | |
| 1056 | imidazol-2-ylamino-$(CH_2)_3$ | H | H | H | $NHSO_2$-t-Bu | |
| 1057 | imidazol-2-ylamino-$(CH_2)_3$ | H | H | H | $NHSO_2NHPh$ | |
| 1058 | imidazol-2-ylamino-$(CH_2)_3$ | H | H | H | $NHSO_2NHC_6H_4$-(2-$CH_3$) | |
| 1059 | imidazol-2-ylamino-$(CH_2)_3$ | H | H | H | $NHSO_2NHC_6H_4$-(3-$CH_3$) | |
| 1060 | imidazol-2-ylamino-$(CH_2)_3$ | H | H | H | $NHSO_2NHC_6H_4$-(4-$CH_3$) | |
| 1060a | imidazol-2-ylamino-$(CH_2)_3$ | H | H | H | $NHSO_2NHC_6C_3$-(2,6-$Me_2$) | |
| 1060b | imidazol-2-ylamino-$(CH_2)_3$ | H | H | H | $NHSO_2NHC_6C_2$-(2,4,6-$Me_3$) | |
| 1061 | imidazol-2-ylamino-$(CH_2)_3$ | H | H | H | $NHSO_2NH$(2-pyridyl) | |
| 1062 | imidazol-2-ylamino-$(CH_2)_3$ | H | H | H | $NHSO_2NH$(3-pyridyl) | |
| 1063 | imidazol-2-ylamino-$(CH_2)_3$ | H | H | H | $NHSO_2NH$(4-pyridyl) | |
| 1064 | imidazol-2-ylamino-$(CH_2)_3$ | H | H | H | $NHSO_2NH$(2-thiazolyl) | |
| 1065 | imidazol-2-ylamino-$(CH_2)_3$ | H | H | H | $NHSO_2NH$(4-thiazolyl) | |
| 1066 | imidazol-2-ylamino-$(CH_2)_3$ | H | H | H | $NHSO_2NH$(4-isoxazolyl) | |
| 1067 | imidazol-2-ylamino-$(CH_2)_3$ | H | H | H | $NHSO_2$[4-(3,5-dimethyl)isoxazolyl] | |
| 1068 | imidazol-2-ylamino-$(CH_2)_3$ | H | H | H | $NHSO_2NHC_6H_4$-(2-Br) | |
| 1069 | imidazol-2-ylamino-$(CH_2)_3$ | H | H | H | $NHSO_2NHC_6H_4$-(3-Br) | |
| 1070 | imidazol-2-ylamino-$(CH_2)_3$ | H | H | H | $NHSO_2NHC_6H_4$-(4-Br) | |
| 1071 | imidazol-2-ylamino-$(CH_2)_3$ | H | H | H | $NHSO_2NHC_6H_4$-(3-F) | |
| 1072 | imidazol-2-ylamino-$(CH_2)_3$ | H | H | H | $NHSO_2NHC_6H_4$-(4-F) | |
| 1073 | imidazol-2-ylamino-$(CH_2)_3$ | H | H | H | $NHSO_2NH$(2-naphthyl) | |
| 1074 | imidazol-2-ylamino-$(CH_2)_3$ | H | H | H | $NHSO_2NH$(1-naphthyl) | |
| 1074a | imidazol-2-ylamino-$(CH_2)_3$ | H | H | H | $NHSO_2NHC_6H_4$-(4-Ph) | |
| 1074b | imidazol-2-ylamino-$(CH_2)_3$ | H | H | H | $NHSO_2NHC_6H_2$-(4-Ph-2,6-dimethyl) | |
| 1074c | imidazol-2-ylamino-$(CH_2)_3$ | H | H | H | $NHSO_2NHC_6H_2$-(4-Ph-2,6-dichloro) | |
| 1075 | imidazol-2-ylamino-$(CH_2)_3$ | H | H | H | $NHSO_2NHCH=CH-Ph$ | |
| 1076 | imidazol-2-ylamino-$(CH_2)_3$ | H | H | H | $NHSO_2NHCH_2Ph$ | |
| 1077 | imidazol-2-ylamino-$(CH_2)_3$ | H | H | H | $NHSO_2NHCH_2CH=CH-Ph$ | |

TABLE 1-continued

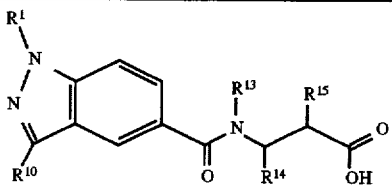

| Ex. No. | R¹ | R¹⁰ | R¹³ | R¹⁴ | R¹⁵ | MS |
|---|---|---|---|---|---|---|
| 1077a | imidazol-2-ylamino-$(CH_2)_3$ | H | H | H | $NHSO_2NH$-cyclohexyl | |
| 1078 | imidazol-2-ylamino-$(CH_2)_3$ | H | H | H | $NHSO_2NH$-n-Bu | |
| 1079 | imidazol-2-ylamino-$(CH_2)_3$ | H | H | H | $NHSO_2NH$-i-Bu | |
| 1080 | imidazol-2-ylamino-$(CH_2)_3$ | H | H | H | $NHSO_2NH$-t-Bu | |
| 1081 | pyridin-2-ylamino-$(CH_2)_3$ | H | H | H | $NHCO_2CH_2Ph$ | 517.3 |
| 1082 | pyridin-2-ylamino-$(CH_2)_3$ | H | H | H | $NHCO_2CH_2C_6H_4$-(2-$CH_3$) | |
| 1083 | pyridin-2-ylamino-$(CH_2)_3$ | H | H | H | $NHCO_2CH_2C_6H_4$-(3-$CH_3$) | |
| 1084 | pyridin-2-ylamino-$(CH_2)_3$ | H | H | H | $NHCO_2CH_2C_6H_4$-(4-$CH_3$) | |
| 1085 | pyridin-2-ylamino-$(CH_2)_3$ | H | H | H | $NHCO_2CH_2$(2-pyridinyl) | |
| 1086 | pyridin-2-ylamino-$(CH_2)_3$ | H | H | H | $NHCO_2CH_2$(3-pyridinyl) | |
| 1087 | pyridin-2-ylamino-$(CH_2)_3$ | H | H | H | $NHCO_2CH_2$(4-pyridinyl) | |
| 1088 | pyridin-2-ylamino-$(CH_2)_3$ | H | H | H | $NHCO_2CH_2$(2-thiazolyl) | |
| 1089 | pyridin-2-ylamino-$(CH_2)_3$ | H | H | H | $NHCO_2CH_2$(4-thiazolyl) | |
| 1090 | pyridin-2-ylamino-$(CH_2)_3$ | H | H | H | $NHCO_2CH_2$(5-thiazolyl) | |
| 1091 | pyridin-2-ylamino-$(CH_2)_3$ | H | H | H | $NHCO_2CH_2$(4-isoxazolyl) | |
| 1092 | pyridin-2-ylamino-$(CH_2)_3$ | H | H | H | $NHCO_2CH_2$(2-thienyl) | |
| 1093 | pyridin-2-ylamino-$(CH_2)_3$ | H | H | H | $NHCO_2$n-Bu | |
| 1094 | pyridin-2-ylamino-$(CH_2)_3$ | H | H | H | $NHCO_2$i-Bu | 483.5 |
| 1095 | pyridin-2-ylamino-$(CH_2)_3$ | H | H | H | $NHCO_2$t-Bu | |
| 1095a | pyridin-2-ylamino-$(CH_2)_3$ | H | H | H | NHCOPh | 487.3 |
| 1096 | pyridin-2-ylamino-$(CH_2)_3$ | H | H | H | $NHCOCH_2Ph$ | 501.4 |
| 1097 | pyridin-2-ylamino-$(CH_2)_3$ | H | H | H | $NHCOCH_2C_6H_4$-(2-$CH_3$) | |
| 1098 | pyridin-2-ylamino-$(CH_2)_3$ | H | H | H | $NHCOCH_2$—$C_6H_4$-(3-$CH_3$) | |
| 1099 | pyridin-2-ylamino-$(CH_2)_3$ | H | H | H | $NHCOCH_2C_6H_4$-(4-$CH_3$) | |
| 1099a | pyridin-2-ylamino-$(CH_2)_3$ | H | H | H | $NHCOCH_2CH_2Ph$ | 515.4 |
| 1099b | pyridin-2-ylamino-$(CH_2)_3$ | H | H | H | NHCOCH=CHPh | 513.3 |
| 1100 | pyridin-2-ylamino-$(CH_2)_3$ | H | H | H | $NHCOCH_2$(2-pyridinyl) | |
| 1101 | pyridin-2-ylamino-$(CH_2)_3$ | H | H | H | $NHCOCH_2$(3-pyridinyl) | |
| 1102 | pyridin-2-ylamino-$(CH_2)_3$ | H | H | H | $NHCOCH_2$(4-pyridinyl) | |
| 1103 | pyridin-2-ylamino-$(CH_2)_3$ | H | H | H | $NHCOCH_2$(2-thiazolyl) | |
| 1104 | pyridin-2-ylamino-$(CH_2)_3$ | H | H | H | $NHCOCH_2$(4-thiazolyl) | |
| 1105 | pyridin-2-ylamino-$(CH_2)_3$ | H | H | H | $NHCOCH_2$(5-thiazolyl) | |
| 1106 | pyridin-2-ylamino-$(CH_2)_3$ | H | H | H | $NHCOCH_2CH_2CH(CH_3)_2$ | 481.4 |
| 1107 | pyridin-2-ylamino-$(CH_2)_3$ | H | H | H | $NHCOCH_2$(4-isoxazolyl) | |
| 1108 | pyridin-2-ylamino-$(CH_2)_3$ | H | H | H | $NHCOCH_2$(2-thienyl) | |
| 1108a | pyridin-2-ylamino-$(CH_2)_3$ | H | H | H | $NHCOCH_2$(cyclohexyl) | 507.3 |
| 1108b | pyridin-2-ylamino-$(CH_2)_3$ | H | H | H | NHCO-cyclohexyl | 493.4 |
| 1109 | pyridin-2-ylamino-$(CH_2)_3$ | H | H | H | NHCOn-Bu | |
| 1110 | pyridin-2-ylamino-$(CH_2)_3$ | H | H | H | NHCOt-Bu | |
| 1110a | pyridin-2-ylamino-$(CH_2)_3$ | H | H | H | NHCONHPh | 502.4 |
| 1110b | pyridin-2-ylamino-$(CH_2)_3$ | H | H | H | $NHCONHCH_2Ph$ | 516.5 |
| 1111 | pyridin-2-ylamino-$(CH_2)_3$ | H | H | H | $NHSO_2Ph$ | 523.2 |
| 1112 | pyridin-2-ylamino-$(CH_2)_3$ | H | H | H | $NHSO_2C_6H_4$-(2-$CH_3$) | |
| 1113 | pyridin-2-ylamino-$(CH_2)_3$ | H | H | H | $NHSO_2C_6H_4$-(3-$CH_3$) | |
| 1114 | pyridin-2-ylamino-$(CH_2)_3$ | H | H | H | $NHSO_2C_6H_4$-(4-$CH_3$) | |
| 1114a | pyridin-2-ylamino-$(CH_2)_3$ | H | H | H | $NHSO_2C_6H_3$-(2,6-$CH_3$)$_2$ | |
| 1114b | pyridin-2-ylamino-$(CH_2)_3$ | H | H | H | $NHSO_2C_6H_2$-(2,4,6-$CH_3$)$_3$ | 565.2 |
| 1115 | pyridin-2-ylamino-$(CH_2)_3$ | H | H | H | $NHSO_2$(2-pyridyl) | |
| 1116 | pyridin-2-ylamino-$(CH_2)_3$ | H | H | H | $NHSO_2$(3-pyridyl) | |
| 1117 | pyridin-2-ylamino-$(CH_2)_3$ | H | H | H | $NHSO_2$(4-pyridyl) | |
| 1117a | pyridin-2-ylamino-$(CH_2)_3$ | H | H | H | $NHSO_2$(2-thienyl) | 529.2 |
| 1117b | pyridin-2-ylamino-$(CH_2)_3$ | H | H | H | $NHSO_2$-[3-(2,5-dichloro)thienyl] | 597.1 |
| 1118 | pyridin-2-ylamino-$(CH_2)_3$ | H | H | H | $NHSO_2$(2-thiazolyl) | |
| 1119 | pyridin-2-ylamino-$(CH_2)_3$ | H | H | H | $NHSO_2$(4-thiazolyl) | |
| 1119a | pyridin-2-ylamino-$(CH_2)_3$ | H | H | H | $NHSO_2$-[5-(4-methyl-2-amino)thiazolyl] | 559.2 |
| 1120 | pyridin-2-ylamino-$(CH_2)_3$ | H | H | H | $NHSO_2$(4-isoxazolyl) | |
| 1121 | pyridin-2-ylamino-$(CH_2)_3$ | H | H | H | $NHSO_2$-[4-(3,5-dimethyl)isoxazolyl] | 542.2 |
| 1122 | pyridin-2-ylamino-$(CH_2)_3$ | H | H | H | $NHSO_2C_6H_4$-(2-Br) | |
| 1123 | pyridin-2-ylamino-$(CH_2)_3$ | H | H | H | $NHSO_2C_6H_4$-(3-Br) | |
| 1124 | pyridin-2-ylamino-$(CH_2)_3$ | H | H | H | $NHSO_2C_6H_4$-(4-Br) | |
| 1125 | pyridin-2-ylamino-$(CH_2)_3$ | H | H | H | $NHSO_2C_6H_4$-(2-F) | |
| 1126 | pyridin-2-ylamino-$(CH_2)_3$ | H | H | H | $NHSO_2C_6H_4$-(3-F) | |
| 1127 | pyridin-2-ylamino-$(CH_2)_3$ | H | H | H | $NHSO_2C_6H_4$-(4-F) | |

TABLE 1-continued

| Ex. No. | R¹ | R¹⁰ | R¹³ | R¹⁴ | R¹⁵ | MS |
|---|---|---|---|---|---|---|
| 1127a | pyridin-2-ylamino-$(CH_2)_3$ | H | H | H | $NHSO_2C_6H_3$-(2,6-$Cl_2$) | 591.3 |
| 1128 | pyridin-2-ylamino-$(CH_2)_3$ | H | H | H | $NHSO_2$(2-naphthyl) | 573.4 |
| 1129 | pyridin-2-ylamino-$(CH_2)_3$ | H | H | H | $NHSO_2$(1-naphthyl) | 573.2 |
| 1129a | pyridin-2-ylamino-$(CH_2)_3$ | H | H | H | $NHSO_2C_6H_4$-(4-Ph) | 599.4 |
| 1129b | pyridin-2-ylamino-$(CH_2)_3$ | H | H | H | $NHSO_2C_6H_4$-4-(4-pyridyl) | |
| 1129c | pyridin-2-ylamino-$(CH_2)_3$ | H | H | H | $NHSO_2C_6H_4$-4-(2-oxazolyl) | |
| 1129d | pyridin-2-ylamino-$(CH_2)_3$ | H | H | H | $NHSO_2C_6H_4$-4-(3-pyrazolyl) | |
| 1129e | pyridin-2-ylamino-$(CH_2)_3$ | H | H | H | $NHSO_2C_6H_2$-4-Ph-2,6-dimethyl | |
| 1129f | pyridin-2-ylamino-$(CH_2)_3$ | H | H | H | $NHSO_2C_6H_2$-4-(3-pyridyl)-2,6-dimethyl | |
| 1129g | pyridin-2-ylamino-$(CH_2)_3$ | H | H | H | $NHSO_2C_6H_2$-4-(2-oxazolyl)-2,6-dimethyl | |
| 1129h | pyridin-2-ylamino-$(CH_2)_3$ | H | H | H | $NHSO_2C_6H_2$-4-(3-pyrazolyl)-2,6-dimethyl | |
| 1129i | pyridin-2-ylamino-$(CH_2)_3$ | H | H | H | $NHSO_2C_6H_2$-4-Ph-2,6-dichloro | |
| 1129j | pyridin-2-ylamino-$(CH_2)_3$ | H | H | H | $NHSO_2C_6H_4$-4-(2-furyl) | |
| 1129k | pyridin-2-ylamino-$(CH_2)_3$ | H | H | H | $NHSO_2C_6H_2$-4-(3-furyl) | |
| 1129l | pyridin-2-ylamino-$(CH_2)_3$ | H | H | H | $NHSO_2C_6H_2$-4-(3-pyridyl) | |
| 1129m | pyridin-2-ylamino-$(CH_2)_3$ | H | H | H | $NHSO_2C_6H_2$-4-(4-pyridyl)-2,6-dimethyl | |
| 1129n | pyridin-2-ylamino-$(CH_2)_3$ | H | H | H | $NHSO_2C_6H_2$-4-(3-furyl)-2,6-dimethyl | |
| 1129o | pyridin-2-ylamino-$(CH_2)_3$ | H | H | H | $NHSO_2C_6H_2$-4-(2-furyl)-2,6-dichloro | |
| 1130 | pyridin-2-ylamino-$(CH_2)_3$ | H | H | H | $NHSO_2CH=CH-Ph$ | |
| 1131 | pyridin-2-ylamino-$(CH_2)_3$ | H | H | H | $NHSO_2CH_2Ph$ | 537.4 |
| 1132 | pyridin-2-ylamino-$(CH_2)_3$ | H | H | H | $NHSO_2-CH_2CH=CH-Ph$ | |
| 1133 | pyridin-2-ylamino-$(CH_2)_3$ | H | H | H | $NHSO_2$-n-Bu | 503.3 |
| 1134 | pyridin-2-ylamino-$(CH_2)_3$ | H | H | H | $NHSO_2$-i-Bu | |
| 1135 | pyridin-2-ylamino-$(CH_2)_3$ | H | H | H | $NHSO_2$-t-Bu | |
| 1136 | pyridin-2-ylamino-$(CH_2)_3$ | H | H | H | $NHSO_2NHPh$ | |
| 1137 | pyridin-2-ylamino-$(CH_2)_3$ | H | H | H | $NHSO_2NHC_6H_4$-(2-$CH_3$) | |
| 1138 | pyridin-2-ylamino-$(CH_2)_3$ | H | H | H | $NHSO_2NHC_6H_4$-(3-$CH_3$) | |
| 1139 | pyridin-2-ylamino-$(CH_2)_3$ | H | H | H | $NHSO_2NHC_6H_4$-(4-$CH_3$) | |
| 1139a | pyridin-2-ylamino-$(CH_2)_3$ | H | H | H | $NHSO_2NHC_6H_3$-(2,6-$Me_2$) | |
| 1139b | pyridin-2-ylamino-$(CH_2)_3$ | H | H | H | $NHSO_2NHC_6H_2$-(2,4,6-$Me_3$) | 580.3 |
| 1140 | pyridin-2-ylamino-$(CH_2)_3$ | H | H | H | $NHSO_2NH$(2-pyridyl) | |
| 1141 | pyridin-2-ylamino-$(CH_2)_3$ | H | H | H | $NHSO_2NH$(3-pyridyl) | |
| 1142 | pyridin-2-ylamino-$(CH_2)_3$ | H | H | H | $NHSO_2NH$(4-pyridyl) | |
| 1143 | pyridin-2-ylamino-$(CH_2)_3$ | H | H | H | $NHSO_2NH$(2-thiazolyl) | |
| 1144 | pyridin-2-ylamino-$(CH_2)_3$ | H | H | H | $NHSO_2NH$-(4-thiazolyl) | |
| 1145 | pyridin-2-ylamino-$(CH_2)_3$ | H | H | H | $NHSO_2NH$(4-isoxazolyl) | |
| 1146 | pyridin-2-ylamino-$(CH_2)_3$ | H | H | H | $NHSO_2$-[4-(3,5-dimethyl)isoxazolyl] | |
| 1147 | pyridin-2-ylamino-$(CH_2)_3$ | H | H | H | $NHSO_2NHC_6H_4$-(2-Br) | |
| 1148 | pyridin-2-ylamino-$(CH_2)_3$ | H | H | H | $NHSO_2NHC_6H_4$-(3-Br) | |
| 1149 | pyridin-2-ylamino-$(CH_2)_3$ | H | H | H | $NHSO_2NHC_6H_4$-(4-Br) | |
| 1150 | pyridin-2-ylamino-$(CH_2)_3$ | H | H | H | $NHSO_2NHC_6H_4$-(3-F) | |
| 1151 | pyridin-2-ylamino-$(CH_2)_3$ | H | H | H | $NHSO_2NHC_6H_4$-(4-F) | |
| 1152 | pyridin-2-ylamino-$(CH_2)_3$ | H | H | H | $NHSO_2NH$(2-naphthyl) | |
| 1153 | pyridin-2-ylamino-$(CH_2)_3$ | H | H | H | $NHSO_2NH$)1-naphthyl) | |
| 1153a | pyridin-2-ylamino-$(CH_2)_3$ | H | H | H | $NHSO_2NHC_6H_4$-(4-Ph) | |
| 1153b | pyridin-2-ylamino-$(CH_2)_3$ | H | H | H | $NHSO_2NHC_6H_2$-(4-Ph-2,6-dimethyl) | |
| 1153c | pyridin-2-ylamino-$(CH_2)_3$ | H | H | H | $NHSO_2NHC_6H_2$-(4-Ph-2,6-dichloro) | |
| 1154 | pyridin-2-ylamino-$(CH_2)_3$ | H | H | H | $NHSO_2NHCH=CH-Ph$ | |
| 1155 | pyridin-2-ylamino-$(CH_2)_3$ | H | H | H | $NHSO_2NHCH_2Ph$ | 552.4 |
| 1156 | pyridin-2-ylamino-$(CH_2)_3$ | H | H | H | $NHSO_2NHCH_2CH=CH-Ph$ | |

TABLE 1-continued

| Ex. No. | R¹ | R¹⁰ | R¹³ | R¹⁴ | R¹⁵ | MS |
|---|---|---|---|---|---|---|
| 1156a | pyridin-2-ylamino-$(CH_2)_3$ | H | H | H | NHSO—NH-cyclohexyl | 544.4 |
| 1157 | pyridin-2-ylamino-$(CH_2)_3$ | H | H | H | $NHSO_2NH$-n-Bu | |
| 1158 | pyridin-2-ylamino-$(CH_2)_3$ | H | H | H | $NHSO_2NH$-i-Bu | 518.4 |
| 1159 | pyridin-2-ylamino-$(CH_2)_3$ | H | H | H | $NHSO_2NH$-t-Bu | |
| 1160 | tetrahydropyrimidin-2-ylamino-$(CH_2)_3$ | H | H | H | $NHCOOCH_2Ph$ | |
| 1161 | tetrahydropyrimidin-2-ylamino-$(CH_2)_3$ | H | H | H | $NHCO_2CH_2C_6H_4$-(2-$CH_3$) | |
| 1162 | tetrahydropyrimidin-2-ylamino-$(CH_2)_3$ | H | H | H | $NHCO_2CH_2C_6H_4$-(3-$CH_3$) | |
| 1163 | tetrahydropyrimidin-2-ylamino-$(CH_2)_3$ | H | H | H | $NHCO_2CH_2C_6H_4$-(4-$CH_3$) | |
| 1164 | tetrahydropyrimidin-2-ylamino-$(CH_2)_3$ | H | H | H | $NHCO_2CH_2$(2-pyridinyl) | |
| 1165 | tetrahydropyrimidin-2-ylamino-$(CH_2)_3$ | H | H | H | $NHCO_2CH_2$(3-pyridinyl) | |
| 1166 | tetrahydropyrimidin-2-ylamino-$(CH_2)_3$ | H | H | H | $NHCO_2CH_2$(4-pyridinyl) | |
| 1167 | tetrahydropyrimidin-2-ylamino-$(CH_2)_3$ | H | H | H | $NHCO_2CH_2$(2-thiazolyl) | |
| 1168 | tetrahydropyrimidin-2-ylamino-$(CH_2)_3$ | H | H | H | $NHCO_2CH_2$(4-thiazolyl) | |
| 1169 | tetrahydropyrimidin-2-ylamino-$(CH_2)_3$ | H | H, | H | $NHCO_2CH_2$(5-thiazolyl) | |
| 1170 | tetrahydropyrimidin-2-ylamino-$(CH_2)_3$ | H | H | H | $NHCO_2CH_2$(4-isoxazolyl) | |
| 1171 | tetrahydropyrimidin-2-ylamino-$(CH_2)_3$ | H | H | H | $NHCO_2CH_2$(2-thienyl) | |
| 1172 | tetrahydropyrimidin-2-ylamino-$(CH_2)_3$ | H | H | H | $NHCO_2$n-Bu | |
| 1173 | tetrahydropyrimidin-2-ylamino-$(CH_2)_3$ | H | H | H | $NHCO_2$i-Bu | |
| 1174 | tetrahydropyrimidin-2-ylamino-$(CH_2)_3$ | H | H | H | $NHCO_2$t-Bu | |
| 1175 | tetrahydropyrimidin-2-ylamino-$(CH_2)_3$ | H | H | H | $NHSO_2Ph$ | |
| 1176 | tetrahydropyrimidin-2-ylamino-$(CH_2)_3$ | H | H | H | $NHSO_2C_6H_4$-(2-$CH_3$) | |
| 1177 | tetrahydropyrimidin-2-ylamino-$(CH_2)_3$ | H | H | H | $NHSO_2C_6H_4$-(3-$CH_3$) | |
| 1178 | tetrahydropyrimidin-2-ylamino-$(CH_2)_3$ | H | H | H | $NHSO_2C_6H_4$-(4-$CH_3$) | |
| 1178a | tetrahydropyrimidin-2-ylamino-$(CH_2)_3$ | H | H | H | $NHSO_2C_6H_3$-(2,6-$Me_2$) | |
| 1178b | tetrahydropyrimidin-2-ylamino-$(CH_2)_3$ | H | H | H | $NHSO_2C_6H_2$-(2,4,6-$Me_3$) | 570.5 |
| 1179 | tetrahydropyrimidin-2-ylamino-$(CH_2)_3$ | H | H | H | $NHSO_2$(2-pyridyl) | |
| 1180 | tetrahydropyrimidin-2-ylamino-$(CH_2)_3$ | H | H | H | $NHSO_2$(3-pyridyl) | |
| 1181 | tetrahydropyrimidin-2-ylamino-$(CH_2)_3$ | H | H | H | $NHSO_2$(4-pyridyl) | |
| 1181a | tetrahydropyrimidin-2-ylamino-$(CH_2)_3$ | H | H | H | $NHSO_2$(2-thienyl) | |
| 1181b | tetrahydropyrimidin-2-ylamino-$(CH_2)_3$ | H | H | H | $NHSO_2$-[3-(2,5-dichloro)thienyl] | |
| 1182 | tetrahydropyrimidin-2-ylamino-$(CH_2)_3$ | H | H | H | $NHSO_2$(2-thiazolyl) | |
| 1183 | tetrahydropyrimidin-2-ylamino-$(CH_2)_3$ | H | H | H | $NHSO_2$(4-thiazolyl) | |
| 1184 | tetrahydropyrimidin-2-ylamino-$(CH_2)_3$ | H | H | H | $NHSO_2$(4-isoxazolyl) | |
| 1185 | tetrahydropyrimidin-2-ylamino-$(CH_2)_3$ | H | H | H | $NHSO_2$-[4-(3,5-dimethyl)isoxazolyl] | |
| 1186 | tetrahydropyrimidin-2-ylamino-$(CH_2)_3$ | H | H | H | $NHSO_2C_6H_4$-(2-Br) | |
| 1187 | tetrahydropyrimidin-2-ylamino-$(CH_2)_3$ | H | H | H | $NHSO_2C_6H_4$-(3-Br) | |
| 1188 | tetrahydropyrimidin-2-ylamino-$(CH_2)_3$ | H | H | H | $NHSO_2C_6H_4$-(2-F) | |
| 1189 | tetrahydropyrimidin-2-ylamino-$(CH_2)_3$ | H | H | H | $NHSO_2C_6H_4$-(3-F) | |
| 1190 | tetrahydropyrimidin-2-ylamino-$(CH_2)_3$ | H | H | H | $NHSO_2C_6H_4$-(4-F) | |
| 1190a | tetrahydropyrimidin-2-ylamino-$(CH_2)_3$ | H | H | H | $NHSO_2C_6H_3$-(2,6-$Cl_2$) | |
| 1191 | tetrahydropyrimidin-2-ylamino-$(CH_2)_3$ | H | H | H | $NHSO_2$(2-naphthyl) | |
| 1192 | tetrahydropyrimidin-2-ylamino-$(CH_2)_3$ | H | H | H | $NHSO_2$(1-naphthyl) | |
| 1192a | tetrahydropyrimidin-2-ylamino-$(CH_2)_3$ | H | H | H | $NHSO_2C_6H_4$-(4-Ph) | |
| 1192b | tetrahydropyrimidin-2-ylamino-$(CH_2)_3$ | H | H | H | $NHSO_2C_6H_4$-4-(4-pyridyl) | |
| 1192c | tetrahydropyrimidin-2-ylamino-$(CH_2)_3$ | H | H | H | $NHSO_2C_6H_4$-4-(2-oxazolyl) | |
| 1192d | tetrahydropyrimidin-2-ylamino-$(CH_2)_3$ | H | H | H | $NHSO_2C_6H_4$-4-(3-pyrazolyl) | |
| 1192e | tetrahydropyrimidin-2-ylamino-$(CH_2)_3$ | H | H | H | $NHSO_2C_6H_2$-4-Ph-2,6-dimethyl | |
| 1192f | tetrahydropyrimidin-2-ylamino-$(CH_2)_3$ | H | H | H | $NHSO_2C_6H_2$-4-(3-pyridyl)-2,6-dimethyl | |
| 1192g | tetrahydropyrimidin-2-ylamino-$(CH_2)_3$ | H | H | H | $NHSO_2C_6H_2$-4-(2-oxazolyl)-2,6-dimethyl | |
| 1192h | tetrahydropyrimidin-2-ylamino-$(CH_2)_3$ | H | H | H | $NHSO_2C_6H_2$-4-(3-pyrazolyl)-2,6-dimethyl | |
| 1192i | tetrahydropyrimidin-2-ylamino-$(CH_2)_3$ | H | H | H | $NHSO_2C_6H_2$-4-Ph-2,6-dichloro | |
| 1192j | tetrahydropyrimidin-2-ylamino-$(CH_2)_3$ | H | H | H | $NHSO_2C_6H_4$-4-(2-furyl) | |
| 1192k | tetrahydropyrimidin-2-ylamino-$(CH_2)_3$ | H | H | H | $NHSO_2C_6H_4$-4-(3-furyl) | |
| 1192l | tetrahydropyrimidin-2-ylamino-$(CH_2)_3$ | H | H | H | $NHSO_2C_6H_2$-4-(3-pyridyl) | |
| 1192m | tetrahydropyrimidin-2-ylamino-$(CH_2)_3$ | H | H | H | $NHSO_2C_6H_2$-4-(4- | |

TABLE 1-continued

| Ex. No. | R¹ | R¹⁰ | R¹³ | R¹⁴ | R¹⁵ | MS |
|---|---|---|---|---|---|---|
| 1192n | tetrahydropyrimidin-2-ylamino-(CH$_2$)$_3$ | H | H | H | NHSO$_2$C$_6$H$_2$-4-(3-furyl)-pyridyl)-2,6-dimethyl 2,6-dimethyl | |
| 1192o | tetrahydropyrimidin-2-ylamino-(CH$_2$)$_3$ | H | H | H | NHSO$_2$C$_6$H$_2$-4-(2-furyl)-2,6-dichloro | |
| 1193 | tetrahydropyrimidin-2-ylamino-(CH$_2$)$_3$ | H | H | H | NHSO$_2$CH=CHPh | |
| 1194 | tetrahydropyrimidin-2-ylamino-(CH$_2$)$_3$ | H | H | H | NHSO$_2$CH$_2$Ph | |
| 1195 | tetrahydropyrimidin-2-ylamino-(CH$_2$)$_3$ | H | H | H | NHSO$_2$CH$_2$CH=CHPh | |
| 1196 | tetrahydropyrimidin-2-ylamino-(CH$_2$)$_3$ | H | H | H | NHSO$_2$-n-Bu | |
| 1197 | tetrahydropyrimidin-2-ylamino-(CH$_2$)$_3$ | H | H | H | NHSO$_2$-i-Bu | |
| 1197a | tetrahydropyrimidin-2-ylamino-(CH$_2$)$_3$ | H | H | H | NHSO$_2$NHPh | |
| 1197b | tetrahydropyrimidin-2-ylamino-(CH$_2$)$_3$ | H | H | H | NHSO$_2$NHC$_6$H$_4$-(2-CH$_3$) | |
| 1197c | tetrahydropyrimidin-2-ylamino-(CH$_2$)$_3$ | H | H | H | NHSO$_2$NHC$_6$H$_4$-(3-CH$_3$) | |
| 1197d | tetrahydropyrimidin-2-ylamino-(CH$_2$)$_3$ | H | H | H | NHSO$_2$NHC$_6$H$_4$-(4-CH$_3$) | |
| 1197e | tetrahydropyrimidin-2-ylamino-(CH$_2$)$_3$ | H | H | H | NHSO$_2$NHC$_6$C$_3$-(2,6-Me$_2$) | |
| 1197f | tetrahydropyrimidin-2-ylamino-(CH$_2$)$_3$ | H | H | H | NHSO$_2$NHC$_6$C$_2$-(2,4,6-Me$_3$) | |
| 1197g | tetrahydropyrimidin-2-ylamino-(CH$_2$)$_3$ | H | H | H | NHSO$_2$[4-(3,5-dimethyl)isoxazolyl] | |
| 1197h | tetrahydropyrimidin-2-ylamino-(CH$_2$)$_3$ | H | H | H | NHSO$_2$NH(2-naphthyl) | |
| 1197j | tetrahydropyrimidin-2-ylamino-(CH$_2$)$_3$ | H | H | H | NHSO$_2$NH(1-naphthyl) | |
| 1197k | tetrahydropyrimidin-2-ylamino-(CH$_2$)$_3$ | H | H | H | NHSO$_2$NHC$_6$H$_4$-(4-Ph) | |
| 1197m | tetrahydropyrimidin-2-ylamino-(CH$_2$)$_3$ | H | H | H | NHSO$_2$NHC$_6$H$_2$-(4-Ph-2,6-dimethyl) | |
| 1197n | tetrahydropyrimidin-2-ylamino-(CH$_2$)$_3$ | H | H | H | NHSO$_2$NHC$_6$H$_2$-(4-Ph-2,6-dichloro) | |
| 1197p | tetrahydropyrimidin-2-ylamino-(CH$_2$)$_3$ | H | H | H | NHSO$_2$NHCH$_2$Ph | |
| 1198 | imidazolin-2-ylamino-(CH$_2$)$_3$ | H | H | H | NHCOOCH$_2$Ph | 508.6 |
| 1199 | imidazolin-2-ylamino-(CH$_2$)$_3$ | H | H | H | NHCO$_2$CH$_2$C$_6$H$_4$-(2-CH$_3$) | |
| 1200 | imidazolin-2-ylamino-(CH$_2$)$_3$ | H | H | H | NHCO$_2$CH$_2$C$_6$H$_4$-(3-CH$_3$) | |
| 1201 | imidazolin-2-ylamino-(CH$_2$)$_3$ | H | H | H | NHCO$_2$CH$_2$C$_6$H$_4$-(4-CH$_3$) | |
| 1202 | imidazolin-2-ylamino-(CH$_2$)$_3$ | H | H | H | NHCO$_2$CH$_2$(2-pyridinyl) | |
| 1203 | imidazolin-2-ylamino-(CH$_2$)$_3$ | H | H | H | NHCO$_2$CH$_2$(3-pyridinyl) | |
| 1204 | imidazolin-2-ylamino-(CH$_2$)$_3$ | H | H | H | NHCO$_2$CH$_2$(4-pyridinyl) | |
| 1205 | imidazolin-2-ylamino-(CH$_2$)$_3$ | H | H | H | NHCO$_2$CH$_2$(2-thiazolyl) | |
| 1206 | imidazolin-2-ylamino-(CH$_2$)$_3$ | H | H | H | NHCO$_2$CH$_2$(4-thiazolyl) | |
| 1207 | imidazolin-2-ylamino-(CH$_2$)$_3$ | H | H | H | NHCO$_2$CH$_2$(5-thiazolyl) | |
| 1208 | imidazolin-2-ylamino-(CH$_2$)$_3$ | H | H | H | NHCO$_2$CH$_2$(4-isoxazolyl) | |
| 1209 | imidazolin-2-ylamino-(CH$_2$)$_3$ | H | H | H | NHCO$_2$CH$_2$(2-thienyl) | |
| 1210 | imidazolin-2-ylamino-(CH$_2$)$_3$ | H | H | H | NHCO$_2$n-Bu | |
| 1211 | imidazolin-2-ylamino-(CH$_2$)$_3$ | H | H | H | NHCO$_2$i-Bu | |
| 1212 | imidazolin-2-ylamino-(CH$_2$)$_3$ | H | H | H | NHCO$_2$t-Bu | |
| 1213 | imidazolin-2-ylamino-(CH$_2$)$_3$ | H | H | H | NHSO$_2$Ph | 514.3 |
| 1214 | imidazolin-2-ylamino-(CH$_2$)$_3$ | H | H | H | NHSO$_2$C$_6$H$_4$-(2-CH$_3$) | |
| 1215 | imidazolin-2-ylamino-(CH$_2$)$_3$ | H | H | H | NHSO$_2$C$_6$H$_4$-(3-CH$_3$) | |
| 1216 | imidazolin-2-ylamino-(CH$_2$)$_3$ | H | H | H | NHSO$_2$C$_6$H$_4$-(4-CH$_3$) | |
| 1216a | imidazolin-2-ylamino-(CH$_2$)$_3$ | H | H | H | NHSO$_2$C$_6$H$_3$-(2,6-Me$_2$) | |
| 1216b | imidazolin-2-ylamino-(CH$_2$)$_3$ | H | H | H | NHSO$_2$C$_6$H$_2$-(2,4,6-Me$_3$) | 556.4 |
| 1217 | imidazolin-2-ylamino-(CH$_2$)$_3$ | H | H | H | NHSO$_2$(2-pyridyl) | |
| 1218 | imidazolin-2-ylamino-(CH$_2$)$_3$ | H | H | H | NHSO$_2$(3-pyridyl) | |
| 1219 | imidazolin-2-ylamino-(CH$_2$)$_3$ | H | H | H | NHSO$_2$(4-pyridyl) | |
| 1219a | imidazolin-2-ylamino-(CH$_2$)$_3$ | H | H | H | NHSO$_2$(2-thienyl) | |
| 1219b | imidazolin-2-ylamino-(CH$_2$)$_3$ | H | H | H | NHSO$_2$-[3-(2,5-dichloro)thienyl] | |
| 1220 | imidazolin-2-ylamino-(CH$_2$)$_3$ | H | H | H | NHSO$_2$(2-thiazolyl) | |
| 1220a | imidazolin-2-ylamino-(CH$_2$)$_3$ | H | H | H | NHSO$_2$-[5-(4-methyl-2-amino)thiazolyl] | |
| 1221 | imidazolin-2-ylamino-(CH$_2$)$_3$ | H | H | H | NHSO$_2$(4-isoxazolyl) | |
| 1222 | imidazolin-2-ylamino-(CH$_2$)$_3$ | H | H | H | NHSO$_2$-[4-(3,5-dimethyl)isoxazolyl] | |
| 1223 | imidazolin-2-ylamino-(CH$_2$)$_3$ | H | H | H | NHSO$_2$C$_6$H$_4$-(2-Br) | |
| 1224 | imidazolin-2-ylamino-(CH$_2$)$_3$ | H | H | H | NHSO$_2$C$_6$H$_4$-(3-Br) | |
| 1225 | imidazolin-2-ylamino-(CH$_2$)$_3$ | H | H | H | NHSO$_2$C$_6$H$_4$-(2-F) | |
| 1226 | imidazolin-2-ylamino-(CH$_2$)$_3$ | H | H | H | NHSO$_2$C$_6$H$_4$-(3-F) | |
| 1227 | imidazolin-2-ylamino-(CH$_2$)$_3$ | H | H | H | NHSO$_2$C$_6$H$_4$-(4-F) | |
| 1227a | imidazolin-2-ylamino-(CH$_2$)$_3$ | H | H | H | NHSO$_2$C$_6$H$_3$-(2,6-Cl$_2$) | |

TABLE 1-continued

| Ex. No. | R¹ | R¹⁰ | R¹³ | R¹⁴ | R¹⁵ | MS |
|---|---|---|---|---|---|---|
| 1228 | imidazolin-2-ylamino-(CH$_2$)$_3$ | H | H | H | NHSO$_2$(2-naphthyl) | |
| 1229 | imidazolin-2-ylamino-(CH$_2$)$_3$ | H | H | H | NHSO$_2$(1-naphthyl) | |
| 1229a | imidazolin-2-ylamino-(CH$_2$)$_3$ | H | H | H | NHSO$_2$C$_6$H$_4$-(4-Ph) | |
| 1229b | imidazolin-2-ylamino-(CH$_2$)$_3$ | H | H | H | NHSO$_2$C$_6$H$_4$-4-(4-pyridyl) | |
| 1229c | imidazolin-2-ylamino-(CH$_2$)$_3$ | H | H | H | NHSO$_2$C$_6$H$_4$-4-(2-oxazolyl) | |
| 1229d | imidazolin-2-ylamino-(CH$_2$)$_3$ | H | H | H | NHSO$_2$C$_6$H$_4$-4-(3-pyrazolyl) | |
| 1229e | imidazolin-2-ylamino-(CH$_2$)$_3$ | H | H | H | NHSO$_2$C$_6$H$_2$-4-Ph-2,6-dimethyl | |
| 1229f | imidazolin-2-ylamino-(CH$_2$)$_3$ | H | H | H | NHSO$_2$C$_6$H$_2$-4-(3-pyridyl)-2,6-dimethyl | |
| 1229g | imidazolin-2-ylamino-(CH$_2$)$_3$ | H | H | H | NHSO$_2$C$_6$H$_2$-4-(2-oxazolyl)-2,6-dimethyl | |
| 1229h | imidazolin-2-ylamino-(CH$_2$)$_3$ | H | H | H | NHSO$_2$C$_6$H$_2$-4-(3-pyrazolyl)-2,6-dimethyl | |
| 1229i | imidazolin-2-ylamino-(CH$_2$)$_3$ | H | H | H | NHSO$_2$C$_6$H$_2$-4-Ph-2,6-dichloro | |
| 1229j | imidazolin-2-ylamino-(CH$_2$)$_3$ | H | H | H | NHSO$_2$C$_6$H$_4$-4-(2-furyl) | |
| 1229k | imidazolin-2-ylamino-(CH$_2$)$_3$ | H | H | H | NHSO$_2$C$_6$H$_2$-4-(3-furyl) | |
| 1229l | imidazolin-2-ylamino-(CH$_2$)$_3$ | H | H | H | NHSO$_2$C$_6$H$_2$-4-(3-pyridyl) | |
| 1229m | imidazolin-2-ylamino-(CH$_2$)$_3$ | H | H | H | NHSO$_2$C$_6$H$_2$-4-(4-pyridyl)-2,6-dimethyl | |
| 1229n | imidazolin-2-ylamino-(CH$_2$)$_3$ | H | H | H | NHSO$_2$C$_6$H$_2$-4-(3-furyl)-2,6-dimethyl | |
| 1229o | imidazolin-2-ylamino-(CH$_2$)$_3$ | H | H | H | NHSO$_2$C$_6$H$_2$-4-(2-furyl)-2,6-dichloro | |
| 1230 | imidazolin-2-ylamino-(CH$_2$)$_3$ | H | H | H | NHSO$_2$CH=CHPh | |
| 1231 | imidazolin-2-ylamino-(CH$_2$)$_3$ | H | H | H | NHSO$_2$CH$_2$Ph | |
| 1232 | imidazolin-2-ylamino-(CH$_2$)$_3$ | H | H | H | NHSO$_2$CH$_2$CH=CHPh | |
| 1233 | imidazolin-2-ylamino-(CH$_2$)$_3$ | H | H | H | NHSO$_2$-n-Bu | |
| 1234 | imidazolin-2-ylamino-(CH$_2$)$_3$ | H | H | H | NHSO$_2$-i-Bu | |
| 1234a | imidazolin-2-ylamino-(CH$_2$)$_3$ | H | H | H | NHSO$_2$NHPh | |
| 1234b | imidazolin-2-ylamino-(CH$_2$)$_3$ | H | H | H | NHSO$_2$NHC$_6$H$_4$-(2-CH$_3$) | |
| 1234c | imidazolin-2-ylamino-(CH$_2$)$_3$ | H | H | H | NHSO$_2$NHC$_6$H$_4$-(3-CH$_3$) | |
| 1234d | imidazolin-2-ylamino-(CH$_2$)$_3$ | H | H | H | NHSO$_2$NHC$_6$H$_4$-(4-CH$_3$) | |
| 1234e | imidazolin-2-ylamino-(CH$_2$)$_3$ | H | H | H | NHSO$_2$NHC$_6$C$_3$-(2,6-Me$_2$) | |
| 1234f | imidazolin-2-ylamino-(CH$_2$)$_3$ | H | H | H | NHSO$_2$NHC$_6$C$_2$-(2,4,6-Me$_3$) | |
| 1234g | imidazolin-2-ylamino-(CH$_2$)$_3$ | H | H | H | NHSO$_2$NH(2-naphthyl) | |
| 1234h | imidazolin-2-ylamino-(CH$_2$)$_3$ | H | H | H | NHSO$_2$NH)1-naphthyl) | |
| 1234j | imidazolin-2-ylamino-(CH$_2$)$_3$ | H | H | H | NHSO$_2$NHC$_6$H$_4$-(4-Ph) | |
| 1234m | imidazolin-2-ylamino-(CH$_2$)$_3$ | H | H | H | NHSO$_2$NHC$_6$H$_2$-(4-Ph-2,6-dimethyl) | |
| 1234n | imidazolin-2-ylamino-(CH$_2$)$_3$ | H | H | H | NHSO$_2$NHC$_6$H$_2$-(4-Ph-2,6-dichloro) | |
| 1234p | imidazolin-2-ylamino-(CH$_2$)$_3$ | H | H | H | NHSO$_2$NHCH$_2$Ph | |
| 1235 | benzimidazol-2-ylamino-(CH$_2$)$_3$ | H | H | H | NHSO$_2$Ph | |
| 1236 | benzimidazol-2-ylamino-(CH$_2$)$_3$ | H | H | H | NHSO$_2$C$_6$H$_4$-(2-CH$_3$) | |
| 1237 | benzimidazol-2-ylamino-(CH$_2$)$_3$ | H | H | H | NHSO$_2$C$_6$H$_4$-(3-CH$_3$) | |
| 1238 | benzimidazol-2-ylamino-(CH$_2$)$_3$ | H | H | H | NHSO$_2$C$_6$H$_4$-(4-CH$_3$) | |
| 1238a | benzimidazol-2-ylamino-(CH$_2$)$_3$ | H | H | H | NHSO$_2$C$_6$H$_3$-(2,6-Me$_2$) | |
| 1238b | benzimidazol-2-ylamino-(CH$_2$)$_3$ | H | H | H | NHSO$_2$C$_6$H$_2$-(2,4,6-Me$_3$) | |
| 1239 | benzimidazol-2-ylamino-(CH$_2$)$_3$ | H | H | H | NHSO$_2$(2-pyridyl) | |
| 1240 | benzimidazol-2-ylamino-(CH$_2$)$_3$ | H | H | H | NHSO$_2$(3-pyridyl) | |
| 1241 | benzimidazol-2-ylamino-(CH$_2$)$_3$ | H | H | H | NHSO$_2$(4-pyridyl) | |
| 1241a | benzimidazol-2-ylamino-(CH$_2$)$_3$ | H | H | H | NHSO$_2$(2-thienyl) | |
| 1241b | benzimidazol-2-ylamino-(CH$_2$)$_3$ | H | H | H | NHSO$_2$-[3-(2,5-dichloro)thienyl] | |
| 1242 | benzimidazol-2-ylamino-(CH$_2$)$_3$ | H | H | H | NHSO$_2$(2-thiazolyl) | |
| 1242a | benzimidazol-2-ylamino-(CH$_2$)$_3$ | H | H | H | NHSO$_2$-[5-(4-methyl-2-amino)thiazolyl] | |
| 1243 | benzimidazol-2-ylamino-(CH$_2$)$_3$ | H | H | H | NHSO$_2$(4-isoxazolyl) | |
| 1244 | benzimidazol-2-ylamino-(CH$_2$)$_3$ | H | H | H | NHSO$_2$-[4-(3,5- | |

TABLE 1-continued

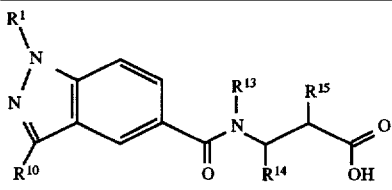

| Ex. No. | R¹ | R¹⁰ | R¹³ | R¹⁴ | R¹⁵ | MS |
|---|---|---|---|---|---|---|
| | | | | | dimethyl)isoxazolyl] | |
| 1245 | benzimidazol-2-ylamino-(CH$_2$)$_3$ | H | H | H | NHSO$_2$C$_6$H$_4$-(2-Br) | |
| 1246 | benzimidazol-2-ylamino-(CH$_2$)$_3$ | H | H | H | NHSO$_2$C$_6$H$_4$-(3-Br) | |
| 1247 | benzimidazol-2-ylamino-(CH$_2$)$_3$ | H | H | H | NHSO$_2$C$_6$H$_4$-(2-F) | |
| 1248 | benzimidazol-2-ylamino-(CH$_2$)$_3$ | H | H | H | NHSO$_2$C$_6$H$_4$-(3-F) | |
| 1249 | benzimidazol-2-ylamino-(CH$_2$)$_3$ | H | H | H | NHSO$_2$C$_6$H$_4$-(4-F) | |
| 1249a | benzimidazol-2-ylamino-(CH$_2$)$_3$ | H | H | H | NHSO$_2$C$_6$H$_3$-(2,6-Cl$_2$) | |
| 1249b | benzimidazol-2-ylamino-(CH$_2$)$_3$ | H | H | H | NHSO$_2$(2-naphthyl) | |
| 1249c | benzimidazol-2-ylamino-(CH$_2$)$_3$ | H | H | H | NHSO$_2$(1-naphthyl) | |
| 1249d | benzimidazol-2-ylamino-(CH$_2$)$_3$ | H | H | H | NHSO$_2$C$_6$H$_4$-(4-Ph) | |
| 1249e | benzimidazol-2-ylamino(CH$_2$)$_3$ | H | H | H | NHSO$_2$C$_6$H$_2$-(4-Ph-2,6-dimethyl) | |
| 1249f | benzimidazol-2-ylamino-(CH$_2$)$_3$ | H | H | H | NHSO$_2$C$_6$H$_2$-(4-Ph-2,6-dichloro) | |
| 1249g | benzimidazol-2-ylamino-(CH$_2$)$_3$ | H | H | H | NHSO$_2$CH=CHPh | |
| 1249h | benzimidazol-2-ylamino-(CH$_2$)$_3$ | H | H | H | NHSO$_2$CH$_2$Ph | |
| 1249j | benzimidazol-2-ylamino-(CH$_2$)$_3$ | H | H | H | NHSO$_2$CH$_2$CH=CHPh | |
| 1249k | benzimidazol-2-ylamino-(CH$_2$)$_3$ | H | H | H | NHSO$_2$-n-Bu | |
| 1249m | benzimidazol-2-ylamino-(CH$_2$)$_3$ | H | H | H | NHSO$_2$-i-Bu | |
| 1249n | benzimidazol-2-ylamino-(CH$_2$)$_3$ | H | H | H | NHSO$_2$NHPh | |
| 1249p | benzimidazol-2-ylamino-(CH$_2$)$_3$ | H | H | H | NHSO$_2$NHC$_6$H$_4$-(2-CH$_3$) | |
| 1249q | benzimidazol-2-ylamino-(CH$_2$)$_3$ | H | H | H | NHSO$_2$NHC$_6$H$_4$-(3-CH$_3$) | |
| 1249r | benzimidazol-2-ylamino-(CH$_2$)$_3$ | H | H | H | NHSO$_2$NHC$_6$H$_4$-(4-CH$_3$) | |
| 1249s | benzimidazol-2-ylamino-(CH$_2$)$_3$ | H | H | H | NHSO$_2$NHC$_6$C$_3$-(2,6-Me$_2$) | |
| 1249t | benzimidazol-2-ylamino-(CH$_2$)$_3$ | H | H | H | NHSO$_2$NHC$_6$C$_2$-(2,4,6-Me$_3$) | |
| 1249u | benzimidazol-2-ylamino-(CH$_2$)$_3$ | H | H | H | NHSO$_2$NH(2-naphthyl) | |
| 1249v | benzimidazol-2-ylamino-(CH$_2$)$_3$ | H | H | H | NHSO$_2$NH)1-naphthyl) | |
| 1249w | benzimidazol-2-ylamino-(CH$_2$)$_3$ | H | H | H | NHSO$_2$NHC$_6$H$_4$-(4-Ph) | |
| 1249x | benzimidazol-2-ylamino-(CH$_2$)$_3$ | H | H | H | NHSO$_2$NHC$_6$H$_2$-(4-Ph-2,6-dimethyl) | |
| 1249y | benzimidazol-2-ylamino-(CH$_2$)$_3$ | H | H | H | NHSO$_2$NHC$_6$H$_2$-(4-Ph-2,6-dichloro) | |
| 1249z | benzimidazol-2-ylamino-(CH$_2$)$_3$ | H | H | H | NHSO$_2$NHCH$_2$Ph | |
| 1250 | benzimidazol-2-ylamino-(CH$_2$)$_3$ | H | H | H | NHCO$_2$CH$_2$Ph | |
| 1251 | benzimidazol-2-ylamino-(CH$_2$)$_3$ | H | H | H | NHCO$_2$n-Bu | |
| 1252 | benzimidazol-2-ylamino-(CH$_2$)$_3$ | H | H | H | NHCO$_2$i-Bu | |
| 1253 | 2-aminopyridin-6-yl-(CH$_2$)$_3$ | H | H | H | NHSO$_2$Ph | |
| 1254 | 2-aminopyridin-6-yl-(CH$_2$)$_3$ | H | H | H | NHSO$_2$C$_6$H$_4$-(2-CH$_3$) | |
| 1255 | 2-aminopyridin-6-yl-(CH$_2$)$_3$ | H | H | H | NHSO$_2$C$_6$H$_4$-(3-CH$_3$) | |
| 1256 | 2-aminopyridin-6-yl-(CH$_2$)$_3$ | H | H | H | NHSO$_2$C$_6$H$_4$-(4-CH$_3$) | |
| 1256a | 2-aminopyridin-6-yl-(CH$_2$)$_3$ | H | H | H | NHSO$_2$C$_6$H$_3$-(2,6-Me$_2$) | |
| 1256b | 2-aminopyridin-6-yl-(CH$_2$)$_3$ | H | H | H | NHSO$_2$C$_6$H$_2$-(2,4,6-Me$_3$) | |
| 1257 | 2-aminopyridin-6-yl-(CH$_2$)$_3$ | H | H | H | NHSO$_2$(2-pyridyl) | |
| 1258 | 2-aminopyridin-6-yl-(CH$_2$)$_3$ | H | H | W | NHSO$_2$(3-pyridyl) | |
| 1259 | 2-aminopyridin-6-yl-(CH$_2$)$_3$ | H | H | H | NHSO$_2$(4-pyridyl) | |
| 1260 | 2-aminopyridin-6-yl-(CH$_2$)$_3$ | H | H | H | NHSO$_2$(2-thiazolyl) | |
| 1261 | 2-aminopyridin-6-yl-(CH$_2$)$_3$ | H | H | H | NHSO$_2$(4-isoxazolyl) | |
| 1262 | 2-aminopyridin-6-yl-(CH$_2$)$_3$ | H | H | H | NHSO$_2$-[4-(3,5-dimethyl)isoxazolyl] | |
| 1263 | 2-aminopyridin-6-yl-(CH$_2$)$_3$ | H | H | H | NHSO$_2$C$_6$H$_4$-(2-Br) | |
| 1264 | 2-aminopyridin-6-yl-(CH$_2$)$_3$ | H | H | H | NHSO$_2$C$_6$H$_4$-(3-Br) | |
| 1265 | 2-aminopyridin-6-yl-(CH$_2$)$_3$ | H | H | H | NHSO$_2$C$_6$H$_4$-(2-F) | |
| 1266 | 2-aminopyridin-6-yl-(CH$_2$)$_3$ | H | H | H | NHSO$_2$C$_6$H$_4$-(3-F) | |
| 1267 | 2-aminopyridin-6-yl-(CH$_2$)$_3$ | H | H | H | NHSO$_2$C$_6$H$_4$-(4-F) | |
| 1267a | 2-aminopyridin-6-yl-(CH$_2$)$_3$ | H | H | H | NHSO$_2$C$_6$H$_3$-(2,6-Cl$_2$) | |
| 1267b | 2-aminopyridin-6-yl-(CH$_2$)$_3$ | H | H | H | NHSO$_2$(2-naphthyl) | |
| 1267c | 2-aminopyridin-6-yl-(CH$_2$)$_3$ | H | H | H | NHSO$_2$(1-naphthyl) | |
| 1267d | 2-aminopyridin-6-yl-(CH$_2$)$_3$ | H | H | H | NHSO$_2$C$_6$H$_4$-(4-Ph) | |
| 1267e | 2-aminopyridin-6-yl-(CH$_2$)$_3$ | H | H | H | NHSO$_2$C$_6$H$_2$-(4-Ph-2,6-dimethyl) | |
| 1267f | 2-aminopyridin-6-yl-(CH$_2$)$_3$ | H | H | H | NHSO$_2$C$_6$H$_2$-(4-Ph-2,6-dichloro) | |
| 1267g | 2-aminopyridin-6-yl-(CH$_2$)$_3$ | H | H | H | NHSO$_2$CH=CHPh | |
| 1267h | 2-aminopyridin-6-yl-(CH$_2$)$_3$ | H | H | H | NHSO$_2$CH$_2$Ph | |
| 1267j | 2-aminopyridin-6-yl-(CH$_2$)$_3$ | H | H | H | NHSO$_2$CH$_2$CH=CHPh | |

TABLE 1-continued

| Ex. No. | R¹ | R¹⁰ | R¹³ | R¹⁴ | R¹⁵ | MS |
|---|---|---|---|---|---|---|
| 1267k | 2-aminopyridin-6-yl-$(CH_2)_3$ | H | H | H | $NHSO_2$-n-Bu | |
| 1267m | 2-aminopyridin-6-yl-$(CH_2)_3$ | H | H | H | $NHSO_2$-i-Bu | |
| 1267n | 2-aminopyridin-6-yl-$(CH_2)_3$ | H | H | H | $NHSO_2NHPh$ | |
| 1267p | 2-aminopyridin-6-yl-$(CH_2)_3$ | H | H | H | $NHSO_2NHC_6H_4$-(2-$CH_3$) | |
| 1267q | 2-aminopyridin-6-yl-$(CH_2)_3$ | H | H | H | $NHSO_2NHC_6H_4$-(3-$CH_3$) | |
| 1267r | 2-aminopyridin-6-yl-$(CH_2)_3$ | H | H | H | $NHSO_2NHC_6H_4$-(4-$CH_3$) | |
| 1267s | 2-aminopyridin-6-yl-$(CH_2)_3$ | H | H | H | $NHSO_2NHC_6C_3$-(2,6-$Me_2$) | |
| 1267t | 2-aminopyridin-6-yl-$(CH_2)_3$ | H | H | H | $NHSO_2NHC_6C_2$-(2,4,6-$Me_3$) | |
| 1267u | 2-aminopyridin-6-yl-$(CH_2)_3$ | H | H | H | $NHSO_2NH$(2-naphthyl) | |
| 1267v | 2-aminopyridin-6-yl-$(CH_2)_3$ | H | H | H | $NHSO_2NH$)1-naphthyl) | |
| 1267w | 2-aminopyridin-6-yl-$(CH_2)_3$ | H | H | H | $NHSO_2NHC_6H_4$-(4-Ph) | |
| 1267x | 2-aminopyridin-6-yl-$(CH_2)_3$ | H | H | H | $NHSO_2NHC_6H_2$-(4-Ph-2,6-dimethyl) | |
| 1267y | 2-aminopyridin-6-yl-$(CH_2)_3$ | H | H | H | $NHSO_2NHC_6H_2$-(4-Ph-2,6-dichloro) | |
| 1268 | 2-aminopyridin-6-yl-$(CH_2)_3$ | H | H | H | $NHCO_2CH_2Ph$ | |
| 1269 | 2-aminopyridin-6-yl-$(CH_2)_3$ | H | H | H | $NHCO_2$n-Bu | |
| 1270 | 2-aminopyridin-6-yl-$(CH_2)_3$ | H | H | H | $NHCO_2$i-Bu | |
| 1271 | 2-iminoazepin-7-yl-$(CH_2)_3$ | H | H | H | $NHSO_2Ph$ | |
| 1274 | imidazol-4-ylamino-$(CH_2)_3$ | H | H | H | $NHSO_2Ph$ | |
| 1279 | 2-iminoazepin-7-yl-$(CH_2)_3$ | H | H | H | $NHSO_2$(4-isoxazolyl) | |
| 1282 | imidazol-4-ylamino-$(CH_2)_3$ | H | H | H | $NHSO_2$(4-isoxazolyl) | |
| 1287 | 2-iminoazepin-7-yl-$(CH_2)_3$ | H | H | H | $NHSO_2$-[4-(3,5-dimethyl)isoxazolyl] | |
| 1290 | imidazol-4-ylamino-$(CH_2)_3$ | H | H | H | $NHSO_2$-[4-(3,5-dimethyl)isoxazolyl] | |
| 1295 | imidazol-2-ylamino-$(CH_2)_3$ | H | H | 3-pyridinyl | H | |
| 1296 | pyridin-2-ylamino-$(CH_2)_3$ | H | H | 3-pyridinyl | H | |
| 1297 | imidazolin-2-ylamino-$(CH_2)_3$ | H | H | 3-pyridinyl | H | |
| 1298 | tetrahydropyrimidin-2-ylamino-$(CH_2)_3$ | H | H | 3-pyridinyl | H | |
| 1299 | benzimidazol-2-ylamino-$(CH_2)_3$ | H | H | 3-pyridinyl | H | |
| 1300 | 2-aminopyridin-6-yl-$(CH_2)_3$ | H | H | 3-pyridinyl | H | |
| 1301 | 2-iminoazepin-7-yl-$(CH_2)_3$ | H | H | 3-pyridinyl | H | |
| 1304 | imidazol-4-ylamino-$(CH_2)_3$ | H | H | 3-pyridinyl | H | |
| 1309 | imidazol-2-ylamino-$(CH_2)_3$ | H | H | (3,4-methylene-dioxy)phenyl | H | |
| 1310 | pyridin-2-ylamino-$(CH_2)_3$ | H | H | (3,4-methylene-dioxy)phenyl | H | |
| 1311 | imidazolin-2-ylamino-$(CH_2)_3$ | H | H | (3,4-methylene-dioxy)phenyl | H | |
| 1312 | tetrahydropyrimidin-2-ylamino-$(CH_2)_3$ | H | H | (3,4-methylene-dioxy)phenyl | H | |
| 1313 | benzimidazol-2-ylamino-$(CH_2)_3$ | H | H | (3,4-methylene-dioxy)phenyl | H | |
| 1314 | 2-aminopyridin-6-yl-$(CH_2)_3$ | H | H | (3,4-methylene-dioxy)phenyl | H | |
| 1315 | 2-iminoazepin-7-yl-$(CH_2)_3$ | H | H | (3,4-methylene-dioxy)phenyl | H | |
| 1318 | imidazol-4-ylamino-$(CH_2)_3$ | H | H | (3,4-methylene-dioxy)phenyl | H | |
| 1323 | imidazol-2-ylamino-$(CH_2)_3$ | H | H | 3-pyridinyl | $NHSO_2Ph$ | |
| 1324 | pyridin-2-ylamino-$(CH_2)_3$ | H | H | 3-pyridinyl | $NHSO_2Ph$ | |
| 1325 | imidazol-2-ylamino-$(CH_2)_3$ | H | H | (3,4-methylene-dioxy)phenyl | $NHSO_2Ph$ | |
| 1326 | pyridin-2-ylamino-$(CH_2)_3$ | H | H | (3,4-methylene-dioxy)phenyl | $NHSO_2Ph$ | |
| 1326a | pyridinyl-2-ylamino$(CH_2)_2CH(Ph)$ | H | H | H | $NHSO_2C_6H_2$-(2,4,6-$CH_3)_3$ | 641.4 |
| 1326b | pyridin-2-ylamino-$(CH_2)_2CH(CH_3)$ | H | H | H | $NHSO_2C_6H_2$-(2,4,6-$CH_3)_3$ | 579.4 |
| 1326c | pyridin-2-ylamino-$CH_2CH(CH_3)CH_2$ | H | H | H | $NHSO_2C_6H_2$-(2,4,6-$CH_3)_3$ | 579.5 |
| 1326d | pyridin-2-ylamino-$(CH_2)_3$ | $CH_3$ | H | H | $NHSO_2C_6H_2$-(2,4,6-$CH_3)_3$ | |
| 1326e | pyridin-2-ylamino-$(CH_2)_3$ | $C_2H_5$ | H | H | $NHSO_2C_6H_2$-(2,4,6-$CH_3)_3$ | |
| 1326f | pyridin-2-ylamino-$(CH_2)_3$ | Ph | H | H | $NHSO_2C_6H_2$-(2,4,6-$CH_3)_3$ | 641.4 |
| 1326g | pyridin-2-ylamino-$(CH_2)_3$ | $CH_2CH_2Ph$ | H | H | $NHSO_2C_6H_2$-(2,4,6-$CH_3)_3$ | 669.5 |
| 1326h | pyridin-2-ylamino-$(CH_2)_3$ | H | $CH_3$ | H | $NHSO_2C_6H_2$-(2,4,6-$CH_3)_3$ | 579.4 |
| 1326i | imidazol-2-ylamino-$(CH_2)_2$ | H | H | Me | $NHSO_2C_6H_2$-(2,4,6-$CH_3)_3$ | 568.3 |

TABLE 1-continued

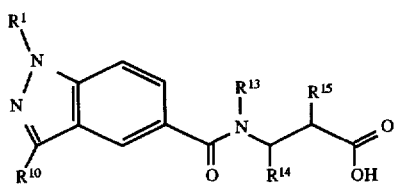

| Ex. No. | R¹ | R¹⁰ | R¹³ | R¹⁴ | R¹⁵ | MS |
|---|---|---|---|---|---|---|
| 1327 | imidazol-2-ylamino-$(CH_2)_2$ | H | H | H | $NHSO_2Ph$ | |
| 1327a | imidazol-2-ylamino-$(CH_2)_2$ | H | H | H | $NHCO_2CH_2Ph$ | |
| 1327b | imidazol-2-ylamino-carbonyl-$(CH_2)_2$ | H | H | H | $NHSO_2C_6H_2$-$(2,4,6$-$CH_3)_3$ | 568.5 |
| 1328 | pyridin-2-ylamino-$(CH_2)_2$ | H | H | H | $NHSO_2Ph$ | |
| 1328a | pyridin-2-ylamino-$(CH_2)_2$ | H | H | H | $NHCO_2CH_2Ph$ | |
| 1328b | pyridin-2-ylamino-carbonyl-$(CH_2)_2$ | H | H | H | $NHSO_2C_6H_2$-$(2,4,6$-$CH_3)_3$ | |
| 1329 | imidazolin-2-ylamino-$(CH_2)_2$ | H | H | H | $NHSO_2Ph$ | |
| 1329a | imidazolin-2-ylamino-$(CH_2)_2$ | H | H | H | $NHCO_2CH_2Ph$ | 494.3 |
| 1330 | tetrahydropyrimidin-2-ylamino-$(CH_2)_2$ | H | H | H | $NHSO_2Ph$ | |
| 1330a | tetrahydropyrimidin-2-ylamino-$(CH_2)_2$ | H | H | H | $NHCO_2CH_2Ph$ | |
| 1331 | benzimidazol-2-ylamino-$(CH_2)_2$ | H | H | H | $NHSO_2Ph$ | |
| 1331a | benzimidazol-2-ylamino-$(CH_2)_2$ | H | H | H | $NHCO_2CH_2Ph$ | |
| 1331b | benzimidazol-2-ylamino-carbonyl-$(CH_2)_2$ | H | H | H | $NHSO_2C_6H_2$-$(2,4,6$-$CH_3)_3$ | |
| 1332 | 2-aminopyridin-6-yl-$(CH_2)_2$ | H | H | H | $NHSO_2Ph$ | |
| 1332a | 2-aminopyridin-6-yl-$(CH_2)_2$ | H | H | H | $NHCO_2CH_2Ph$ | |
| 1333 | 2-iminoazepin-7-yl-$(CH_2)_2$ | H | H | H | $NHSO_2Ph$ | |
| 1333a | 2-iminoazepin-7-yl-$(CH_2)_2$ | H | H | H | $NHCO_2CH_2Ph$ | |
| 1336 | imidazol-4-ylamino-$(CH_2)_2$ | H | H | H | $NHSO_2Ph$ | |
| 1336a | imidazol-4-ylamino-$(CH_2)_2$ | H | H | H | $NHCO_2CH_2Ph$ | |
| 1341 | imidazol-2-ylamino-$(CH_2)_4$ | H | H | H | $NHSO_2Ph$ | |
| 1341a | imidazol-2-ylamino-$(CH_2)_4$ | H | H | H | $NHCO_2CH_2Ph$ | |
| 1342 | pyridin-2-ylamino-$(CH_2)_4$ | H | H | H | $NHSO_2Ph$ | |
| 1342a | pyridin-2-ylamino-$(CH_2)_4$ | H | H | H | $NHCO_2CH_2Ph$ | |
| 1343 | imidazolin-2-ylamino-$(CH_2)_4$ | H | H | H | $NHSO_2Ph$ | |
| 1343a | imidazolin-2-ylamino-$(CH_2)_4$ | H | H | H | $NHCO_2CH_2Ph$ | 522.3 |
| 1344 | tetrahydropyrimidin-2-ylamino-$(CH_2)_4$ | H | H | H | $NHSO_2Ph$ | |
| 1344a | tetrahydropyrimidin-2-ylamino-$(CH_2)_4$ | H | H | H | $NHCO_2CH_2Ph$ | |
| 1345 | benzimidazol-2-ylamino-$(CH_2)_4$ | H | H | H | $NHSO_2Ph$ | |
| 1345a | benzimidazol-2-ylamino-$(CH_2)_4$ | H | H | H | $NHCO_2CH_2Ph$ | |
| 1346 | 2-aminopyridin-6-yl-$(CH_2)_4$ | H | H | H | $NHSO_2Ph$ | |
| 1346a | 2-aminopyridin-6-yl-$(CH_2)_4$ | H | H | H | $NHCO_2CH_2Ph$ | |
| 1347 | 2-iminoazepin-7-yl-$(CH_2)_4$ | H | H | H | $NHSO_2Ph$ | |
| 1347a | 2-iminoazepin-7-yl-$(CH_2)_4$ | H | H | H | $NHCO_2CH_2Ph$ | |
| 1350 | imidazol-4-ylamino-$(CH_2)_4$ | H | H | H | $NHSO_2Ph$ | |
| 1350a | imidazol-4-ylamino-$(CH_2)_4$ | H | H | H | $NHCO_2CH_2Ph$ | |
| 1351 | imidazol-2-ylamino-$CH_2(o$-$C_6H_4)$—$CH_2$ | H | H | H | $NHSO_2$-$(1$-naphthyl$)$ | |
| 1352 | imidazol-2-ylamino-$CH_2(o$-$C_6H_4)$—$CH_2$ | H | H | H | $NHCO_2CH_2Ph$ | |
| 1353 | imidazol-2-ylamino-$CH_2(o$-$C_6H_4)$—$CH_2$ | H | H | H | $NHSO_2C_6C_2$-$(2,4,6$-$Me_3)$ | |
| 1354 | pyridin-2-ylamino-$CH_2(o$-$C_6H_4)$—$CH_2$ | H | H | H | $NHSO_2$-$(1$-naphthyl$)$ | |
| 1355 | pyridin-2-ylamino-$CH_2(o$-$C_6H_4)$—$CH_2$ | H | H | H | $NHCO_2CH_2Ph$ | |
| 1356 | pyridin-2-ylamino-$CH_2(o$-$C_6H_4)$—$CH_2$ | H | H | H | $NHSO_2C_6C_2$-$(2,4,6$-$Me_3)$ | |
| 1357 | imidazolin-2-ylamino-$CH_2(o$-$C_6H_4)$—$CH_2$ | H | H | H | $NHSO_2$-$(1$-naphthyl$)$ | |
| 1358 | imidazolin-2-ylamino-$CH_2(o$-$C_6H_4)$—$CH_2$ | H | H | H | $NHCO_2CH_2Ph$ | |
| 1359 | imidazolin-2-ylamino-$CH_2(o$-$C_6H_4)$—$CH_2$ | H | H | H | $NHSO_2C_6C_2$-$(2,4,6$-$Me_3)$ | |
| 1360 | imidazolin-2-ylamino-$(o$-$C_6H_4)$—$CH_2$ | H | H | H | $NHSO_2$-$(1$-naphthyl$)$ | |
| 1361 | imidazolin-2-ylamino-$(o$-$C_6H_4)$—$CH_2$ | H | H | H | $NHCO_2CH_2Ph$ | |
| 1362 | imidazolin-2-ylamino-$(o$-$C_6H_4)$—$CH_2$ | H | H | H | $NHSO_2C_6H_2$-$(2,4,6$-$Me_3)$ | |

TABLE 2

| Ex. No. | R$^{1a}$ | R$^{10}$ | R$^{13}$ | R$^{14}$ | R$^{15}$ | MS |
|---|---|---|---|---|---|---|
| 2001 | imidazol-2-ylamino-(CH$_2$)$_3$ | H | H | H | H | |
| 2002 | pyridin-2-ylamino-(CH$_2$)$_3$ | H | H | H | NHCOOCH$_2$Ph | |
| 2003 | imidazolin-2-yl amino-(CH$_2$)$_3$ | H | H | H | NHCO$_2$CH$_2$C$_6$H$_4$-(2-CH$_3$) | |
| 2004 | tetrahydropyrimidin-2-ylamino-(CH$_2$)$_3$ | H | H | H | NHCO$_2$CH$_2$C$_6$H$_4$-(3-CH$_3$) | |
| 2005 | benzimidazol-2-ylamino-(CH$_2$)$_3$ | H | H | H | NHCO$_2$CH$_2$C$_6$H$_4$-(4-CH$_3$) | |
| 2006 | 2-aminopyridin-6-yl-(CH$_2$)$_3$ | H | H | H | NHCO$_2$CH$_2$(2-pyridinyl) | |
| 2007 | 2-iminoazepin-7-yl-(CH$_2$)$_3$ | H | H | H | NHCO$_2$CH$_2$(3-pyridinyl) | |
| 2010 | imidazol-4-ylamino-(CH$_2$)$_3$ | H | H | H | NHCO$_2$CH$_2$(2-thiazolyl) | |
| 2015 | imidazol-2-ylamino-(CH$_2$)$_3$ | H | H | H | NHCO$_2$CH$_2$(4-isoxazolyl) | |
| 2016 | pyridin-2-ylamino-(CH$_2$)$_3$ | H | H | H | NHCO$_2$CH$_2$(2-thienyl) | |
| 2017 | imidazolin-2-ylamino-(CH$_2$)$_3$ | H | H | H | NHCO$_2$n-Bu | |
| 2018 | tetrahydropyrimidin-2-ylamino-(CH$_2$)$_3$ | H | H | H | NHCO$_2$i-Bu | |
| 2019 | benzimidazol-2-ylamino-(CH$_2$)$_3$ | H | H | H | NHCO$_2$t-Bu | |
| 2020 | 2-aminopyridin-6-yl-(CH$_2$)$_3$ | H | H | H | NHSO$_2$Ph | |
| 2021 | 2-iminoazepin-7-yl-(CH$_2$)$_3$ | H | H | H | NHSO$_2$C$_6$H$_4$-(2-CH$_3$) | |
| 2024 | imidazol-4-ylamino-(CH$_2$)$_3$ | H | H | H | NHSO$_2$(2-pyridyl) | |
| 2029 | imidazol-2-ylamino-(CH$_2$)$_3$ | H | H | H | NHSO$_2$(4-isoxazolyl) | |
| 2030 | pyridin-2-ylamino-(CH$_2$)$_3$ | H | H | H | NHSO$_2$-[4-(3,5-dimethyl)isoxazolyl] | |
| 2031 | imidazolin-2-ylamino-(CH$_2$)$_3$ | H | H | H | NHSO$_2$C$_6$H$_4$-(2-Br) | |
| 2032 | tetrahydropyrimidin-2-ylamino-(CH$_2$)$_3$ | H | H | H | NHSO$_2$C$_6$H$_4$-(3-Br) | |
| 2033 | benzimidazol-2-ylamino-(CH$_2$)$_3$ | H | H | H | NHSO$_2$C$_6$H$_4$-(4-Br) | |
| 2034 | 2-aminopyridin-6-yl-(CH$_2$)$_3$ | H | H | H | NHSO$_2$C$_6$H$_4$-(2-F) | |
| 2035 | 2-iminoazepin-7-yl-(CH$_2$)$_3$ | H | H | H | NHSO$_2$C$_6$H$_4$-(3-F) | |
| 2038 | imidazol-4-ylamino-(CH$_2$)$_3$ | H | H | H | NHSO$_2$(1-naphthyl) | |
| 2043 | imidazol-2-ylamino-(CH$_2$)$_3$ | H | H | H | NHSO$_2$-i-Bu | |
| 2044 | pyridin-2-ylamino-(CH$_2$)$_3$ | H | H | H | NHSO$_2$-t-Bu | |
| 2045 | imidazol-2-ylamino-(CH$_2$)$_3$ | H | H | (3,4-methylenedioxy)phenyl | H | |
| 2046 | pyridin-2-ylamino-(CH$_2$)$_3$ | H | H | (3,4-methylenedioxy)phenyl | H | |
| 2047 | imidazolin-2-ylamino-(CH$_2$)$_3$ | H | H | (3,4-methylenedioxy)phenyl | H | |
| 2048 | tetrahydropyrimidin-2-ylamino-(CH$_2$)$_3$ | H | H | (3,4-methylenedioxy)phenyl | H | |
| 2049 | benzimidazol-2-ylamino-(CH$_2$)$_3$ | H | H | (3,4-methylenedioxy)phenyl | H | |
| 2050 | 2-aminopyridin-6-yl-(CH$_2$)$_3$ | H | H | (3,4-methylenedioxy)phenyl | H | |
| 2051 | 2-iminoazepin-7-yl-(CH$_2$)$_3$ | H | H | (3,4-methylenedioxy)phenyl | H | |
| 2054 | imidazol-4-ylamino-(CH$_2$)$_3$ | H | H | (3,4-methylenedioxy)phenyl | H | |
| 2059 | imidazol-2-ylamino-(CH$_2$)$_3$ | H | H | 3-pyridinyl | H | |
| 2060 | pyridin-2-ylamino-(CH$_2$)$_3$ | H | H | 3-pyridinyl | H | |
| 2061 | imidazolin-2-ylamino-(CH$_2$)$_3$ | H | H | 3-pyridinyl | H | |
| 2062 | tetrahydropyrimidin-2-ylamino-(CH$_2$)$_3$ | H | H | 3-pyridinyl | H | |
| 2063 | benzimidazol-2-ylamino-(CH$_2$)$_3$ | H | H | 3-pyridinyl | H | |
| 2064 | 2-aminopyridin-6-yl-(CH$_2$)$_3$ | H | H | 3-pyridinyl | H | |
| 2065 | 2-iminoazepin-7-yl-(CH$_2$)$_3$ | H | H | 3-pyridinyl | H | |
| 2068 | imidazol-4-ylamino-(CH$_2$)$_3$ | H | H | 3-pyridinyl | H | |
| 2073 | imidazolin-2-ylamino-(CH$_2$)$_3$ | H | H | H | NHCOOCH$_2$Ph | 508.3 |
| 2075 | imidazol-2-ylamino-(CH$_2$)$_3$ | H | H | H | NHCO$_2$CH$_2$Ph | |
| 2076 | imidazol-2-ylamino-(CH$_2$)$_3$ | H | H | H | NHCO$_2$CH$_2$C$_6$H$_4$-(3-CH$_3$) | |
| 2077 | imidazol-2-ylamino-(CH$_2$)$_3$ | H | H | H | NHCO$_2$CH$_2$(3-pyridinyl) | |

TABLE 2-continued

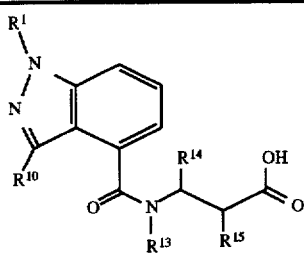

| Ex. No. | R¹ᵃ | R¹⁰ | R¹³ | R¹⁴ | R¹⁵ | MS |
|---|---|---|---|---|---|---|
| 2078 | imidazol-2-ylamino-(CH₂)₃ | H | H | H | NHCO₂CH₂(2-thiazolyl) | |
| 2079 | imidazol-2-ylamino-(CH₂)₃ | H | H | H | NHCO₂CH₂(2-thienyl) | |
| 2080 | imidazol-2-ylamino-(CH₂)₃ | H | H | H | NHCO₂CH₂(5-isoxazolyl) | |
| 2081 | imidazol-2-ylamino-(CH₂)₃ | H | H | H | NHCO₂n-Bu | |
| 2082 | imidazol-2-ylamino-(CH₂)₃ | H | H | H | NHCOPh | |
| 2083 | imidazol-2-ylamino-(CH₂)₃ | H | H | H | NHCOCH₂Ph | |
| 2084 | imidazol-2-ylamino-(CH₂)₃ | H | H | H | NHCOCH₂CH₂Ph | |
| 2085 | imidazol-2-ylamino-(CH₂)₃ | H | H | H | NHCOCH=CHPh | |
| 2086 | imidazol-2-ylamino-(CH₂)₃ | H | H | H | NHCOCH₂(3-pyridinyl) | |
| 2087 | imidazol-2-ylamino-(CH₂)₃ | H | H | H | NHCOCH₂(2-thienyl) | |
| 2088 | imidazol-2-ylamino-(CH₂)₃ | H | H | H | NHCOCH₂(cyclohexyl) | |
| 2089 | imidazol-2-ylamino-(CH₂)₃ | H | H | H | NHCOn-Bu | |
| 2090 | imidazol-2-ylamino-(CH₂)₃ | H | H | H | NHCONHCH₂Ph | |
| 2091 | imidazol-2-ylamino-(CH₂)₃ | H | H | H | NHSO₂Ph | |
| 2092 | imidazol-2-ylamino-(CH₂)₃ | H | H | H | NHSO₂C₆H₄-(4-CH₃) | |
| 2093 | imidazol-2-ylamino-(CH₂)₃ | H | H | H | NHSO₂C₆H₃-(2,6-CH₃)₂ | 540.3 |
| 2094 | imidazol-2-ylamino-(CH₂)₃ | H | H | H | NHSO₂C₆H₂-(2,4,6-CH₃)₃ | 554.4 |
| 2095 | imidazol-2-ylamino-(CH₂)₃ | H | H | H | NHSO₂(3-pyridyl) | |
| 2096 | imidazol-2-ylamino-(CH₂)₃ | H | H | H | NHSO₂(2-thienyl) | |
| 2097 | imidazol-2-ylamino-(CH₂)₃ | H | H | H | NHSO₂(2-thiazolyl) | |
| 2098 | imidazol-2-ylamino-(CH₂)₃ | H | H | H | NHSO₂[4-(3,5-dimethyl)isoxazolyl] | |
| 2099 | imidazol-2-ylamino-(CH₂)₃ | H | H | H | NHSO₂C₆H₄-(4-Br) | |
| 2100 | imidazol-2-ylamino-(CH₂)₃ | H | H | H | NHSO₂C₆H₄-(4-F) | |
| 2101 | imidazol-2-ylamino-(CH₂)₃ | H | H | H | NHSO₂C₆H₃-(2,6-Cl₂) | |
| 2102 | imidazol-2-ylamino-(CH₂)₃ | H | H | H | NHSO₂(2-naphthyl) | |
| 2103 | imidazol-2-ylamino-(CH₂)₃ | H | H | H | NHSO₂(1-naphthyl) | 562.4 |
| 2104 | imidazol-2-ylamino-(CH₂)₃ | H | H | H | NHSO₂C₆H₄-4-Ph | 588.4 |
| 2104a | imidazol-2-ylamino-(CH₂)₃ | H | H | H | NHSO₂C₆H₄-4-(4-pyridyl) | |
| 2104b | imidazol-2-ylamino-(CH₂)₃ | H | H | H | NHSO₂C₆H₄-4-(2-oxazolyl) | |
| 2104c | imidazol-2-ylamino-(CH₂)₃ | H | H | H | NHSO₂C₆H₄-4-(3-pyrazolyl) | |
| 2105 | imidazol-2-ylamino-(CH₂)₃ | H | H | H | NHSO₂C₆H₂-4-Ph-2,6-dimethyl | 616.3 |
| 2105a | imidazol-2-ylamino-(CH₂)₃ | H | H | H | NHSO₂C₆H₂-4-(3-pyridyl)-2,6-dimethyl | |
| 2105b | imidazol-2-ylamino-(CH₂)₃ | H | H | H | NHSO₂C₆H₂-4-(2-oxazolyl)-2,6-dimethyl | |
| 2105c | imidazol-2-ylamino-(CH₂)₃ | H | H | H | NHSO₂C₆H₂-4-(3-pyrazolyl)-2,6-dimethyl | |
| 2106 | imidazol-2-ylamino-(CH₂)₃ | H | H | H | NHSO₂C₆H₂-4-Ph-2,6-dichloro | |
| 2107 | imidazol-2-ylamino-(CH₂)₃ | H | H | H | NHSO₂C₆H-4-Ph-2,6-dimethyl-3-chloro | |
| 2108 | imidazol-2-ylamino-(CH₂)₃ | H | H | H | NHSO₂CH₂Ph | |
| 2109 | imidazol-2-ylamino-(CH₂)₃ | H | H | H | NHSO₂-n-Bu | |
| 2110 | imidazol-2-ylamino-(CH₂)₃ | H | H | H | NHSO₂NHPh | |
| 2111 | imidazol-2-ylamino-(CH₂)₃ | H | H | H | NHSO₂NHC₆H₄-(4-CH₃) | |
| 2112 | imidazol-2-ylamino-(CH₂)₃ | H | H | H | NHSO₂NHC₆C₃-(2,6-Me₂) | |
| 2113 | imidazol-2-ylamino-(CH₂)₃ | H | H | H | NHSO₂NHC₆C₂-(2,4,6-Me₃) | |
| 2114 | imidazol-2-ylamino-(CH₂)₃ | H | H | H | NHSO₂NH(3-pyridyl) | |
| 2115 | imidazol-2-ylamino-(CH₂)₃ | H | H | H | NHSO₂[4-(3,5-dimethyl)isoxazolyl] | |
| 2116 | imidazol-2-ylamino-(CH₂)₃ | H | H | H | NHSO₂NHC₆H₄-(4-Br) | |
| 2117 | imidazol-2-ylamino-(CH₂)₃ | H | H | H | NHSO₂NHC₆H₄-(4-F) | |
| 2118 | imidazol-2-ylamino-(CH₂)₃ | H | H | H | NHSO₂NH(2-naphthyl) | |
| 2119 | imidazol-2-ylamino-(CH₂)₃ | H | H | H | NHSO₂NH(1-naphthyl) | |
| 2120 | imidazol-2-ylamino-(CH₂)₃ | H | H | H | NHSO₂NHC₆H₄-(4-Ph) | |
| 2121 | imidazol-2-ylamino-(CH₂)₃ | H | H | H | NHSO₂NHC₆H₂-(4-Ph-2,6-dimethyl) | |

TABLE 2-continued

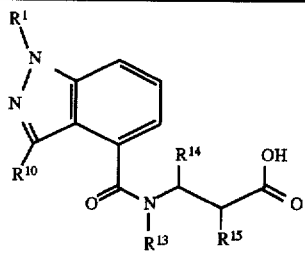

| Ex. No. | $R^{1a}$ | $R^{10}$ | $R^{13}$ | $R^{14}$ | $R^{15}$ | MS |
|---|---|---|---|---|---|---|
| 2122 | imidazol-2-ylamino-$(CH_2)_3$ | H | H | H | $NHSO_2NHC_6H_2$-(4-Ph-2,6-dichloro) | |
| 2123 | imidazol-2-ylamino-$(CH_2)_3$ | H | H | H | $NHSO_2NHCH_2Ph$ | |
| 2124 | imidazol-2-ylamino-$(CH_2)_3$ | H | H | H | $NHSO_2NH$-n-Bu | |
| 2125 | pyridin-2-ylamino-$(CH_2)_3$ | H | H | H | $NHCO_2CH_2C_6H_4$-(3-$CH_3$) | |
| 2126 | pyridin-2-ylamino-$(CH_2)_3$ | H | H | H | $NHCO_2CH_2$(3-pyridinyl) | |
| 2127 | pyridin-2-ylamino-$(CH_2)_3$ | H | H | H | $NHCO_2CH_2$(2-thiazolyl) | |
| 2128 | pyridin-2-ylamino-$(CH_2)_3$ | H | H | H | $NHCO_2CH_2$(4-isoxazolyl) | |
| 2129 | pyridin-2-ylamino-$(CH_2)_3$ | H | H | H | $NHCO_2$i-Bu | |
| 2130 | pyridin-2-ylamino-$(CH_2)_3$ | H | H | H | NHCOPh | |
| 2131 | pyridin-2-ylamino-$(CH_2)_3$ | H | H | H | $NHCOCH_2Ph$ | |
| 2132 | pyridin-2-ylamino-$(CH_2)_3$ | H | H | H | $NHCOCH_2CH_2Ph$ | |
| 2133 | pyridin-2-ylamino-$(CH_2)_3$ | H | H | H | NHCOCH=CHPh | |
| 2134 | pyridin-2-ylamino-$(CH_2)_3$ | H | H | H | $NHCOCH_2$(3-pyridinyl) | |
| 2135 | pyridin-2-ylamino-$(CH_2)_3$ | H | H | H | $NHCOCH_2$(2-thienyl) | |
| 2136 | pyridin-2-ylamino-$(CH_2)_3$ | H | H | H | $NHCOCH_2$(cyclohexyl) | |
| 2137 | pyridin-2-ylamino-$(CH_2)_3$ | H | H | H | NHCOn-Bu | |
| 2138 | pyridin-2-ylamino-$(CH_2)_3$ | H | H | H | $NHCONHCH_2Ph$ | |
| 2139 | pyridin-2-ylamino-$(CH_2)_3$ | H | H | H | $NHSO_2Ph$ | |
| 2140 | pyridin-2-ylamino-$(CH_2)_3$ | H | H | H | $NHSO_2C_6H_4$-(4-$CH_3$) | |
| 2141 | pyridin-2-ylamino-$(CH_2)_3$ | H | H | H | $NHSO_2C_6H_3$-(2,6-$CH_3$)$_2$ | |
| 2142 | pyridin-2-ylamino-$(CH_2)_3$ | H | H | H | $NHSO_2C_6H_2$-(2,4,6-$CH_3$)$_3$ | 565.4 |
| 2143 | pyridin-2-ylamino-$(CH_2)_3$ | H | H | H | $NHSO_2$(3-pyridyl) | |
| 2144 | pyridin-2-ylamino-$(CH_2)_3$ | H | H | H | $NHSO_2$(2-thienyl) | |
| 2145 | pyridin-2-ylamino-$(CH_2)_3$ | H | H | H | $NHSO_2$(2-thiazolyl) | |
| 2146 | pyridin-2-ylamino-$(CH_2)_3$ | H | H | H | $NHSO_2C_6H_4$-(4-Br) | |
| 2147 | pyridin-2-ylamino-$(CH_2)_3$ | H | H | H | $NHSO_2C_6H_4$-(4-F) | |
| 2148 | pyridin-2-ylamino-$(CH_2)_3$ | H | H | H | $NHSO_2C_6H_3$-(2,6-$Cl_2$) | |
| 2149 | pyridin-2-ylamino-$(CH_2)_3$ | H | H | H | $NHSO_2$(2-naphthyl) | |
| 2150 | pyridin-2-ylamino-$(CH_2)_3$ | H | H | H | $NHSO_2$(1-naphthyl) | |
| 2151 | pyridin-2-ylamino-$(CH_2)_3$ | H | H | H | $NHSO_2C_6H_4$-(4-Ph) | |
| 2151a | pyridin-2-ylamino-$(CH_2)_3$ | H | H | H | $NHSO_2C_6H_4$-4-(4-pyridyl) | |
| 2151b | pyridin-2-ylamino-$(CH_2)_3$ | H | H | H | $NHSO_2C_6H_4$-4-(2-oxazolyl) | |
| 2151c | pyridin-2-ylamino-$(CH_2)_3$ | H | H | H | $NHSO_2C_6H_4$-4-(3-pyrazolyl) | |
| 2152 | pyridin-2-ylamino-$(CH_2)_3$ | H | H | H | $NHSO_2C_6H_2$-4-Ph-2,6-dimethyl | |
| 2152a | pyridin-2-ylamino-$(CH_2)_3$ | H | H | H | $NHSO_2C_6H_2$-4-(3-pyridyl)-2,6-dimethyl | |
| 2152b | pyridin-2-ylamino-$(CH_2)_3$ | H | H | H | $NHSO_2C_6H_2$-4-(2-oxazolyl)-2,6-dimethyl | |
| 2152c | pyridin-2-ylamino-$(CH_2)_3$ | H | H | H | $NHSO_2C_6H_2$-4-(3-pyrazolyl)-2,6-dimethyl | |
| 2153 | pyridin-2-ylamino-$(CH_2)_3$ | H | H | H | $NHSO_2C_6H_2$-4-Ph-2,6-dichloro | |
| 2154 | pyridin-2-ylamino-$(CH_2)_3$ | H | H | H | $NHSO_2CH_2Ph$ | |
| 2155 | pyridin-2-ylamino-$(CH_2)_3$ | H | H | H | $NHSO_2$-n-Bu | |
| 2156 | pyridin-2-ylamino-$(CH_2)_3$ | H | H | H | $NHSO_2NHPh$ | |
| 2157 | pyridin-2-ylamino-$(CH_2)_3$ | H | H | H | $NHSO_2NHC_6H_4$-(4-$CH_3$) | |
| 2158 | pyridin-2-ylamino-$(CH_2)_3$ | H | H | H | $NHSO_2NHC_6C_3$-(2,6-$Me_2$) | |
| 2159 | pyridin-2-ylamino-$(CH_2)_3$ | H | H | H | $NHSO_2NHC_6C_2$-(2,4,6-$Me_3$) | |
| 2160 | pyridin-2-ylamino-$(CH_2)_3$ | H | H | H | $NHSO_2NH$(3-pyridyl) | |
| 2161 | pyridin-2-ylamino-$(CH_2)_3$ | H | H | H | $NHSO_2$-[4-(3,5-dimethyl)isoxazolyl] | |
| 2162 | pyridin-2-ylamino-$(CH_2)_3$ | H | H | H | $NHSO_2NHC_6H_4$-(4-Br) | |
| 2163 | pyridin-2-ylamino-$(CH_2)_3$ | H | H | H | $NHSO_2NHC_6H_4$-(4-F) | |
| 2164 | pyridin-2-ylamino-$(CH_2)_3$ | H | H | H | $NHSO_2NH$(2-naphthyl) | |
| 2165 | pyridin-2-ylamino-$(CH_2)_3$ | H | H | H | $NHSO_2NH$)1-naphthyl) | |
| 2166 | pyridin-2-ylamino-$(CH_2)_3$ | H | H | H | $NHSO_2NHC_6H_4$-(4-Ph) | |
| 2167 | pyridin-2-ylamino-$(CH_2)_3$ | H | H | H | $NHSO_2NHC_6H_2$-(4-Ph-2,6- | |

TABLE 2-continued

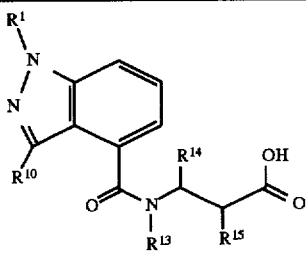

| Ex. No. | $R^{1a}$ | $R^{10}$ | $R^{13}$ | $R^{14}$ | $R^{15}$ | MS |
|---|---|---|---|---|---|---|
| | | | | | dimethyl) | |
| 2168 | pyridin-2-ylamino-$(CH_2)_3$ | H | H | H | $NHSO_2NHC_6H_2$-(4-Ph-2,6-dichloro) | |
| 2169 | pyridin-2-ylamino-$(CH_2)_3$ | H | H | H | $NHSO_2NHCH_2Ph$ | |
| 2170 | pyridin-2-ylamino-$(CH_2)_3$ | H | H | H | $NHSO_2NH$-n-Bu | |
| 2171 | tetrahydropyrimidin-2-ylamino-$(CH_2)_3$ | H | H | H | $NHCOOCH_2Ph$ | |
| 2172 | tetrahydropyrimidin-2-ylamino-$(CH_2)_3$ | H | H | H | $NHCO_2CH_2C_6H_4$-(4-$CH_3$) | |
| 2173 | tetrahydropyrimidin-2-ylamino-$(CH_2)_3$ | H | H | H | $NHCO_2CH_2$(3-pyridinyl) | |
| 2173 | tetrahydropyrimidin-2-ylamino-$(CH_2)_3$ | H | H | H | $NHCO_2CH_2$(2-thiazolyl) | |
| 2175 | tetrahydropyrimidin-2-ylamino-$(CH_2)_3$ | H | H | H | $NHCO_2CH_2$(2-thienyl) | |
| 2176 | tetrahydropyrimidin-2-ylamino-$(CH_2)_3$ | H | H | H | $NHCO_2$-n-Bu | |
| 2177 | tetrahydropyrimidin-2-ylamino-$(CH_2)_3$ | H | H | H | $NHSO_2Ph$ | |
| 2178 | tetrahydropyrimidin-2-ylamino-$(CH_2)_3$ | H | H | H | $NHSO_2C_6H_4$-(4-$CH_3$) | |
| 2179 | tetrahydropyrimidin-2-ylamino-$(CH_2)_3$ | H | H | H | $NHSO_2C_6H_3$-(2,6-$Me_2$) | |
| 2180 | tetrahydropyrimidin-2-ylamino-$(CH_2)_3$ | H | H | H | $NHSO_2C_6H_2$-(2,4,6-$Me_3$) | |
| 2181 | tetrahydropyrimidin-2-ylamino-$(CH_2)_3$ | H | H | H | $NHSO_2$(3-pyridyl) | |
| 2182 | tetrahydropyrimidin-2-ylamino-$(CH_2)_3$ | H | H | H | $NHSO_2$(2-thienyl) | |
| 2183 | tetrahydropyrimidin-2-ylamino-$(CH_2)_3$ | H | H | H | $NHSO_2$(2-thiazolyl) | |
| 2184 | tetrahydropyrimidin-2-ylamino-$(CH_2)_3$ | H | H | H | $NHSO_2C_6H_4$-(2-Br) | |
| 2185 | tetrahydropyrimidin-2-ylamino-$(CH_2)_3$ | H | H | H | $NHSO_2C_6H_4$-(4-F) | |
| 2186 | tetrahydropyrimidin-2-ylamino-$(CH_2)_3$ | H | H | H | $NHSO_2C_6H_3$-(2,6-$Cl_2$) | |
| 2187 | tetrahydropyrimidin-2-ylamino-$(CH_2)_3$ | H | H | H | $NHSO_2$(2-naphthyl) | |
| 2188 | tetrahydropyrimidin-2-ylamino-$(CH_2)_3$ | H | H | H | $NHSO_2$(1-naphthyl) | |
| 2189 | tetrahydropyrimidin-2-ylamino-$(CH_2)_3$ | H | H | H | $NHSO_2C_6H_4$-(4-Ph) | |
| 2189a | tetrahydropyrimidin-2-ylamino-$(CH_2)_3$ | H | H | H | $NHSO_2C_6H_4$-4-(4-pyridyl) | |
| 2189b | tetrahydropyrimidin-2-ylamino-$(CH_2)_3$ | H | H | H | $NHSO_2C_6H_4$-4-(2-oxazolyl) | |
| 2189c | tetrahydropyrimidin-2-ylamino-$(CH_2)_3$ | H | H | H | $NHSO_2C_6H_4$-4-(3-pyrazolyl) | |
| 2190 | tetrahydropyrimidin-2-ylamino-$(CH_2)_3$ | H | H | H | $NHSO_2C_6H_2$-4-Ph-2,6-dimethyl | |
| 2190a | tetrahydropyrimidin-2-ylamino-$(CH_2)_3$ | H | H | H | $NHSO_2C_6H_2$-4-(3-pyridyl)-2,6-dimethyl | |
| 2190b | tetrahydropyrimidin-2-ylamino-$(CH_2)_3$ | H | H | H | $NHSO_2C_6H_2$-4-(2-oxazolyl)-2,6-dimethyl | |
| 2190c | tetrahydropyrimidin-2-ylamino-$(CH_2)_3$ | H | H | H | $NHSO_2C_6H_2$-4-(3-pyrazolyl)-2,6-dimethyl | |
| 2191 | tetrahydropyrimidin-2-ylamino-$(CH_2)_3$ | H | H | H | $NHSO_2C_6H_2$-4-Ph-2,6-dichloro | |
| 2192 | tetrahydropyrimidin-2-ylamino-$(CH_2)_3$ | H | H | H | $NHSO_2CH_2Ph$ | |
| 2193 | tetrahydropyrimidin-2-ylamino-$(CH_2)_3$ | H | H | H | $NHSO_2$-n-Bu | |
| 2194 | tetrahydropyrimidin-2-ylamino-$(CH_2)_3$ | H | H | H | $NHSO_2NHPh$ | |
| 2195 | tetrahydropyrimidin-2-ylamino-$(CH_2)_3$ | H | H | H | $NHSO_2NHC_6H_4$-(4-$CH_3$) | |
| 2196 | tetrahydropyrimidin-2-ylamino-$(CH_2)_3$ | H | H | H | $NHSO_2NHC_6C_3$-(2,6-$Me_2$) | |
| 2197 | tetrahydropyrimidin-2-ylamino-$(CH_2)_3$ | H | H | H | $NHSO_2NHC_6C_2$-(2,4,6-$Me_3$) | |
| 2198 | tetrahydropyrimidin-2-ylamino-$(CH_2)_3$ | H | H | H | $NHSO_2$[4-(3,5-dimethyl)isoxazolyl] | |
| 2199 | tetrahydropyrimidin-2-ylamino-$(CH_2)_3$ | H | H | H | $NHSO_2NH$(2-naphthyl) | |
| 2200 | tetrahydropyrimidin-2-ylamino-$(CH_2)_3$ | H | H | H | $NHSO_2NH$(1-naphthyl) | |
| 2201 | tetrahydropyrimidin-2-ylamino-$(CH_2)_3$ | H | H | H | $NHSO_2NHC_6H_4$-(4-Ph) | |
| 2202 | tetrahydropyrimidin-2-ylamino-$(CH_2)_3$ | H | H | H | $NHSO_2NHC_6H_2$-(4-Ph-2,6-dimethyl) | |
| 2203 | tetrahydropyrimidin-2-ylamino-$(CH_2)_3$ | H | H | H | $NHSO_2NHC_6H_2$-(4-Ph-2,6-dichloro) | |
| 2204 | tetrahydropyrimidin-2-ylamino-$(CH_2)_3$ | H | H | H | $NHSO_2NHCH_2Ph$ | |
| 2205 | imidazolin-2-ylamino-$(CH_2)_3$ | H | H | H | $NHCO_2CH_2C_6H_4$-(4-$CH_3$) | |
| 2206 | imidazolin-2-ylamino-$(CH_2)_3$ | H | H | H | $NHCO_2CH_2$(3-pyridinyl) | |
| 2207 | imidazolin-2-ylamino-$(CH_2)_3$ | H | H | H | $NHCO_2CH_2$(2-thiazolyl) | |
| 2208 | imidazolin-2-ylamino-$(CH_2)_3$ | H | H | H | $NHCO_2CH_2$(2-thienyl) | |
| 2209 | imidazolin-2-ylamino-$(CH_2)_3$ | H | H | H | $NHCO_2$i-Bu | |
| 2210 | imidazolin-2-ylamino-$(CH_2)_3$ | H | H | H | $NHSO_2Ph$ | |

TABLE 2-continued

| Ex. No. | R¹ᵃ | R¹⁰ | R¹³ | R¹⁴ | R¹⁵ | MS |
|---|---|---|---|---|---|---|
| 2211 | imidazolin-2-ylamino-(CH₂)₃ | H | H | H | NHSO₂C₆H₄-(3-CH₃) | |
| 2212 | imidazolin-2-ylamino-(CH₂)₃ | H | H | H | NHSO₂C₆H₃-(2,6-Me₂) | |
| 2213 | imidazolin-2-ylamino-(CH₂)₃ | H | H | H | NHSO₂C₆H₂-(2,4,6-Me₃) | |
| 2214 | imidazolin-2-ylamino-(CH₂)₃ | H | H | H | NHSO₂(3-pyridyl) | |
| 2215 | imidazolin-2-ylamino-(CH₂)₃ | H | H | H | NHSO₂(2-thienyl) | |
| 2216 | imidazolin-2-ylamino-(CH₂)₃ | H | H | H | NHSO₂(2-thiazolyl) | |
| 2217 | imidazolin-2-ylamino-(CH₂)₃ | H | H | H | NHSO₂-[4-(3,5-dimethyl)isoxazolyl] | |
| 2218 | imidazolin-2-ylamino-(CH₂)₃ | H | H | H | NHSO₂C₆H₄-(3-Br) | |
| 2218 | imidazolin-2-ylamino-(CH₂)₃ | H | H | H | NHSO₂C₆H₄-(4-F) | |
| 2219 | imidazolin-2-ylamino-(CH₂)₃ | H | H | H | NHSO₂C₆H₃-(2,6-Cl₂) | |
| 2220 | imidazolin-2-ylamino-(CH₂)₃ | H | H | H | NHSO₂(2-naphthyl) | |
| 2221 | imidazolin-2-ylamino-(CH₂)₃ | H | H | H | NHSO₂(1-naphthyl) | |
| 2222 | imidazolin-2-ylamino-(CH₂)₃ | H | H | H | NHSO₂C₆H₄-(4-Ph) | |
| 2222a | imidazolin-2-ylamino-(CH₂)₃ | H | H | H | NHSO₂C₆H₄-4-(4-pyridyl) | |
| 2222b | imidazolin-2-ylamino-(CH₂)₃ | H | H | H | NHSO₂C₆H₄-4-(2-oxazolyl) | |
| 2222c | imidazolin-2-ylamino-(CH₂)₃ | H | H | H | NHSO₂C₆H₄-4-(3-pyrazolyl) | |
| 2223 | imidazolin-2-ylamino-(CH₂)₃ | H | H | H | NHSO₂C₆H₂-4-Ph-2,6-dimethyl | |
| 2223a | imidazolin-2-ylamino-(CH₂)₃ | H | H | H | NHSO₂C₆H₂-4-(3-pyridyl)-2,6-dimethyl | |
| 2223b | imidazolin-2-ylamino-(CH₂)₃ | H | H | H | NHSO₂C₆H₂-4-(2-oxazolyl)-2,6-dimethyl | |
| 2223c | imidazolin-2-ylamino-(CH₂)₃ | H | H | H | NHSO₂C₆H₂-4-(3-pyrazolyl)-2,6-dimethyl | |
| 2224 | imidazolin-2-ylamino-(CH₂)₃ | H | H | H | NHSO₂C₆H₂-4-Ph-2,6-dichloro | |
| 2225 | imidazolin-2-ylamino-(CH₂)₃ | H | H | H | NHSO₂CH₂Ph | |
| 2226 | imidazolin-2-ylamino-(CH₂)₃ | H | H | H | NHSO₂-n-Bu | |
| 2227 | imidazolin-2-ylamino-(CH₂)₃ | H | H | H | NHSO₂NHPh | |
| 2228 | imidazolin-2-ylamino-(CH₂)₃ | H | H | H | NHSO₂NHC₆H₄-(4-CH₃) | |
| 2229 | imidazolin-2-ylamino-(CH₂)₃ | H | H | H | NHSO₂NHC₆C₃-(2,6-Me₂) | |
| 2230 | imidazolin-2-ylamino-(CH₂)₃ | H | H | H | NHSO₂NHC₆C₂-(2,4,6-Me₃) | |
| 2231 | imidazolin-2-ylamino-(CH₂)₃ | H | H | H | NHSO₂NH(2-naphthyl) | |
| 2232 | imidazolin-2-ylamino-(CH₂)₃ | H | H | H | NHSO₂NH)1-naphthyl) | |
| 2233 | imidazolin-2-ylamino-(CH₂)₃ | H | H | H | NHSO₂NHC₆H₄-(4-Ph) | |
| 2234 | imidazolin-2-ylamino-(CH₂)₃ | H | H | H | NHSO₂NHC₆H₂-4-Ph-2,6-dimethyl | |
| 2235 | imidazolin-2-ylamino-(CH₂)₃ | H | H | H | NHSO₂NHC₆H₂-4-Ph-2,6-dichloro | |
| 2236 | imidazolin-2-ylamino-(CH₂)₃ | H | H | H | NHSO₂NHCH₂Ph | |
| 2237 | benzimidazol-2-ylamino-(CH₂)₃ | H | H | H | NHSO₂Ph | |
| 2238 | benzimidazol-2-ylamino-(CH₂)₃ | H | H | H | NHSO₂C₆H₄-(3-CH₃) | |
| 2239 | benzimidazol-2-ylamino-(CH₂)₃ | H | H | H | NHSO₂C₆H₃-(2,6-Me₂) | |
| 2240 | benzimidazol-2-ylamino-(CH₂)₃ | H | H | H | NHSO₂C₆H₂-(2,4,6-Me₃) | |
| 2241 | benzimidazol-2-ylamino-(CH₂)₃ | H | H | H | NHSO₂(4-pyridyl) | |
| 2242 | benzimidazol-2-ylamino-(CH₂)₃ | H | H | H | NHSO₂(2-thienyl) | |
| 2243 | benzimidazol-2-ylamino-(CH₂)₃ | H | H | H | NHSO₂(2-thiazolyl) | |
| 2244 | benzimidazol-2-ylamino-(CH₂)₃ | H | H | H | NHSO₂-[4-(3,5-dimethyl)isoxazolyl] | |
| 2245 | benzimidazol-2-ylamino-(CH₂)₃ | H | H | H | NHSO₂C₆H₄-(3-Br) | |
| 2246 | benzimidazol-2-ylamino-(CH₂)₃ | H | H | H | NHSO₂C₆H₄-(3-F) | |
| 2247 | benzimidazol-2-ylamino-(CH₂)₃ | H | H | H | NHSO₂C₆H₃-(2,6-Cl₂) | |
| 2248 | benzimidazol-2-ylamino-(CH₂)₃ | H | H | H | NHSO₂(2-naphthyl) | |
| 2249 | benzimidazol-2-ylamino-(CH₂)₃ | H | H | H | NHSO₂(1-naphthyl) | |
| 2250 | benzimidazol-2-ylamino-(CH₂)₃ | H | H | H | NHSO₂C₆H₄-(4-Ph) | |
| 2251 | benzimidazol-2-ylamino-(CH₂)₃ | H | H | H | NHSO₂C₆H₂-4-Ph-2,6-dimethyl | |
| 2252 | benzimidazol-2-ylamino-(CH₂)₃ | H | H | H | NHSO₂C₆H₂-4-Ph-2,6- | |

TABLE 2-continued

[Structure: indazole with R¹ on N, R¹⁰ on C3, and at position connected to C(=O)-N(R¹³)-CH(R¹⁴)-CH(R¹⁵)-C(=O)OH]

| Ex. No. | R¹ᵃ | R¹⁰ | R¹³ | R¹⁴ | R¹⁵ | MS |
|---|---|---|---|---|---|---|
| 2253 | benzimidazol-2-ylamino-(CH₂)₃ | H | H | H | NHSO₂CH₂Ph dichloro | |
| 2254 | benzimidazol-2-ylamino-(CH₂)₃ | H | H | H | NHSO₂-i-Bu | |
| 2255 | benzimidazol-2-ylamino-(CH₂)₃ | H | H | H | NHSO₂NHPh | |
| 2256 | benzimidazol-2-ylamino-(CH₂)₃ | H | H | H | NHSO₂NHC₆H₄-(4-CH₃) | |
| 2257 | benzimidazol-2-ylamino-(CH₂)₃ | H | H | H | NHSO₂NHC₆C₃-(2,6-Me₂) | |
| 2258 | benzimidazol-2-ylamino-(CH₂)₃ | H | H | H | NHSO₂NHC₆C₂-(2,4,6-Me₃) | |
| 2259 | benzimidazol-2-ylamino-(CH₂)₃ | H | H | H | NHSO₂NH(2-naphthyl) | |
| 2260 | benzimidazol-2-ylamino-(CH₂)₃ | H | H | H | NHSO₂NH)1-naphthyl) | |
| 2261 | benzimidazol-2-ylamino-(CH₂)₃ | H | H | H | NHSO₂NHC₆H₄-(4-Ph) | |
| 2262 | benzimidazol-2-ylamino-(CH₂)₃ | H | H | H | NHSO₂NHC₆H₂-4-Ph-2,6-dimethyl | |
| 2263 | benzimidazol-2-ylamino-(CH₂)₃ | H | H | H | NHSO₂NHC₆H₂-4-Ph-2,6-dichloro | |
| 2264 | benzimidazol-2-ylamino-(CH₂)₃ | H | H | H | NHSO₂NHCH₂Ph | |
| 2265 | benzimidazol-2-ylamino-(CH₂)₃ | H | H | H | NHCO₂CH₂Ph | |
| 2266 | benzimidazol-2-ylamino-(CH₂)₃ | H | H | H | NHCO₂i-Bu | |
| 2267 | 2-aminopyridin-6-yl-(CH₂)₃ | H | H | H | NHSO₂C₆H₄-(4-CH₃) | |
| 2268 | 2-aminopyridin-6-yl-(CH₂)₃ | H | H | H | NHSO₂C₆H₃-(2,6-Me₂) | |
| 2269 | 2-aminopyridin-6-yl-(CH₂)₃ | H | H | H | NHSO₂C₆H₂-(2,4,6-Me₃) | |
| 2270 | 2-aminopyridin-6-yl-(CH₂)₃ | H | H | H | NHSO₂(3-pyridyl) | |
| 2271 | 2-aminopyridin-6-yl-(CH₂)₃ | H | H | H | NHSO₂(2-thiazolyl) | |
| 2272 | 2-aminopyridin-6-yl-(CH₂)₃ | H | H | H | NHSO₂(4-isoxazolyl) | |
| 2273 | 2-aminopyridin-6-yl-(CH₂)₃ | H | H | H | NHSO₂C₆H₄-(3-Br) | |
| 2274 | 2-aminopyridin-6-yl-(CH₂)₃ | H | H | H | NHSO₂C₆H₄-(3-F) | |
| 2275 | 2-aminopyridin-6-yl-(CH₂)₃ | H | H | H | NHSO₂C₆H₃-(2,6-Cl₂) | |
| 2276 | 2-aminopyridin-6-yl-(CH₂)₃ | H | H | H | NHSO₂(2-naphthyl) | |
| 2277 | 2-aminopyridin-6-yl-(CH₂)₃ | H | H | H | NHSO₂(1-naphthyl) | |
| 2278 | 2-aminopyridin-6-yl-(CH₂)₃ | H | H | H | NHSO₂C₆H₄-(4-Ph) | |
| 2279 | 2-aminopyridin-6-yl-(CH₂)₃ | H | H | H | NHSO₂C₆H₂-4-Ph-2,6-dimethyl | |
| 2280 | 2-aminopyridin-6-yl-(CH₂)₃ | H | H | H | NHSO₂C₆H₂-4-Ph-2,6-dichloro | |
| 2281 | 2-aminopyridin-6-yl-(CH₂)₃ | H | H | H | NHSO₂CH₂Ph | |
| 2282 | 2-aminopyridin-6-yl-(CH₂)₃ | H | H | H | NHSO₂-i-Bu | |
| 2283 | 2-aminopyridin-6-yl-(CH₂)₃ | H | H | H | NHSO₂NHPh | |
| 2284 | 2-aminopyridin-6-yl-(CH₂)₃ | H | H | H | NHSO₂NHC₆H₄-(4-CH₃) | |
| 2285 | 2-aminopyridin-6-yl-(CH₂)₃ | H | H | H | NHSO₂NHC₆C₃-(2,6-Me₂) | |
| 2286 | 2-aminopyridin-6-yl-(CH₂)₃ | H | H | H | NHSO₂NHC₆C₂-(2,4,6-Me₃) | |
| 2287 | 2-aminopyridin-6-yl-(CH₂)₃ | H | H | H | NHSO₂NH(2-naphthyl) | |
| 2288 | 2-aminopyridin-6-yl-(CH₂)₃ | H | H | H | NHSO₂NH)1-naphthyl) | |
| 2289 | 2-aminopyridin-6-yl-(CH₂)₃ | H | H | H | NHSO₂NHC₆H₄-(4-Ph) | |
| 2290 | 2-aminopyridin-6-yl-(CH₂)₃ | H | H | H | NHSO₂NHC₆H₂-4-Ph-2,6-dimethyl | |
| 2291 | 2-aminopyridin-6-yl-(CH₂)₃ | H | H | H | NHSO₂NHC₆H₂-4-Ph-2,6-dichloro | |
| 2292 | 2-aminopyridin-6-yl-(CH₂)₃ | H | H | H | NHCO₂n-Bu | |
| 2293 | 2-aminopyridin-6-yl-(CH₂)₃ | H | H | H | NHCO₂i-Bu | |
| 2294 | 2-iminoazepin-7-yl-(CH₂)₃ | H | H | H | NHSO₂Ph | |
| 2295 | imidazol-4-ylamino-(CH₂)₃ | H | H | H | NHSO₂Ph | |
| 2296 | 2-iminoazepin-7-yl-(CH₂)₃ | H | H | H | NHSO₂(4-isoxazolyl) | |
| 2297 | imidazol-4-ylamino-(CH₂)₃ | H | H | H | NHSO₂(4-isoxazolyl) | |
| 2298 | 2-iminoazepin-7-yl-(CH₂)₃ | H | H | H | NHSO₂-[4-(3,5-dimethyl)isoxazolyl] | |
| 2299 | imidazol-4-ylamino-(CH₂)₃ | H | H | H | NHSO₂-[4-(3,5-dimethyl)isoxazolyl] | |
| 2300 | imidazol-2-ylamino-(CH₂)₃ | H | H | 3-pyridinyl | NHSO₂Ph | |
| 2301 | pyridin-2-ylamino-(CH₂)₃ | H | H | 3-pyridinyl | NHSO₂Ph | |
| 2302 | imidazol-2-ylamino-(CH₂)₃ | H | H | (3,4-methylenedioxy)phenyl | NHSO₂Ph | |
| 2303 | pyridin-2-ylamino-(CH₂)₃ | H | H | (3,4-methylene- | NHSO₂Ph | |

TABLE 2-continued

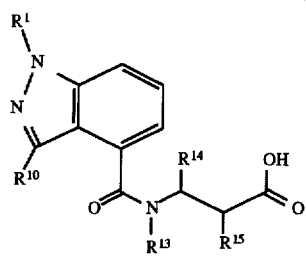

| Ex. No. | $R^{1a}$ | $R^{10}$ | $R^{13}$ | $R^{14}$ | $R^{15}$ | MS |
|---|---|---|---|---|---|---|
| | | | | dioxy)phenyl | | |
| 2304 | imidazol-2-ylamino-$(CH_2)_2$ | H | H | H | $NHSO_2Ph$ | |
| 2305 | imidazol-2-ylamino-$(CH_2)_2$ | H | H | H | $NHCO_2CH_2Ph$ | |
| 2306 | imidazol-2-ylamino-carbonyl-$(CH_2)_2$ | H | H | H | $NHSO_2C_6H_2$-$(2,4,6$-$CH_3)_3$ | |
| 2307 | pyridin-2-ylamino-$(CH_2)_2$ | H | H | H | $NHSO_2Ph$ | |
| 2308 | pyridin-2-ylamino-$(CH_2)_2$ | H | H | H | $NHCO_2CH_2Ph$ | |
| 2309 | pyridin-2-ylamino-carbonyl-$(CH_2)_2$ | H | H | H | $NHSO_2C_6H_2$-$(2,4,6$-$CH_3)_3$ | |
| 2310 | imidazolin-2-ylamino-$(CH_2)_2$ | H | H | H | $NHSO_2Ph$ | |
| 2311 | imidazolin-2-ylamino-$(CH_2)_2$ | H | H | H | $NHCO_2CH_2Ph$ | |
| 2312 | tetrahydropyrimidin-2-ylamino-$(CH_2)_2$ | H | H | H | $NHSO_2Ph$ | |
| 2313 | tetrahydropyrimidin-2-ylamino-$(CH_2)_2$ | H | H | H | $NHCO_2CH_2Ph$ | |
| 2314 | benzimidazol-2-ylamino-$(CH_2)_2$ | H | H | H | $NHSO_2Ph$ | |
| 2315 | benzimidazol-2-ylamino-$(CH_2)_2$ | H | H | H | $NHCO_2CH_2Ph$ | |
| 2316 | benzimidazol-2-ylamino-carbonyl-$(CH_2)_2$ | H | H | H | $NHSO_2C_6H_2$-$(2,4,6$-$CH_3)_3$ | |
| 2317 | 2-aminopyridin-6-yl-$(CH_2)_2$ | H | H | H | $NHSO_2Ph$ | |
| 2318 | 2-aminopyridin-6-yl-$(CH_2)_2$ | H | H | H | $NHCO_2CH_2Ph$ | |
| 2319 | 2-iminoazepin-7-yl-$(CH_2)_2$ | H | H | H | $NHSO_2Ph$ | |
| 2320 | 2-iminoazepin-7-yl-$(CH_2)_2$ | H | H | H | $NHCO_2CH_2Ph$ | |
| 2321 | imidazol-4-ylamino-$(CH_2)_2$ | H | H | H | $NHSO_2Ph$ | |
| 2322 | imidazol-4-ylamino-$(CH_2)_2$ | H | H | H | $NHCO_2CH_2Ph$ | |
| 2323 | imidazol-2-ylamino-$(CH_2)_4$ | H | H | H | $NHSO_2Ph$ | |
| 2324 | imidazol-2-ylamino-$(CH_2)_4$ | H | H | H | $NHCO_2CH_2Ph$ | |
| 2325 | pyridin-2-ylamino-$(CH_2)_4$ | H | H | H | $NHSO_2Ph$ | |
| 2326 | pyridin-2-ylamino-$(CH_2)_4$ | H | H | H | $NHCO_2CH_2Ph$ | |
| 2327 | imidazolin-2-ylamino-$(CH_2)_4$ | H | H | H | $NHSO_2Ph$ | |
| 2328 | imidazolin-2-ylamino-$(CH_2)_4$ | H | H | H | $NHCO_2CH_2Ph$ | 522.3 |
| 2329 | tetrahydropyrimidin-2-ylamino-$(CH_2)_4$ | H | H | H | $NHSO_2Ph$ | |
| 2330 | tetrahydropyrimidin-2-ylamino-$(CH_2)_4$ | H | H | H | $NHCO_2CH_2Ph$ | |
| 2331 | benzimidazol-2-ylamino-$(CH_2)_4$ | H | H | H | $NHSO_2Ph$ | |
| 2332 | benzimidazol-2-ylamino-$(CH_2)_4$ | H | H | H | $NHCO_2CH_2Ph$ | |
| 2333 | 2-aminopyridin-6-yl-$(CH_2)_4$ | H | H | H | $NHSO_2Ph$ | |
| 2334 | 2-aminopyridin-6-yl-$(CH_2)_4$ | H | H | H | $NHCO_2CH_2Ph$ | |
| 2335 | 2-iminoazepin-7-yl-$(CH_2)_4$ | H | H | H | $NHSO_2Ph$ | |
| 2336 | 2-iminoazepin-7-yl-$(CH_2)_4$ | H | H | H | $NHCO_2CH_2Ph$ | |
| 2337 | imidazol-4-ylamino-$(CH_2)_4$ | H | H | H | $NHSO_2Ph$ | |
| 2338 | imidazol-4-ylamino-$(CH_2)_4$ | H | H | H | $NHCO_2CH_2Ph$ | |
| 2339 | imidazol-2-ylamino-$CH_2(o$-$C_6H_4)$—$CH_2$ | H | H | H | $NHSO_2$-$(1$-naphthyl$)$ | |
| 2340 | imidazol-2-ylamino-$CH_2(o$-$C_6H_4)$—$CH_2$ | H | H | H | $NHCO_2CH_2Ph$ | |
| 2341 | imidazol-2-ylamino-$CH_2(o$-$C_6H_4)$—$CH_2$ | H | H | H | $NHSO_2C_6C_2$-$(2,4,6$-$Me_3)$ | |
| 2342 | pyridin-2-ylamino-$CH_2(o$-$C_6H_4)$—$CH_2$ | H | H | H | $NHSO_2$-$(1$-naphthyl$)$ | |
| 2343 | pyridin-2-ylamino-$CH_2(o$-$C_6H_4)$—$CH_2$ | H | H | H | $NHCO_2CH_2Ph$ | |
| 2344 | pyridin-2-ylamino-$CH_2(o$-$C_6H_4)$—$CH_2$ | H | H | H | $NHSO_2C_6C_2$-$(2,4,6$-$Me_3)$ | |
| 2345 | imidazolin-2-ylamino-$CH_2(o$-$C_6H_4)$—$CH_2$ | H | H | H | $NHSO_2$-$(1$-naphthyl$)$ | |
| 2346 | imidazolin-2-ylamino-$CH_2(o$-$C_6H_4)$—$CH_2$ | H | H | H | $NHCO_2CH_2Ph$ | |
| 2347 | imidazolin-2-ylamino-$CH_2(o$-$C_6H_4)$—$CH_2$ | H | H | H | $NHSO_2C_6C_2$-$(2,4,6$-$Me_3)$ | |
| 2348 | imidazolin-2-ylamino-$(o$-$C_6H_4)$—$CH_2$ | H | H | H | $NHSO_2$-$(1$-naphthyl$)$ | |
| 2349 | imidazolin-2-ylamino-$(o$-$C_6H_4)$—$CH_2$ | H | H | H | $NHCO_2CH_2Ph$ | |
| 2350 | imidazolin-2-ylamino-$(o$-$C_6H_4)$—$CH_2$ | H | H | H | $NHSO_2C_6C_2$-$(2,4,6$-$Me_3)$ | |

TABLE 3

| Ex. No. | R¹ | R⁹ | R¹⁴ | R¹⁵ | MS |
|---|---|---|---|---|---|
| 3001 | imidazol-2-ylamino-(CH₂)₃ | H | H | H | |
| 3002 | pyridin-2-ylamino-(CH₂)₃ | H | H | NHCOOCH₂Ph | |
| 3002a | imidazolin-2-ylamino-(CH₂)₃ | H | H | NHCOOCH₂Ph | |
| 3002b | tetrahydropyrimidin-2-ylamino-(CH₂)₃ | H | H | NHCO₂CH₂Ph | |
| 3002c | imidazol-2-ylamino-(CH₂)₃ | H | H | NHCO₂CH₂Ph | |
| 3003 | imidazol-2-ylamino-(CH₂)₃ | H | H | NHCO₂CH₂C₆H₄-(2-CH₃) | |
| 3004 | tetrahydropyrimidin-2-ylamino-(CH₂)₃ | H | H | NHCO₂CH₂C₆H₄-(3-CH₃) | |
| 3005 | benzimidazol-2-ylamino-(CH₂)₃ | H | H | NHCO₂CH₂C₆H₄-(4-CH₃) | |
| 3006 | 2-aminopyridin-6-yl-(CH₂)₃ | H | H | NHCO₂CH₂(2-pyridinyl) | |
| 3007 | 2-iminoazepin-7-yl-(CH₂)₃ | H | H | NHCO₂CH₂(3-pyridinyl) | |
| 3010 | imidazol-4-ylamino-(CH₂)₃ | H | H | NHCO₂CH₂(2-thiazolyl) | |
| 3015 | imidazol-2-ylamino-(CH₂)₃ | H | H | NHCO₂CH₂(4-isoxazolyl) | |
| 3016 | pyridin-2-ylamino-(CH₂)₃ | H | H | NHCO₂CH₂(2-thienyl) | |
| 3017 | imidazolin-2-ylamino-(CH₂)₃ | H | H | NHCO₂n-Bu | |
| 3018 | tetrahydropyrimidin-2-ylamino-(CH₂)₃ | H | H | NHCO₂i-Bu | |
| 3019 | benzimidazol-2-ylamino-(CH₂)₃ | H | H | NHCO₂t-Bu | |
| 3020 | 2-aminopyridin-6-yl-(CH₂)₃ | H | H | NHSO₂Ph | |
| 3020a | pyridin-2-ylamino-(CH₂)₃ | H | H | NHSO₂Ph | |
| 3020b | imidazolin-2-ylamino-(CH₂)₃ | H | H | NHSO₂Ph | |
| 3020c | tetrahydropyrimidin-2-ylamino-(CH₂)₃ | H | H | NHSO₂Ph | |
| 3020d | imidazol-2-ylamino-(CH₂)₃ | H | H | NHSO₂Ph | |
| 3021 | 2-iminoazepin-7-yl-(CH₂)₃ | H | H | NHSO₂C₆H₄-(2-CH₃) | |
| 3021a | imidazol-2-ylamino-(CH₂)₃ | H | H | NHSO₂C₆H₃-(2,6-Me₂) | |
| 3021b | imidazol-2-ylamino-(CH₂)₃ | H | H | NHSO₂C₆H₂-(2,4,6-Me₃) | |
| 3021c | imidazol-2-ylamino-(CH₂)₃ | H | H | NHSO₂C₆H₂-(2,6-Me₂-4-Ph) | |
| 3021d | pyridin-2-ylamino-(CH₂)₃ | H | H | NHSO₂C₆H₂-(2,6-Me₂-4-Ph) | |
| 3021e | imidazolin-2-ylamino-(CH₂)₃ | H | H | NHSO₂C₆H₂-(2,6-Me₂-4-Ph) | |
| 3021f | tetrahydropyrimidin-2-ylamino-(CH₂)₃ | H | H | NHSO₂C₆H₂-(2,6-Me₂-4-Ph) | |
| 3021g | imidazol-2-ylamino-(CH₂)₃ | H | H | NHSO₂C₆H₂-(2,6-Me₂-4-(3-pyridyl) | |
| 3021h | imidazol-2-ylamino-(CH₂)₃ | H | H | NHSO₂C₆H₂-(2,6-Me₂-4-(4-pyridyl) | |
| 3021i | imidazol-2-ylamino-(CH₂)₃ | H | H | NHSO₂C₆H₂-(2,6-Me₂-4-(2-furyl) | |
| 3021j | imidazol-2-ylamino-(CH₂)₃ | H | H | NHSO₂C₆H₂-(2,6-Me₂-4-(3-furyl) | |
| 3021k | imidazol-2-ylamino-(CH₂)₃ | H | H | NHSO₂C₆H₂-(2,6-Me₂-4-(5-pyrazolyl)) | |
| 3021l | pyridin-2-ylamino-(CH₂)₃ | H | H | NHSO₂C₆H₂-(2,4,6-Me₃) | |
| 3021m | pyridin-2-ylamino-(CH₂)₃ | H | H | NHSO₂C₆H₂-(2,6-Me₂-4-(3-pyridyl)) | |
| 3021n | pyridin-2-ylamino-(CH₂)₃ | H | H | NHSO₂C₆H₂-(2,6-Me₂-4-(4-pyridyl)) | |
| 3021o | pyridin-2-ylamino-(CH₂)₃ | H | H | NHSO₂C₆H₂(2,6-Me₂-4-(2-furyl)) | |
| 3021p | pyridin-2-ylamino-(CH₂)₃ | H | H | NHSO₂C₆H₂-(2,6-Me₂-4-(3-furyl)) | |
| 3021q | pyridin-2-ylamino-(CH₂)₃ | H | H | NHSO₂C₆H₂-(2,6-Me₂-4-(5-pyrazolyl)) | |
| 3021r | imidazolin-2-ylamino-(CH₂)₃ | H | H | NHSO₂C₆H₂-(2,4,6-Me₃) | |
| 3021s | imidazolin-2-ylamino-(CH₂)₃ | H | H | NHSO₂C₆H₂-(2,6-Me₂-4-(3-pyridyl)) | |
| 3021t | imidazolin-2-ylamino-(CH₂)₃ | H | H | NHSO₂C₆H₂- (2,6-Me₂-4-(4-pyridyl)) | |
| 3021u | imidazolin-2-ylamino-(CH₂)₃ | H | H | NHSO₂C₆H₂-(2,6-Me₂-4-(2-furyl)) | |
| 3021v | imidazolin-2-ylamino-(CH₂)₃ | H | H | NHSO₂C₆H₂-(2,6-Me₂-4-(3-furyl)) | |
| 3021w | imidazolin-2-ylamino-(CH₂)₃ | H | H | NHSO₂C₆H₂-(2,6-Me₂-4-(5-pyrazolyl)) | |
| 3024 | imidazol-4-ylamino-(CH₂)₃ | H | H. | NHSO₂(2-pyridyl) | |
| 3029 | imidazol-2-ylamino-(CH₂)₃ | H | H | NHSO₂(4-isoxazolyl) | |
| 3030 | pyridin-2-ylamino-(CH₂)₃ | H | H | NHSO₂-[4-(3,5-dimethyl)isoxazolyl] | |
| 3030a | imidazolin-2-ylamino-(CH₂)₃ | H | H | NHSO₂-[4-(3,5-dimethyl)isoxazolyl] | |
| 3030b | tetrahydropyrimidin-2-ylamino-(CH₂)₃ | H | H | NHSO₂-[4-(3,5 dimethyl)isoxazolyl] | |
| 3030c | imidazol-2-ylamino-(CH₂)₃ | H | H | NHSO₂-[4-(3,5-dimethyl)isoxazolyl] | |
| 3031 | imidazolin-2-ylamino-(CH₂)₃ | H | H | NHSO₂C₆H₄-(2-Br) | |
| 3032 | tetrahydropyrimidin-2-ylamino-(CH₂)₃ | H | H | NHSO₂C₆H₄-(3-Br) | |
| 3033 | benzimidazol-2-ylamino-(CH₂)₃ | H | H | NHSO₂C₆H₄-(4-Br) | |
| 3034 | 2-aminopyridin-6-yl-(CH₂)₃ | H | H | NHSO₂C₆H₄-(2-F) | |
| 3035 | 2-iminoazepin-7-yl-(CH₂)₃ | H | H | NHSO₂C₆H₄-(3-F) | |
| 3038 | imidazol-2-ylamino-(CH₂)₃ | H | H | NHSO₂(1-naphthyl) | |
| 3038a | imidazol-2-ylamino-(CH₂)₃ | H | H | NHSO₂C₆H₃-(2,6-Cl₂) | |
| 3038b | imidazol-2-ylamino-(CH₂)₃ | H | H | NHSO₂C₆H₂-(2,6-Cl₂-4-Ph) | |
| 3043 | imidazol-2-ylamino-(CH₂)₃ | H | H | NHSO₂-i-Bu | |
| 3044 | pyridin-2-ylamino-(CH₂)₃ | H | H | NHSO₂-t-Bu | |
| 3045 | imidazol-2-ylamino-(CH₂)₃ | H | (3,4-methylenedioxy)phenyl | | |
| 3046 | pyridin-2-ylamino-(CH₂)₃ | H | (3,4-methylenedioxy)phenyl | H | |
| 3047 | imidazolin-2-ylamino-(CH₂)₃ | H | (3,4-methylenedioxy)phenyl | H | |
| 3048 | tetrahydropyrimidin-2-ylamino-(CH₂)₃ | H | (3,4-methylenedioxy)phenyl | H | |
| 3049 | benzimidazol-2-ylamino-(CH₂)₃ | H | (3,4-methylenedioxy)phenyl | H | |
| 3050 | 2-aminopyridin-6-yl-(CH₂)₃ | H | (3,4-methylenedioxy)phenyl | H | |

TABLE 3-continued

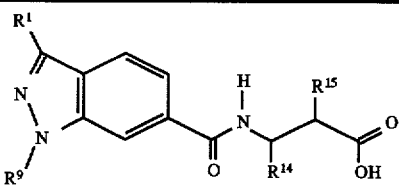

| Ex. No. | $R^1$ | $R^9$ | $R^{14}$ | $R^{15}$ | MS |
|---|---|---|---|---|---|
| 3051 | 2-iminoazepin-7-yl-$(CH_2)_3$ | H | (3,4-methylenedioxy)phenyl | H | |
| 3054 | imidazol-4-ylamino-$(CH_2)_3$ | H | (3,4-methylenedioxy)phenyl | H | |
| 3059 | imidazol-2-ylamino-$(CH_2)_3$ | H | 3-pyridinyl | H | |
| 3060 | pyridin-2-ylamino-$(CH_2)_3$ | H | 3-pyridinyl | H | |
| 3061 | imidazolin-2-ylamino-$(CH_2)_3$ | H | 3-pyridinyl | H | |
| 3062 | tetrahydropyrimidin-2-ylamino-$(CH_2)_3$ | H | 3-pyridinyl | H | |
| 3063 | benzimidazol-2-ylamino-$(CH_2)_3$ | H | 3-pyridinyl | H | |
| 3064 | 2-aminopyridin-6-yl-$(CH_2)_3$ | H | 3-pyridinyl | H | |
| 3065 | 2-iminoazepin-7-yl-$(CH_2)_3$ | H | 3-pyridinyl | H | |
| 3068 | imidazol-4-ylamino-$(CH_2)_3$ | H | 3-pyridinyl | H | |
| 3068a | imidazol-2-ylamino-$CH_2(o-C_6H_4)$ | H | H | $NHSO_2$-(1-naphthyl) | |
| 3068b | imidazol-2-ylamino-$CH_2(o-C_6H_4)$ | H | H | $NHCO_2CH_2Ph$ | |
| 3068c | imidazol-2-ylamino-$CH_2(o-C_6H_4)$ | H | H | $NHSO_2C_6C_2$-(2,4,6-$Me_3$) | |
| 3068d | pyridin-2-ylamino-$CH_2(o-C_6H_4)$ | H | H | $NHSO_2$-(1-naphthyl) | |
| 3068e | pyridin-2-ylamino-$CH_2(o-C_6H_4)$ | H | H | $NHCO_2CH_2Ph$ | |
| 3068f | pyridin-2-ylamino-$CH_2(o-C_6H_4)$ | H | H | $NHSO_2C_6C_2$-(2,4,6-$Me_3$) | |
| 3068g | imidazolin-2-ylamino-$CH_2(o-C_6H_4)$ | H | H | $NHSO_2$-(1-naphthyl) | |
| 3068h | imidazolin-2-ylamino-$CH_2(6-C_6H_4)$ | H | H | $NHCO_2CH_2Ph$ | |
| 3068i | imidazolin-2-ylamino-$CH_2(o-C_6H_4)$ | H | H | $NHSO_2C_6C_2$-(2,4,6-$Me_3$) | |
| 3068j | imidazolin-2-ylamino-$(m-C_6H_4)$ | H | H | $NHSO_2$-(1-naphthyl) | |
| 3068k | imidazolin-2-ylamino-$(m-C_6H_4)$ | H | H | $NHCO_2CH_2Ph$ | |
| 3068l | imidazolin-2-ylamino-$(m-C_6H_4)$ | H | H | $NHSO_2C_6C_2$-(2,4,6-$Me_3$) | |
| 3075 | imidazol-2-ylamino-$(CH_2)_3$ | $CH_3$ | H | $NHCO_2CH_2Ph$ | |
| 3076 | imidazol-2-ylamino-$(CH_2)_3$ | $CH_3$ | H | $NHCO_2CH_2C_6H_4$-(3-$CH_3$) | |
| 3077 | imidazol-2-ylamino-$(CH_2)_3$ | $CH_3$ | H | $NHCO_2CH_2$(3-pyridinyl) | |
| 3078 | imidazol-2-ylamino-$(CH_2)_3$ | $CH_3$ | H | $NHCO_2CH_2$(2-thiazolyl) | |
| 3079 | imidazol-2-ylamino-$(CH_2)_3$ | $CH_3$ | H | $NHCO_2CH_2$(2-thienyl) | |
| 3080 | imidazol-2-ylamino-$(CH_2)_3$ | $CH_3$ | H | $NHCO_2CH_2$(5-isoxazolyl) | |
| 3081 | imidazol-2-ylamino-$(CH_2)_3$ | $CH_3$ | H | $NHCO_2$n-Bu | |
| 3082 | imidazol-2-ylamino-$(CH_2)_3$ | $CH_3$ | H | NHCOPh | |
| 3083 | imidazol-2-ylamino-$(CH_2)_3$ | $CH_3$ | H | $NHCOCH_2Ph$ | * |
| 3084 | imidazol-2-ylamino-$(CH_2)_3$ | $CH_3$ | H | $NHCOCH_2CH_2Ph$ | |
| 3085 | imidazol-2-ylamino-$(CH_2)_3$ | $CH_3$ | H | NHCOCH=CHPh | |
| 3086 | imidazol-2-ylamino-$(CH_2)_3$ | $CH_3$ | H | $NHCOCH_2$(3-pyridinyl) | |
| 3087 | imidazol-2-ylamino-$(CH_2)_3$ | $CH_3$ | H | $NHCOCH_2$(2-thienyl) | |
| 3088 | imidazol-2-ylamino-$(CH_2)_3$ | $CH_3$ | H | $NHCOCH_2$(cyclohexyl) | |
| 3089 | imidazol-2-ylamino-$(CH_2)_3$ | $CH_3$ | H | NHCOn-Bu | |
| 3090 | imidazol-2-ylamino-$(CH_2)_3$ | $CH_3$ | H | $NHCONHCH_2Ph$ | |
| 3091 | imidazol-2-ylamino-$(CH_2)_3$ | $CH_3$ | H | $NHSO_2Ph$ | |
| 3092 | imidazol-2-ylamino-$(CH_2)_3$ | $CH_3$ | H | $NHSO_2C_6H_4$-(4-$CH_3$) | |
| 3093 | imidazol-2-ylamino-$(CH_2)_3$ | $CH_3$ | H | $NHSO_2C_6H_3$-(2,6-$CH_3$)$_2$ | 554.4 |
| 3094 | imidazol-2-ylamino-$(CH_2)_3$ | $CH_3$ | H | $NHSO_2C_6H_2$-(2,4,6-$CH_3$)$_3$ | 568.4 |
| 3095 | imidazol-2-ylamino-$(CH_2)_3$ | $CH_3$ | H | $NHSO_2$(3-pyridyl) | |
| 3096 | imidazol-2-ylamino-$(CH_2)_3$ | $CH_3$ | H | $NHSO_2$(2-thienyl) | |
| 3097 | imidazol-2-ylamino-$(CH_2)_3$ | $CH_3$ | H | $NHSO_2$(2-thiazolyl) | |
| 3098 | imidazol-2-ylamino-$(CH_2)_3$ | $CH_3$ | H | $NHSO_2$[4-(3,5-dimethyl)isoxazolyl] | |
| 3099 | imidazol-2-ylamino-$(CH_2)_3$ | $CH_3$ | H | $NHSO_2C_6H_4$-(4-Br) | |
| 3100 | imidazol-2-ylamino-$(CH_2)_3$ | $CH_3$ | H | $NHSO_2C_6H_4$-(4-F) | |
| 3101 | imidazol-2-ylamino-$(CH_2)_3$ | $CH_3$ | H | $NHSO_2C_6H_3$-(2,6-$Cl_2$) | 594.3 |
| 3102 | imidazol-2-ylamino-$(CH_2)_3$ | $CH_3$ | H | $NHSO_2$(2-naphthyl) | |
| 3103 | imidazol-2-ylamino-$(CH_2)_3$ | $CH_3$ | H | $NHSO_2$(1-naphthyl) | |
| 3104 | imidazol-2-ylamino-$(CH_2)_3$ | $CH_3$ | H | $NHSO_2C_6H_4$-(4-Ph) | |
| 3104a | imidazol-2-ylamino-$(CH_2)_3$ | $CH_3$ | H | $NHSO_2C_6H_4$-4-(4-pyridyl) | |
| 3104b | imidazol-2-ylamino-$(CH_2)_3$ | $CH_3$ | H | $NHSO_2C_6H_4$-4-(2-oxazolyl) | |
| 3104c | imidazol-2-ylamino-$(CH_2)_3$ | $CH_3$ | H | $NHSO_2C_6H_4$-4-(3-pyrazolyl) | |
| 3105 | imidazol-2-ylamino-$(CH_2)_3$ | $CH_3$ | H | $NHSO_2C_6H_2$-(4-Ph-2,6-dimethyl) | 630.3 |
| 3105a | imidazol-2-ylamino-$(CH_2)_3$ | $CH_3$ | H | $NHSO_2C_6H_2$-4-(3-pyridyl)-2,6-dimethyl | |
| 3105b | imidazol-2-ylamino-$(CH_2)_3$ | $CH_3$ | H | $NHSO_2C_6H_2$-4-(2-oxazolyl)-2,6-dimethyl | |
| 3105c | imidazol-2-ylamino-$(CH_2)_3$ | $CH_3$ | H | $NHSO_2C_6H_2$-4-(3-pyrazolyl)-2,6-dimethyl | |
| 3105d | imidazol-2-ylamino-$(CH_2)_3$ | $CH_3$ | H | $NHSO_2C_6H_2$-4-(4-pyridyl)-2,6-dimethyl | |
| 3105e | imidazol-2-ylamino-$(CH_2)_3$ | $CH_3$ | H | $NHSO_2C_6H_2$-4-(2-furyl)-2,6-dimethyl | |
| 3105f | imidazol-2-ylamino-$(CH_2)_3$ | $CH_3$ | H | $NHSO_2C_6H_2$-4-(3-furyl)-2,6-dimethyl | |
| 3106 | imidazol-2-ylamino-$(CH_2)_3$ | $CH_3$ | H | $NHSO_2C_6H_2$-(4-Ph-2,6-dichloro) | 670.3 |
| 3107 | imidazol-2-ylamino-$(CH_2)_3$ | $CH_3$ | H | $NHSO_2C_6H$-(4-Ph-2,6-dimethyl-3-chloro) | |
| 3108 | imidazol-2-ylamino-$(CH_2)_3$ | $CH_3$ | H | $NHSO_2CH_2Ph$ | |
| 3109 | imidazol-2-ylamino-$(CH_2)_3$ | $CH_3$ | H | $NHSO_2$-n-Bu | |
| 3110 | imidazol-2-ylamino-$(CH_2)_3$ | $CH_3$ | H | $NHSO_2NHPh$ | |

TABLE 3-continued

| Ex. No. | R¹ | R⁹ | R¹⁴ | R¹⁵ | MS |
|---|---|---|---|---|---|
| 3111 | imidazol-2-ylamino-(CH₂)₃ | CH₃ | H | NHSO₂NHC₆H₄-(4-CH₃) | |
| 3112 | imidazol-2-ylamino-(CH₂)₃ | CH₃ | H | NHSO₂NHC₅C₃-(2,6-Me₂) | |
| 3113 | imidazol-2-ylamino-(CH₂)₃ | CH₃ | H | NHSO₂NHC₅C₂-(2,4,6-Me₃) | |
| 3114 | imidazol-2-ylamino-(CH₂)₃ | CH₃ | H | NHSO₂NH(3-pyridyl) | |
| 3115 | imidazol-2-ylamino-(CH₂)₃ | CH₃ | H | NHSO₂[4-(3,5-dimethyl)isoxazolyl] | |
| 3116 | imidazol-2-ylamino-(CH₂)₃ | CH₃ | H | NHSO₂NHC₆H₄-(4-Br) | |
| 3117 | imidazol-2-ylamino-(CH₂)₃ | CH₃ | H | NHSO₂NHC₆H₄-(4-F) | |
| 3118 | imidazol-2-ylamino-(CH₂)₃ | CH₃ | H | NHSO₂NH(2-naphthyl) | |
| 3119 | imidazol-2-ylamino-(CH₂)₃ | CH₃ | H | NHSO₂NH(1-naphthyl) | |
| 3120 | imidazol-2-ylamino-(CH₂)₃ | CH₃ | H | NHSO₂NHC₆H₄-(4-Ph) | |
| 3121 | imidazol-2-ylamino-(CH₂)₃ | CH₃ | H | NHSO₂NHC₆H₂-(4-Ph-2,6-dimethyl) | |
| 3122 | imidazol-2-ylamino-(CH₂)₃ | CH₃ | H | NHSO₂NHC₆H₂-(4-Ph-2,6-dichloro) | |
| 3123 | imidazol-2-ylamino-(CH₂)₃ | CH₃ | H | NHSO₂NHCH₂Ph | |
| 3124 | imidazol-2-ylamino-(CH₂)₃ | CH₃ | H | NHSO₂NH-n-Bu | |
| 3125 | pyridin-2-ylamino-(CH₂)₃ | CH₃ | H | NHCO₂CH₂C₆H₄-(3-CH₃) | |
| 3126 | pyridin-2-ylamino-(CH₂)₃ | CH₃ | H | NHCO₂CH₂(3-pyridinyl) | |
| 3127 | pyridin-2-ylamino-(CH₂)₃ | CH₃ | H | NHCO₂CH₂(2-thiazolyl) | |
| 3128 | pyridin-2-ylamino-(CH₂)₃ | CH₃ | H | NHCO₂CH₂(4-isoxazolyl) | |
| 3129 | pyridin-2-ylamino-(CH₂)₃ | CH₃ | H | NHCO₂i-Bu | |
| 3130 | pyridin-2-ylamino-(CH₂)₃ | CH₃ | H | NHCOPh | |
| 3131 | pyridin-2-ylamino-(CH₂)₃ | CH₃ | H | NHCOCH₂Ph | |
| 3132 | pyridin-2-ylamino-(CH₂)₃ | CH₃ | H | NHCOCH₂CH₂Ph | |
| 3133 | pyridin-2-ylamino-(CH₂)₃ | CH₃ | H | NHCOCH=CHPh | |
| 3134 | pyridin-2-ylamino-(CH₂)₃ | CH₃ | H | NHCOCH₂(3-pyridinyl) | |
| 3135 | pyridin-2-ylamino-(CH₂)₃ | CH₃ | H | NHCOCH₂(2-thienyl) | |
| 3136 | pyridin-2-ylamino-(CH₂)₃ | CH₃ | H | NHCOCH₂(cyclohexyl) | |
| 3137 | pyridin-2-ylamino-(CH₂)₃ | CH₃ | H | NHCOn-Bu | |
| 3138 | pyridin-2-ylamino-(CH₂)₃ | CH₃ | H | NHCONHCH₂Ph | |
| 3139 | pyridin-2-ylamino-(CH₂)₃ | CH₃ | H | NHSO₂Ph | |
| 3140 | pyridin-2-ylamino-(CH₂)₃ | CH₃ | H | NHSO₂C₆H₄-(4-CH₃) | |
| 3141 | pyridin-2-ylamino-(CH₂)₃ | CH₃ | H | NHSO₂C₆H₃-(2,6-CH₃)₂ | |
| 3142 | pyridin-2-ylamino-(CH₂)₃ | CH₃ | H | NHSO₂C₆H₂-(2,4,6-CH₃)₃ | 579.4 |
| 3143 | pyridin-2-ylamino-(CH₂)₃ | CH₃ | H | NHSO₂(3-pyridyl) | |
| 3144 | pyridin-2-ylamino-(CH₂)₃ | CH₃ | H | NHSO₂(2-thienyl) | |
| 3145 | pyridin-2-ylamino-(CH₂)₃ | CH₃ | H | NHSO₂(2-thiazolyl) | |
| 3146 | pyridin-2-ylamino-(CH₂)₃ | CH₃ | H | NHSO₂C₆H₄-(4-Br) | |
| 3147 | pyridin-2-ylamino-(CH₂)₃ | CH₃ | H | NHSO₂C₆H₄-(4-F) | |
| 3148 | pyridin-2-ylamino-(CH₂)₃ | CH₃ | H | NHSO₂C₆H₃-(2,6-Cl₂) | |
| 3149 | pyridin-2-ylamino-(CH₂)₃ | CH₃ | H | NHSO₂(2-naphthyl) | |
| 3150 | pyridin-2-ylamino-(CH₂)₃ | CH₃ | H | NHSO₂(1-naphthyl) | |
| 3151 | pyridin-2-ylamino-(CH₂)₃ | CH₃ | H | NHSO₂C₆H₄-(4-Ph) | |
| 3151a | pyridin-2-ylamino-(CH₂)₃ | CH₃ | H | NHSO₂C₆H₄-4-(4-pyridyl) | |
| 3151b | pyridin-2-ylamino-(CH₂)₃ | CH₃ | H | NHSO₂C₆H₄-4-(2-oxazolyl) | |
| 3151c | pyridin-2-ylamino-(CH₂)₃ | CH₃ | H | NHSO₂C₆H₄-4-(3-pyrazolyl) | |
| 3152 | pyridin-2-ylamino-(CH₂)₃ | CH₃ | H | NHSO₂C₆H₂-(4-Ph-2,6-dimethyl) | |
| 3152a | pyridin-2-ylamino-(CH₂)₃ | CH₃ | H | NHSO₂C₆H₂-4-(3-pyridyl)-2,6-dimethyl | |
| 3152b | pyridin-2-ylamino-(CH₂)₃ | CH₃ | H | NHSO₂C₆H₂-4-(2-oxazolyl)-2,6-dimethyl | |
| 3152c | pyridin-2-ylamino-(CH₂)₃ | CH₃ | H | NHSO₂C₆H₂-4-(3-pyrazolyl)-2,6-dimethyl | |
| 3152d | pyridin-2-ylamino-(CH₂)₃ | CH₃ | H | NHSO₂C₆H₂-4-(4-pyridyl)-2,6-dimethyl | |
| 3152e | pyridin-2-ylamino-(CH₂)₃ | CH₃ | H | NHSO₂C₆H₂-4-(2-furyl)-2,6-dimethyl | |
| 3152f | pyridin-2-ylamino-(CH₂)₃ | CH₃ | H | NHSO₂C₆H₂-4-(3-furyl)-2,6-dimethyl | |
| 3153 | pyridin-2-ylamino-(CH₂)₃ | CH₃ | H | NHSO₂C₆H₂-(4-Ph-2,6-dichloro) | |
| 3154 | pyridin-2-ylamino-(CH₂)₃ | CH₃ | H | NHSO₂CH₂Ph | |
| 3155 | pyridin-2-ylamino-(CH₂)₃ | CH₃ | H | NHSO₂-n-Bu | |
| 3156 | pyridin-2-ylamino-(CH₂)₃ | CH₃ | H | NHSO₂NHPh | |
| 3157 | pyridin-2-ylamino-(CH₂)₃ | CH₃ | H | NHSO₂NHC₆H₄-(4-CH₃) | |
| 3158 | pyridin-2-ylamino-(CH₂)₃ | CH₃ | H | NHSO₂NHC₆C₃-(2,6-Me₂) | |
| 3159 | pyridin-2-ylamino-(CH₂)₃ | CH₃ | H | NHSO₂NHC₆C₂-(2,4,6-Me₃) | |
| 3160 | pyridin-2-ylamino-(CH₂)₃ | CH₃ | H | NHSO₂NH(3-pyridyl) | |
| 3161 | pyridin-2-ylamino-(CH₂)₃ | CH₃ | H | NHSO₂-[4-(3,5-dimethyl)isoxazolyl] | |
| 3162 | pyridin-2-ylamino-(CH₂)₃ | CH₃ | H | NHSO₂NHC₆H₄-(4-Br) | |
| 3163 | pyridin-2-ylamino-(CH₂)₃ | CH₃ | H | NHSO₂NHC₆H₄-(4-F) | |
| 3164 | pyridin-2-ylamino-(CH₂)₃ | CH₃ | H | NHSO₂NH(2-naphthyl) | |
| 3165 | pyridin-2-ylamino-(CH₂)₃ | CH₃ | H | NHSO₂NH)1-naphthyl) | |
| 3166 | pyridin-2-ylamino-(CH₂)₃ | CH₃ | H | NHSO₂NHC₆H₄-(4-Ph) | |
| 3167 | pyridin-2-ylamino-(CH₂)₃ | CH₃ | H | NHSO₂NHC₆H₂-(4-Ph-2,6-dimethyl) | |
| 3168 | pyridin-2-ylamino-(CH₂)₃ | CH₃ | H | NHSO₂NHC₆H₂-(4-Ph-2,6-dichloro) | |

TABLE 3-continued

| Ex. No. | R¹ | R⁹ | R¹⁴ | R¹⁵ | MS |
|---|---|---|---|---|---|
| 3169 | pyridin-2-ylamino-$(CH_2)_3$ | $CH_3$ | H | $NHSO_2NHCH_2Ph$ | |
| 3170 | pyridin-2-ylamino-$(CH_2)_3$ | $CH_3$ | H | $NHSO_2NH$-n-Bu | |
| 3171 | tetrahydropyrimidin-2-ylamino-$(CH_2)_3$ | $CH_3$ | H | $NHCOOCH_2Ph$ | |
| 3172 | tetrahydropyrimidin-2-ylamino-$(CH_2)_3$ | $CH_3$ | H | $NHCO_2CH_2C_6H_4$-(4-$CH_3$) | |
| 3173 | tetrahydropyrimidin-2-ylamino-$(CH_2)_3$ | $CH_3$ | H | $NHCO_2CH_2$(3-pyridinyl) | |
| 3173 | tetrahydropyrimidin-2-ylamino-$(CH_2)_3$ | $CH_3$ | H | $NHCO_2CH_2$(2-thiazolyl) | |
| 3175 | tetrahydropyrimidin-2-ylamino-$(CH_2)_3$ | $CH_3$ | H | $NHCO_2CH_2$(2-thienyl) | |
| 3176 | tetrahydropyrimidin-2-ylamino-$(CH_2)_3$ | $CH_3$ | H | $NHCO_2$n-Bu | |
| 3177 | tetrahydropyrimidin-2-ylamino-$(CH_2)_3$ | $CH_3$ | H | $NHSO_2Ph$ | |
| 3178 | tetrahydropyrimidin-2-ylamino-$(CH_2)_3$ | $CH_3$ | H | $NHSO_2C_6H_4$-(4-$CH_3$) | |
| 3179 | tetrahydropyrimidin-2-ylamino-$(CH_2)_3$ | $CH_3$ | H | $NHSO_2C_6H_3$-(2,6-$Me_2$) | |
| 3180 | tetrahydropyrimidin-2-ylamino-$(CH_2)_3$ | $CH_3$ | H | $NHSO_2C_6H_2$-(2,4,6-$Me_3$) | |
| 3181 | tetrahydropyrimidin-2-ylamino-$(CH_2)_3$ | $CH_3$ | H | $NHSO_2$(3-pyridyl) | |
| 3182 | tetrahydropyrimidin-2-ylamino-$(CH_2)_3$ | $CH_3$ | H | $NHSO_2$(2-thienyl) | |
| 3183 | tetrahydropyrimidin-2-ylamino-$(CH_2)_3$ | $CH_3$ | H | $NHSO_2$(2-thiazolyl) | |
| 3184 | tetrahydropyrimidin-2-ylamino-$(CH_2)_3$ | $CH_3$ | H | $NHSO_2C_6H_4$-(2-Br) | |
| 3185 | tetrahydropyrimidin-2-ylamino-$(CH_2)_3$ | $CH_3$ | H | $NHSO_2C_6H_4$-(4-F) | |
| 3186 | tetrahydropyrimidin-2-ylamino-$(CH_2)_3$ | $CH_3$ | H | $NHSO_2C_6H_3$-(2,6-$Cl_2$) | |
| 3187 | tetrahydropyrimidin-2-ylamino-$(CH_2)_3$ | $CH_3$ | H | $NHSO_2$(2-naphthyl) | |
| 3188 | tetrahydropyrimidin-2-ylamino-$(CH_2)_3$ | $CH_3$ | H | $NHSO_2$(1-naphthyl) | |
| 3189 | tetrahydropyrimidin-2-ylamino-$(CH_2)_3$ | $CH_3$ | H | $NHSO_2C_6H_4$-(4-Ph) | |
| 3189a | tetrahydropyrimidin-2-ylamino-$(CH_2)_3$ | $CH_3$ | H | $NHSO_2C_6H_4$-4-(4-pyridyl) | |
| 3189b | tetrahydropyrimidin-2-ylamino-$(CH_2)_3$ | $CH_3$ | H | $NHSO_2C_6H_4$-4-(2-oxazolyl) | |
| 3189c | tetrahydropyrimidin-2-ylamino-$(CH_2)_3$ | $CH_3$ | H | $NHSO_2C_6H_4$-4-(3-pyrazolyl) | |
| 3190 | tetrahydropyrimidin-2-ylamino-$(CH_2)_3$ | $CH_3$ | H | $NHSO_2C_6H_2$-(4-Ph-2,6-dimethyl) | |
| 3190a | tetrahydropyrimidin-2-ylamino-$(CH_2)_3$ | $CH_3$ | H | $NHSO_2C_6H_2$-4-(3-pyridyl)-2,6-dimethyl | |
| 3190b | tetrahydropyrimidin-2-ylamino-$(CH_2)_3$ | $CH_3$ | H | $NHSO_2C_6H_2$-4-(2-oxazolyl)-2,6-dimethyl | |
| 3190c | tetrahydropyrimidin-2-ylamino-$(CH_2)_3$ | $CH_3$ | H | $NHSO_2C_6H_2$-4-(3-pyrazolyl)-2,6-dimethyl | |
| 3190d | tetrahydropyrimidin-2-ylamino-$(CH_2)_3$ | $CH_3$ | H | $NHSO_2C_6H_2$-4-(4-pyridyl)-2,6-dimethyl | |
| 3190e | tetrahydropyrimidin-2-ylamino-$(CH_2)_3$ | $CH_3$ | H | $NHSO_2C_6H_2$-4-(2-furyl)-2,6-dimethyl | |
| 3190f | tetrahydropyrimidin-2-ylamino-$(CH_2)_3$ | $CH_3$ | H | $NHSO_2C_6H_2$-4-(3-furyl)-2,6-dimethyl | |
| 3191 | tetrahydropyrimidin-2-ylamino-$(CH_2)_3$ | $CH_3$ | H | $NHSO_2C_6H_2$-(4-Ph-2,6-dichloro) | |
| 3192 | tetrahydropyrimidin-2-ylamino-$(CH_2)_3$ | $CH_3$ | H | $NHSO_2CH_2Ph$ | |
| 3193 | tetrahydropyrimidin-2-ylamino-$(CH_2)_3$ | $CH_3$ | H | $NHSO_2$-n-Bu | |
| 3194 | tetrahydropyrimidin-2-ylamino-$(CH_2)_3$ | $CH_3$ | H | $NHSO_2NHPh$ | |
| 3195 | tetrahydropyrimidin-2-ylamino-$(CH_2)_3$ | $CH_3$ | H | $NHSO_2NHC_6H_4$-(4-$CH_3$) | |
| 3196 | tetrahydropyrimidin-2-ylamino-$(CH_2)_3$ | $CH_3$ | H | $NHSO_2NHC_6C_3$-(2,6-$Me_2$) | |
| 3197 | tetrahydropyrimidin-2-ylamino-$(CH_2)_3$ | $CH_3$ | H | $NHSO_2NHC_6C_2$-(2,4,6-$Me_3$) | |
| 3198 | tetrahydropyrimidin-2-ylamino-$(CH_2)_3$ | $CH_3$ | H | $NHSO_2$[4-(3,5-dimethyl)isoxazolyl] | |
| 3199 | tetrahydropyrimidin-2-ylamino-$(CH_2)_3$ | $CH_3$ | H | $NHSO_2NH$(2-naphthyl) | |
| 3200 | tetrahydropyrimidin-2-ylamino-$(CH_2)_3$ | $CH_3$ | H | $NHSO_2NH$(1-naphthyl) | |
| 3201 | tetrahydropyrimidin-2-ylamino-$(CH_2)_3$ | $CH_3$ | H | $NHSO_2NHC_6H_4$-(4-Ph) | |
| 3202 | tetrahydropyrimidin-2-ylamino-$(CH_2)_3$ | $CH_3$ | H | $NHSO_2NHC_6H_2$-(4-Ph-2,6-dimethyl) | |
| 3203 | tetrahydropyrimidin-2-ylamino-$(CH_2)_3$ | $CH_3$ | H | $NHSO_2NHC_6H_2$-(4-Ph-2,6-dichloro) | |
| 3204 | tetrahydropyrimidin-2-ylamino-$(CH_2)_3$ | $CH_3$ | H | $NHSO_2NHCH_2Ph$ | |
| 3205 | imidazolin-2-ylamino-$(CH_2)_3$ | $CH_3$ | H | $NHCO_2CH_2C_6H_4$-(4-$CH_3$) | |
| 3206 | imidazolin-2-ylamino-$(CH_2)_3$ | $CH_3$ | H | $NHCO_2CH_2$(3-pyridinyl) | |
| 3207 | imidazolin-2-ylamino-$(CH_2)_3$ | $CH_3$ | H | $NHCO_2CH_2$(2-thiazolyl) | |
| 3208 | imidazolin-2-ylamino-$(CH_2)_3$ | $CH_3$ | H | $NHCO_2CH_2$(2-thienyl) | |
| 3209 | imidazolin-2-ylamino-$(CH_2)_3$ | $CH_3$ | H | $NHCO_2$i-Bu | |
| 3210 | imidazolin-2-ylamino-$(CH_2)_3$ | $CH_3$ | H | $NHSO_2Ph$ | |
| 3211 | imidazolin-2-ylamino-$(CH_2)_3$ | $CH_3$ | H | $NHSO_2C_6H_4$-(3-$CH_3$) | |
| 3212 | imidazolin-2-ylamino-$(CH_2)_3$ | $CH_3$ | H | $NHSO_2C_6H_3$-(2,6-$Me_2$) | |
| 3213 | imidazolin-2-ylamino-$(CH_2)_3$ | $CH_3$ | H | $NHSO_2C_6H_2$-(2,4,6-$Me_3$) | |
| 3214 | imidazolin-2-ylamino-$(CH_2)_3$ | $CH_3$ | H | $NHSO_2$(3-pyridyl) | |
| 3215 | imidazolin-2-ylamino-$(CH_2)_3$ | $CH_3$ | H | $NHSO_2$(2-thienyl) | |
| 3216 | imidazolin-2-ylamino-$(CH_2)_3$ | $CH_3$ | H | $NHSO_2$(2-thiazolyl) | |
| 3217 | imidazolin-2-ylamino-$(CH_2)_3$ | $CH_3$ | H | $NHSO_2$-[4-(3,5-dimethyl)isoxazolyl] | |
| 3218 | imidazolin-2-ylamino-$(CH_2)_3$ | $CH_3$ | H | $NHSO_2C_6H_4$-(3-Br) | |
| 3218a | imidazolin-2-ylamino-$(CH_2)_3$ | $CH_3$ | H | $NHSO_2C_6H_4$-(4-F) | |
| 3219 | imidazolin-2-ylamino-$(CH_2)_3$ | $CH_3$ | H | $NHSO_2C_6H_3$-(2,6-$Cl_2$) | |
| 3220 | imidazolin-2-ylamino-$(CH_2)_3$ | $CH_3$ | H | $NHSO_2$(2-naphthyl) | |
| 3221 | imidazolin-2-ylamino-$(CH_2)_3$ | $CH_3$ | H | $NHSO_2$(1-naphthyl) | |
| 3222 | imidazolin-2-ylamino-$(CH_2)_3$ | $CH_3$ | H | $NHSO_2C_6H_4$-(4-Ph) | |
| 3222a | imidazolin-2-ylamino-$(CH_2)_3$ | $CH_3$ | H | $NHSO_2C_6H_4$-4-(4-pyridyl) | |
| 3222b | imidazolin-2-ylamino-$(CH_2)_3$ | $CH_3$ | H | $NHSO_2C_6H_4$-4-(2-oxazolyl) | |
| 3222c | imidazolin-2-ylamino-$(CH_2)_3$ | $CH_3$ | H | $NHSO_2C_6H_4$-4-(3-pyrazolyl) | |

TABLE 3-continued

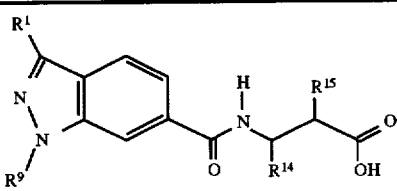

| Ex. No. | R$^1$ | R$^9$ | R$^{14}$ | R$^{15}$ | MS |
|---|---|---|---|---|---|
| 3223 | imidazolin-2-ylamino-(CH$_2$)$_3$ | CH$_3$ | H | NHSO$_2$C$_6$H$_2$-(4-Ph-2,6-dimethyl) | |
| 3223a | imidazolin-2-ylamino-(CH$_2$)$_3$ | CH$_3$ | H | NHSO$_2$C$_6$H$_2$-4-(3-pyridyl)-2,6-dimethyl | |
| 3223b | imidazolin-2-ylamino-(CH$_2$)$_3$ | CH$_3$ | H | NHSO$_2$C$_6$H$_2$-4-(2-oxazolyl)-2,6-dimethyl | |
| 3223c | imidazolin-2-ylamino-(CH$_2$)$_3$ | CH$_3$ | H | NHSO$_2$C$_6$H$_2$-4-(3-pyrazolyl)-2,6-dimethyl | |
| 3223d | imidazolin-2-ylamino-(CH$_2$)$_3$ | CH$_3$ | H | NHSO$_2$C$_6$H$_2$-4-(4-pyridyl)-2,6-dimethyl | |
| 3223e | imidazolin-2-ylamino-(CH$_2$)$_3$ | CH$_3$ | H | NHSO$_2$C$_6$H$_2$-4-(2-furyl)-2,6-dimethyl | |
| 3223f | imidazolin-2-ylamino-(CH$_2$)$_3$ | CH$_3$ | H | NHSO$_2$C$_6$H$_2$-4-(3-furyl)-2,6-dimethyl | |
| 3224 | imidazolin-2-ylamino-(CH$_2$)$_3$ | CH$_3$ | H | NHSO$_2$C$_6$H$_2$-(4-Ph-2,6-dichloro) | |
| 3225 | imidazolin-2-ylamino-(CH$_2$)$_3$ | CH$_3$ | H | NHSO$_2$CH$_2$Ph | |
| 3226 | imidazolin-2-ylamino-(CH$_2$)$_3$ | CH$_3$ | H | NHSO$_2$-n-Bu | |
| 3227 | imidazolin-2-ylamino-(CH$_2$)$_3$ | CH$_3$ | H | NHSO$_2$NHPh | |
| 3228 | imidazolin-2-ylamino-(CH$_2$)$_3$ | CH$_3$ | H | NHSO$_2$NHC$_6$H$_4$-(4-CH$_3$) | |
| 3229 | imidazolin-2-ylamino-(CH$_2$)$_3$ | CH$_3$ | H | NHSO$_2$NHC$_6$C$_3$-(2,6-Me$_2$) | |
| 3230 | imidazolin-2-ylamino-(CH$_2$)$_3$ | CH$_3$ | H | NHSO$_2$NHC$_6$C$_2$-(2,4,6-Me$_3$) | |
| 3231 | imidazolin-2-ylamino-(CH$_2$)$_3$ | CH$_3$ | H | NHSO$_2$NH(2-naphthyl) | |
| 3232 | imidazolin-2-ylamino-(CH$_2$)$_3$ | CH$_3$ | H | NHSO$_2$NH)1-naphthyl) | |
| 3233 | imidazolin-2-ylamino-(CH$_2$)$_3$ | CH$_3$ | H | NHSO$_2$NHC$_6$H$_4$-(4-Ph) | |
| 3234 | imidazolin-2-ylamino-(CH$_2$)$_3$ | CH$_3$ | H | NHSO$_2$NHC$_6$H$_2$-(4-Ph-2,6-dimethyl) | |
| 3235 | imidazolin-2-ylamino-(CH$_2$)$_3$ | CH$_3$ | H | NHSO$_2$NHC$_6$H$_2$-(4-Ph-2,6-dichloro) | |
| 3236 | imidazolin-2-ylamino-(CH$_2$)$_3$ | CH$_3$ | H | NHSO$_2$NHCH$_2$Ph | |
| 3237 | benzimidazol-2-ylamino-(CH$_2$)$_3$ | CH$_3$ | H | NHSO$_2$Ph | |
| 3238 | benzimidazol-2-ylamino-(CH$_2$)$_3$ | CH$_3$ | H | NHSO$_2$C$_6$H$_4$-(3-CH$_3$) | |
| 3239 | benzimidazol-2-ylamino-(CH$_2$)$_3$ | CH$_3$ | H | NHSO$_2$C$_6$H$_3$-(2,6-Me$_2$) | |
| 3240 | benzimidazol-2-ylamino-(CH$_2$)$_3$ | CH$_3$ | H | NHSO$_2$C$_6$H$_2$-(2,4,6-Me$_3$) | |
| 3241 | benzimidazol-2-ylamino-(CH$_2$)$_3$ | CH$_3$ | H | NHSO$_2$(4-pyridyl) | |
| 3242 | benzimidazol-2-ylamino-(CH$_2$)$_3$ | CH$_3$ | H | NHSO$_2$(2-thienyl) | |
| 3243 | benzimidazol-2-ylamino-(CH$_2$)$_3$ | CH$_3$ | H | NHSO$_2$(2-thiazolyl) | |
| 3244 | benzimidazol-2-ylamino-(CH$_2$)$_3$ | CH$_3$ | H | NHSO$_2$-[4-(3,5-dimethyl)isoxazolyl] | |
| 3245 | benzimidazol-2-ylamino-(CH$_2$)$_3$ | CH$_3$ | H | NHSO$_2$C$_6$H$_4$-(3-Br) | |
| 3246 | benzimidazol-2-ylamino-(CH$_2$)$_3$ | CH$_3$ | H | NHSO$_2$C$_6$H$_4$-(3-F) | |
| 3247 | benzimidazol-2-ylamino-(CH$_2$)$_3$ | CH$_3$ | H | NHSO$_2$C$_6$H$_3$-(2,6-Cl$_2$) | |
| 3248 | benzimidazol-2-ylamino-(CH$_2$)$_3$ | CH$_3$ | H | NHSO$_2$(2-naphthyl) | |
| 3249 | benzimidazol-2-ylamino-(CH$_2$)$_3$ | CH$_3$ | H | NHSO$_2$(1-naphthyl) | |
| 3250 | benzimidazol-2-ylamino-(CH$_2$)$_3$ | CH$_3$ | H | NHSO$_2$C$_6$H$_4$-(4-Ph) | |
| 3251 | benzimidazol-2-ylamino-(CH$_2$)$_3$ | CH$_3$ | H | NHSO$_2$C$_6$H$_2$-(4-Ph-2,6-dimethyl) | |
| 3252 | benzimidazol-2-ylamino-(CH$_2$)$_3$ | CH$_3$ | H | NHSO$_2$C$_6$H$_2$-(4-Ph-2,6-dichloro) | |
| 3253 | benzimidazol-2-ylamino-(CH$_2$)$_3$ | CH$_3$ | H | NHSO$_2$CH$_2$Ph | |
| 3254 | benzimidazol-2-ylamino-(CH$_2$)$_3$ | CH$_3$ | H | NHSO$_2$-i-Bu | |
| 3255 | benzimidazol-2-ylamino-(CH$_2$)$_3$ | CH$_3$ | H | NHSO$_2$NHPh | |
| 3256 | benzimidazol-2-ylamino-(CH$_2$)$_3$ | CH$_3$ | H | NHSO$_2$NHC$_6$H$_4$-(4-CH$_3$) | |
| 3257 | benzimidazol-2-ylamino-(CH$_2$)$_3$ | CH$_3$ | H | NHSO$_2$NHC$_6$C$_3$-(2,6-Me$_2$) | |
| 3258 | benzimidazol-2-ylamino-(CH$_2$)$_3$ | CH$_3$ | H | NHSO$_2$NHC$_6$C$_2$-(2,4,6-Me$_3$) | |
| 3259 | benzimidazol-2-ylamino-(CH$_2$)$_3$ | CH$_3$ | H | NHSO$_2$NH(2-naphthyl) | |
| 3260 | benzimidazol-2-ylamino-(CH$_2$)$_3$ | CH$_3$ | H | NHSO$_2$NH)1-naphthyl) | |
| 3261 | benzimidazol-2-ylamino-(CH$_2$)$_3$ | CH$_3$ | H | NHSO$_2$NHC$_6$H$_4$-(4-Ph) | |
| 3262 | benzimidazol-2-ylamino-(CH$_2$)$_3$ | CH$_3$ | H | NHSO$_2$NHC$_6$H$_2$-(4-Ph-2,6-dimethyl) | |
| 3263 | benzimidazol-2-ylamino-(CH$_2$)$_3$ | CH$_3$ | H | NHSO$_2$NHC$_6$H$_2$-(4-Ph-2,6-dichloro) | |
| 3264 | benzimidazol-2-ylamino-(CH$_2$)$_3$ | CH$_3$ | H | NHSO$_2$NHCH$_2$Ph | |
| 3265 | benzimidazol-2-ylamino-(CH$_2$)$_3$ | CH$_3$ | H | NHCO$_2$CH$_2$Ph | |
| 3266 | benzimidazol-2-ylamino-(CH$_2$)$_3$ | CH$_3$ | H | NHCO$_2$i-Bu | |
| 3267 | 2-aminopyridin-6-yl-(CH$_2$)$_3$ | CH$_3$ | H | NHSO$_2$C$_6$H$_4$-(4-CH$_3$) | |
| 3268 | 2-aminopyridin-6-yl-(CH$_2$)$_3$ | CH$_3$ | H | NHSO$_2$C$_6$H$_2$-(2,6-Me$_2$) | |
| 3269 | 2-aminopyridin-6-yl-(CH$_2$)$_3$ | CH$_3$ | H | NHSO$_2$C$_6$H$_2$-(2,4,6-Me$_3$) | |
| 3270 | 2-aminopyridin-6-yl-(CH$_2$)$_3$ | CH$_3$ | H | NHSO$_2$(3-pyridyl) | |
| 3271 | 2-aminopyridin-6-yl-(CH$_2$)$_3$ | CH$_3$ | H | NHSO$_2$(2-thiazolyl) | |
| 3272 | 2-aminopyridin-6-yl-(CH$_2$)$_3$ | CH$_3$ | H | NHSO$_2$(4-isoxazolyl) | |
| 3273 | 2-aminopyridin-6-yl-(CH$_2$)$_3$ | CH$_3$ | H | NHSO$_2$C$_6$H$_4$-(3-Br) | |
| 3274 | 2-aminopyridin-6-yl-(CH$_2$)$_3$ | CH$_3$ | H | NHSO$_2$C$_6$H$_4$-(3-F) | |
| 3275 | 2-aminopyridin-6-yl-(CH$_2$)$_3$ | CH$_3$ | H | NHSO$_2$C$_6$H$_3$-(2,6-Cl$_2$) | |
| 3276 | 2-aminopyridin-6-yl-(CH$_2$)$_3$ | CH$_3$ | H | NHSO$_2$(2-naphthyl) | |
| 3277 | 2-aminopyridin-6-yl-(CH$_2$)$_3$ | CH$_3$ | H | NHSO$_2$(1-naphthyl) | |
| 3278 | 2-aminopyridin-6-yl-(CH$_2$)$_3$ | CH$_3$ | H | NHSO$_2$C$_6$H$_4$-(4-Ph) | |
| 3279 | 2-aminopyridin-6-yl-(CH$_2$)$_3$ | CH$_3$ | H | NHSO$_2$C$_6$H$_2$-(4-Ph-2,6-dimethyl) | |
| 3280 | 2-aminopyridin-6-yl-(CH$_2$)$_3$ | CH$_3$ | H | NHSO$_2$C$_6$H$_2$-(4-Ph-2,6-dichloro) | |
| 3281 | 2-aminopyridin-6-yl-(CH$_2$)$_3$ | CH$_3$ | H | NHSO$_2$CH$_2$Ph | |
| 3282 | 2-aminopyridin-6-yl-(CH$_2$)$_3$ | CH$_3$ | H | NHSO$_2$-i-Bu | |
| 3283 | 2-aminopyridin-6-yl-(CH$_2$)$_3$ | CH$_3$ | H | NHSO$_2$NHPh | |

TABLE 3-continued

| Ex. No. | R¹ | R⁹ | R¹⁴ | R¹⁵ | MS |
|---|---|---|---|---|---|
| 3284 | 2-aminopyridin-6-yl-(CH₂)₃ | CH₃ | H | NHSO₂NHC₆H₄-(4-CH₃) | |
| 3285 | 2-aminopyridin-6-yl-(CH₂)₃ | CH₃ | H | NHSO₂NHC₆C₃-(2,6-Me₂) | |
| 3286 | 2-aminopyridin-6-yl-(CH₂)₃ | CH₃ | H | NHSO₂NHC₆C₂-(2,4,6-Me₃) | |
| 3287 | 2-aminopyridin-6-yl-(CH₂)₃ | CH₃ | H | NHSO₂NH(2-naphthyl) | |
| 3288 | 2-aminopyridin-6-yl-(CH₂)₃ | CH₃ | H | NHSO₂NH)1-naphthyl) | |
| 3289 | 2-aminopyridin-6-yl-(CH₂)₃ | CH₃ | H | NHSO₂NHC₆H₄-(4-Ph) | |
| 3290 | 2-aminopyridin-6-yl-(CH₂)₃ | CH₃ | H | NHSO₂NHC₆H₂-(4-Ph-2,6-dimethyl) | |
| 3291 | 2-aminopyridin-6-yl-(CH₂)₃ | CH₃ | H | NHSO₂NHC₆H₂-(4-Ph-2,6-dichloro) | |
| 3292 | 2-aminopyridin-6-yl-(CH₂)₃ | CH₃ | H | NHCO₂n-Bu | |
| 3293 | 2-aminopyridin-6-yl-(CH₂)₃ | CH₃ | H | NHCO₂i-Bu | |
| 3294 | 2-iminoazepin-7-yl-(CH₂)₃ | CH₃ | H | NHSO₂Ph | |
| 3295 | imidazol-4-ylamino-(CH₂)₃ | CH₃ | H | NHSO₂Ph | |
| 3296 | 2-iminoazepin-7-yl-(CH₂)₃ | CH₃ | H | NHSO₂(4-isoxazolyl) | |
| 3297 | imidazol-4-ylamino-(CH₂)₃ | CH₃ | H | NHSO₂(4-isoxazolyl) | |
| 3298 | 2-iminoazepin-7-yl-(CH₂)₃ | CH₃ | H | NHSO₂-[4-(3,5-dimethyl)isoxazolyl] | |
| 3299 | imidazol-4-ylamino-(CH₂)₃ | CH₃ | H | NHSO₂-[4-(3,5-dimethyl)isoxazolyl] | |
| 3300 | imidazol-2-ylamino-(CH₂)₃ | CH₃ | 3-pyridinyl | NHSO₂Ph | |
| 3301 | pyridin-2-ylamino-(CH₂)₃ | CH₃ | 3-pyridinyl | NHSO₂Ph | |
| 3302 | imidazol-2-ylamino-(CH₂)₃ | CH₃ | (3,4-methylenedioxy)phenyl | NHSO₂Ph | |
| 3303 | pyridin-2-ylamino-(CH₂)₃ | CH₃ | (3,4-methylenedioxy)phenyl | NHSO₂Ph | |
| 3304 | imidazol-2-ylamino-(CH₂)₂ | CH₃ | H | NHSO₂Ph | |
| 3305 | imidazol-2-ylamino-(CH₂)₂ | CH₃ | H | NHCO₂CH₂Ph | |
| 3306 | imidazol-2-ylamino-carbonyl-(CH₂)₂ | CH₃ | H | NHSO₂C₆H₂-(2,4,6-CH₃)₃ | |
| 3307 | pyridin-2-ylamino-(CH₂)₂ | CH₃ | H | NHSO₂Ph | |
| 3308 | pyridin-2-ylamino-(CH₂)₂ | CH₃ | H | NHCO₂CH₂Ph | |
| 3309 | pyridin-2-ylamino-carbonyl-(CH₂)₂ | CH₃ | H | NHSO₂C₆H₂-(2,4,6-CH₃)₃ | |
| 3310 | imidazolin-2-ylamino-(CH₂)₂ | CH₃ | H | NHSO₂Ph | |
| 3311 | imidazolin-2-ylamino-(CH₂)₂ | CH₃ | H | NHCO₂CH₂Ph | |
| 3312 | tetrahydropyrimidin-2-ylamino-(CH₂)₂ | CH₃ | H | NHSO₂Ph | |
| 3313 | tetrahydropyrimidin-2-ylamino-(CH₂)₂ | CH₃ | H | NHCO₂CH₂Ph | |
| 3314 | benzimidazol-2-ylamino-(CH₂)₂ | CH₃ | H | NHSO₂Ph | |
| 3315 | benzimidazol-2-ylamino-(CH₂)₂ | CH₃ | H | NHCO₂CH₂Ph | |
| 3316 | benzimidazol-2-ylamino-carbonyl-(CH₂)₂ | CH₃ | H | NHSO₂C₆H₂-(2,4,6-CH₃)₃ | |
| 3317 | 2-aminopyridin-6-yl-(CH₂)₂ | CH₃ | H | NHSO₂Ph | |
| 3318 | 2-aminopyridin-6-yl-(CH₂)₂ | CH₃ | H | NHCO₂CH₂Ph | |
| 3319 | 2-iminoazepin-7-yl-(CH₂)₂ | CH₃ | H | NHSO₂Ph | |
| 3320 | 2-iminoazepin-7-yl-(CH₂)₂ | CH₃ | H | NHCO₂CH₂Ph | |
| 3321 | imidazol-4-ylamino-(CH₂)₂ | CH₃ | H | NHSO₂Ph | |
| 3322 | imidazol-4-ylamino-(CH₂)₂ | CH₃ | H | NHCO₂CH₂Ph | |
| 3323 | imidazol-2-ylamino-(CH₂)₄ | CH₃ | H | NHSO₂Ph | |
| 3324 | imidazol-2-ylamino-(CH₂)₄ | CH₃ | H | NHCO₂CH₂Ph | |
| 3325 | pyridin-2-ylamino-(CH₂)₄ | CH₃ | H | NHSO₂Ph | |
| 3326 | pyridin-2-ylamino-(CH₂)₄ | CH₃ | H | NHCO₂CH₂Ph | |
| 3327 | imidazolin-2-ylamino-(CH₂)₄ | CH₃ | H | NHSO₂Ph | |
| 3328 | tetrahydropyrimidin-2-ylamino-(CH₂)₄ | CH₃ | H | NHSO₂Ph | |
| 3329 | tetrahydropyrimidin-2-ylamino-(CH₂)₄ | CH₃ | H | NHCO₂CH₂Ph | |
| 3330 | benzimidazol-2-ylamino-(CH₂)₄ | CH₃ | H | NHSO₂Ph | |
| 3331 | benzimidazol-2-ylamino-(CH₂)₄ | CH₃ | H | NHCO₂CH₂Ph | |
| 3332 | 2-aminopyridin-6-yl-(CH₂)₄ | CH₃ | H | NHSO₂Ph | |
| 3333 | 2-aminopyridin-6-yl-(CH₂)₄ | CH₃ | H | NHCO₂CH₂Ph | |
| 3334 | 2-iminoazepin-7-yl-(CH₂)₄ | CH₃ | H | NHSO₂Ph | |
| 3335 | 2-iminoazepin-7-yl-(CH₂)₄ | CH₃ | H | NHCO₂CH₂Ph | |
| 3336 | imidazol-4-ylamino-(CH₂)₄ | CH₃ | H | NHSO₂Ph | |
| 3337 | imidazol-4-ylamino-(CH₂)₄ | CH₃ | H | NHCO₂CH₂Ph | |
| 3338 | imidazol-2-ylamino-(CH₂)₃ | CH₂Ph | H | NHSO₂C₆H₂-(2,4,6-CH₃)₃ | |
| 3339 | pyridin-2-ylamino-(CH₂)₃ | CH₂Ph | H | NHSO₂C₆H₂-(2,4,6-CH₃)₃ | |
| 3340 | imidazol-2-ylamino-(CH₂)₃ | CH₂CH₃ | H | NHSO₂C₆H₂-(2,4,6-CH₃)₃ | |
| 3341 | imidazol-2-ylamino-(CH₂)₃ | CH(CH₃)₂ | H | NHSO₂C₆H₂-(2,4,6-CH₃)₃ | |
| 3342 | imidazol-2-ylamino-(CH₂)₃ | cyclopropyl | H | NHSO₂C₆H₂-(2,4,6-CH₃)₃ | |
| 3343 | imidazol-2-ylamino-(CH₂)₃ | CH₂-cyclopropyl | H | NHSO₂C₆H₂-(2,4,6-CH₃)₃ | |
| 3344 | imidazol-2-ylamino-(CH₂)₃ | CH₂COOH | H | NHSO₂C₆H₂-(2,4,6-CH₃)₃ | |
| 3345 | imidazol-2-ylamino-(CH₂)₃ | (CH₂)₂NMe₂ | H | NHSO₂C₆H₂-(2,4,6-CH₃)₃ | |
| 3346 | imidazol-2-ylamino-(CH₂)₃ | CH₂CH₂OMe | H | NHSO₂C₆H₂-(2,4,6-CH₃)₃ | |
| 3347 | imidazol-2-ylamino-(CH₂)₃ | CH₂CH₂Ph | H | NHSO₂C₆H₂-(2,4,6-CH₃)₃ | |
| 3348 | imidazol-2-ylamino-(CH₂)₃ | CH₂CH₂OH | H | NHSO₂C₆H₂-(2,4,6-CH₃)₃ | |
| 3349 | imidazol-2-ylamino-(CH₂)₃ | CH₂CH₃ | H | NHSO₂C₆H₂-(2,6-CH₃)₂-4-Ph | |

TABLE 3-continued

| Ex. No. | R¹ | R⁹ | R¹⁴ | R¹⁵ | MS |
|---|---|---|---|---|---|
| 3350 | imidazol-2-ylamino-(CH₂)₃ | CH(CH₃)₂ | H | NHSO₂C₆H₂-(2,6-CH₃)₂-4-Ph | |
| 3351 | imidazol-2-ylamino-(CH₂)₃ | cyclopropyl | H | NHSO₂C₆H₂-(2,6-CH₃)₂-4-Ph | |
| 3352 | imidazol-2-ylamino-(CH₂)₃ | CH₂-cyclopropyl | H | NHSO₂C₆H₂-(2,6-CH₃)₂-4-Ph | |
| 3353 | imidazol-2-ylamino-(CH₂)₃ | CH₂COOH | H | NHSO₂C₆H₂-(2,6-CH₃)₂-4-Ph | |
| 3354 | imidazol-2-ylamino-(CH₂)₃ | (CH₂)₂NMe₂ | H | NHSO₂C₆H₂-(2,6-CH₃)₂-4-Ph | |
| 3355 | imidazol-2-ylamino-(CH₂)₃ | CH₂CH₂OMe | H | NHSO₂C₆H₂-(2,6-CH₃)₂-4-Ph | |
| 3356 | imidazol-2-ylamino-(CH₂)₃ | CH₂CH₂Ph | H | NHSO₂C₆H₂-(2,6-CH₃)₂-4-Ph | |
| 3357 | imidazol-2-ylamino-(CH₂)₃ | CH₂CH₂OH | H | NHSO₂C₆H₂-(2,6-CH₃)₂-4-Ph | |
| 3358 | imidazol-2-ylamino-CH₂(o-C₆H₄) | CH₃ | H | NHSO₂-(1-naphthyl) | |
| 3359 | imidazol-2-ylamino-CH₂(o-C₆H₄) | CH₃ | H | NHCO₂CH₂Ph | |
| 3360 | imidazol-2-ylamino-CH₂(o-C₆H₄) | CH₃ | H | NHSO₂C₆C₂-(2,4,6-Me₃) | |
| 3361 | pyridin-2-ylamino-CH₂(o-C₆H₄) | CH₃ | H | NHSO₂-(1-naphthyl) | |
| 3362 | pyridin-2-ylamino-CH₂(o-C₆H₄) | CH₃ | H | NHCO₂CH₂Ph | |
| 3363 | pyridin-2-ylamino-CH₂(o-C₆H₄) | CH₃ | H | NHSO₂C₆C₂-(2,4,6-Me₃) | |
| 3364 | imidazolin-2-ylamino-CH₂(o-C₆H₄) | CH₃ | H | NHSO₂-(1-naphthyl) | |
| 3365 | imidazolin-2-ylamino-CH₂(o-C₆H₄) | CH₃ | H | NHCO₂CH₂Ph | |
| 3366 | imidazolin-2-ylamino-CH₂(o-C₆H₄) | CH₃ | H | NHSO₂C₆C₂-(2,4,6-Me₃) | |
| 3367 | imidazolin-2-ylamino-(m-C₆H₄) | CH₃ | H | NHSO₂-(1-naphthyl) | |
| 3368 | imidazolin-2-ylamino-(m-C₆H₄) | CH₃ | H | NHCO₂CH₂Ph | |
| 3369 | imidazolin-2-ylamino-(m-C₆H₄) | CH₃ | H | NHSO₂C₆C₂-(2,4,6-Me₃) | |

TABLE 4

| Ex. No. | R¹ | R⁹ | R¹⁴ | R¹⁵ | MS |
|---|---|---|---|---|---|
| 4001 | imidazol-2-ylamino-(CH₂)₃ | H | H | H | |
| 4002 | pyridin-2-ylamino-(CH₂)₃ | H | H | NHCOOCH₂Ph | |
| 4002a | imidazolin-2-ylamino-(CH₂)₃ | H | H | NHCOOCH₂Ph | |
| 4002b | tetrahydropyrimidin-2-ylamino-(CH₂)₃ | H | H | NHCO₂CH₂Ph | |
| 4002c | imidazol-2-ylamino-(CH₂)₃ | H | H | NHCO₂CH₂Ph | |
| 4003 | imidazolin-2-ylamino-(CH₂)₃ | H | H | NHCO₂CH₂C₆H₄-(2-CH₃) | |
| 4004 | tetrahydropyrimidin-2-ylamino-(CH₂)₃ | H | H | NHCO₂CH₂C₆H₄-(3-CH₃) | |
| 4005 | benzimidazol-2-ylamino-(CH₂)₃ | H | H | NHCO₂CH₂C₆H₄-(4-CH₃) | |
| 4006 | 2-aminopyridin-6-yl-(CH₂)₃ | H | H | NHCO₂CH₂(2-pyridinyl) | |
| 4007 | 2-iminoazepin-7-yl-(CH₂)₃ | H | H | NHCO₂CH₃(3-pyridinyl) | |
| 4010 | imidazol-4-ylamino-(CH₂)₃ | H | H | NHCO₂CH₂(2-thiazolyl) | |
| 4015 | imidazol-2-ylamino-(CH₂)₃ | H | H | NHCO₂CH₂(4-isoxazolyl) | |
| 4016 | pyridin-2-ylamino-(CH₂)₃ | H | H | NHCO₂CH₂(2-thienyl) | |
| 4017 | imidazol-2-ylamino-(CH₂)₃ | H | H | NHCO₂n-Bu | |
| 4018 | tetrahydropyrimidin-2-ylamino-(CH₂)₃ | H | H | NHCO₂i-Bu | |
| 4019 | benzimidazol-2-ylamino-(CH₂)₃ | H | H | NHCO₂t-Bu | |
| 4020 | 2-aminopyridin-6-yl-(CH₂)₃ | H | H | NHSO₂Ph | |
| 4020a | pyridin-2-ylamino-(CH₂)₃ | H | H | NHSO₂Ph | |
| 4020b | imidazolin-2-ylamino-(CH₂)₃ | H | H | NHSO₂Ph | |
| 4020c | tetrahydropyrimidin-2-ylamino-(CH₂)₃ | H | H | NHSO₂Ph | |
| 4020d | imidazol-2-ylamino-(CH₂)₃ | H | H | NHSO₂Ph | |
| 4021 | 2-iminoazepin-7-yl-(CH₂)₃ | H | H | NHSO₂C₆H₄-(2-CH₃) | |
| 4021a | imidazol-2-ylamino-(CH₂)₃ | H | H | NHSO₂C₆H₃-(2,6-Me₂) | |
| 4021b | imidazol-2-ylamino-(CH₂)₃ | H | H | NHSO₂C₆H₂-(2,4,6-Me₃) | |
| 4021c | imidazol-2-ylamino-(CH₂)₃ | H | H | NHSO₂C₆H₂-(2,6-Me₂-4-Ph) | |
| 4021d | pyridin-2-ylamino-(CH₂)₃ | H | H | NHSO₂C₆H₂-(2,6-Me₂-4-Ph) | |
| 4021e | imidazolin-2-ylamino-(CH₂)₃ | H | H | NHSO₂C₆H₂-(2,6-Me₂-4-Ph) | |

TABLE 4-continued

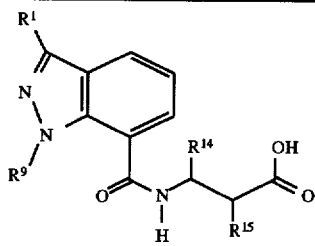

| Ex. No. | $R^1$ | $R^9$ | $R^{14}$ | $R^{15}$ | MS |
|---|---|---|---|---|---|
| 4021f | tetrahydropyrimidin-2-ylamino-$(CH_2)_3$ | H | H | $NHSO_2C_6H_2$-(2,6-$Me_2$-4-Ph) | |
| 4024 | imidazol-4-ylamino-$(CH_2)_3$ | H | H | $NHSO_2$(2-pyridyl) | |
| 4029 | imidazol-2-ylamino-$(CH_2)_3$ | H | H | $NHSO_2$(4-isoxazolyl) | |
| 4030 | pyridin-2-ylamino-$(CH_2)_3$ | H | H | $NHSO_2$-[4-(3,5-dimethyl)isoxazolyl] | |
| 4030a | imidazolin-2-ylamino-$(CH_2)_3$ | H | H | $NHSO_2$-[4-(3,5-dimethyl)isoxazolyl] | |
| 4030b | tetrahydropyrimidin-2-ylamino-$(CH_2)_3$ | H | H | $NHSO_2$-[4-(3,5-dimethyl)isoxazolyl] | |
| 4030c | imidazol-2-ylamino-$(CH_2)_3$ | H | H | $NHSO_2$-[4-(3,5-dimethyl)isoxazolyl] | |
| 4031 | imidazolin-2-ylamino-$(CH_2)_3$ | H | H | $NHSO_2C_6H_4$-(2-Br) | |
| 4032 | tetrahydropyrimidin-2-ylamino-$(CH_2)_3$ | H | H | $NHSO_2C_6H_4$-(3-Br) | |
| 4033 | benzimidazol-2-ylamino-$(CH_2)_3$ | H | H | $NHSO_2C_6H_4$-(4-Br) | |
| 4034 | 2-aminopyridin-6-yl-$(CH_2)_3$ | H | H | $NHSO_2C_6H_4$-(2-F) | |
| 4035 | 2-iminoazepin-7-yl-$(CH_2)_3$ | H | H | $NHSO_2C_6H_4$-(3-F) | |
| 4038 | imidazol-2-ylamino-$(CH_2)_3$ | H | H | $NHSO_2$(1-naphthyl) | |
| 4038a | imidazol-2-ylamino-$(CH_2)_3$ | H | H | $NHSO_2C_6H_3$-(2,6-$Cl_2$) | |
| 4038b | imidazol-2-ylamino-$(CH_2)_3$ | H | H | $NHSO_2C_6H_2$-(2,6-$Cl_2$-4-Ph) | |
| 4043 | imidazol-2-ylamino-$(CH_2)_3$ | H | H | $NHSO_2$-i-Bu | |
| 4044 | pyridin-2-ylamino-$(CH_2)_3$ | H | H | $NHSO_2$-t-Bu | |
| 4045 | imidazol-2-ylamino-$(CH_2)_3$ | H | (3,4-methylenedioxy)phenyl | H | |
| 4046 | pyridin-2-ylamino-$(CH_2)_3$ | H | (3,4-methylenedioxy)phenyl | H | |
| 4047 | imidazolin-2-ylamino-$(CH_2)_3$ | H | (3,4-methylenedioxy)phenyl | H | |
| 4048 | tetrahydropyrimidin-2-ylamino-$(CH_2)_3$ | H | (3,4-methylenedioxy)phenyl | H | |
| 4049 | benzimidazol-2-ylamino-$(CH_2)_3$ | H | (3,4-methylenedioxy)phenyl | H | |
| 4050 | 2-aminopyridin-6-yl-$(CH_2)_3$ | H | (3,4-methylenedioxy)phenyl | H | |
| 4051 | 2-iminoazepin-7-yl-$(CH_2)_3$ | H | (3,4-methylenedioxy)phenyl | H | |
| 4054 | imidazol-4-ylamino-$(CH_2)_3$ | H | (3,4-methylenedioxy)phenyl | H | |
| 4059 | imidazol-2-ylamino-$(CH_2)_3$ | H | 3-pyridinyl | H | |
| 4060 | pyridin-2-ylamino-$(CH_2)_3$ | H | 3-pyridinyl | H | |
| 4061 | imidazol-2-ylamino-$(CH_2)_3$ | H | 3-pyridinyl | H | |
| 4062 | tetrahydropyrimidin-2-ylamino-$(CH_2)_3$ | H | 3-pyridinyl | H | |
| 4063 | benzimidazol-2-ylamino-$(CH_2)_3$ | H | 3-pyridinyl | H | |
| 4064 | 2-aminopyridin-6-yl-$(CH_2)_3$ | H | 3-pyridinyl | H | |
| 4065 | 2-iminoazepin-7-yl-$(CH_2)_3$ | H | 3-pyridinyl | H | |
| 4068 | imidazol-4-ylamino-$(CH_2)_3$ | H | 3-pyridinyl | H | |
| 4068a | imidazol-2-ylamino-$CH_2$(o-$C_6H_4$) | H | H | $NHSO_2$-(1-naphthyl) | |
| 4068b | imidazol-2-ylamino-$CH_2$(o-$C_6H_4$) | H | H | $NHCO_2CH_2Ph$ | |
| 4068c | imidazol-2-ylamino-$CH_2$(o-$C_6H_4$) | H | H | $NHSO_2C_6C_2$-(2,4,6-$Me_3$) | |
| 4068d | pyridin-2-ylamino-$CH_2$(o-$C_6H_4$) | H | H | $NHSO_2$-(1-naphthyl) | |
| 4068e | pyridin-2-ylamino-$CH_2$(o-$C_6H_4$) | H | H | $NHCO_2CH_2Ph$ | |
| 4068f | pyridin-2-ylamino-$CH_2$(o-$C_6H_4$) | H | H | $NHSO_2C_6C_2$-(2,4,6-$Me_3$) | |
| 4068g | imidazolin-2-ylamino-$CH_2$(o-$C_6H_4$) | H | H | $NHSO_2$-(1-naphthyl) | |
| 4068h | imidazolin-2-ylamino-$CH_2$(o-$C_6H_4$) | H | H | $NHCO_2CH_2Ph$ | |
| 4068i | imidazolin-2-ylamino-$CH_2$(o-$C_6H_4$) | H | H | $NHSO_2C_6C_2$-(2,4,6-$Me_3$) | |
| 4068j | imidazolin-2-ylamino-(m-$C_6H_4$) | H | H | $NHSO_2$-(1-naphthyl) | |
| 4068k | imidazolin-2-ylamino-(m-$C_6H_4$) | H | H | $NHCO_2CH_2Ph$ | |
| 4068l | imidazolin-2-ylamino-(m-$C_6H_4$) | H | H | $NHSO_2C_6C_2$-(2,4,6-$Me_3$) | |
| 4075 | imidazol-2-ylamino-$(CH_2)_3$ | $CH_3$ | H | $NHCO_2CH_2Ph$ | |
| 4076 | imidazol-2-ylamino-$(CH_2)_3$ | $CH_3$ | H | $NHCO_2CH_2C_6H_4$-(3-$CH_3$) | |
| 4077 | imidazol-2-ylamino-$(CH_2)_3$ | $CH_3$ | H | $NHCO_2CH_2$(3-pyridinyl) | |
| 4078 | imidazol-2-ylamino-$(CH_2)_3$ | $CH_3$ | H | $NHCO_2CH_2$(2-thiazolyl) | |
| 4079 | imidazol-2-ylamino-$(CH_2)_3$ | $CH_3$ | H | $NHCO_2CH_2$(2-thienyl) | |
| 4080 | imidazol-2-ylamino-$(CH_2)_3$ | $CH_3$ | H | $NHCO_2CH_2$(5-isoxazolyl) | |
| 4081 | imidazol-2-ylamino-$(CH_2)_3$ | $CH_3$ | H | $NHCO_2$n-Bu | |
| 4082 | imidazol-2-ylamino-$(CH_2)_3$ | $CH_3$ | H | NHCOPh | |
| 4083 | imidazol-2-ylamino-$(CH_2)_3$ | $CH_3$ | H | $NHCOCH_2Ph$ | |
| 4084 | imidazol-2-ylamino-$(CH_2)_3$ | $CH_3$ | H | $NHCOCH_2CH_2Ph$ | |
| 4085 | imidazol-2-ylamino-$(CH_2)_3$ | $CH_3$ | H | NHCOCH=CHPh | |
| 4086 | imidazol-2-ylamino-$(CH_2)_3$ | $CH_3$ | H | $NHCOCH_2$(3-pyridinyl) | |
| 4087 | imidazol-2-ylamino-$(CH_2)_3$ | $CH_3$ | H | $NHCOCH_2$(2-thienyl) | |
| 4088 | imidazol-2-ylamino-$(CH_2)_3$ | $CH_3$ | H | $NHCOCH_2$(cyclohexyl) | |
| 4089 | imidazol-2-ylamino-$(CH_2)_3$ | $CH_3$ | H | NHCOn-Bu | |
| 4090 | imidazol-2-ylamino-$(CH_2)_3$ | $CH_3$ | H | $NHCONHCH_2Ph$ | |
| 4091 | imidazol-2-ylamino-$(CH_2)_3$ | $CH_3$ | H | $NHSO_2Ph$ | |
| 4092 | imidazol-2-ylamino-$(CH_2)_3$ | $CH_3$ | H | $NHSO_2C_6H_4$-(4-$CH_3$) | |
| 4093 | imidazol-2-ylamino-$(CH_2)_3$ | $CH_3$ | H | $NHSO_2C_6H_3$-(2,6-$CH_3$)$_2$ | |

TABLE 4-continued

[Structure: indazole with R¹ at 3-position, R⁹ on N1, 7-position bears C(O)NH-CH(R¹⁴)-CH(R¹⁵)-COOH]

| Ex. No. | R¹ | R⁹ | R¹⁴ | R¹⁵ | MS |
|---|---|---|---|---|---|
| 4094 | imidazol-2-ylamino-(CH₂)₃ | CH₃ | H | NHSO₂C₆H₂-(2,4,6-CH₃)₃ | |
| 4095 | imidazol-2-ylamino-(CH₂)₃ | CH₃ | H | NHSO₂(3-pyridyl) | |
| 4096 | imidazol-2-ylamino-(CH₂)₃ | CH₃ | H | NHSO₂(2-thienyl) | |
| 4097 | imidazol-2-ylamino-(CH₂)₃ | CH₃ | H | NHSO₂(2-thiazolyl) | |
| 4098 | imidazol-2-ylamino-(CH₂)₃ | CH₃ | H | NHSO₂[4-(3,5-dimethyl)isoxazolyl] | |
| 4099 | imidazol-2-ylamino-(CH₂)₃ | CH₃ | H | NHSO₂C₆H₄-(4-Br) | |
| 4100 | imidazol-2-ylamino-(CH₂)₃ | CH₃ | H | NHSO₂C₆H₄-(4-F) | |
| 4101 | imidazol-2-ylamino-(CH₂)₃ | CH₃ | H | NHSO₂C₆H₃-(2,6-Cl₂) | |
| 4102 | imidazol-2-ylamino-(CH₂)₃ | CH₃ | H | NHSO₂(2-naphthyl) | |
| 4103 | imidazol-2-ylamino-(CH₂)₃ | CH₃ | H | NHSO₂(1-naphthyl) | |
| 4104 | imidazol-2-ylamino-(CH₂)₃ | CH₃ | H | NHSO₂C₆H₄-(4-Ph) | |
| 4104a | imidazol-2-ylamino-(CH₂)₃ | CH₃ | H | NHSO₂C₆H₄-4-(4-pyridyl) | |
| 4104b | imidazol-2-ylamino-(CH₂)₃ | CH₃ | H | NHSO₂C₆H₄-4-(2-oxazolyl) | |
| 4104c | imidazol-2-ylamino-(CH₂)₃ | CH₃ | H | NHSO₂C₆H₄-4-(3-pyrazolyl) | |
| 4105 | imidazol-2-ylamino-(CH₂)₃ | CH₃ | H | NHSO₂C₆H₂-4-(4-Ph-2,6-dimethyl) | |
| 4105a | imidazol-2-ylamino-(CH₂)₃ | CH₃ | H | NHSO₂C₆H₂-4-(3-pyridyl)-2,6-dimethyl | |
| 4105b | imidazol-2-ylamino-(CH₂)₃ | CH₃ | H | NHSO₂C₆H₂-4-(2-oxazolyl)-2,6-dimethyl | |
| 4105c | imidazol-2-ylamino-(CH₂)₃ | CH₃ | H | NHSO₂C₆H₂-4-(3-pyrazolyl)-2,6-dimethyl | |
| 4106 | imidazol-2-ylamino-(CH₂)₃ | CH₃ | H | NHSO₂C₆H₂-(4-Ph-2,6-dichloro) | |
| 4107 | imidazol-2-ylamino-(CH₂)₃ | CH₃ | H | NHSO₂C₆H-(4-Ph-2,6-dimethyl-3-chloro) | |
| 4108 | imidazol-2-ylamino-(CH₂)₃ | CH₃ | H | NHSO₂CH₂Ph | |
| 4109 | imidazol-2-ylamino-(CH₂)₃ | CH₃ | H | NHSO₂-n-Bu | |
| 4110 | imidazol-2-ylamino-(CH₂)₃ | CH₃ | H | NHSO₂NHPh | |
| 4111 | imidazol-2-ylamino-(CH₂)₃ | CH₃ | H | NHSO₂NHC₆H₄-(4-CH₃) | |
| 4112 | imidazol-2-ylamino-(CH₂)₃ | CH₃ | H | NHSO₂NHC₆C₃-(2,6-Me₂) | |
| 4113 | imidazol-2-ylamino-(CH₂)₃ | CH₃ | H | NHSO₂NHC₆C₂-(2,4,6-Me₃) | |
| 4114 | imidazol-2-ylamino-(CH₂)₃ | CH₃ | H | NHSO₂NH(3-pyridyl) | |
| 4115 | imidazol-2-ylamino-(CH₂)₃ | CH₃ | H | NHSO₂[4-(3,5-dimethyl)isoxazolyl] | |
| 4116 | imidazol-2-ylamino-(CH₂)₃ | CH₃ | H | NHSO₂NHC₆H₄-(4-Br) | |
| 4117 | imidazol-2-ylamino-(CH₂)₃ | CH₃ | H | NHSO₂NHC₆H₄-(4-F) | |
| 4118 | imidazol-2-ylamino-(CH₂)₃ | CH₃ | H | NHSO₂NH(2-naphthyl) | |
| 4119 | imidazol-2-ylamino-(CH₂)₃ | CH₃ | H | NHSO₂NH(1-naphthyl) | |
| 4120 | imidazol-2-ylamino-(CH₂)₃ | CH₃ | H | NHSO₂NHC₆H₄-(4-Ph) | |
| 4121 | imidazol-2-ylamino-(CH₂)₃ | CH₃ | H | NHSO₂NHC₆H₂-(4-Ph-2,6-dimethyl) | |
| 4122 | imidazol-2-ylamino-(CH₂)₃ | CH₃ | H | NHSO₂NHC₆H₂-(4-Ph-2,6-dichloro) | |
| 4123 | imidazol-2-ylamino-(CH₂)₃ | CH₃ | H | NHSO₂NHCH₂Ph | |
| 4124 | imidazol-2-ylamino-(CH₂)₃ | CH₃ | H | NHSO₂NH-n-Bu | |
| 4125 | pyridin-2-ylamino-(CH₂)₃ | CH₃ | H | NHCO₂CH₂C₆H₄-(3-CH₃) | |
| 4126 | pyridin-2-ylamino-(CH₂)₃ | CH₃ | H | NHCO₂CH₂(3-pyridinyl) | |
| 4127 | pyridin-2-ylamino-(CH₂)₃ | CH₃ | H | NHCO₂CH₂(2-thiazolyl) | |
| 4128 | pyridin-2-ylamino-(CH₂)₃ | CH₃ | H | NHCO₂CH₂(4-isoxazolyl) | |
| 4129 | pyridin-2-ylamino-(CH₂)₃ | CH₃ | H | NHCO₂i-Bu | |
| 4130 | pyridin-2-ylamino-(CH₂)₃ | CH₃ | H | NHCOPh | |
| 4131 | pyridin-2-ylamino-(CH₂)₃ | CH₃ | H | NHCOCH₂Ph | |
| 4132 | pyridin-2-ylamino-(CH₂)₃ | CH₃ | H | NHCOCH₂CH₂Ph | |
| 4133 | pyridin-2-ylamino-(CH₂)₃ | CH₃ | H | NHCOCH=CHPh | |
| 4134 | pyridin-2-ylamino-(CH₂)₃ | CH₃ | H | NHCOCH₂(3-pyridinyl) | |
| 4135 | pyridin-2-ylamino-(CH₂)₃ | CH₃ | H | NHCOCH₂(2-thienyl) | |
| 4136 | pyridin-2-ylamino-(CH₂)₃ | CH₃ | H | NHCOCH₂(cyclohexyl) | |
| 4137 | pyridin-2-ylamino-(CH₂)₃ | CH₃ | H | NHCOn-Bu | |
| 4138 | pyridin-2-ylamino-(CH₂)₃ | CH₃ | H | NHCONHCH₂Ph | |
| 4139 | pyridin-2-ylamino-(CH₂)₃ | CH₃ | H | NHSO₂Ph | |
| 4140 | pyridin-2-ylamino-(CH₂)₃ | CH₃ | H | NHSO₂C₆H₄-(4-CH₃) | |
| 4141 | pyridin-2-ylamino-(CH₂)₃ | CH₃ | H | NHSO₂C₆H₃-(2,6-CH₃)₂ | |
| 4142 | pyridin-2-ylamino-(CH₂)₃ | CH₃ | H | NHSO₂C₆H₂-(2,4,6-CH₃)₃ | |
| 4143 | pyridin-2-ylamino-(CH₂)₃ | CH₃ | H | NHSO₂(3-pyridyl) | |
| 4144 | pyridin-2-ylamino-(CH₂)₃ | CH₃ | H | NHSO₂(2-thienyl) | |
| 4145 | pyridin-2-ylamino-(CH₂)₃ | CH₃ | H | NHSO₂(2-thiazolyl) | |
| 4146 | pyridin-2-ylamino-(CH₂)₃ | CH₃ | H | NHSO₂C₆H₄-(4-Br) | |
| 4147 | pyridin-2-ylamino-(CH₂)₃ | CH₃ | H | NHSO₂C₆H₄-(4-F) | |
| 4148 | pyridin-2-ylamino-(CH₂)₃ | CH₃ | H | NHSO₂C₆H₃-(2,6-Cl₂) | |
| 4149 | pyridin-2-ylamino-(CH₂)₃ | CH₃ | H | NHSO₂(2-naphthyl) | |
| 4150 | pyridin-2-ylamino-(CH₂)₃ | CH₃ | H | NHSO₂(1-naphthyl) | |
| 4151 | pyridin-2-ylamino-(CH₂)₃ | CH₃ | H | NHSO₂C₆H₄-(4-Ph) | |

TABLE 4-continued

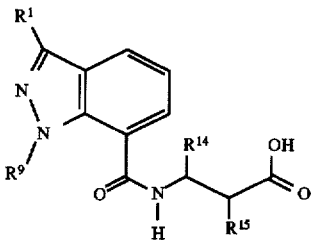

| Ex. No. | R¹ | R⁹ | R¹⁴ | R¹⁵ | MS |
|---|---|---|---|---|---|
| 4151a | pyridin-2-ylamino-(CH₂)₃ | CH₃ | H | NHSO₂C₆H₄-4-(4-pyridyl) | |
| 4151b | pyridin-2-ylamino-(CH₂)₃ | CH₃ | H | NHSO₂C₆H₄-4-(2-oxazolyl) | |
| 4151c | pyridin-2-ylamino-(CH₂)₃ | CH₃ | H | NHSO₂C₆H₄-4-(3-pyrazolyl) | |
| 4152 | pyridin-2-ylamino-(CH₂)₃ | CH₃ | H | NHSO₂C₆H₂-(4-Ph-2,6-dimethyl) | |
| 4152a | pyridin-2-ylamino-(CH₂)₃ | CH₃ | H | NHSO₂C₆H₂-4-(3-pyridyl)-2,6-dimethyl | |
| 4152b | pyridin-2-ylamino-(CH₂)₃ | CH₃ | H | NHSO₂C₆H₂-4-(2-oxazolyl)-2,6-dimethyl | |
| 4152c | pyridin-2-ylamino-(CH₂)₃ | CH₃ | H | NHSO₂C₆H₂-4-(3-pyrazolyl)-2,6-dimethyl | |
| 4153 | pyridin-2-ylamino-(CH₂)₃ | CH₃ | H | NHSO₂C₆H₂-(4-Ph-2,6-dichloro) | |
| 4154 | pyridin-2-ylamino-(CH₂)₃ | CH₃ | H | NHSO₂CH₂Ph | |
| 4155 | pyridin-2-ylamino-(CH₂)₃ | CH₃ | H | NHSO₂-n-Bu | |
| 4156 | pyridin-2-ylamino-(CH₂)₃ | CH₃ | H | NHSO₂NHPh | |
| 4157 | pyridin-2-ylamino-(CH₂)₃ | CH₃ | H | NHSO₂NHC₆H₄-(4-CH₃) | |
| 4158 | pyridin-2-ylamino-(CH₂)₃ | CH₃ | H | NHSO₂NHC₆C₃-(2,6-Me₂) | |
| 4159 | pyridin-2-ylamino-(CH₂)₃ | CH₃ | H | NHSO₂NHC₆C₂-(2,4,6-Me₃) | |
| 4160 | pyridin-2-ylamino-(CH₂)₃ | CH₃ | H | NHSO₂NH(3-pyridyl) | |
| 4161 | pyridin-2-ylamino-(CH₂)₃ | CH₃ | H | NHSO₂-[4-(3,5-dimethyl)isoxazolyl] | |
| 4162 | pyridin-2-ylamino-(CH₂)₃ | CH₃ | H | NHSO₂NHC₆H₄-(4-Br) | |
| 4163 | pyridin-2-ylamino-(CH₂)₃ | CH₃ | H | NHSO₂NHC₆H₄-(4-F) | |
| 4164 | pyridin-2-ylamino-(CH₂)₃ | CH₃ | H | NHSO₂NH(2-naphthyl) | |
| 4165 | pyridin-2-ylamino-(CH₂)₃ | CH₃ | H | NHSO₂NH)1-naphthyl) | |
| 4166 | pyridin-2-ylamino-(CH₂)₃ | CH₃ | H | NHSO₂NHC₆H₄-(4-Ph) | |
| 4167 | pyridin-2-ylamino-(CH₂)₃ | CH₃ | H | NHSO₂NHC₆H₂-(4-Ph-2,6-dimethyl) | |
| 4168 | pyridin-2-ylamino-(CH₂)₃ | CH₃ | H | NHSO₂NHC₆H₂-(4-Ph-2,6-dichloro) | |
| 4169 | pyridin-2-ylamino-(CH₂)₃ | CH₃ | H | NHSO₂NHCH₂Ph | |
| 4170 | pyridin-2-ylamino-(CH₂)₃ | CH₃ | H | NHSO₂NH-n-Bu | |
| 4171 | tetrahydropyrimidin-2-ylamino-(CH₂)₃ | CH₃ | H | NHCOOCH₂Ph | |
| 4172 | tetrahydropyrimidin-2-ylamino-(CH₂)₃ | CH₃ | H | NHCO₂CH₂C₆H₄-(4-CH₃) | |
| 4173 | tetrahydropyrimidin-2-ylamino-(CH₂)₃ | CH₃ | H | NHCO₂CH₃(3-pyridinyl) | |
| 4173 | tetrahydropyrimidin-2-ylamino-(CH₂)₃ | CH₃ | H | NHCO₂CH₂(2-thiazolyl) | |
| 4175 | tetrahydropyrimidin-2-ylamino-(CH₂)₃ | CH₃ | H | NHCO₂CH₂(2-thienyl) | |
| 4176 | tetrahydropyrimidin-2-ylamino-(CH₂)₃ | CH₃ | H | NHCO₂n-Bu | |
| 4177 | tetrahydropyrimidin-2-ylamino-(CH₂)₃ | CH₃ | H | NHSO₂Ph | |
| 4178 | tetrahydropyrimidin-2-ylamino-(CH₂)₃ | CH₃ | H | NHSO₂C₆H₄-(4-CH₃) | |
| 4179 | tetrahydropyrimidin-2-ylamino-(CH₂)₃ | CH₃ | H | NHSO₂C₆H₃-(2,6-Me₂) | |
| 4180 | tetrahydropyrimidin-2-ylamino-(CH₂)₃ | CH₃ | H | NHSO₂C₆H₂-(2,4,6-Me₃) | |
| 4181 | tetrahydropyrimidin-2-ylamino-(CH₂)₃ | CH₃ | H | NHSO₂(3-pyridyl) | |
| 4182 | tetrahydropyrimidin-2-ylamino-(CH₂)₃ | CH₃ | H | NHSO₂(2-thienyl) | |
| 4183 | tetrahydropyrimidin-2-ylamino-(CH₂)₃ | CH₃ | H | NHSO₂(2-thiazolyl) | |
| 4184 | tetrahydropyrimidin-2-ylamino-(CH₂)₃ | CH₃ | H | NHSO₂C₆H₄-(2-Br) | |
| 4185 | tetrahydropyrimidin-2-ylamino-(CH₂)₃ | CH₃ | H | NHSO₂C₆H₄-(4-F) | |
| 4186 | tetrahydropyrimidin-2-ylamino-(CH₂)₃ | CH₃ | H | NHSO₂C₆H₃-(2,6-Cl₂) | |
| 4187 | tetrahydropyrimidin-2-ylamino-(CH₂)₃ | CH₃ | H | NHSO₂(2-naphthyl) | |
| 4188 | tetrahydropyrimidin-2-ylamino-(CH₂)₃ | CH₃ | H | NHSO₂(1-naphthyl) | |
| 4189 | tetrahydropyrimidin-2-ylamino-(CH₂)₃ | CH₃ | H | NHSO₂C₆H₄-(4-Ph) | |
| 4189a | tetrahydropyrimidin-2-ylamino-(CH₂)₃ | CH₃ | H | NHSO₂C₆H₄-4-(4-pyridyl) | |
| 4189b | tetrahydropyrimidin-2-ylamino-(CH₂)₃ | CH₃ | H | NHSO₂C₆H₄-4-(2-oxazolyl) | |
| 4189c | tetrahydropyrimidin-2-ylamino-(CH₂)₃ | CH₃ | H | NHSO₂C₆H₄-4-(3-pyrazolyl) | |
| 4190 | tetrahydropyrimidin-2-ylamino-(CH₂)₃ | CH₃ | H | NHSO₂C₆H₂-(4-Ph-2-6-dimethyl) | |
| 4190a | tetrahydropyrimidin-2-ylamino-(CH₂)₃ | CH₃ | H | NHSO₂C₆H₂-4-(3-pyridyl)-2,6-dimethyl | |
| 4190b | tetrahydropyrimidin-2-ylamino-(CH₂)₃ | CH₃ | H | NHSO₂C₆H₂-4-(2-oxazolyl)-2,6-dimethyl | |
| 4190c | tetrahydropyrimidin-2-ylamino-(CH₂)₃ | CH₃ | H | NHSO₂C₆H₂-4-(3-pyrazolyl)-2,6-dimethyl | |
| 4191 | tetrahydropyrimidin-2-ylamino-(CH₂)₃ | CH₃ | H | NHSO₂C₆H₂-(4-Ph-2,6-dichloro) | |
| 4192 | tetrahydropyrimidin-2-ylamino-(CH₂)₃ | CH₃ | H | NHSO₂CH₂Ph | |
| 4193 | tetrahydropyrimidin-2-ylamino-(CH₂)₃ | CH₃ | H | NHSO₂-n-Bu | |
| 4194 | tetrahydropyrimidin-2-ylamino-(CH₂)₃ | CH₃ | H | NHSO₂NHPh | |
| 4195 | tetrahydropyrimidin-2-ylamino-(CH₂)₃ | CH₃ | H | NHSO₂NHC₆H₄-(4-CH₃) | |
| 4196 | tetrahydropyrimidin-2-ylamino-(CH₂)₃ | CH₃ | H | NHSO₂NHC₆C₃-(2,6-Me₂) | |
| 4197 | tetrahydropyrimidin-2-ylamino-(CH₂)₃ | CH₃ | H | NHSO₂NHC₆C₂-(2,4,6-Me₃) | |
| 4198 | tetrahydropyrimidin-2-ylamino-(CH₂)₃ | CH₃ | H | NHSO₂[4-(3,5-dimethyl)isoxazolyl] | |
| 4199 | tetrahydropyrimidin-2-ylamino-(CH₂)₃ | CH₃ | H | NHSO₂NH(2-naphthyl) | |
| 4200 | tetrahydropyrimidin-2-ylamino-(CH₂)₃ | CH₃ | H | NHSO₂NH(1-naphthyl) | |
| 4201 | tetrahydropyrimidin-2-ylamino-(CH₂)₃ | CH₃ | H | NHSO₂NHC₆H₄-(4-Ph) | |
| 4202 | tetrahydropyrimidin-2-ylamino-(CH₂)₃ | CH₃ | H | NHSO₂NHC₆H₂-(4-Ph-2,6-dimethyl) | |
| 4203 | tetrahydropyrimidin-2-ylamino-(CH₂)₃ | CH₃ | H | NHSO₂NHC₆H₂-(4-Ph-2,6-dichloro) | |

TABLE 4-continued

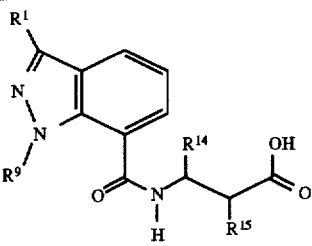

| Ex. No. | R¹ | R⁹ | R¹⁴ | R¹⁵ | MS |
|---|---|---|---|---|---|
| 4204 | tetrahydropyrimidin-2-ylamino-(CH₂)₃ | CH₃ | H | NHSO₂NHCH₂Ph | |
| 4205 | imidazolin-2-ylamino-(CH₂)₃ | CH₃ | H | NHCO₂CH₂C₆H₄-(4-CH₃) | |
| 4206 | imidazolin-2-ylamino-(CH₂)₃ | CH₃ | H | NHCO₂CH₂(3-pyridinyl) | |
| 4207 | imidazolin-2-ylamino-(CH₂)₃ | CH₃ | H | NHCO₂CH₂(2-thiazolyl) | |
| 4208 | imidazolin-2-ylamino-(CH₂)₃ | CH₃ | H | NHCO₂CH₂(2-thienyl) | |
| 4209 | imidazolin-2-ylamino-(CH₂)₃ | CH₃ | H | NHCO₂i-Bu | |
| 4210 | imidazolin-2-ylamino-(CH₂)₃ | CH₃ | H | NHSO₂Ph | |
| 4211 | imidazolin-2-ylamino-(CH₂)₃ | CH₃ | H | NHSO₂C₆H₄-(3-CH₃) | |
| 4212 | imidazolin-2-ylamino-(CH₂)₃ | CH₃ | H | NHSO₂C₆H₃-(2,6-Me₂) | |
| 4213 | imidazolin-2-ylamino-(CH₂)₃ | CH₃ | H | NHSO₂C₆H₂-(2,4,6-Me₃) | |
| 4214 | imidazolin-2-ylamino-(CH₂)₃ | CH₃ | H | NHSO₂(3-pyridyl) | |
| 4215 | imidazolin-2-ylamino-(CH₂)₃ | CH₃ | H | NHSO₂(2-thienyl) | |
| 4216 | imidazolin-2-ylamino-(CH₂)₃ | CH₃ | H | NHSO₂(2-thiazolyl) | |
| 4217 | imidazolin-2-ylamino-(CH₂)₃ | CH₃ | H | NHSO₂-[4-(3,5-dimethyl)isoxazolyl] | |
| 4218 | imidazolin-2-ylamino-(CH₂)₃ | CH₃ | H | NHSO₂C₆H₄-(3-Br) | |
| 4218a | imidazolin-2-ylamino-(CH₂)₃ | CH₃ | H | NHSO₂C₆H₄-(4-F) | |
| 4219 | imidazolin-2-ylamino-(CH₂)₃ | CH₃ | H | NHSO₂C₆H₃-(2,6-Cl₂) | |
| 4220 | imidazolin-2-ylamino-(CH₂)₃ | CH₃ | H | NHSO₂(2-naphthyl) | |
| 4221 | imidazolin-2-ylamino-(CH₂)₃ | CH₃ | H | NHSO₂(1-naphthyl) | |
| 4222 | imidazolin-2-ylamino-(CH₂)₃ | CH₃ | H | NHSO₂C₆H₄-(4-Ph) | |
| 4223 | imidazolin-2-ylamino-(CH₂)₃ | CH₃ | H | NHSO₂C₆H₂-(4-Ph-2,6-dimethyl) | |
| 4224 | imidazolin-2-ylamino-(CH₂)₃ | CH₃ | H | NHSO₂C₆H₂-(4-Ph-2,6-dichloro) | |
| 4225 | imidazolin-2-ylamino-(CH₂)₃ | CH₃ | H | NHSO₂CH₂Ph | |
| 4226 | imidazolin-2-ylamino-(CH₂)₃ | CH₃ | H | NHSO₂-n-Bu | |
| 4227 | imidazolin-2-ylamino-(CH₂)₃ | CH₃ | H | NHSO₂NHPh | |
| 4228 | imidazolin-2-ylamino-(CH₂)₃ | CH₃ | H | NHSO₂NHC₆H₄-(4-CH₃) | |
| 4229 | imidazolin-2-ylamino-(CH₂)₃ | CH₃ | H | NHSO₂NHC₆C₃-(2,6-Me₂) | |
| 4230 | imidazolin-2-ylamino-(CH₂)₃ | CH₃ | H | NHSO₂NHC₆C₂-(2,4,6-Me₃) | |
| 4231 | imidazolin-2-ylamino-(CH₂)₃ | CH₃ | H | NHSO₂NH(2-naphthyl) | |
| 4232 | imidazolin-2-ylamino-(CH₂)₃ | CH₃ | H | NHSO₂NH)1-naphthyl) | |
| 4233 | imidazolin-2-ylamino-(CH₂)₃ | CH₃ | H | NHSO₂NHC₆H₄-(4-Ph) | |
| 4234 | imidazolin-2-ylamino-(CH₂)₃ | CH₃ | H | NHSO₂NHC₆H₂-(4-Ph-2,6-dimethyl) | |
| 4235 | imidazolin-2-ylamino-(CH₂)₃ | CH₃ | H | NHSO₂NHC₆H₂-(4-Ph-2,6-dichloro) | |
| 4236 | imidazolin-2-ylamino-(CH₂)₃ | CH₃ | H | NHSO₂NHCH₂Ph | |
| 4237 | benzimidazol-2-ylamino-(CH₂)₃ | CH₃ | H | NHSO₂Ph | |
| 4238 | benzimidazol-2-ylamino-(CH₂)₃ | CH₃ | H | NHSO₂C₆H₄-(3-CH₃) | |
| 4239 | benzimidazol-2-ylamino-(CH₂)₃ | CH₃ | H | NHSO₂C₆H₃-(2,6-Me₂) | |
| 4240 | benzimidazol-2-ylamino-(CH₂)₃ | CH₃ | H | NHSO₂C₆H₂-(2,4,6-Me₃) | |
| 4241 | benzimidazol-2-ylamino-(CH₂)₃ | CH₃ | H | NHSO₂(4-pyridyl) | |
| 4242 | benzimidazol-2-ylamino-(CH₂)₃ | CH₃ | H | NHSO₂(2-thienyl) | |
| 4243 | benzimidazol-2-ylamino-(CH₂)₃ | CH₃ | H | NHSO₂(2-thiazolyl) | |
| 4244 | benzimidazol-2-ylamino-(CH₂)₃ | CH₃ | H | NHSO₂-[4-(3,5-dimethyl)isoxazolyl] | |
| 4245 | benzimidazol-2-ylamino-(CH₂)₃ | CH₃ | H | NHSO₂C₆H₄-(3-Br) | |
| 4246 | benzimidazol-2-ylamino-(CH₂)₃ | CH₃ | H | NHSO₂C₆H₄-(3-F) | |
| 4247 | benzimidazol-2-ylamino-(CH₂)₃ | CH₃ | H | NHSO₂C₆H₃-(2,6-Cl₂) | |
| 4248 | benzimidazol-2-ylamino-(CH₂)₃ | CH₃ | H | NHSO₂(2-naphthyl) | |
| 4249 | benzimidazol-2-ylamino-(CH₂)₃ | CH₃ | H | NHSO₂(1-naphthyl) | |
| 4250 | benzimidazol-2-ylamino-(CH₂)₃ | CH₃ | H | NHSO₂C₆H₄-(4-Ph) | |
| 4250a | benzimidazol-2-ylamino-(CH₂)₃ | CH₃ | H | NHSO₂C₆H₄-4-(4-pyridyl) | |
| 4250b | benzimidazol-2-ylamino-(CH₂)₃ | CH₃ | H | NHSO₂C₆H₄-4-(2-oxazolyl) | |
| 4250c | benzimidazol-2-ylamino-(CH₂)₃ | CH₃ | H | NHSO₂C₆H₄-4-(3-pyrazolyl) | |
| 4251 | benzimidazol-2-ylamino-(CH₂)₃ | CH₃ | H | NHSO₂C₆H₂-(4-Ph-2,6-dimethyl) | |
| 4251a | benzimidazol-2-ylamino-(CH₂)₃ | CH₃ | H | NHSO₂C₆H₂-4-(3-pyridyl)-2,6-dimethyl) | |
| 4251b | benzimidazol-2-ylamino-(CH₂)₃ | CH₃ | H | NHSO₂C₆H₂-4-(2-oxazolyl)-2,6-dimethyl) | |
| 4251c | benzimidazol-2-ylamino-(CH₂)₃ | CH₃ | H | NHSO₂C₆H₂-4-(2-pyrazolyl)-2,6-dimethyl) | |
| 4252 | benzimidazol-2-ylamino-(CH₂)₃ | CH₃ | H | NHSO₂C₆H₂-(4-Ph-2,6-dichloro) | |
| 4253 | benzimidazol-2-ylamino-(CH₂)₃ | CH₃ | H | NHSO₂CH₂Ph | |
| 4254 | benzimidazol-2-ylamino-(CH₂)₃ | CH₃ | H | NHSO₂-i-Bu | |
| 4255 | benzimidazol-2-ylamino-(CH₂)₃ | CH₃ | H | NHSO₂NHPh | |
| 4256 | benzimidazol-2-ylamino-(CH₂)₃ | CH₃ | H | NHSO₂NHC₆H₄-(4-CH₃) | |
| 4257 | benzimidazol-2-ylamino-(CH₂)₃ | CH₃ | H | NHSO₂NHC₆C₃-(2,6-Me₂) | |
| 4258 | benzimidazol-2-ylamino-(CH₂)₃ | CH₃ | H | NHSO₂NHC₆C₂-(2,4,6-Me₃) | |
| 4259 | benzimidazol-2-ylamino-(CH₂)₃ | CH₃ | H | NHSO₂NH(2-naphthyl) | |
| 4260 | benzimidazol-2-ylamino-(CH₂)₃ | CH₃ | H | NHSO₂NH)1-naphthyl) | |

TABLE 4-continued

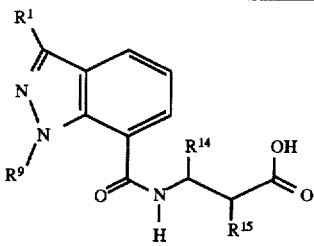

| Ex. No. | $R^1$ | $R^9$ | $R^{14}$ | $R^{15}$ | MS |
|---|---|---|---|---|---|
| 4261 | benzimidazol-2-ylamino-$(CH_2)_3$ | $CH_3$ | H | $NHSO_2NHC_6H_4$-(4-Ph) | |
| 4262 | benzimidazol-2-ylamino-$(CH_2)_3$ | $CH_3$ | H | $NHSO_2NHC_6H_4$-(4-Ph-2,6-dimethyl) | |
| 4263 | benzimidazol-2-ylamino-$(CH_2)_3$ | $CH_3$ | H | $NHSO_2NHC_6H_4$-(4-Ph-2,6-dichloro) | |
| 4264 | benzimidazol-2-ylamino-$(CH_2)_3$ | $CH_3$ | H | $NHSO_2NHCH_2Ph$ | |
| 4265 | benzimidazol-2-ylamino-$(CH_2)_3$ | $CH_3$ | H | $NHCO_2CH_2Ph$ | |
| 4266 | benzimidazol-2-ylamino-$(CH_2)_3$ | $CH_3$ | H | $NHCO_2$i-Bu | |
| 4267 | 2-aminopyridin-6-yl-$(CH_2)_3$ | $CH_3$ | H | $NHSO_2C_6H_4$-(4-$CH_3$) | |
| 4268 | 2-aminopyridin-6-yl-$(CH_2)_3$ | $CH_3$ | H | $NHSO_2C_6H_3$-(2,6-$Me_2$) | |
| 4269 | 2-aminopyridin-6-yl-$(CH_2)_3$ | $CH_3$ | H | $NHSO_2C_6H_2$-(2,4,6-$Me_3$) | |
| 4270 | 2-aminopyridin-6-yl-$(CH_2)_3$ | $CH_3$ | H | $NHSO_2$(3-pyridyl) | |
| 4271 | 2-aminopyridin-6-yl-$(CH_2)_3$ | $CH_3$ | H | $NHSO_2$(2-thiazolyl) | |
| 4272 | 2-aminopyridin-6-yl-$(CH_2)_3$ | $CH_3$ | H | $NHSO_2$(4-isoxazolyl) | |
| 4273 | 2-aminopyridin-6-yl-$(CH_2)_3$ | $CH_3$ | H | $NHSO_2C_6H_4$-(3-Br) | |
| 4274 | 2-aminopyridin-6-yl-$(CH_2)_3$ | $CH_3$ | H | $NHSO_2C_6H_4$-(3-F) | |
| 4275 | 2-aminopyridin-6-yl-$(CH_2)_3$ | $CH_3$ | H | $NHSO_2C_6H_3$-(2,6-$Cl_2$) | |
| 4276 | 2-aminopyridin-6-yl-$(CH_2)_3$ | $CH_3$ | H | $NHSO_2$(2-naphthyl) | |
| 4277 | 2-aminopyridin-6-yl-$(CH_2)_3$ | $CH_3$ | H | $NHSO_2$(1-naphthyl) | |
| 4278 | 2-aminopyridin-6-yl-$(CH_2)_3$ | $CH_3$ | H | $NHSO_2C_6H_4$-(4-Ph) | |
| 4279 | 2-aminopyridin-6-yl-$(CH_2)_3$ | $CH_3$ | H | $NHSO_2C_6H_2$-(4-Ph-2,6-dimethyl) | |
| 4280 | 2-aminopyridin-6-yl-$(CH_2)_3$ | $CH_3$ | H | $NHSO_2C_6H_2$-(4-Ph-2,6-dichloro) | |
| 4281 | 2-aminopyridin-6-yl-$(CH_2)_3$ | $CH_3$ | H | $NHSO_2CH_2Ph$ | |
| 4282 | 2-aminopyridin-6-yl-$(CH_2)_3$ | $CH_3$ | H | $NHSO_2$-i-Bu | |
| 4283 | 2-aminopyridin-6-yl-$(CH_2)_3$ | $CH_3$ | H | $NHSO_2NHPh$ | |
| 4284 | 2-aminopyridin-6-yl-$(CH_2)_3$ | $CH_3$ | H | $NHSO_2NHC_6H_4$-(4-$CH_3$) | |
| 4285 | 2-aminopyridin-6-yl-$(CH_2)_3$ | $CH_3$ | H | $NHSO_2NHC_6C_3$-(2,6-$Me_2$) | |
| 4286 | 2-aminopyridin-6-yl-$(CH_2)_3$ | $CH_3$ | H | $NHSO_2NHC_6C_2$-(2,4,6-$Me_3$) | |
| 4287 | 2-aminopyridin-6-yl-$(CH_2)_3$ | $CH_3$ | H | $NHSO_2NH$(2-naphthyl) | |
| 4288 | 2-aminopyridin-6-yl-$(CH_2)_3$ | $CH_3$ | H | $NHSO_2NH$)1-naphthyl) | |
| 4289 | 2-aminopyridin-6-yl-$(CH_2)_3$ | $CH_3$ | H | $NHSO_2NHC_6H_4$-(4-Ph) | |
| 4290 | 2-aminopyridin-6-yl-$(CH_2)_3$ | $CH_3$ | H | $NHSO_2NHC_6H_2$-(4-Ph-2,6-dimethyl) | |
| 4291 | 2-aminopyridin-6-yl-$(CH_2)_3$ | $CH_3$ | H | $NHSO_2NHC_6H_2$-(4-Ph-2,6-dichloro) | |
| 4292 | 2-aminopyridin-6-yl-$(CH_2)_3$ | $CH_3$ | H | $NHCO_2$n-Bu | |
| 4293 | 2-aminopyridin-6-yl-$(CH_2)_3$ | $CH_3$ | H | $NHCO_2$i-Bu | |
| 4294 | 2-iminoazepin-7-yl-$(CH_2)_3$ | $CH_3$ | H | $NHSO_2Ph$ | |
| 4295 | imidazol-4-ylamino-$(CH_2)_3$ | $CH_3$ | H | $NHSO_2Ph$ | |
| 4296 | 2-iminoazepin-7-yl-$(CH_2)_3$ | $CH_3$ | H | $NHSO_2$(4-isoxazolyl) | |
| 4297 | imidazol-4-ylamino-$(CH_2)_3$ | $CH_3$ | H | $NHSO_2$(4-isoxazolyl) | |
| 4298 | 2-iminoazepin-7-yl-$(CH_2)_3$ | $CH_3$ | H | $NHSO_2$-[4-(3,5-dimethyl)isoxazolyl] | |
| 4299 | imidazol-4-ylamino-$(CH_2)_3$ | $CH_3$ | H | $NHSO_2$-[4-(3,5-dimethyl)isoxazolyl] | |
| 4300 | imidazol-2-ylamino-$(CH_2)_3$ | $CH_3$ | 3-pyridinyl | $NHSO_2Ph$ | |
| 4301 | pyridin-2-ylamino-$(CH_2)_3$ | $CH_3$ | 3-pyridinyl | $NHSO_2Ph$ | |
| 4302 | imidazol-2-ylamino-$(CH_2)_3$ | $CH_3$ | (3,4-methylenedioxy)phenyl | $NHSO_2Ph$ | |
| 4303 | pyridin-2-ylamino-$(CH_2)_3$ | $CH_3$ | (3,4-methylenedioxy)phenyl | $NHSO_2Ph$ | |
| 4304 | imidazol-2-ylamino-$(CH_2)_2$ | $CH_3$ | H | $NHSO_2Ph$ | |
| 4305 | imidazol-2-ylamino-$(CH_2)_2$ | $CH_3$ | H | $NHCO_2CH_2Ph$ | |
| 4306 | imidazol-2-ylamino-carbonyl-$(CH_2)_2$ | $CH_3$ | H | $NHSO_2C_6H_2$-(2,4,6-$CH_3$) | |
| 4307 | pyridin-2-ylamino-$(CH_2)_2$ | $CH_3$ | H | $NHSO_2Ph$ | |
| 4308 | pyridin-2-ylamino-$(CH_2)_2$ | $CH_3$ | H | $NHCO_2CH_2Ph$ | |
| 4309 | pyridin-2-ylamino-carbonyl-$(CH_2)_2$ | $CH_3$ | H | $NHSO_2C_6H_2$-(2,4,6-$CH_3$)$_3$ | |
| 4310 | imidazolin-2-ylamino-$(CH_2)_2$ | $CH_3$ | H | $NHSO_2Ph$ | |
| 4311 | imidazolin-2-ylamino-$(CH_2)_2$ | $CH_3$ | H | $NHCO_2CH_2Ph$ | |
| 4312 | tetrahydropyrimidin-2-ylamino-$(CH_2)_2$ | $CH_3$ | H | $NHSO_2Ph$ | |
| 4313 | tetrahydropyrimidin-2-ylamino-$(CH_2)_2$ | $CH_3$ | H | $NHCO_2CH_2Ph$ | |
| 4314 | benzimidazol-2-ylamino-$(CH_2)_2$ | $CH_3$ | H | $NHSO_2Ph$ | |
| 4315 | benzimidazol-2-ylamino-$(CH_2)_2$ | $CH_3$ | H | $NHCO_2CH_2Ph$ | |
| 4316 | benzimidazol-2-ylamino-carbonyl-$(CH_2)_2$ | $CH_3$ | H | $NHSO_2C_6H_2$-(2,4,6-$CH_3$)$_3$ | |
| 4317 | 2-aminopyridin-6-yl-$(CH_2)_2$ | $CH_3$ | H | $NHSO_2Ph$ | |
| 4318 | 2-aminopyridin-6-yl-$(CH_2)_2$ | $CH_3$ | H | $NHCO_2CH_2Ph$ | |
| 4319 | 2-iminoazepin-7-yl-$(CH_2)_2$ | $CH_3$ | H | $NHSO_2Ph$ | |
| 4320 | 2-iminoazepin-7-yl-$(CH_2)_2$ | $CH_3$ | H | $NHCO_2CH_2Ph$ | |
| 4321 | imidazol-4-ylamino-$(CH_2)_2$ | $CH_3$ | H | $NHSO_2Ph$ | |
| 4322 | imidazol-4-ylamino-$(CH_2)_2$ | $CH_3$ | H | $NHCO_2CH_2Ph$ | |
| 4323 | imidazol-2-ylamino-$(CH_2)_4$ | $CH_3$ | H | $NHSO_2Ph$ | |
| 4324 | imidazol-2-ylamino-$(CH_2)_4$ | $CH_3$ | H | $NHCO_2CH_2Ph$ | |

TABLE 4-continued

| Ex. No. | R¹ | R⁹ | R¹⁴ | R¹⁵ | MS |
|---|---|---|---|---|---|
| 4325 | pyridin-2-ylamino-(CH₂)₄ | CH₃ | H | NHSO₂Ph | |
| 4326 | pyridin-2-ylamino-(CH₂)₄ | CH₃ | H | NHCO₂CH₂Ph | |
| 4327 | imidazolin-2-ylamino-(CH₂)₄ | CH₃ | H | NHSO₂Ph | |
| 4328 | tetrahydropyrimidin-2-ylamino-(CH₂)₄ | CH₃ | H | NHSO₂Ph | |
| 4329 | tetrahydropyrimidin-2-ylamino-(CH₂)₄ | CH₃ | H | NHCO₂CH₂Ph | |
| 4330 | benzimidazol-2-ylamino-(CH₂)₄ | CH₃ | H | NHSO₂Ph | |
| 4331 | benzimidazol-2-ylamino-(CH₂)₄ | CH₃ | H | NHCO₂CH₂Ph | |
| 4332 | 2-aminopyridin-6-yl-(CH₂)₄ | CH₃ | H | NHSO₂Ph | |
| 4333 | 2-aminopyridin-6-yl-(CH₂)₄ | CH₃ | H | NHCO₂CH₂Ph | |
| 4334 | 2-iminoazepin-7-yl-(CH₂)₄ | CH₃ | H | NHSO₂Ph | |
| 4335 | 2-iminoazepin-7-yl-(CH₂)₄ | CH₃ | H | NHCO₂CH₂Ph | |
| 4336 | imidazol-4-ylamino-(CH₂)₄ | CH₃ | H | NHSO₂Ph | |
| 4337 | imidazol-4-ylamino-(CH₂)₄ | CH₃ | H | NHCO₂CH₂Ph | |
| 4338 | imidazol-2-ylamino-(CH₂)₃ | CH₂Ph | H | NHSO₂C₆H₂-(2,4,6-CH₃) | |
| 4339 | pyridin-2-ylamino-(CH₂)₃ | CH₂Ph | H | NHSO₂C₆H₂-(2,4,6-CH₃) | |
| 4340 | imidazol-2-ylamino-(CH₂)₃ | CH₂CH₃ | H | NHSO₂C₆H₂-(2,4,6-CH₃) | |
| 4341 | imidazol-2-ylamino-(CH₂)₃ | CH(CH₃)₂ | H | NHSO₂C₆H₂-(2,4,6-CH₃) | |
| 4342 | imidazol-2-ylamino-(CH₂)₃ | cyclopropyl | H | NHSO₂C₆H₂-(2,4,6-CH₃) | |
| 4343 | imidazol-2-ylamino-(CH₂)₃ | CH₂-cyclopropyl | H | NHSO₂C₆H₂-(2,4,6-CH₃) | |
| 4344 | imidazol-2-ylamino-(CH₂)₃ | CH₂COOH | H | NHSO₂C₆H₂-(2,4,6-CH₃) | |
| 4345 | imidazol-2-ylamino-(CH₂)₃ | (CH₂)₂NMe₂ | H | NHSO₂C₆H₂-(2,4,6-CH₃) | |
| 4346 | imidazol-2-ylamino-(CH₂)₃ | CH₂CH₂OMe | H | NHSO₂C₆H₂-(2,4,6-CH₃) | |
| 4347 | imidazol-2-ylamino-(CH₂)₃ | CH₂CH₂Ph | H | NHSO₂C₆H₂-(2,4,6-CH₃) | |
| 4348 | imidazol-2-ylamino-(CH₂)₃ | CH₂CH₂OH | H | NHSO₂C₆H₂-(2,4,6-CH₃) | |
| 4349 | imidazol-2-ylamino-(CH₂)₃ | CH₂CH₃ | H | NHSO₂C₆H₂-(2,6-CH₃)₂-4-Ph | |
| 4350 | imidazol-2-ylamino-(CH₂)₃ | CH(CH₃)₂ | H | NHSO₂C₆H₂-(2,6-CH₃)₂-4-Ph | |
| 4351 | imidazol-2-ylamino-(CH₂)₃ | cyclopropyl | H | NHSO₂C₆H₂-(2,6-CH₃)₂-4-Ph | |
| 4352 | imidazol-2-ylamino-(CH₂)₃ | CH₂-cyclopropyl | H | NHSO₂C₆H₂-(2,6-CH₃)₂-4-Ph | |
| 4353 | imidazol-2-ylamino-(CH₂)₃ | CH₂COOH | H | NHSO₂C₆H₂-(2,6-CH₃)₂-4-Ph | |
| 4354 | imidazol-2-ylamino-(CH₂)₃ | (CH₂)₂NMe₂ | H | NHSO₂C₆H₂-(2,6-CH₃)₂-4-Ph | |
| 4355 | imidazol-2-ylamino-(CH₂)₃ | CH₂CH₂OMe | H | NHSO₂C₆H₂-(2,6-CH₃)₂-4-Ph | |
| 4356 | imidazol-2-ylamino-(CH₂)₃ | CH₂CH₂Ph | H | NHSO₂C₆H₂-(2,6-CH₃)₂-4-Ph | |
| 4357 | imidazol-2-ylamino-(CH₂)₃ | CH₂CH₂OH | H | NHSO₂C₆H₂-(2,6-CH₃)₂-4-Ph | |
| 4358 | imidazol-2-ylamino-(CH₂)₃ | CH₃ | H | NHSO₂-(1-naphthyl) | |
| 4359 | imidazol-2-ylamino-(CH₂)₃ | CH₃ | H | NHCO₂CH₂Ph | |
| 4360 | imidazol-2-ylamino-(CH₂)₃ | CH₃ | H | NHSO₂C₆C₂-(2,4,6-Me₃) | |
| 4361 | pyridin-2-ylamino-CH₂(o-C₆H₄) | CH₃ | H | NHSO₂-(1-naphthyl) | |
| 4362 | pyridin-2-ylamino-CH₂(o-C₆H₄) | CH₃ | H | NHCO₂CH₂Ph | |
| 4363 | pyridin-2-ylamino-CH₂(o-C₆H₄) | CH₃ | H | NHSO₂C₆C₂-(2,4,6-Me₃) | |
| 4364 | imidazolin-2-ylamino-CH₂(o-C₆H₄) | CH₃ | H | NHSO₂-(1-naphthyl) | |
| 4365 | imidazolin-2-ylamino-CH₂(o-C₆H₄) | CH₃ | H | NHCO₂CH₂Ph | |
| 4366 | imidazolin-2-ylamino-CH₂(o-C₆H₄) | CH₃ | H | NHSO₂C₆C₂-(2,4,6-Me₃) | |
| 4367 | imidazolin-2-ylamino-(m-C₆H₄) | CH₃ | H | NHSO₂-(1-naphthyl) | |
| 4368 | imidazolin-2-ylamino-(m-C₆H₄) | CH₃ | H | NHCO₂CH₂Ph | |
| 4369 | imidazolin-2-ylamino-(m-C₆H₄) | CH₃ | H | NHSO₂C₆C₂-(2,4,6-Me₃) | |

TABLE 5

| Ex. No. | R¹ | R¹⁴ | R¹⁵ | MS |
|---|---|---|---|---|
| 5001 | imidazol-2-ylamino-(CH₂)₃ | H | H | |
| 5002 | pyridin-2-ylamino-(CH₂)₃ | H | NHCOOCH₂Ph | |

TABLE 5-continued

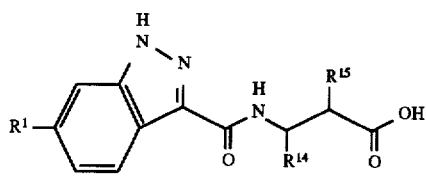

| Ex. No. | $R^1$ | $R^{14}$ | $R^{15}$ | MS |
|---|---|---|---|---|
| 5003 | imidazolin-2-yl amino-$(CH_2)_3$ | H | $NHCO_2CH_2C_6H_4$-(2-$CH_3$) | |
| 5004 | tetrahydropyrimidin-2-ylamino-$(CH_2)_3$ | H | $NHCO_2CH_2C_6H_4$-(3-$CH_3$) | |
| 5005 | benzimidazol-2-ylamino-$(CH_2)_3$ | H | $NHCO_2CH_2C_6H_4$-(4-$CH_3$) | |
| 5006 | 2-aminopyridin-6-yl-$(CH_2)_3$ | H | $NHCO_2CH_2$(2-pyridinyl) | |
| 5007 | 2-iminoazepin-7-yl-$(CH_2)_3$ | H | $NHCO_2CH_2$(3-pyridinyl) | |
| 5010 | imidazol-4-ylamino-$(CH_2)_3$ | H | $NHCO_2CH_2$(2-thiazolyl) | |
| 5015 | imidazol-2-ylamino-$(CH_2)_3$ | H | $NHCO_2CH_2$(4-isoxazolyl) | |
| 5016 | pyridin-2-ylamino-$(CH_2)_3$ | H | $NHCO_2CH_2$(2-thienyl) | |
| 5017 | imidazolin-2-ylamino-$(CH_2)_3$ | H | $NHCO_2$n-Bu | |
| 5018 | tetrahydropyrimidin-2-ylamino-$(CH_2)_3$ | H | $NHCO_2$i-Bu | |
| 5019 | benzimidazol-2-ylamino-$(CH_2)_3$ | H | $NHCO_2$t-Bu | |
| 5020 | 2-aminopyridin-6-yl-$(CH_2)_3$ | H | $NHSO_2$Ph | |
| 5021 | 2-iminoazepin-7-yl-$(CH_2)_3$ | H | $NHSO_2C_6H_4$-(2-$CH_3$) | |
| 5024 | imidazol-4-ylamino-$(CH_2)_3$ | H | $NHSO_2$(2-pyridyl) | |
| 5029 | imidazol-2-ylamino-$(CH_2)_3$ | H | $NHSO_2$(4-isoxazolyl) | |
| 5030 | pyridin-2-ylamino-$(CH_2)_3$ | H | $NHSO_2$-[4-(3,5-dimethyl)isoxazolyl] | |
| 5031 | imidazolin-2-ylamino-$(CH_2)_3$ | H | $NHSO_2C_6H_4$-(2-Br) | |
| 5032 | tetrahydropyrimidin-2-ylamino-$(CH_2)_3$ | H | $NHSO_2C_6H_4$-(3-Br) | |
| 5033 | benzimidazol-2-ylamino-$(CH_2)_3$ | H | $NHSO_2C_6H_4$-(4-Br) | |
| 5034 | 2-aminopyridin-6-yl-$(CH_2)_3$ | H | $NHSO_2C_6H_4$-(2-F) | |
| 5035 | 2-iminoazepin-7-yl-$(CH_2)_3$ | H | $NHSO_2C_6H_4$-(3-F) | |
| 5038 | imidazol-4-ylamino-$(CH_2)_3$ | H | $NHSO_2$(1-naphthyl) | |
| 5043 | imidazol-2-ylamino-$(CH_2)_3$ | H | $NHSO_2$-i-Bu | |
| 5044 | pyridin-2-ylamino-$(CH_2)_3$ | H | $NHSO_2$-t-Bu | |
| 5045 | imidazol-2-ylamino-$(CH_2)_3$ | (3,4-methylenedioxy)phenyl | H | |
| 5046 | pyridin-2-ylamino-$(CH_2)_3$ | (3,4-methylenedioxy)phenyl | H | |
| 5047 | imidazolin-2-ylamino-$(CH_2)_3$ | (3,4-methylenedioxy)phenyl | H | |
| 5048 | tetrahydropyrimidin-2-ylamino-$(CH_2)_3$ | (3,4-methylenedioxy)phenyl | H | |
| 5049 | benzimidazol-2-ylamino-$(CH_2)_3$ | (3,4-methylenedioxy)phenyl | H | |
| 5050 | 2-aminopyridin-6-yl-$(CH_2)_3$ | (3,4-methylenedioxy)phenyl | H | |
| 5051 | 2-iminoazepin-7-yl-$(CH_2)_3$ | (3,4-methylenedioxy)phenyl | H | |
| 5054 | imidazol-4-ylamino-$(CH_2)_3$ | (3,4-methylenedioxy)phenyl | H | |
| 5059 | imidazol-2-ylamino-$(CH_2)_3$ | 3-pyridinyl | H | |
| 5060 | pyridin-2-ylamino-$(CH_2)_3$ | 3-pyridinyl | H | |
| 5061 | imidazolin-2-ylamino-$(CH_2)_3$ | 3-pyridinyl | H | |
| 5062 | tetrahydropyrimidin-2-ylamino-$(CH_2)_3$ | 3-pyridinyl | H | |
| 5063 | benzimidazol-2-ylamino-$(CH_2)_3$ | 3-pyridinyl | H | |
| 5064 | 2-aminopyridin-6-yl-$(CH_2)_3$ | 3-pyridinyl | H | |
| 5065 | 2-iminoazepin-7-yl-$(CH_2)_3$ | 3-pyridinyl | H | |
| 5068 | imidazol-4-ylamino-$(CH_2)_3$ | 3-pyridinyl | H | |
| 5069 | imidazol-2-ylamino-$CH_2$(o-$C_6H_4$) | H | $NHSO_2$-(1-naphthyl) | |
| 5070 | imidazol-2-ylamino-$CH_2$(o-$C_6H_4$) | H | $NHCO_2CH_2$Ph | |
| 5071 | imidazol-2-ylamino-$CH_2$(o-$C_6H_4$) | H | $NHSO_2C_6C_2$-(2,4,6-$Me_3$) | |
| 5072 | pyridin-2-ylamino-$CH_2$(o-$C_6H_4$) | H | $NHSO_2$-(1-naphthyl) | |
| 5073 | pyridin-2-ylamino-$CH_2$(o-$C_6H_4$) | H | $NHCO_2CH_2$Ph | |
| 5074 | pyridin-2-ylamino-$CH_2$(o-$C_6H_4$) | H | $NHSO_2C_6C_2$-(2,4,6-$Me_3$) | |
| 5075 | imidazolin-2-ylamino-$CH_2$(o-$C_6H_4$) | H | $NHSO_2$-(1-naphthyl) | |
| 5076 | imidazolin-2-ylamino-$CH_2$(o-$C_6H_4$) | H | $NHCO_2CH_2$Ph | |
| 5077 | imidazolin-2-ylamino-$CH_2$(o-$C_6H_4$) | H | $NHSO_2C_6C_2$-(2,4,6-$Me_3$) | |
| 5078 | imidazolin-2-ylamino-(m-$C_6H_4$) | H | $NHSO_2$-(1-naphthyl) | |
| 5079 | imidazolin-2-ylamino-(m-$C_6H_4$) | H | $NHCO_2CH_2$Ph | |
| 5080 | imidazolin-2-ylamino-(m-$C_6H_4$) | H | $NHSO_2C_6C_2$-(2,4,6-$Me_3$) | |

TABLE 6

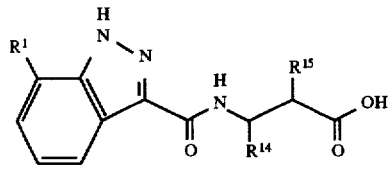

| Ex. No. | R¹ | R¹⁴ | R¹⁵ | MS |
|---|---|---|---|---|
| 6001 | imidazol-2-ylamino-(CH$_2$)$_3$ | H | H | |
| 6002 | pyridin-2-ylamino-(CH$_2$)$_3$ | H | NHCOOCH$_2$Ph | |
| 6003 | imidazolin-2-yl amino-(CH$_2$)$_3$ | H | NHCO$_2$CH$_2$C$_6$H$_4$-(2-CH$_3$) | |
| 6004 | tetrahydropyrimidin-2-ylamino-(CH$_2$)$_3$ | H | NHCO$_2$CH$_2$C$_6$H$_4$-(3-CH$_3$) | |
| 6005 | benzimidazol-2-ylamino-(CH$_2$)$_3$ | H | NHCO$_2$CH$_2$C$_6$H$_4$-(4-CH$_3$) | |
| 6006 | 2-aminopyridin-6-yl-(CH$_2$)$_3$ | H | NHCO$_2$CH$_2$(2-pyridinyl) | |
| 6007 | 2-iminoazepin-7-yl-(CH$_2$)$_3$ | H | NHCO$_2$CH$_2$(3-pyridinyl) | |
| 6010 | imidazol-4-ylamino-(CH$_2$)$_3$ | H | NHCO$_2$CH$_2$(2-thiazolyl) | |
| 6015 | imidazol-2-ylamino-(CH$_2$)$_3$ | H | NHCO$_2$CH$_2$(4-isoxazolyl) | |
| 6016 | pyridin-2-ylamino-(CH$_2$)$_3$ | H | NHCO$_2$CH$_2$(2-thienyl) | |
| 6017 | imidazolin-2-ylamino-(CH$_2$)$_3$ | H | NHCO$_2$n-Bu | |
| 6018 | tetrahydropyrimidin-2-ylamino-(CH$_2$)$_3$ | H | NHCO$_2$i-Bu | |
| 6019 | benzimidazol-2-ylamino-(CH$_2$)$_3$ | H | NHCO$_2$t-Bu | |
| 6020 | 2-aminopyridin-6-yl-(CH$_2$)$_3$ | H | NHSO$_2$Ph | |
| 6021 | 2-iminoazepin-7-yl-(CH$_2$)$_3$ | H | NHSO$_2$C$_6$H$_4$-(2-CH$_3$) | |
| 6024 | imidazol-4-ylamino-(CH$_2$)$_3$ | H | NHSO$_2$(2-pyridyl) | |
| 6029 | imidazol-2-ylamino-(CH$_2$)$_3$ | H | NHSO$_2$(4-isoxazolyl) | |
| 6030 | pyridin-2-ylamino-(CH$_2$)$_3$ | H | NHSO$_2$-[4-(3,5-dimethyl)isoxazolyl] | |
| 6031 | imidazolin-2-ylamino-(CH$_2$)$_3$ | H | NHSO$_2$C$_6$H$_4$-(2-Br) | |
| 6032 | tetrahydropyrimidin-2-ylamino-(CH$_2$)$_3$ | H | NHSO$_2$C$_6$H$_4$-(3-Br) | |
| 6033 | benzimidazol-2-ylamino-(CH$_2$)$_3$ | H | NHSO$_2$C$_6$H$_4$-(4-Br) | |
| 6034 | 2-aminopyridin-6-yl-(CH$_2$)$_3$ | H | NHSO$_2$C$_6$H$_4$-(2-F) | |
| 6035 | 2-iminoazepin-7-yl-(CH$_2$)$_3$ | H | NHSO$_2$C$_6$H$_4$-(3-F) | |
| 6038 | imidazol-4-ylamino-(CH$_2$)$_3$ | H | NHSO$_2$(1-naphthyl) | |
| 6043 | imidazol-2-ylamino-(CH$_2$)$_3$ | H | NHSO$_2$-i-Bu | |
| 6044 | pyridin-2-ylamino-(CH$_2$)$_3$ | H | NHSO$_2$-t-Bu | |
| 6045 | imidazol-2-ylamino-(CH$_2$)$_3$ | (3,4-methylenedioxy)phenyl | H | |
| 6046 | pyridin-2-ylamino-(CH$_2$)$_3$ | (3,4-methylenedioxy)phenyl | H | |
| 6047 | imidazolin-2-ylamino-(CH$_2$)$_3$ | (3,4-methylenedioxy)phenyl | H | |
| 6048 | tetrahydropyrimidin-2-ylamino-(CH$_2$)$_3$ | (3,4-methylenedioxy)phenyl | H | |
| 6049 | benzimidazol-2-ylamino-(CH$_2$)$_3$ | (3,4-methylenedioxy)phenyl | H | |
| 6050 | 2-aminopyridin-6-yl-(CH$_2$)$_3$ | (3,4-methylenedioxy)phenyl | H | |
| 6051 | 2-iminoazepin-7-yl-(CH$_2$)$_3$ | (3,4-methylenedioxy)phenyl | H | |
| 6054 | imidazol-4-ylamino-(CH$_2$)$_3$ | (3,4-methylenedioxy)phenyl | H | |
| 6059 | imidazol-2-ylamino-(CH$_2$)$_3$ | 3-pyridinyl | H | |
| 6060 | pyridin-2-ylamino-(CH$_2$)$_3$ | 3-pyridinyl | H | |
| 6061 | imidazolin-2-ylamino-(CH$_2$)$_3$ | 3-pyridinyl | H | |
| 6062 | tetrahydropyrimidin-2-ylamino-(CH$_2$)$_3$ | 3-pyridinyl | H | |
| 6063 | benzimidazol-2-ylamino-(CH$_2$)$_3$ | 3-pyridinyl | H | |
| 6064 | 2-aminopyridin-6-yl-(CH$_2$)$_3$ | 3-pyridinyl | H | |
| 6065 | 2-iminoazepin-7-yl-(CH$_2$)$_3$ | 3-pyridinyl | H | |
| 6068 | imidazol-4-ylamino-(CH$_2$)$_3$ | 3-pyridinyl | H | |
| 6069 | imidazol-2-ylamino-CH$_2$(o-C$_6$H$_4$) | H | NHSO$_2$-(1-naphthyl) | |
| 6070 | imidazol-2-ylamino-CH$_2$(o-C$_6$H$_4$) | H | NHCO$_2$CH$_2$Ph | |
| 6071 | imidazol-2-ylamino-CH$_2$(o-C$_6$H$_4$) | H | NHSO$_2$C$_6$C$_2$-(2,4,6-Me$_3$) | |
| 6072 | pyridin-2-ylamino-CH$_2$(o-C$_6$H$_4$) | H | NHSO$_2$-(1-naphthyl) | |
| 6073 | pyridin-2-ylamino-CH$_2$(o-C$_6$H$_4$) | H | NHCO$_2$CH$_2$Ph | |
| 6074 | pyridin-2-ylamino-CH$_2$(o-C$_6$H$_4$) | H | NHSO$_2$C$_6$C$_2$-(2,4,6-Me$_3$) | |
| 6075 | imidazolin-2-ylamino-CH$_2$(o-C$_6$H$_4$) | H | NHSO$_2$-(1-naphthyl) | |
| 6076 | imidazolin-2-ylamino-CH$_2$(o-C$_6$H$_4$) | H | NHCO$_2$CH$_2$Ph | |
| 6077 | imidazolin-2-ylamino-CH$_2$(o-C$_6$H$_4$) | H | NHSO$_2$C$_6$C$_2$-(2,4,6-Me$_3$) | |
| 6078 | imidazolin-2-ylamino-(m-C$_6$H$_4$) | H | NHSO$_2$-(1-naphthyl) | |
| 6079 | imidazolin-2-ylamino-(m-C$_6$H$_4$) | H | NHCO$_2$CH$_2$Ph | |
| 6080 | imidazolin-2-ylamino-(m-C$_6$H$_4$) | H | NHSO$_2$C$_6$C$_2$-(2,4,6-Me$_3$) | |

TABLE 7

| Ex. No. | R¹ | R¹⁰ | X¹ | X³ | X⁴ | R¹⁵ | MS |
|---|---|---|---|---|---|---|---|
| 7001 | imidazol-2-ylamino-(CH₂)₃ | H | N | CH | CH | NHCO₂CH₂Ph | |
| 7002 | imidazol-2-ylamino-(CH₂)₃ | CH₃ | CH | N | CH | NHCO₂n-Bu | |
| 7003 | imidazol-2-ylamino-(CH₂)₃ | H | N | CH | CH | NHCO₂i-Bu | |
| 7004 | imidazol-2-ylamino-(CH₂)₃ | H | CH | N | CH | NHCOPh | |
| 7005 | imidazol-2-ylamino-(CH₂)₃ | H | CH | CH | N | NHCOCH₂Ph | |
| 7006 | imidazol-2-ylamino-(CH₂)₃ | H | N | N | CH | NHCOCH₂CH₂Ph | |
| 7007 | imidazol-2-ylamino-(CH₂)₃ | CH₃ | N | CH | CH | NHCOCH=CHPh | |
| 7008 | imidazol-2-ylamino-(CH₂)₃ | H | CH | N | CH | NHCOn-Bu | |
| 7009 | imidazol-2-ylamino-(CH₂)₃ | H | N | CH | CH | NHSO₂Ph | |
| 7010 | imidazol-2-ylamino-(CH₂)₃ | H | CH | N | CH | NHSO₂C₆H₄-(2-CH₃) | |
| 7011 | imidazol-2-ylamino-(CH₂)₃ | H | CH | CH | N | NHSO₂C₆H₄-(3-CH₃) | |
| 7012 | imidazol-2-ylamino-(CH₂)₃ | H | N | N | CH | NHSO₂C₆H₄-(4-CH₃) | |
| 7013 | imidazol-2-ylamino-(CH₂)₃ | H | N | CH | CH | NHSO₂C₆H₃-(2,6-CH₃)₂ | |
| 7014 | imidazol-2-ylamino-(CH₂)₃ | H | CH | N | CH | NHSO₂C₆H₂-(2,4,6-CH₃)₃ | |
| 7015 | imidazol-2-ylamino-(CH₂)₃ | H | N | CH | CH | NHSO₂(2-pyridyl) | |
| 7016 | imidazol-2-ylamino-(CH₂)₃ | H | CH | N | CH | NHSO₂(3-pyridyl) | |
| 7017 | imidazol-2-ylamino-(CH₂)₃ | CH₃ | CH | CH | N | NHSO₂(4-pyridyl) | |
| 7018 | imidazol-2-ylamino-(CH₂)₃ | H | N | N | CH | NHSO₂(2-thienyl) | |
| 7019 | imidazol-2-ylamino-(CH₂)₃ | H | N | CH | CH | NHSO₂[4-(3,5-dimethyl)isoxazolyl] | |
| 7020 | imidazol-2-ylamino-(CH₂)₃ | H | CH | N | CH | NHSO₂C₆H₃-(2,6-Cl₂) | |
| 7021 | imidazol-2-ylamino-(CH₂)₃ | H | N | CH | CH | NHSO₂(2-naphthyl) | |
| 7022 | imidazol-2-ylamino-(CH₂)₃ | H | CH | N | CH | NHSO₂(1-naphthyl) | |
| 7023 | imidazol-2-ylamino-(CH₂)₃ | H | N | CH | CH | NHSO₂C₆H₄-(4-Ph) | |
| 7024 | imidazol-2-ylamino-(CH₂)₃ | H | CH | N | CH | NHSO₂C₆H₂-(4-Ph-2,6-dimethyl) | |
| 7025 | imidazol-2-ylamino-(CH₂)₃ | H | N | CH | CH | NHSO₂C₆H₂-(4-Ph-2,6-dichloro) | |
| 7026 | imidazol-2-ylamino-(CH₂)₃ | H | CH | N | CH | NHSO₂C₆H₄-4-(4-pyridyl) | |
| 7027 | imidazol-2-ylamino-(CH₂)₃ | H | N | CH | CH | NHSO₂C₆H₄-4-(4-pyridyl)-2,6-dimethyl | |
| 7028 | imidazol-2-ylamino-(CH₂)₃ | H | CH | N | CH | NHSO₂C₆H₄-4-(4-pyridyl)-2,6-dichloro | |
| 7029 | imidazol-2-ylamino-(CH₂)₃ | H | CH | N | CH | NHSO₂C₆H₄-4-(2-oxazolyl) | |
| 7030 | imidazol-2-ylamino-(CH₂)₃ | H | CH | N | CH | NHSO₂C₆H₄-4-(2-oxazolyl)-2,6-dimethyl | |
| 7031 | imidazol-2-ylamino-(CH₂)₃ | H | N | CH | CH | NHSO₂C₆H₄-4-(2-oxazolyl)-2,6-dichloro | |
| 7031a | imidazol-2-ylamino-(CH₂)₃ | H | N | CH | CH | NHSO₂C₆H₄-4-(2-pyridyl)-2,6-dimethyl | |
| 7031b | imidazol-2-ylamino-(CH₂)₃ | H | N | CH | CH | NHSO₂C₆H₄-4-(2-furyl)-2,6-dimethyl | |
| 7031c | imidazol-2-ylamino-(CH₂)₃ | H | N | CH | CH | NHSO₂C₆H₄-4-(3-furyl)2,6-dimethyl | |
| 7031d | imidazol-2-ylamino-(CH₂)₃ | H | N | CH | CH | NHSO₂C₆H₄-4-(5-pyrazolyl)-2,6-dimethyl | |
| 7032 | imidazol-2-ylamino-(CH₂)₃ | H | CH | N | CH | NHSO₂CH₂Ph | |
| 7033 | imidazol-2-ylamino-(CH₂)₃ | H | N | CH | CH | NHSO₂-n-Bu | |
| 7034 | imidazol-2-ylamino-(CH₂)₃ | H | CH | N | CH | NHSO₂NHPh | |
| 7035 | imidazol-2-ylamino-(CH₂)₃ | H | CH | CH | N | NHSO₂NHC₆H₃-(2,6-Me₂) | |
| 7036 | imidazol-2-ylamino-(CH₂)₃ | H | N | N | CH | NHSO₂NHC₆H₂-(2,4,6-Me₃) | |
| 7037 | imidazol-2-ylamino-(CH₂)₃ | H | N | CH | CH | NHSO₂NH(2-naphthyl) | |
| 7038 | imidazol-2-ylamino-(CH₂)₃ | H | CH | N | CH | NHSO₂NH(1-naphthyl) | |
| 7039 | imidazol-2-ylamino-(CH₂)₃ | H | N | CH | CH | NHSO₂NHC₆H₄-(4-Ph) | |
| 7040 | imidazol-2-ylamino-(CH₂)₃ | H | CH | N | CH | NHSO₂NHC₆H₂-(4-Ph-2,6-dimethyl) | |
| 7041 | imidazol-2-ylamino-(CH₂)₃ | H | CH | CH | N | NHSO₂C₆H₂-(4-Ph-2,6-dichloro) | |
| 7042 | imidazol-2-ylamino-(CH₂)₃ | H | N | N | CH | NHSO₂NHCH₂Ph | |
| 7043 | imidazol-2-ylamino-(CH₂)₃ | H | N | CH | CH | NHSO₂NH-n-Bu | |
| 7044 | imidazol-2-ylamino-(CH₂)₃ | H | CH | N | CH | NHSO₂NH-i-Bu | |
| 7045 | imidazol-2-ylamino-(CH₂)₃ | CH₃ | N | CH | CH | NHSO₂NH-t-Bu | |
| 7046 | pyridin-2-ylamino-(CH₂)₃ | H | CH | N | CH | NHCO₂CH₂Ph | |
| 7047 | pyridin-2-ylamino-(CH₂)₃ | H | CH | CH | N | NHCO₂n-Bu | |
| 7048 | pyridin-2-ylamino-(CH₂)₃ | H | N | N | CH | NHCO₂i-Bu | |
| 7049 | pyridin-2-ylamino-(CH₂)₃ | H | N | CH | CH | NHCOPh | |
| 7050 | pyridin-2-ylamino-(CH₂)₃ | H | CH | N | CH | NHCOCH₂Ph | |
| 7051 | pyridin-2-ylamino-(CH₂)₃ | H | N | CH | CH | NHCOCH₂CH₂Ph | |
| 7052 | pyridin-2-ylamino-(CH₂)₃ | H | CH | N | CH | NHCOCH=CHPh | |
| 7053 | pyridin-2-ylamino-(CH₂)₃ | H | CH | CH | N | NHCOn-Bu | |
| 7054 | pyridin-2-ylamino-(CH₂)₃ | H | N | CH | CH | NHSO₂Ph | |
| 7055 | pyridin-2-ylamino-(CH₂)₃ | H | CH | N | CH | NHSO₂C₆H₄-(2-CH₃) | |
| 7056 | pyridin-2-ylamino-(CH₂)₃ | H | CH | CH | N | NHSO₂C₆H₄-(3-CH₃) | |
| 7057 | pyridin-2-ylamino-(CH₂)₃ | H | N | N | CH | NHSO₂C₆H₄-(4-CH₃) | |
| 7058 | pyridin-2-ylamino-(CH₂)₃ | H | N | CH | CH | NHSO₂C₆H₃-(2,6-CH₃)₂ | |
| 7059 | pyridin-2-ylamino-(CH₂)₃ | H | CH | N | CH | NHSO₂C₆H₂-(2,4,6-CH₃)₃ | |
| 7060 | pyridin-2-ylamino-(CH₂)₃ | H | N | CH | CH | NHSO₂(2-pyridyl) | |
| 7061 | pyridin-2-ylamino-(CH₂)₃ | CH₃ | CH | N | CH | NHSO₂(3-pyridyl) | |
| 7062 | pyridin-2-ylamino-(CH₂)₃ | H | CH | CH | N | NHSO₂(4-pyridyl) | |
| 7063 | pyridin-2-ylamino-(CH₂)₃ | H | N | N | CH | NHSO₂(2-thienyl) | |

TABLE 7-continued

| Ex. No. | R¹ | R¹⁰ | X¹ | X³ | X⁴ | R¹⁵ | MS |
|---|---|---|---|---|---|---|---|
| 7064 | pyridin-2-ylamino-(CH₂)₃ | H | N | CH | CH | NHSO₂[4-(3,5-dimethyl)isoxazolyl] | |
| 7065 | pyridin-2-ylamino-(CH₂)₃ | H | CH | N | CH | NHSO₂C₆H₃-(2,6-Cl₂) | |
| 7066 | pyridin-2-ylamino-(CH₂)₃ | H | N | CH | CH | NHSO₂(2-naphthyl) | |
| 7067 | pyridin-2-ylamino-(CH₂)₃ | H | CH | N | CH | NHSO₂(1-naphthyl) | |
| 7068 | pyridin-2-ylamino-(CH₂)₃ | H | N | CH | CH | NHSO₂C₆H₄-(4-Ph) | |
| 7069 | pyridin-2-ylamino-(CH₂)₃ | H | CH | N | CH | NHSO₂C₆H₄-(4-Ph-2,6-dimethyl) | |
| 7070 | pyridin-2-ylamino-(CH₂)₃ | H | N | CH | CH | NHSO₂C₆H₄-(4-Ph-2,6-dichloro) | |
| 7071 | pyridin-2-ylamino-(CH₂)₃ | H | CH | N | CH | NHSO₂C₆H₄-4-(4-pyridyl) | |
| 7072 | pyridin-2-ylamino-(CH₂)₃ | H | N | CH | CH | NHSO₂C₆H₄-4-(4-pyridyl)-2,6-dimethyl | |
| 7073 | pyridin-2-ylamino-(CH₂)₃ | H | CH | N | CH | NHSO₂C₆H₄-4-(4-pyridyl)-2,6-dichloro | |
| 7074 | pyridin-2-ylamino-(CH₂)₃ | H | CH | N | CH | NHSO₂C₆H₄-(2-oxazolyl) | |
| 7075 | pyridin-2-ylamino-(CH₂)₃ | H | CH | N | CH | NHSO₂C₆H₄-4-(2-oxazolyl)-2,6-dimethyl | |
| 7076 | pyridin-2-ylamino-(CH₂)₃ | H | N | CH | CH | NHSO₂C₆H₄-4-(2-oxazolyl)-2,6-dichloro | |
| 7076a | pyridin-2-ylamino-(CH₂)₃ | H | N | CH | CH | NHSO₂C₆H₄-4-(3-pyridyl)-2,6-dimethyl | |
| 7076b | pyridin-2-ylamino-(CH₂)₃ | H | N | CH | CH | NHSO₂C₆H₄-4-(2-furyl)-2,6-dimethyl | |
| 7076c | pyridin-2-ylamino-(CH₂)₃ | H | N | CH | CH | NHSO₂C₆H₄-4-(3-furyl)-2,6-dimethyl | |
| 7076d | pyridin-2-ylamino-(CH₂)₃ | H | N | CH | CH | NHSO₂C₆H₄-4-(5-pyrazolyl)-2,6-dimethyl | |
| 7077 | pyridin-2-ylamino-(CH₂)₃ | CH₃ | CH | CH | N | NHSO₂CH₂Ph | |
| 7078 | pyridin-2-ylamino-(CH₂)₃ | H | N | N | CH | NHSO₂-n-Bu | |
| 7079 | pyridin-2-ylamino-(CH₂)₃ | H | N | CH | CH | NHSO₂NHPh | |
| 7080 | pyridin-2-ylamino-(CH₂)₃ | H | CH | N | CH | NHSO₂NHC₆H₃-(2,6-Me₂) | |
| 7081 | pyridin-2-ylamino-(CH₂)₃ | H | N | CH | CH | NHSO₂NHC₆H₂-(2,4,6-Me₃) | |
| 7082 | pyridin-2-ylamino-(CH₂)₃ | H | CH | N | CH | NHSO₂NH(2-naphthyl) | |
| 7083 | pyridin-2-ylamino-(CH₂)₃ | H | CH | CH | N | NHSO₂NH(1-naphthyl) | |
| 7084 | pyridin-2-ylamino-(CH₂)₃ | H | N | N | CH | NHSO₂NHC₆H₄-(4-Ph) | |
| 7085 | pyridin-2-ylamino-(CH₂)₃ | H | N | CH | CH | NHSO₂NHC₆H₂-(4-Ph-2,6-dimethyl) | |
| 7086 | pyridin-2-ylamino-(CH₂)₃ | H | CH | N | CH | NHSO₂NHC₆H₂-(4-Ph-2,6-dichloro) | |
| 7087 | pyridin-2-ylamino-(CH₂)₃ | H | N | CH | CH | NHSO₂NHCH₂Ph | |
| 7088 | pyridin-2-ylamino-(CH₂)₃ | H | CH | N | CH | NHSO₂NH-n-Bu | |
| 7089 | pyridin-2-ylamino-(CH₂)₃ | H | CH | CH | N | NHSO₂NH-i-Bu | |
| 7090 | pyridin-2-ylamino-(CH₂)₃ | H | N | N | CH | NHSO₂NH-t-Bu | |
| 7091 | tetrahydropyrimidin-2-ylamino-(CH₂)₃ | C₂H₅ | N | CH | CH | NHCO₂CH₂Ph | |
| 7092 | tetrahydropyrimidin-2-ylamino-(CH₂)₃ | H | CH | N | CH | NHCO₂n-Bu | |
| 7093 | tetrahydropyrimidin-2-ylamino-(CH₂)₃ | H | N | CH | CH | NHCO₂i-Bu | |
| 7094 | tetrahydropyrimidin-2-ylamino-(CH₂)₃ | H | CH | N | CH | NHCOPh | |
| 7095 | tetrahydropyrimidin-2-ylamino-(CH₂)₃ | H | CH | CH | N | NHCOCH₂Ph | |
| 7096 | tetrahydropyrimidin-2-ylamino-(CH₂)₃ | H | N | N | CH | NHCOCH₂CH₂Ph | |
| 7097 | tetrahydropyrimidin-2-ylamino-(CH₂)₃ | H | N | CH | CH | NHCOCH=CHPh | |
| 7098 | tetrahydropyrimidin-2-ylamino-(CH₂)₃ | H | CH | N | CH | NHCOn-Bu | |
| 7099 | tetrahydropyrimidin-2-ylamino-(CH₂)₃ | H | N | CH | CH | NHSO₂Ph | |
| 7100 | tetrahydropyrimidin-2-ylamino-(CH₂)₃ | H | CH | N | CH | NHSO₂C₆H₄-(2-CH₃) | |
| 7101 | tetrahydropyrimidin-2-ylamino-(CH₂)₃ | H | CH | CH | N | NHSO₂C₆H₄-(3-CH₃) | |
| 7102 | tetrahydropyrimidin-2-ylamino-(CH₂)₃ | H | N | N | CH | NHSO₂C₆H₄-(4-CH₃) | |
| 7103 | tetrahydropyrimidin-2-ylamino-(CH₂)₃ | H | N | CH | CH | NHSO₂C₆H₃-(2,6-CH₃)₂ | |
| 7104 | tetrahydropyrimidin-2-ylamino-(CH₂)₃ | H | CH | N | CH | NHSO₂C₆H₂-(2,4,6-CH₃)₃ | |
| 7105 | tetrahydropyrimidin-2-ylamino-(CH₂)₃ | H | N | CH | CH | NHSO₂(2-pyridyl) | |
| 7106 | tetrahydropyrimidin-2-ylamino-(CH₂)₃ | H | CH | N | CH | NHSO₂(3-pyridyl) | |
| 7107 | tetrahydropyrimidin-2-ylamino-(CH₂)₃ | H | CH | CH | N | NHSO₂(4-pyridyl) | |
| 7108 | tetrahydropyrimidin-2-ylamino-(CH₂)₃ | CH₃ | N | N | CH | NHSO₂(2-thienyl) | |
| 7109 | tetrahydropyrimidin-2-ylamino-(CH₂)₃ | H | N | CH | CH | NHSO₂[4-(3,5-dimethyl)isoxazolyl] | |
| 7110 | tetrahydropyrimidin-2-ylamino-(CH₂)₃ | H | CH | N | CH | NHSO₂C₆H₃-(2,6-Cl₂) | |
| 7111 | tetrahydropyrimidin-2-ylamino-(CH₂)₃ | H | N | CH | CH | NHSO₂(2-naphthyl) | |
| 7112 | tetrahydropyrimidin-2-ylamino-(CH₂)₃ | H | CH | N | CH | NHSO₂(1-naphthyl) | |
| 7113 | tetrahydropyrimidin-2-ylamino-(CH₂)₃ | H | N | CH | CH | NHSO₂C₆H₄-(4-Ph) | |
| 7114 | tetrahydropyrimidin-2-ylamino-(CH₂)₃ | H | CH | N | CH | NHSO₂C₆H₂-(4-Ph-2,6-dimethyl) | |
| 7115 | tetrahydropyrimidin-2-ylamino-(CH₂)₃ | H | N | CH | CH | NHSO₂C₆H₂-(4-Ph-2,6-dichloro) | |
| 7116 | tetrahydropyrimidin-2-ylamino-(CH₂)₃ | H | CH | N | CH | NHSO₂C₆H₄-4-(4-pyridyl) | |
| 7117 | tetrahydropyrimidin-2-ylamino-(CH₂)₃ | H | N | CH | CH | NHSO₂C₆H₄-4-(4-pyridyl)-2,6-dimethyl | |
| 7118 | tetrahydropyrimidin-2-ylamino-(CH₂)₃ | H | CH | N | CH | NHSO₂C₆H₄-4-(4-pyridyl)-2,6-dichloro | |
| 7119 | tetrahydropyrimidin-2-ylamino-(CH₂)₃ | H | CH | N | CH | NHSO₂C₆H₄-(2-oxazolyl) | |
| 7120 | tetrahydropyrimidin-2-ylamino-(CH₂)₃ | H | CH | N | CH | NHSO₂C₆H₄-4-(2-oxazolyl)-2,6-dimethyl | |
| 7121 | tetrahydropyrimidin-2-ylamino-(CH₂)₃ | H | N | CH | CH | NHSO₂C₆H₄-4-(2-oxazolyl)-2,6-dichloro | |
| 7121a | tetrahydropyrimidin-2-ylamino-(CH₂)₃ | H | N | CH | CH | NHSO₂C₆H₄-4-(3-pyridyl)-2,6-dimethyl | |
| 7121b | tetrahydropyrimidin-2-ylamino-(CH₂)₃ | H | N | CH | CH | NHSO₂C₆H₄-4-(2-furyl)-2,6-dimethyl | |
| 7121c | tetrahydropyrimidin-2-ylamino-(CH₂)₃ | H | N | CH | CH | NHSO₂C₆H₄-4-(3-furyl)-2,6-dimethyl | |
| 7121d | tetrahydropyrimidin-2-ylamino-(CH₂)₃ | H | N | CH | CH | NHSO₂C₆H₄-4-(5-pyrazolyl)-2,6-dimethyl | |
| 7122 | tetrahydropyrimidin-2-ylamino-(CH₂)₃ | CH₃ | CH | N | CH | NHSO₂CH₂Ph | |

TABLE 7-continued

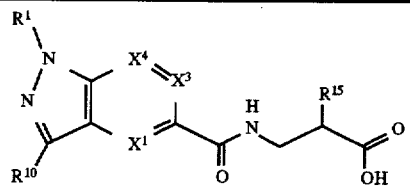

| Ex. No. | R¹ | R¹⁰ | X¹ | X³ | X⁴ | R¹⁵ | MS |
|---|---|---|---|---|---|---|---|
| 7123 | tetrahydropyrimidin-2-ylamino-(CH₂)₃ | H | N | CH | CH | NHSO₂-n-Bu | |
| 7124 | tetrahydropyrimidin-2-ylamino-(CH₂)₃ | H | CH | N | CH | NHSO₂NHPh | |
| 7125 | tetrahydropyrimidin-2-ylamino-(CH₂)₃ | H | CH | CH | N | NHSO₂NHC₆H₃-(2,6-Me₂) | |
| 7126 | tetrahydropyrimidin-2-ylamino-(CH₂)₃ | H | N | N | CH | NHSO₂NHC₆H₂-(2,4,6-Me₃) | |
| 7127 | tetrahydropyrimidin-2-ylamino-(CH₂)₃ | H | N | CH | CH | NHSO₂NH(2-naphthyl) | |
| 7128 | tetrahydropyrimidin-2-ylamino-(CH₂)₃ | H | CH | N | CH | NHSO₂NH(1-naphthyl) | |
| 7129 | tetrahydropyrimidin-2-ylamino-(CH₂)₃ | H | N | CH | CH | NHSO₂NHC₆H₄-(4-Ph) | |
| 7130 | tetrahydropyrimidin-2-ylamino-(CH₂)₃ | H | CH | N | CH | NHSO₂NHC₆H₂-(4-Ph-2,6-dimethyl) | |
| 7131 | tetrahydropyrimidin-2-ylamino-(CH₂)₃ | H | CH | CH | N | NHSO₂NHC₆H₂-(4-Ph-2,6-dichloro) | |
| 7132 | tetrahydropyrimidin-2-ylamino-(CH₂)₃ | H | N | N | CH | NHSO₂NHCH₂Ph | |
| 7133 | tetrahydropyrimidin-2-ylamino-(CH₂)₃ | H | N | CH | CH | NHSO₂NH-n-Bu | |
| 7134 | tetrahydropyrimidin-2-ylamino-(CH₂)₃ | H | CH | N | CH | NHSO₂NH-i-Bu | |
| 7135 | tetrahydropyrimidin-2-ylamino-(CH₂)₃ | H | N | CH | CH | NHSO₂NH-t-Bu | |
| 7136 | imidazolin-2-ylamino-(CH₂)₃ | H | CH | N | CH | NHCO₂CH₂Ph | |
| 7137 | imidazolin-2-ylamino-(CH₂)₃ | H | CH | CH | N | NHCO₂n-Bu | |
| 7138 | imidazolin-2-ylamino-(CH₂)₃ | H | N | N | CH | NHCO₂i-Bu | |
| 7139 | imidazolin-2-ylamino-(CH₂)₃ | H | N | CH | CH | NHCOPh | |
| 7140 | imidazolin-2-ylamino-(CH₂)₃ | H | CH | N | CH | NHCOCH₂Ph | |
| 7141 | imidazolin-2-ylamino-(CH₂)₃ | H | N | CH | CH | NHCOCH₂CH₂Ph | |
| 7142 | imidazolin-2-ylamino-(CH₂)₃ | CH₃ | CH | N | CH | NHCOCH=CHPh | |
| 7143 | imidazolin-2-ylamino-(CH₂)₃ | H | CH | CH | N | NHCOn-Bu | |
| 7144 | imidazolin-2-ylamino-(CH₂)₃ | H | N | CH | CH | NHSO₂Ph | |
| 7145 | imidazolin-2-ylamino-(CH₂)₃ | H | CH | N | CH | NHSO₂C₆H₄-(2-CH₃) | |
| 7146 | imidazolin-2-ylamino-(CH₂)₃ | H | CH | CH | N | NHSO₂C₆H₄-(3-CH₃) | |
| 7147 | imidazolin-2-ylamino-(CH₂)₃ | H | N | N | CH | NHSO₂C₆H₄-(4-CH₃) | |
| 7148 | imidazolin-2-ylamino-(CH₂)₃ | H | N | CH | CH | NHSO₂C₆H₃-(2,6-CH₃)₂ | |
| 7149 | imidazolin-2-ylamino-(CH₂)₃ | H | CH | N | CH | NHSO₂C₆H₂-(2,4,6-CH₃)₃ | |
| 7150 | imidazolin-2-ylamino-(CH₂)₃ | H | N | CH | CH | NHSO₂(2-pyridyl) | |
| 7151 | imidazolin-2-ylamino-(CH₂)₃ | H | CH | N | CH | NHSO₂(3-pyridyl) | |
| 7152 | imidazolin-2-ylamino-(CH₂)₃ | H | CH | CH | N | NHSO₂(4-pyridyl) | |
| 7153 | imidazolin-2-ylamino-(CH₂)₃ | H | N | N | CH | NHSO₂(2-thienyl) | |
| 7154 | imidazolin-2-ylamino-(CH₂)₃ | H | N | CH | CH | NHSO₂[4-(3,5-dimethyl)isoxazolyl] | |
| 7155 | imidazolin-2-ylamino-(CH₂)₃ | H | CH | N | CH | NHSO₂C₆H₃-(2,6-Cl₂) | |
| 7156 | imidazolin-2-ylamino-(CH₂)₃ | H | N | CH | CH | NHSO₂(2-naphthyl) | |
| 7157 | imidazolin-2-ylamino-(CH₂)₃ | H | CH | N | CH | NHSO₂(1-naphthyl) | |
| 7158 | imidazolin-2-ylamino-(CH₂)₃ | H | N | CH | CH | NHSO₂C₆H₄-(4-Ph) | |
| 7159 | imidazolin-2-ylamino-(CH₂)₃ | H | CH | N | CH | NHSO₂C₆H₂-(4-Ph-2,6-dimethyl) | |
| 7160 | imidazolin-2-ylamino-(CH₂)₃ | H | N | CH | CH | NHSO₂C₆H₂-(4-Ph-2,6-dichloro) | |
| 7161 | imidazolin-2-ylamino-(CH₂)₃ | H | CH | N | CH | NHSO₂C₆H₄-4-(4-pyridyl) | |
| 7162 | imidazolin-2-ylamino-(CH₂)₃ | H | N | CH | CH | NHSO₂C₆H₄-4-(4-pyridyl)-2,6-dimethyl | |
| 7163 | imidazolin-2-ylamino-(CH₂)₃ | H | CH | N | CH | NHSO₂C₆H₄-4-(4-pyridyl)-2,6-dichloro | |
| 7164 | imidazolin-2-ylamino-(CH₂)₃ | H | CH | N | CH | NHSO₂C₆H₄-4-(2-oxazolyl) | |
| 7165 | imidazolin-2-ylamino-(CH₂)₃ | H | CH | N | CH | NHSO₂C₆H₄-4-(2-oxazolyl)-2,6-dimethyl | |
| 7166 | imidazolin-2-ylamino-(CH₂)₃ | H | N | CH | CH | NHSO₂C₆H₄-4-(2-oxazolyl)-2,6-dichloro | |
| 7166a | imidazolin-2-ylamino-(CH₂)₃ | H | N | CH | CH | NHSO₂C₆H₄-4-(3-pyridyl)-2,6-dimethyl | |
| 7166b | imidazolin-2-ylamino-(CH₂)₃ | H | N | CH | CH | NHSO₂C₆H₄-4-(2-furyl)-2,6-dimethyl | |
| 7166c | imidazolin-2-ylamino-(CH₂)₃ | H | N | CH | CH | NHSO₂C₆H₄-4-(3-furyl)-2,6-dimethyl | |
| 7166d | imidazolin-2-ylamino-(CH₂)₃ | H | N | CH | CH | NHSO₂C₆H₄-4-(5-pyrazolyl)-2,6-dimethyl | |
| 7167 | imidazolin-2-ylamino-(CH₂)₃ | H | CH | CH | N | NHSO₂CH₂Ph | |
| 7168 | imidazolin-2-ylamino-(CH₂)₃ | H | N | N | CH | NHSO₂-n-Bu | |
| 7169 | imidazolin-2-ylamino-(CH₂)₃ | Br | N | CH | CH | NHSO₂NHPh | |
| 7170 | imidazolin-2-ylamino-(CH₂)₃ | H | CH | N | CH | NHSO₂NHC₆H₃-(2,6-Me₂) | |
| 7171 | imidazolin-2-ylamino-(CH₂)₃ | H | N | CH | CH | NHSO₂NHC₆H₂-(2,4,6-Me₃) | |
| 7172 | imidazolin-2-ylamino-(CH₂)₃ | H | CH | N | CH | NHSO₂NH(2-naphthyl) | |
| 7173 | imidazolin-2-ylamino-(CH₂)₃ | H | CH | CH | N | NHSO₂NH(1-naphthyl) | |
| 7174 | imidazolin-2-ylamino-(CH₂)₃ | H | N | N | CH | NHSO₂NHC₆H₄-(4-Ph) | |
| 7175 | imidazolin-2-ylamino-(CH₂)₃ | H | N | CH | CH | NHSO₂NHC₆H₂-(4-Ph-2,6-dimethyl) | |
| 7176 | imidazolin-2-ylamino-(CH₂)₃ | H | CH | N | CH | NHSO₂NHC₆H₂-(4-Ph-2,6-dichloro) | |
| 7177 | imidazolin-2-ylamino-(CH₂)₃ | H | N | CH | CH | NHSO₂NHCH₂Ph | |
| 7178 | imidazolin-2-ylamino-(CH₂)₃ | H | CH | N | CH | NHSO₂NH-n-Bu | |
| 7179 | imidazolin-2-ylamino-(CH₂)₃ | H | CH | CH | N | NHSO₂NH-i-Bu | |
| 7180 | imidazolin-2-ylamino-(CH₂)₃ | H | N | N | CH | NHSO₂NH-t-Bu | |
| 7181 | benzimidazol-2-ylamino-(CH₂)₃ | H | N | CH | CH | NHCO₂CH₂Ph | |
| 7182 | benzimidazol-2-ylamino-(CH₂)₃ | H | CH | N | CH | NHCO₂n-Bu | |
| 7183 | benzimidazol-2-ylamino-(CH₂)₃ | H | N | CH | CH | NHCO₂i-Bu | |
| 7184 | benzimidazol-2-ylamino-(CH₂)₃ | H | CH | N | CH | NHCOPh | |
| 7185 | benzimidazol-2-ylamino-(CH₂)₃ | H | CH | CH | N | NHCOCH₂Ph | |

TABLE 7-continued

| Ex. No. | R¹ | R¹⁰ | X¹ | X³ | X⁴ | R¹⁵ | MS |
|---------|-----|-----|----|----|----|-----|-----|
| 7186 | benzimidazol-2-ylamino-(CH₂)₃ | H | N | N | CH | NHCOCH₂CH₂Ph | |
| 7187 | benzimidazol-2-ylamino-(CH₂)₃ | H | N | CH | CH | NHCOCH=CHPh | |
| 7188 | benzimidazol-2-ylamino-(CH₂)₃ | CH₃ | CH | N | CH | NHCOn-Bu | |
| 7189 | benzimidazol-2-ylamino-(CH₂)₃ | H | N | CH | CH | NHSO₂Ph | |
| 7190 | benzimidazol-2-ylamino-(CH₂)₃ | H | CH | N | CH | NHSO₂C₆H₄-(2-CH₃) | |
| 7191 | benzimidazol-2-ylamino-(CH₂)₃ | H | CH | CH | N | NHSO₂C₆H₄-(3-CH₃) | |
| 7192 | benzimidazol-2-ylamino-(CH₂)₃ | H | N | N | CH | NHSO₂C₆H₄-(4-CH₃) | |
| 7193 | benzimidazol-2-ylamino-(CH₂)₃ | H | N | CH | CH | NHSO₂C₆H₃-(2,6-CH₃)₂ | |
| 7194 | benzimidazol-2-ylamino-(CH₂)₃ | H | CH | N | CH | NHSO₂C₆H₂-(2,4,6-CH₃)₃ | |
| 7195 | benzimidazol-2-ylamino-(CH₂)₃ | H | N | CH | CH | NHSO₂(2-pyridyl) | |
| 7196 | benzimidazol-2-ylamino-(CH₂)₃ | H | CH | N | CH | NHSO₂(3-pyridyl) | |
| 7197 | benzimidazol-2-ylamino-(CH₂)₃ | H | CH | CH | N | NHSO₂(4-pyridyl) | |
| 7198 | benzimidazol-2-ylamino-(CH₂)₃ | H | N | N | CH | NHSO₂(2-thienyl) | |
| 7199 | benzimidazol-2-ylamino-(CH₂)₃ | H | N | CH | CH | NHSO₂[4-(3,5-dimethyl)isoxazolyl] | |
| 7200 | benzimidazol-2-ylamino-(CH₂)₃ | H | CH | N | CH | NHSO₂C₆H₃-(2,6-Cl₂) | |
| 7201 | benzimidazol-2-ylamino-(CH₂)₃ | H | N | CH | CH | NHSO₂(2-naphthyl) | |
| 7202 | benzimidazol-2-ylamino-(CH₂)₃ | H | CH | N | CH | NHSO₂(1-naphthyl) | |
| 7203 | benzimidazol-2-ylamino-(CH₂)₃ | H | N | CH | CH | NHSO₂C₆H₄-(4-Ph) | |
| 7204 | benzimidazol-2-ylamino-(CH₂)₃ | H | CH | N | CH | NHSO₂C₆H₂-(4-Ph-2,6-dimethyl) | |
| 7205 | benzimidazol-2-ylamino-(CH₂)₃ | H | N | CH | CH | NHSO₂C₆H₂-(4-Ph-2,6-dichloro) | |
| 7206 | benzimidazol-2-ylamino-(CH₂)₃ | H | CH | N | CH | NHSO₂C₆H₄-4-(4-pyridyl) | |
| 7207 | benzimidazol-2-ylamino-(CH₂)₃ | H | N | CH | CH | NHSO₂C₆H₄-4-(4-pyridyl)-2,6-dimethyl | |
| 7208 | benzimidazol-2-ylamino-(CH₂)₃ | H | CH | N | CH | NHSO₂C₆H₄-4-(4-pyridyl)-2,6-dichloro | |
| 7209 | benzimidazol-2-ylamino-(CH₂)₃ | H | CH | N | CH | NHSO₂C₆H₄-4-(2-oxazolyl) | |
| 7210 | benzimidazol-2-ylamino-(CH₂)₃ | H | CH | N | CH | NHSO₂C₆H₄-4-(2-oxazolyl)-2,6-dimethyl | |
| 7211 | benzimidazol-2-ylamino-(CH₂)₃ | H | N | CH | CH | NHSO₂C₆H₄-4-(2-oxazolyl)-2,6-dichloro | |
| 7211a | benzimidazol-2-ylamino-(CH₂)₃ | H | N | CH | CH | NHSO₂C₆H₄-4-(2-pyridyl)-2,6-dimethyl | |
| 7211b | benzimidazol-2-ylamino-(CH₂)₃ | H | N | CH | CH | NHSO₂C₆H₄-4-(2-furyl)-2,6-dimethyl | |
| 7211c | benzimidazol-2-ylamino-(CH₂)₃ | H | N | CH | CH | NHSO₂C₆H₄-4-(3-furyl)-2,6-dimethyl | |
| 7211d | benzimidazol-2-ylamino-(CH₂)₃ | H | N | CH | CH | NHSO₂C₆H₄-4-(5-pyrazolyl)-2,6-dimethyl | |
| 7212 | benzimidazol-2-ylamino-(CH₂)₃ | CH₃ | CH | N | CH | NHSO₂CH₂Ph | |
| 7213 | benzimidazol-2-ylamino-(CH₂)₃ | H | N | CH | CH | NHSO₂-n-Bu | |
| 7214 | benzimidazol-2-ylamino-(CH₂)₃ | H | CH | N | CH | NHSO₂NHPh | |
| 7215 | benzimidazol-2-ylamino-(CH₂)₃ | H | CH | CH | N | NHSO₂NHC₆H₃-(2,6-Me₂) | |
| 7216 | benzimidazol-2-ylamino-(CH₂)₃ | H | N | N | CH | NHSO₂NHC₆H₂-(2,4,6-Me₃) | |
| 7217 | benzimidazol-2-ylamino-(CH₂)₃ | H | N | CH | CH | NHSO₂NH(2-naphthyl) | |
| 7218 | benzimidazol-2-ylamino-(CH₂)₃ | H | CH | N | CH | NHSO₂NH(1-naphthyl) | |
| 7219 | benzimidazol-2-ylamino-(CH₂)₃ | H | N | CH | CH | NHSO₂NHC₆H₄-(4-Ph) | |
| 7220 | benzimidazol-2-ylamino-(CH₂)₃ | H | CH | N | CH | NHSO₂NHC₆H₂-(4-Ph-2,6-dimethyl) | |
| 7221 | benzimidazol-2-ylamino-(CH₂)₃ | H | CH | CH | N | NHSO₂NHC₆H₂-(4-Ph-2,6-dichloro) | |
| 7222 | benzimidazol-2-ylamino-(CH₂)₃ | H | N | N | CH | NHSO₂NHCH₂Ph | |
| 7223 | benzimidazol-2-ylamino-(CH₂)₃ | H | N | CH | CH | NHSO₂NH-n-Bu | |
| 7224 | benzimidazol-2-ylamino-(CH₂)₃ | H | CH | N | CH | NHSO₂NH-i-Bu | |
| 7225 | benzimidazol-2-ylamino-(CH₂)₃ | H | N | CH | CH | NHSO₂NH-t-Bu | |
| 7226 | 2-aminopyridin-6-yl-(CH₂)₂ | H | CH | N | CH | NHSO₂CH₂Ph | |
| 7227 | 2-aminopyridin-6-yl-(CH₂)₂ | H | CH | CH | N | NHCO₂n-Bu | |
| 7228 | 2-aminopyridin-6-yl-(CH₂)₂ | H | N | N | CH | NHCO₂i-Bu | |
| 7229 | 2-aminopyridin-6-yl-(CH₂)₂ | H | N | CH | CH | NHCOPh | |
| 7230 | 2-aminopyridin-6-yl-(CH₂)₂ | H | CH | N | CH | NHCOCH₂Ph | |
| 7231 | 2-aminopyridin-6-yl-(CH₂)₂ | H | N | CH | CH | NHCOCH₂CH₂Ph | |
| 7232 | 2-aminopyridin-6-yl-(CH₂)₂ | H | CH | N | CH | NHCOCH=CHPh | |
| 7233 | 2-aminopyridin-6-yl-(CH₂)₂ | H | CH | CH | N | NHCOn-Bu | |
| 7234 | 2-aminopyridin-6-yl-(CH₂)₂ | H | N | CH | CH | NHSO₂Ph | |
| 7235 | 2-aminopyridin-6-yl-(CH₂)₂ | H | CH | N | CH | NHSO₂C₆H₄-(2-CH₃) | |
| 7236 | 2-aminopyridin-6-yl-(CH₂)₂ | H | CH | CH | N | NHSO₂C₆H₄-(3-CH₃) | |
| 7237 | 2-aminopyridin-6-yl-(CH₂)₂ | H | N | N | CH | NHSO₂C₆H₄-(4-CH₃) | |
| 7238 | 2-aminopyridin-6-yl-(CH₂)₂ | H | N | CH | CH | NHSO₂C₆H₃-(2,6-CH₃)₂ | |
| 7239 | 2-aminopyridin-6-yl-(CH₂)₂ | H | CH | N | CH | NHSO₂C₆H₂-(2,4,6-CH₃)₃ | |
| 7240 | 2-aminopyridin-6-yl-(CH₂)₂ | H | N | CH | CH | NHSO₂(2-pyridyl) | |
| 7241 | 2-aminopyridin-6-yl-(CH₂)₂ | H | CH | N | CH | NHSO₂(3-pyridyl) | |
| 7242 | 2-aminopyridin-6-yl-(CH₂)₂ | H | CH | CH | N | NHSO₂(4-pyridyl) | |
| 7243 | 2-aminopyridin-6-yl-(CH₂)₂ | H | N | N | CH | NHSO₂(2-thienyl) | |
| 7244 | 2-aminopyridin-6-yl-(CH₂)₂ | CH₃ | N | CH | CH | NHSO₂[4-(3,5-dimethyl)isoxazolyl] | |
| 7245 | 2-aminopyridin-6-yl-(CH₂)₂ | H | CH | N | CH | NHSO₂C₆H₃-(2,6-Cl₂) | |
| 7246 | 2-aminopyridin-6-yl-(CH₂)₂ | H | N | CH | CH | NHSO₂(2-naphthyl) | |
| 7247 | 2-aminopyridin-6-yl-(CH₂)₂ | H | CH | N | CH | NHSO₂(1-naphthyl) | |
| 7248 | 2-aminopyridin-6-yl-(CH₂)₂ | H | N | CH | CH | NHSO₂C₆H₄-(4-Ph) | |

TABLE 7-continued

| Ex. No. | R¹ | R¹⁰ | X¹ | X³ | X⁴ | R¹⁵ | MS |
|---|---|---|---|---|---|---|---|
| 7249 | 2-aminopyridin-6-yl-(CH₂)₂ | H | CH | N | CH | NHSO₂C₆H₂-(4-Ph-2,6-dimethyl) | |
| 7250 | 2-aminopyridin-6-yl-(CH₂)₂ | H | N | CH | CH | NHSO₂C₆H₂-(4-Ph-2,6-dichloro) | |
| 7251 | 2-aminopyridin-6-yl-(CH₂)₂ | H | CH | N | CH | NHSO₂C₆H₄-4-(4-pyridyl) | |
| 7252 | 2-aminopyridin-6-yl-(CH₂)₂ | H | N | CH | CH | NHSO₂C₆H₄-4-(4-pyridyl)-2,6-dimethyl | |
| 7253 | 2-aminopyridin-6-yl-(CH₂)₂ | H | CH | N | CH | NHSO₂C₆H₄-4-(4-pyridyl)-2,6-dichloro | |
| 7254 | 2-aminopyridin-6-yl-(CH₂)₂ | H | CH | N | CH | NHSO₂C₆H₄-4-(2-oxazolyl) | |
| 7255 | 2-aminopyridin-6-yl-(CH₂)₂ | H | CH | N | CH | NHSO₂C₆H₄-4-(2-oxazolyl)-2,6-dimethyl | |
| 7256 | 2-aminopyridin-6-yl-(CH₂)₂ | H | N | CH | CH | NHSO₂C₆H₄-4-(2-oxazolyl)-2,6-dichloro | |
| 7256a | 2-aminopyridin-6-yl-(CH₂)₂ | H | N | CH | CH | NHSO₂C₆H₄-4-(3-pyridyl)-2,6-dimethyl | |
| 7256b | 2-aminopyridin-6-yl-(CH₂)₂ | H | N | CH | CH | NHSO₂C₆H₄-4-(2-furyl)-2,6-dimethyl | |
| 7256c | 2-aminopyridin-6-yl-(CH₂)₂ | H | N | CH | CH | NHSO₂C₆H₄-4-(3-furyl)-2,6-dimethyl | |
| 7256d | 2-aminopyridin-6-yl-(CH₂)₂ | H | N | CH | CH | NHSO₂C₆H₄-4-(5-pyrazolyl)-2,6-dimethyl | |
| 7257 | 2-aminopyridin-6-yl-(CH₂)₂ | H | CH | CH | N | NHSO₂CH₂Ph | |
| 7258 | 2-aminopyridin-6-yl-(CH₂)₂ | H | N | N | CH | NHSO₂-n-Bu | |
| 7259 | 2-aminopyridin-6-yl-(CH₂)₂ | H | N | CH | CH | NHSO₂NHPh | |
| 7260 | 2-aminopyridin-6-yl-(CH₂)₂ | H | CH | N | CH | NHSO₂NHC₆H₃-(2,6-Me₂) | |
| 7261 | 2-aminopyridin-6-yl-(CH₂)₂ | H | N | CH | CH | NHSO₂NHC₆H₂-(2,4,6-Me₃) | |
| 7262 | 2-aminopyridin-6-yl-(CH₂)₂ | H | CH | N | CH | NHSO₂NH(2-naphthyl) | |
| 7263 | 2-aminopyridin-6-yl-(CH₂)₂ | H | CH | CH | N | NHSO₂NH(1-naphthyl) | |
| 7264 | 2-aminopyridin-6-yl-(CH₂)₂ | H | N | N | CH | NHSO₂NHC₆H₄-(4-Ph) | |
| 7265 | 2-aminopyridin-6-yl-(CH₂)₂ | H | N | CH | CH | NHSO₂NHC₆H₂-(4-Ph-2,6-dimethyl) | |
| 7266 | 2-aminopyridin-6-yl-(CH₂)₂ | H | CH | N | CH | NHSO₂NHC₆H₂-(4-Ph-2,6-dichloro) | |
| 7267 | 2-aminopyridin-6-yl-(CH₂)₂ | H | N | CH | CH | NHSO₂NHCH₂Ph | |
| 7268 | 2-aminopyridin-6-yl-(CH₂)₂ | H | CH | N | CH | NHSO₂NH-n-Bu | |
| 7269 | 2-aminopyridin-6-yl-(CH₂)₂ | H | CH | CH | N | NHSO₂NH-i-Bu | |
| 7270 | 2-aminopyridin-6-yl-(CH₂)₂ | H | N | N | CH | NHSO₂NH-t-Bu | |
| 7271 | imidazol-2-ylamino-CH₂(o-C₆H₄)-CH₂ | H | N | CH | CH | NHSO₂-(1-naphthyl) | |
| 7272 | imidazol-2-ylamino-CH₂(o-C₆H₄)-CH₂ | H | N | CH | CH | NHCO₂CH₂Ph | |
| 7273 | imidazol-2-ylamino-CH₂(o-C₆H₄)-CH₂ | H | N | CH | CH | NHSO₂C₆C₂-(2,4,6-Me₃) | |
| 7274 | pyridin-2-ylamino-CH₂(o-C₆H₄)-CH₂ | H | N | CH | CH | NHSO₂-(1-naphthyl) | |
| 7275 | pyridin-2-ylamino-CH₂(o-C₆H₄)-CH₂ | H | N | CH | CH | NHCO₂CH₂Ph | |
| 7276 | pyridin-2-ylamino-CH₂(o-C₆H₄)-CH₂ | H | N | CH | CH | NHSO₂C₆C₂-(2,4,6-Me₃) | |
| 7277 | imidazolin-2-ylamino-CH₂(o-C₆H₄)-CH₂ | H | N | CH | CH | NHSO₂-(1-naphthyl) | |
| 7278 | imidazolin-2-ylamino-CH₂(o-C₆H₄)-CH₂ | H | N | CH | CH | NHCO₂CH₂Ph | |
| 7279 | imidazolin-2-ylamino-CH₂(o-C₆H₄)-CH₂ | H | N | CH | CH | NHSO₂C₆C₂-(2,4,6-Me₃) | |
| 7280 | imidazolin-2-ylamino-(o-C₆H₄)-CH₂ | H | N | CH | CH | NHSO₂-(1-naphthyl) | |
| 7281 | imidazolin-2-ylamino-(o-C₆H₄)-CH₂ | H | N | CH | CH | NHCO₂CH₂Ph | |
| 7282 | imidazolin-2-ylamino-(o-C₆H₄)-CH₂ | H | N | CH | CH | NHSO₂C₆C₂-(2,4,6-Me₃) | |

TABLE 8

| Ex. No. | R¹ | R⁹ | X¹ | X³ | X⁴ | R¹⁵ | MS |
|---|---|---|---|---|---|---|---|
| 8001 | imidazol-2-ylamino-(CH₂)₃ | H | CH | CH | N | NHCO₂CH₂Ph | |
| 8002 | imidazol-2-ylamino-(CH₂)₃ | CH₃ | CH | N | CH | NHCO₂n-Bu | |
| 8003 | imidazol-2-ylamino-(CH₂)₃ | H | CH | CH | N | NHCO₂i-Bu | |
| 8004 | imidazol-2-ylamino-(CH₂)₃ | CH₃ | N | CH | CH | NHCOPh | |
| 8005 | imidazol-2-ylamino-(CH₂)₃ | H | CH | CH | N | NHCOCH₂Ph | |
| 8006 | imidazol-2-ylamino-(CH₂)₃ | CH₃ | N | N | CH | NHCOCH₂CH₂Ph | |
| 8007 | imidazol-2-ylamino-(CH₂)₃ | CH₃ | CH | CH | N | NHCOCH=CHPh | |
| 8008 | imidazol-2-ylamino-(CH₂)₃ | H | CH | N | CH | NHCOn-Bu | |
| 8009 | imidazol-2-ylamino-(CH₂)₃ | CH₃ | CH | CH | N | NHSO₂Ph | |
| 8010 | imidazol-2-ylamino-(CH₂)₃ | H | N | CH | CH | NHSO₂C₆H₄-(2-CH₃) | |
| 8011 | imidazol-2-ylamino-(CH₂)₃ | H | CH | CH | N | NHSO₂C₆H₄-(3-CH₃) | |
| 8012 | imidazol-2-ylamino-(CH₂)₃ | H | N | N | CH | NHSO₂C₆H₄-(4-CH₃) | |

TABLE 8-continued

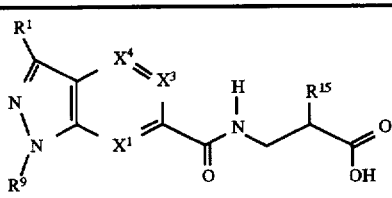

| Ex. No. | R¹ | R⁹ | X¹ | X³ | X⁴ | R¹⁵ | MS |
|---|---|---|---|---|---|---|---|
| 8013 | imidazol-2-ylamino-(CH₂)₃ | CH₃ | CH | CH | N | NHSO₂C₆H₃-(2,6-CH₃)₂ | |
| 8014 | imidazol-2-ylamino-(CH₂)₃ | H | CH | CH | N | NHSO₂C₆H₂-(2,4,6-CH₃)₃ | |
| 8015 | imidazol-2-ylamino-(CH₂)₃ | CH₃ | CH | CH | N | NHSO₂(2-pyridyl) | |
| 8016 | imidazol-2-ylamino-(CH₂)₃ | H | N | CH | CH | NHSO₂(3-pyridyl) | |
| 8017 | imidazol-2-ylamino-(CH₂)₃ | CH₃ | CH | CH | N | NHSO₂(4-pyridyl) | |
| 8018 | imidazol-2-ylamino-(CH₂)₃ | H | N | N | CH | NHSO₂(2-thienyl) | |
| 8019 | imidazol-2-ylamino-(CH₂)₃ | CH₃ | CH | CH | N | NHSO₂[4-(3,5-dimethyl)isoxazolyl] | |
| 8020 | imidazol-2-ylamino-(CH₂)₃ | H | CH | CH | N | NHSO₂C₆H₃-(2,6-Cl₂) | |
| 8021 | imidazol-2-ylamino-(CH₂)₃ | CH₃ | CH | CH | N | NHSO₂(2-naphthyl) | |
| 8022 | imidazol-2-ylamino-(CH₂)₃ | H | CH | CH | N | NHSO₂(1-naphthyl) | |
| 8023 | imidazol-2-ylamino-(CH₂)₃ | CH₃ | CH | CH | N | NHSO₂C₆H₄-(4-Ph) | |
| 8024 | imidazol-2-ylamino-(CH₂)₃ | H | CH | CH | N | NHSO₂C₆H₂-(4-Ph-2,6-dimethyl) | |
| 8025 | imidazol-2-ylamino-(CH₂)₃ | H | CH | CH | N | NHSO₂C₆H₂-(4-Ph-2,6-dichloro) | |
| 8026 | imidazol-2-ylamino-(CH₂)₃ | CH₃ | CH | CH | N | NHSO₂C₆H₄-4-(4-pyridyl) | |
| 8027 | imidazol-2-ylamino-(CH₂)₃ | CH₃ | CH | CH | N | NHSO₂C₆H₄-4-(4-pyridyl)-2,6-dimethyl | |
| 8028 | imidazol-2-ylamino-(CH₂)₃ | H | N | CH | CH | NHSO₂C₆H₄-4-(4-pyridyl)-2,6-dichloro | |
| 8029 | imidazol-2-ylamino-(CH₂)₃ | CH₃ | CH | CH | N | NHSO₂C₆H₄-4-(2-oxazolyl) | |
| 8030 | imidazol-2-ylamino-(CH₂)₃ | CH₃ | CH | CH | N | NHSO₂C₆H₄-4-(2-oxazolyl)-2,6-dimethyl | |
| 8031 | imidazol-2-ylamino-(CH₂)₃ | H | CH | CH | N | NHSO₂C₆H₄-4-(2-oxazolyl)-2,6-dichloro | |
| 8031a | imidazol-2-ylamino-(CH₂)₃ | CH₃ | CH | CH | N | NHSO₂C₆H₄-4-(3-pyridyl)-2,6-dimethyl | |
| 8031b | imidazol-2-ylamino-(CH₂)₃ | H | CH | CH | N | NHSO₂C₆H₄-4-(2-furyl)-2,6-dimethyl | |
| 8031c | imidazol-2-ylamino-(CH₂)₃ | H | CH | CH | N | NHSO₂C₆H₄-4-(3-furyl)-2,6-dimethyl | |
| 8031d | imidazol-2-ylamino-(CH₂)3 | CH₃ | CH | CH | N | NHSO₂C₆H₄-4-(5-pyrazolyl)-2,6-dimethyl | |
| 8032 | imidazol-2-ylamino-(CH₂)₃ | H | CH | N | CH | NHSO₂CH₂Ph | |
| 8033 | imidazol-2-ylamino-(CH₂)₃ | H | CH | CH | N | NHSO₂-n-Bu | |
| 8034 | imidazol-2-ylamino-(CH₂)₃ | H | N | CH | CH | NHSO₂NHPh | |
| 8035 | imidazol-2-ylamino-(CH₂)₃ | CH₃ | CH | CH | N | NHSO₂NHC₆H₃-(2,6-Me₂) | |
| 8036 | imidazol-2-ylamino-(CH₂)₃ | H | N | N | CH | NHSO₂NHC₆H₂-(2,4,6-Me₃) | |
| 8037 | imidazol-2-ylamino-(CH₂)₃ | H | CH | CH | N | NHSO₂NH(2-naphthyl) | |
| 8038 | imidazol-2-ylamino-(CH₂)₃ | CH₃ | CH | N | CH | NHSO₂NH(1-naphthyl) | |
| 8039 | imidazol-2-ylamino-(CH₂)₃ | H | CH | CH | N | NHSO₂NHC₆H₄-(4-Ph) | |
| 8040 | imidazol-2-ylamino-(CH₂)₃ | H | CH | CH | CH | NHSO₂NHC₆H₂-(4-Ph-2,6-dimethyl) | |
| 8041 | imidazol-2-ylamino-(CH₂)₃ | CH₃ | CH | CH | N | NHSO₂NHC₆H₂-(4-Ph-2,6-dichloro) | |
| 8042 | imidazol-2-ylamino-(CH₂)₃ | H | N | N | CH | NHSO₂NHCH₂Ph | |
| 8043 | imidazol-2-ylamino-(CH₂)₃ | H | CH | CH | N | NHSO₂NH-n-Bu | |
| 8044 | imidazol-2-ylamino-(CH₂)₃ | H | CH | N | CH | NHSO₂NH-i-Bu | |
| 8045 | imidazol-2-ylamino-(CH₂)₃ | CH₃ | CH | CH | N | NHSO₂NH-t-Bu | |
| 8046 | pyridin-2-ylamino-(CH₂)₃ | H | N | CH | CH | NHCO₂CH₂Ph | |
| 8047 | pyridin-2-ylamino-(CH₂)₃ | CH₃ | CH | CH | N | NHCO₂n-Bu | |
| 8048 | pyridin-2-ylamino-(CH₂)₃ | H | N | N | CH | NHCO₂i-Bu | |
| 8049 | pyridin-2-ylamino-(CH₂)₃ | CH₃ | CH | CH | N | NHCOPh | |
| 8050 | pyridin-2-ylamino-(CH₂)₃ | H | CH | N | CH | NHCOCH₂Ph | |
| 8051 | pyridin-2-ylamino-(CH₂)₃ | CH₃ | CH | CH | N | NHCOCH₂CH₂Ph | |
| 8052 | pyridin-2-ylamino-(CH₂)₃ | CH₃ | N | CH | CH | NHCOCH=CHPh | |
| 8053 | pyridin-2-ylamino-(CH₂)₃ | H | CH | CH | N | NHCOn-Bu | |
| 8054 | pyridin-2-ylamino-(CH₂)₃ | CH₃ | CH | CH | N | NHSO₂Ph | |
| 8055 | pyridin-2-ylamino-(CH₂)₃ | H | N | CH | CH | NHSO₂C₆H₄-(2-CH₃) | |
| 8056 | pyridin-2-ylamino-(CH₂)₃ | H | CH | CH | N | NHSO₂C₆H₄-(3-CH₃) | |
| 8057 | pyridin-2-ylamino-(CH₂)₃ | H | N | N | CH | NHSO₂C₆H₄-(4-CH₃) | |
| 8058 | pyridin-2-ylamino-(CH₂)₃ | CH₃ | CH | CH | N | NHSO₂C₆H₃-(2,6-CH₃)₂ | |
| 8059 | pyridin-2-ylamino-(CH₂)₃ | H | CH | CH | N | NHSO₂C₆H₂-(2,4,6-CH₃)₃ | |
| 8060 | pyridin-2-ylamino-(CH₂)₃ | CH₃ | CH | CH | N | NHSO₂(2-pyridyl) | |
| 8061 | pyridin-2-ylamino-(CH₂)₃ | H | N | CH | CH | NHSO₂(3-pyridyl) | |

TABLE 8-continued

| Ex. No. | R¹ | R⁹ | X¹ | X³ | X⁴ | R¹⁵ | MS |
|---|---|---|---|---|---|---|---|
| 8062 | pyridin-2-ylamino-(CH₂)₃ | CH₃ | CH | CH | N | NHSO₂(4-pyridyl) | |
| 8063 | pyridin-2-ylamino-(CH₂)₃ | H | N | N | CH | NHSO₂(2-thienyl) | |
| 8064 | pyridin-2-ylamino-(CH₂)₃ | CH₃ | CH | CH | N | NHSO₂[4-(3,5-dimethyl)isoxazolyl] | |
| 8065 | pyridin-2-ylamino-(CH₂)₃ | H | CH | CH | N | NHSO₂C₆H₃-(2,6-Cl₂) | |
| 8066 | pyridin-2-ylamino-(CH₂)₃ | CH₃ | CH | CH | N | NHSO₂(2-naphthyl) | |
| 8067 | pyridin-2-ylamino-(CH₂)₃ | H | CH | CH | N | NHSO₂(1-naphthyl) | |
| 8068 | pyridin-2-ylamino-(CH₂)₃ | CH₃ | CH | CH | N | NHSO₂C₆H₄-(4-Ph) | |
| 8069 | pyridin-2-ylamino-(CH₂)₃ | H | CH | CH | N | NHSO₂C₆H₂-(4-Ph-2,6-dimethyl) | |
| 8070 | pyridin-2-ylamino-(CH₂)₃ | H | CH | CH | N | NHSO₂C₆H₂-(4-Ph-2,6-dichloro) | |
| 8071 | pyridin-2-ylamino-(CH₂)₃ | CH₃ | CH | CH | N | NHSO₂C₆H₄-4-(4-pyridyl) | |
| 8072 | pyridin-2-ylamino-(CH₂)₃ | CH₃ | CH | CH | N | NHSO₂C₆H₄-4-(4-pyridyl)-2,6-dimethyl | |
| 8073 | pyridin-2-ylamino-(CH₂)₃ | H | N | CH | CH | NHSO₂C₆H₄-4-(4-pyridyl)-2,6-dichloro | |
| 8074 | pyridin-2-ylamino-(CH₂)₃ | CH₃ | CH | CH | N | NHSO₂C₆H₄-4-(2-oxazolyl) | |
| 8075 | pyridin-2-ylamino-(CH₂)₃ | CH₃ | CH | CH | N | NHSO₂C₆H₄-4-(2-oxazolyl)-2,6-dimethyl | |
| 8076 | pyridin-2-ylamino-(CH₂)₃ | H | CH | CH | N | NHSO₂C₆H₄-4-(2-oxazolyl)-2,6-dichloro | |
| 8076a | pyridin-2-ylamino-(CH₂)₃ | CH₃ | CH | CH | N | NHSO₂C₆H₄-4-(3-pyridyl)-2,6-dimethyl | |
| 8076b | pyridin-2-ylamino-(CH₂)₃ | H | CH | CH | N | NHSO₂C₆H₄-4-(2-furyl)-2,6-dimethyl | |
| 8076c | pyridin-2-ylamino-(CH₂)₃ | H | CH | CH | N | NHSO₂C₆H₄-4-(3-furyl)-2,6-dimethyl | |
| 8076d | pyridin-2-ylamino-(CH₂)₃ | CH₃ | CH | CH | N | NHSO₂C₆H₄-4-(5-pyrazolyl)-2,6-dimethyl | |
| 8077 | pyridin-2-ylamino-(CH₂)₃ | H | CH | CH | N | NHSO₂CH₂Ph | |
| 8078 | pyridin-2-ylamino-(CH₂)₃ | H | N | N | CH | NHSO₂-n-Bu | |
| 8079 | pyridin-2-ylamino-(CH₂)₃ | H | CH | CH | N | NHSO₂NHPh | |
| 8080 | pyridin-2-ylamino-(CH₂)₃ | CH₃ | CH | N | CH | NHSO₂NHC₆H₃-(2,6-Me₂) | |
| 8081 | pyridin-2-ylamino-(CH₂)₃ | H | CH | CH | N | NHSO₂NHC₆H₂-(2,4,6-Me₃) | |
| 8082 | pyridin-2-ylamino-(CH₂)₃ | H | N | CH | CH | NHSO₂NH(2-naphthyl) | |
| 8083 | pyridin-2-ylamino-(CH₂)₃ | CH₃ | CH | CH | N | NHSO₂NH(1-naphthyl) | |
| 8084 | pyridin-2-ylamino-(CH₂)₃ | H | N | N | CH | NHSO₂NHC₆H₄-(4-Ph) | |
| 8085 | pyridin-2-ylamino-(CH₂)₃ | H | CH | CH | N | NHSO₂NHC₆H₂-(4-Ph-2,6-dimethyl) | |
| 8086 | pyridin-2-ylamino-(CH₂)₃ | CH₃ | CH | N | CH | NHSO₂NHC₆H₂-(4-Ph-2,6-dichloro) | |
| 8087 | pyridin-2-ylamino-(CH₂)₃ | H | CH | CH | N | NHSO₂NHCH₂Ph | |
| 8088 | pyridin-2-ylamino-(CH₂)₃ | H | N | CH | CH | NHSO₂NH-n-Bu | |
| 8089 | pyridin-2-ylamino-(CH₂)₃ | H | CH | CH | N | NHSO₂NH-i-Bu | |
| 8090 | pyridin-2-ylamino-(CH₂)₃ | CH₃ | N | N | CH | NHSO₂NH-t-Bu | |
| 8091 | tetrahydropyrimidin-2-ylamino-(CH₂)₃ | H | CH | CH | N | NHCO₂CH₂Ph | |
| 8092 | tetrahydropyrimidin-2-ylamino-(CH₂)₃ | CH₃ | CH | N | CH | NHCO₂n-Bu | |
| 8093 | tetrahydropyrimidin-2-ylamino-(CH₂)₃ | H | CH | CH | N | NHCO₂i-Bu | |
| 8094 | tetrahydropyrimidin-2-ylamino-(CH₂)₃ | CH₃ | N | CH | CH | NHCOPh | |
| 8095 | tetrahydropyrimidin-2-ylamino-(CH₂)₃ | H | CH | CH | N | NHCOCH₂Ph | |
| 8096 | tetrahydropyrimidin-2-ylamino-(CH₂)₃ | CH₃ | N | N | CH | NHCOCH₂CH₂Ph | |
| 8097 | tetrahydropyrimidin-2-ylamino-(CH₂)₃ | CH₃ | CH | CH | N | NHCOCH=CHPh | |
| 8098 | tetrahydropyrimidin-2-ylamino-(CH₂)₃ | H | CH | N | CH | NHCOn-Bu | |
| 8099 | tetrahydropyrimidin-2-ylamino-(CH₂)₃ | CH₃ | CH | CH | N | NHSO₂Ph | |
| 8100 | tetrahydropyrimidin-2-ylamino-(CH₂)₃ | H | N | CH | CH | NHSO₂C₆H₄-(2-CH₃) | |
| 8101 | tetrahydropyrimidin-2-ylamino-(CH₂)₃ | H | CH | CH | N | NHSO₂C₆H₄-(3-CH₃) | |
| 8102 | tetrahydropyrimidin-2-ylamino-(CH₂)₃ | H | N | N | CH | NHSO₂C₆H₄-(4-CH₃) | |
| 8103 | tetrahydropyrimidin-2-ylamino-(CH₂)₃ | CH₃ | CH | CH | N | NHSO₂C₆H₃-(2,6-CH₃)₂ | |
| 8104 | tetrahydropyrimidin-2-ylamino-(CH₂)₃ | H | CH | CH | N | NHSO₂C₆H₂-(2,4,6-CH₃)₃ | |
| 8105 | tetrahydropyrimidin-2-ylamino-(CH₂)₃ | CH₃ | CH | CH | N | NHSO₂(2-pyridyl) | |
| 8106 | tetrahydropyrimidin-2-ylamino-(CH₂)₃ | H | N | CH | CH | NHSO₂(3-pyridyl) | |
| 8107 | tetrahydropyrimidin-2-ylamino-(CH₂)₃ | CH₃ | CH | CH | N | NHSO₂(4-pyridyl) | |
| 8108 | tetrahydropyrimidin-2-ylamino-(CH₂)₃ | H | N | N | CH | NHSO₂(2-thienyl) | |
| 8109 | tetrahydropyrimidin-2-ylamino-(CH₂)₃ | CH₃ | CH | CH | N | NHSO₂[4-(3,5-dimethyl)isoxazolyl] | |

TABLE 8-continued

| Ex. No. | R¹ | R⁹ | X¹ | X³ | X⁴ | R¹⁵ | MS |
|---|---|---|---|---|---|---|---|
| 8110 | tetrahydropyrimidin-2-ylamino-(CH₂)₃ | H | CH | CH | N | NHSO₂C₆H₃-(2,6-Cl₂) | |
| 8111 | tetrahydropyrimidin-2-ylamino-(CH₂)₃ | CH₃ | CH | CH | N | NHSO₂(2-naphthyl) | |
| 8112 | tetrahydropyrimidin-2-ylamino-(CH₂)₃ | H | CH | CH | N | NHSO₂(1-naphthyl) | |
| 8113 | tetrahydropyrimidin-2-ylamino-(CH₂)₃ | CH₃ | CH | CH | N | NHSO₂C₆H₄-(4-Ph) | |
| 8114 | tetrahydropyrimidin-2-ylamino-(CH₂)₃ | H | CH | CH | N | NHSO₂C₆H₂-(4-Ph-2,6-dimethyl) | |
| 8115 | tetrahydropyrimidin-2-ylamino-(CH₂)₃ | H | CH | CH | N | NHSO₂C₆H₂-(4-Ph-2,6-dichloro) | |
| 8116 | tetrahydropyrimidin-2-ylamino-(CH₂)₃ | CH₃ | CH | CH | N | NHSO₂C₆H₄-4-(4-pyridyl) | |
| 8117 | tetrahydropyrimidin-2-ylamino-(CH₂)₃ | CH₃ | CH | CH | N | NHSO₂C₆H₄-4-(4-pyridyl)-2,6-dimethyl | |
| 8118 | tetrahydropyrimidin-2-ylamino-(CH₂)₃ | H | N | CH | CH | NHSO₂C₆H₄-4-(4-pyridyl)-2,6-dichloro | |
| 8119 | tetrahydropyrimidin-2-ylamino-(CH₂)₃ | CH₃ | CH | CH | N | NHSO₂C₆H₄-4-(2-oxazolyl) | |
| 8120 | tetrahydropyrimidin-2-ylamino-(CH₂)₃ | CH₃ | CH | CH | N | NHSO₂C₆H₄-4-(2-oxazolyl)-2,6-dimethyl | |
| 8121 | tetrahydropyrimidin-2-ylamino-(CH₂)₃ | H | CH | CH | N | NHSO₂C₆H₄-4-(2-oxazolyl)-2,6-dichloro | |
| 8121a | tetrahydropyrimidin-2-ylamino-(CH₂)₃ | CH₃ | CH | CH | N | NHSO₂C₆H₄-4-(3-pyridyl)-2,6-dimethyl | |
| 8121b | tetrahydropyrimidin-2-ylamino-(CH₂)₃ | H | CH | CH | N | NHSO₂C₆H₄-4-(2-furyl)-2,6-dimethyl | |
| 8121c | tetrahydropyrimidin-2-ylamino-(CH₂)₃ | H | CH | CH | N | NHSO₂C₆H₄-4-(3-furyl)-2,6-dimethyl | |
| 8121d | tetrahydropyrimidin-2-ylamino-(CH₂)₃ | CH₃ | CH | CH | N | NHSO₂C₆H₄-4-(5-pyrazolyl)-2,6-dimethyl | |
| 8122 | tetrahydropyrimidin-2-ylamino-(CH₂)₃ | H | CH | N | CH | NHSO₂CH₂Ph | |
| 8123 | tetrahydropyrimidin-2-ylamino-(CH₂)₃ | H | CH | CH | N | NHSO₂-n-Bu | |
| 8124 | tetrahydropyrimidin-2-ylamino-(CH₂)₃ | H | N | CH | CH | NHSO₂NHPh | |
| 8125 | tetrahydropyrimidin-2-ylamino-(CH₂)₃ | CH₃ | CH | CH | N | NHSO₂NHC₆H₃-(2,6-Me₂) | |
| 8126 | tetrahydropyrimidin-2-ylamino-(CH₂)₃ | H | N | N | CH | NHSO₂NHC₆H₂-(2,4,6-Me₃) | |
| 8127 | tetrahydropyrimidin-2-ylamino-(CH₂)₃ | H | CH | CH | N | NHSO₂NH(2-naphthyl) | |
| 8128 | tetrahydropyrimidin-2-ylamino-(CH₂)₃ | CH₃ | CH | N | CH | NHSO₂NH(1-naphthyl) | |
| 8129 | tetrahydropyrimidin-2-ylamino-(CH₂)₃ | H | CH | CH | N | NHSO₂NHC₆H₄-(4-Ph) | |
| 8130 | tetrahydropyrimidin-2-ylamino-(CH₂)₃ | H | N | CH | CH | NHSO₂NHC₆H₂-(4-Ph-2,6-dimethyl) | |
| 8131 | tetrahydropyrimidin-2-ylamino-(CH₂)₃ | CH₃ | CH | CH | N | NHSO₂NHC₆H₂-(4-Ph-2,6-dichloro) | |
| 8132 | tetrahydropyrimidin-2-ylamino-(CH₂)₃ | H | N | N | CH | NHSO₂NHCH₂Ph | |
| 8133 | tetrahydropyrimidin-2-ylamino-(CH₂)₃ | H | CH | CH | N | NHSO₂NH-n-Bu | |
| 8134 | tetrahydropyrimidin-2-ylamino-(CH₂)₃ | H | CH | N | CH | NHSO₂NH-i-Bu | |
| 8135 | tetrahydropyrimidin-2-ylamino-(CH₂)₃ | CH₃ | CH | CH | N | NHSO₂NH-t-Bu | |
| 8136 | imidazolin-2-ylamino-(CH₂)₃ | H | N | CH | CH | NHCO₂CH₂Ph | |
| 8137 | imidazolin-2-ylamino-(CH₂)₃ | CH₃ | CH | CH | N | NHCO₂n-Bu | |
| 8138 | imidazolin-2-ylamino-(CH₂)₃ | H | N | N | CH | NHCO₂i-Bu | |
| 8139 | imidazolin-2-ylamino-(CH₂)₃ | CH₃ | CH | CH | N | NHCOPh | |
| 8140 | imidazolin-2-ylamino-(CH₂)₃ | H | CH | N | CH | NHCOCH₂Ph | |
| 8141 | imidazolin-2-ylamino-(CH₂)₃ | CH₃ | CH | CH | N | NHCOCH₂CH₂Ph | |
| 8142 | imidazolin-2-ylamino-(CH₂)₃ | CH₃ | N | CH | CH | NHCOCH=CHPh | |
| 8143 | imidazolin-2-ylamino-(CH₂)₃ | H | CH | CH | N | NHCOn-Bu | |
| 8144 | imidazolin-2-ylamino-(CH₂)₃ | CH₃ | CH | CH | N | NHSO₂Ph | |
| 8145 | imidazolin-2-ylamino-(CH₂)₃ | H | N | CH | CH | NHSO₂C₆H₄-(2-CH₃) | |
| 8146 | imidazolin-2-ylamino-(CH₂)₃ | CH₃ | CH | CH | N | NHSO₂C₆H₄-(3-CH₃) | |
| 8147 | imidazolin-2-ylamino-(CH₂)₃ | H | N | N | CH | NHSO₂C₆H₄-(4-CH₃) | |
| 8148 | imidazolin-2-ylamino-(CH₂)₃ | CH₃ | CH | CH | N | NHSO₂C₆H₃-(2,6-CH₃)₂ | |
| 8149 | imidazolin-2-ylamino-(CH₂)₃ | H | CH | CH | N | NHSO₂C₆H₂-(2,4,6-CH₃)₃ | |
| 8150 | imidazolin-2-ylamino-(CH₂)₃ | CH₃ | CH | CH | N | NHSO₂(2-pyridyl) | |
| 8151 | imidazolin-2-ylamino-(CH₂)₃ | H | N | CH | CH | NHSO₂(3-pyridyl) | |
| 8152 | imidazolin-2-ylamino-(CH₂)₃ | CH₃ | CH | CH | N | NHSO₂(4-pyridyl) | |
| 8153 | imidazolin-2-ylamino-(CH₂)₃ | H | N | N | CH | NHSO₂(2-thienyl) | |
| 8154 | imidazolin-2-ylamino-(CH₂)₃ | CH₃ | CH | CH | N | NHSO₂[4-(3,5-dimethyl)isoxazolyl] | |
| 8155 | imidazolin-2-ylamino-(CH₂)₃ | H | CH | CH | N | NHSO₂C₆H₃-(2,6-Cl₂) | |
| 8156 | imidazolin-2-ylamino-(CH₂)₃ | CH₃ | CH | CH | N | NHSO₂(2-naphthyl) | |
| 8157 | imidazolin-2-ylamino-(CH₂)₃ | H | CH | CH | N | NHSO₂(1-naphthyl) | |
| 8158 | imidazolin-2-ylamino-(CH₂)₃ | CH₃ | CH | CH | N | NHSO₂C₆H₄-(4-Ph) | |

TABLE 8-continued

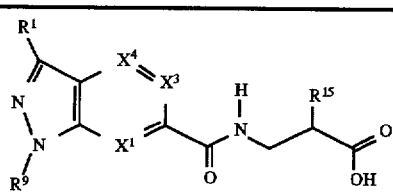

| Ex. No. | R¹ | R⁹ | X¹ | X³ | X⁴ | R¹⁵ | MS |
|---|---|---|---|---|---|---|---|
| 8159 | imidazolin-2-ylamino-(CH₂)₃ | H | CH | CH | N | NHSO₂C₆H₂-(4-Ph-2,6-dimethyl) | |
| 8160 | imidazolin-2-ylamino-(CH₂)₃ | H | CH | CH | N | NHSO₂C₆H₂-(4-Ph-2,6-dichloro) | |
| 8161 | imidazolin-2-ylamino-(CH₂)₃ | CH₃ | CH | CH | N | NHSO₂C₆H₄-4-(4-pyridyl) | |
| 8162 | imidazolin-2-ylamino-(CH₂)₃ | CH₃ | CH | CH | N | NHSO₂C₆H₄-4-(4-pyridyl)-2,6-dimethyl | |
| 8163 | imidazolin-2-ylamino-(CH₂)₃ | H | N | CH | CH | NHSO₂C₆H₄-4-(4-pyridyl)-2,6-dichloro | |
| 8164 | imidazolin-2-ylamino-(CH₂)₃ | CH₃ | CH | CH | N | NHSO₂C₆H₄-4-(2-oxazolyl) | |
| 8165 | imidazolin-2-ylamino-(CH₂)₃ | CH₃ | CH | CH | N | NHSO₂C₆H₄-4-(2-oxazolyl)-2,6-dimethyl | |
| 8166 | imidazolin-2-ylamino-(CH₂)₃ | H | CH | CH | N | NHSO₂C₆H₄-4-(2-oxazolyl)-2,6-dichloro | |
| 8166a | imidazolin-2-ylamino-(CH₂)₃ | CH₃ | CH | CH | N | NHSO₂C₆H₄-4-(3-pyridyl)-2,6-dimethyl | |
| 8166b | imidazolin-2-ylamino-(CH₂)₃ | H | CH | CH | N | NHSO₂C₆H₄-4-(2-furyl)-2,6-dimethyl | |
| 8166c | imidazolin-2-ylamino-(CH₂)₃ | H | CH | CH | N | NHSO₂C₆H₄-4-(3-furyl)-2,6-dimethyl | |
| 8166d | imidazolin-2-ylamino-(CH₂)₃ | CH₃ | CH | CH | N | NHSO₂C₆H₄-4-(5-pyrazolyl)-2,6-dimethyl | |
| 8167 | imidazolin-2-ylamino-(CH₂)₃ | H | CH | CH | N | NHSO₂CH₂Ph | |
| 8168 | imidazolin-2-ylamino-(CH₂)₃ | H | N | N | CH | NHSO₂-n-Bu | |
| 8169 | imidazolin-2-ylamino-(CH₂)₃ | H | CH | CH | N | NHSO₂NHPh | |
| 8170 | imidazolin-2-ylamino-(CH₂)₃ | CH₃ | CH | N | CH | NHSO₂NHC₆H₃-(2,6-Me₂) | |
| 8171 | imidazolin-2-ylamino-(CH₂)₃ | H | CH | CH | N | NHSO₂NHC₆H₂-(2,4,6-Me₃) | |
| 8172 | imidazolin-2-ylamino-(CH₂)₃ | H | N | CH | CH | NHSO₂NH(2-naphthyl) | |
| 8173 | imidazolin-2-ylamino-(CH₂)₃ | CH₃ | CH | CH | N | NHSO₂NH(1-naphthyl) | |
| 8174 | imidazolin-2-ylamino-(CH₂)₃ | H | N | N | CH | NHSO₂NHC₆H₄-(4-Ph) | |
| 8175 | imidazolin-2-ylamino-(CH₂)₃ | H | CH | CH | N | NHSO₂NHC₆H₂-(4-Ph-2,6-dimethyl) | |
| 8176 | imidazolin-2-ylamino-(CH₂)₃ | CH₃ | CH | N | CH | NHSO₂NHC₆H₂-(4-Ph-2,6-dichloro) | |
| 8177 | imidazolin-2-ylamino-(CH₂)₃ | H | CH | CH | N | NHSO₂NHCH₂Ph | |
| 8178 | imidazolin-2-ylamino-(CH₂)₃ | H | N | CH | CH | NHSO₂NH-n-Bu | |
| 8179 | imidazolin-2-ylamino-(CH₂)₃ | H | CH | CH | N | NHSO₂NH-i-Bu | |
| 8180 | imidazolin-2-ylamino-(CH₂)₃ | CH₃ | N | N | CH | NHSO₂NH-t-Bu | |
| 8181 | benzimidazol-2-ylamino-(CH₂)₃ | H | CH | CH | N | NHCO₂CH₂Ph | |
| 8182 | benzimidazol-2-ylamino-(CH₂)₃ | CH₃ | CH | N | CH | NHCO₂n-Bu | |
| 8183 | benzimidazol-2-ylamino-(CH₂)₃ | H | CH | CH | N | NHCO₂i-Bu | |
| 8184 | benzimidazol-2-ylamino-(CH₂)₃ | CH₃ | N | CH | CH | NHCOPh | |
| 8185 | benzimidazol-2-ylamino-(CH₂)₃ | H | CH | CH | N | NHCOCH₂Ph | |
| 8186 | benzimidazol-2-ylamino-(CH₂)₃ | CH₃ | N | N | CH | NHCOCH₂CH₂Ph | |
| 8187 | benzimidazol-2-ylamino-(CH₂)₃ | CH₃ | CH | CH | N | NHCOCH=CHPh | |
| 8188 | benzimidazol-2-ylamino-(CH₂)₃ | H | CH | N | CH | NHCOn-Bu | |
| 8189 | benzimidazol-2-ylamino-(CH₂)₃ | CH₃ | CH | CH | N | NHSO₂Ph | |
| 8190 | benzimidazol-2-ylamino-(CH₂)₃ | H | N | CH | CH | NHSO₂C₆H₄-(2-CH₃) | |
| 8191 | benzimidazol-2-ylamino-(CH₂)₃ | H | CH | CH | N | NHSO₂C₆H₄-(3-CH₃) | |
| 8192 | benzimidazol-2-ylamino-(CH₂)₃ | H | N | N | CH | NHSO₂C₆H₄-(4-CH₃) | |
| 8193 | benzimidazol-2-ylamino-(CH₂)₃ | CH₃ | CH | CH | N | NHSO₂C₆H₃-(2,6-CH₃)₂ | |
| 8194 | benzimidazol-2-ylamino-(CH₂)₃ | H | CH | CH | N | NHSO₂C₆H₂-(2,4,6-CH₃)₃ | |
| 8195 | benzimidazol-2-ylamino-(CH₂)₃ | CH₃ | CH | CH | N | NHSO₂(2-pyridyl) | |
| 8196 | benzimidazol-2-ylamino-(CH₂)₃ | H | N | CH | CH | NHSO₂(3-pyridyl) | |
| 8197 | benzimidazol-2-ylamino-(CH₂)₃ | CH₃ | CH | CH | N | NHSO₂(4-pyridyl) | |
| 8198 | benzimidazol-2-ylamino-(CH₂)₃ | H | N | N | CH | NHSO₂(2-thienyl) | |
| 8199 | benzimidazol-2-ylamino-(CH₂)₃ | CH₃ | CH | CH | N | NHSO₂[4-(3,5-dimethyl)isoxazolyl] | |
| 8200 | benzimidazol-2-ylamino-(CH₂)₃ | H | CH | CH | N | NHSO₂C₆H₃-(2,6-Cl₂) | |
| 8201 | benzimidazol-2-ylamino-(CH₂)₃ | CH₃ | CH | CH | N | NHSO₂(2-naphthyl) | |
| 8202 | benzimidazol-2-ylamino-(CH₂)₃ | H | CH | CH | N | NHSO₂(1-naphthyl) | |
| 8203 | benzimidazol-2-ylamino-(CH₂)₃ | CH₃ | CH | CH | N | NHSO₂C₆H₄-(4-Ph) | |
| 8204 | benzimidazol-2-ylamino-(CH₂)₃ | H | CH | CH | N | NHSO₂C₆H₂-(4-Ph-2,6-dimethyl) | |
| 8205 | benzimidazol-2-ylamino-(CH₂)₃ | H | CH | CH | N | NHSO₂C₆H₂-(4-Ph-2,6-dichloro) | |

TABLE 8-continued

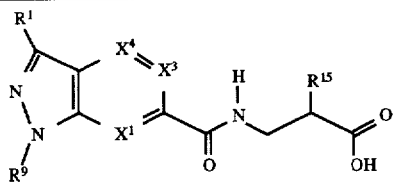

| Ex. No. | R¹ | R⁹ | X¹ | X³ | X⁴ | R¹⁵ | MS |
|---|---|---|---|---|---|---|---|
| 8206 | benzimidazol-2-ylamino-(CH₂)₃ | CH₃ | CH | CH | N | NHSO₂C₆H₄-4-(4-pyridyl) | |
| 8207 | benzimidazol-2-ylamino-(CH₂)₃ | CH₃ | CH | CH | N | NHSO₂C₆H₄-4-(4-pyridyl)-2,6-dimethyl | |
| 8208 | benzimidazol-2-ylamino-(CH₂)₃ | H | N | CH | CH | NHSO₂C₆H₄-4-(4-pyridyl)-2,6-dichloro | |
| 8209 | benzimidazol-2-ylamino-(CH₂)₃ | CH₃ | CH | CH | N | NHSO₂C₆H₄-4-(2-oxazolyl) | |
| 8210 | benzimidazol-2-ylamino-(CH₂)₃ | CH₃ | CH | CH | N | NHSO₂C₆H₄-4-(2-oxazolyl)-2,6-dimethyl | |
| 8211 | benzimidazol-2-ylamino-(CH₂)₃ | H | CH | CH | N | NHSO₂C₆H₄-4-(2-oxazolyl)-2,6-dichloro | |
| 8211a | benzimidazol-2-ylamino-(CH₂)₃ | CH₃ | CH | CH | N | NHSO₂C₆H₄-4-(3-pyridyl)-2,6-dimethyl | |
| 8211b | benzimidazol-2-ylamino-(CH₂)₃ | H | CH | CH | N | NHSO₂C₆H₄-4-(2-furyl)-2,6-dimethyl | |
| 8211c | benzimidazol-2-ylamino-(CH₂)₃ | H | CH | CH | N | NHSO₂C₆H₄-4-(3-furyl)-2,6-dimethyl | |
| 8211d | benzimidazol-2-ylamino-(CH₂)₃ | CH₃ | CH | CH | N | NHSO₂C₆H₄-4-(5-pyrazolyl)-2,6-dimethyl | |
| 8212 | benzimidazol-2-ylamino-(CH₂)₃ | H | CH | N | CH | NHSO₂CH₂Ph | |
| 8213 | benzimidazol-2-ylamino-(CH₂)₃ | H | CH | CH | N | NHSO₂-n-Bu | |
| 8214 | benzimidazol-2-ylamino-(CH₂)₃ | H | N | CH | CH | NHSO₂NHPh | |
| 8215 | benzimidazol-2-ylamino-(CH₂)₃ | CH₃ | CH | CH | N | NHSO₂NHC₆H₃-(2,6-Me₂) | |
| 8216 | benzimidazol-2-ylamino-(CH₂)₃ | H | N | N | CH | NHSO₂NHC₆H₂-(2,4,6-Me₃) | |
| 8217 | benzimidazol-2-ylamino-(CH₂)₃ | H | CH | CH | N | NHSO₂NH(2-naphthyl) | |
| 8218 | benzimidazol-2-ylamino-(CH₂)₃ | CH₃ | CH | N | CH | NHSO₂NH(1-naphthyl) | |
| 8219 | benzimidazol-2-ylamino-(CH₂)₃ | H | CH | CH | N | NHSO₂NHC₆H₄-(4-Ph) | |
| 8220 | benzimidazol-2-ylamino-(CH₂)₃ | H | N | CH | CH | NHSO₂NHC₆H₂-(4-Ph-2,6-dimethyl) | |
| 8221 | benzimidazol-2-ylamino-(CH₂)₃ | CH₃ | CH | CH | N | NHSO₂NHC₆H₂-(4-Ph-2,6-dichloro) | |
| 8222 | benzimidazol-2-ylamino-(CH₂)₃ | H | N | N | CH | NHSO₂NHCH₂Ph | |
| 8223 | benzimidazol-2-ylamino-(CH₂)₃ | H | CH | CH | N | NHSO₂NH-n-Bu | |
| 8224 | benzimidazol-2-ylamino-(CH₂)₃ | H | CH | N | CH | NHSO₂NH-i-Bu | |
| 8225 | benzimidazol-2-ylamino-(CH₂)₃ | CH₃ | CH | CH | N | NHSO₂NH-t-Bu | |
| 8226 | 2-aminopyridin-6-yl-(CH₂)₂ | H | N | CH | CH | NHCO₂CH₂Ph | |
| 8227 | 2-aminopyridin-6-yl-(CH₂)₂ | CH₃ | CH | CH | N | NHCO₂n-Bu | |
| 8228 | 2-aminopyridin-6-yl-(CH₂)₂ | H | N | N | CH | NHCO₂i-Bu | |
| 8229 | 2-aminopyridin-6-yl-(CH₂)₂ | CH₃ | CH | CH | N | NHCOPh | |
| 8230 | 2-aminopyridin-6-yl-(CH₂)₂ | H | CH | N | CH | NHCOCH₂Ph | |
| 8231 | 2-aminopyridin-6-yl-(CH₂)₂ | CH₃ | CH | CH | N | NHCOCH₂CH₂Ph | |
| 8232 | 2-aminopyridin-6-yl-(CH₂)₂ | CH₃ | N | CH | CH | NHCOCH=CHPh | |
| 8233 | 2-aminopyridin-6-yl-(CH₂)₂ | H | CH | CH | N | NHCOn-Bu | |
| 8234 | 2-aminopyridin-6-yl-(CH₂)₂ | CH₃ | CH | CH | N | NHSO₂Ph | |
| 8235 | 2-aminopyridin-6-yl-(CH₂)₂ | H | N | CH | CH | NHSO₂C₆H₄-(2-CH₃) | |
| 8236 | 2-aminopyridin-6-yl-(CH₂)₂ | H | CH | CH | N | NHSO₂C₆H₄-(3-CH₃) | |
| 8237 | 2-aminopyridin-6-yl-(CH₂)₂ | H | N | N | CH | NHSO₂C₆H₄-(4-CH₃) | |
| 8238 | 2-aminopyridin-6-yl-(CH₂)₂ | CH₃ | CH | CH | N | NHSO₂C₆H₃-(2,6-CH₃)₂ | |
| 8239 | 2-aminopyridin-6-yl-(CH₂)₂ | H | CH | CH | N | NHSO₂C₆H₂-(2,4,6-CH₃)₃ | |
| 8240 | 2-aminopyridin-6-yl-(CH₂)₂ | CH₃ | CH | CH | N | NHSO₂(2-pyridyl) | |
| 8241 | 2-aminopyridin-6-yl-(CH₂)₂ | H | N | CH | CH | NHSO₂(3-pyridyl) | |
| 8242 | 2-aminopyridin-6-yl-(CH₂)₂ | CH₃ | CH | CH | N | NHSO₂(4-pyridyl) | |
| 8243 | 2-aminopyridin-6-yl-(CH₂)₂ | H | N | N | CH | NHSO₂(2-thienyl) | |
| 8244 | 2-aminopyridin-6-yl-(CH₂)₂ | CH₃ | CH | CH | N | NHSO₂[4-(3,5-dimethyl)isoxazolyl] | |
| 8245 | 2-aminopyridin-6-yl-(CH₂)₂ | H | CH | CH | N | NHSO₂C₆H₃-(2,6-Cl₂) | |
| 8246 | 2-aminopyridin-6-yl-(CH₂)₂ | CH₃ | CH | CH | N | NHSO₂(2-naphthyl) | |
| 8247 | 2-aminopyridin-6-yl-(CH₂)₂ | H | CH | CH | N | NHSO₂(1-naphthyl) | |
| 8248 | 2-aminopyridin-6-yl-(CH₂)₂ | CH₃ | CH | CH | N | NHSO₂C₆H₄-(4-Ph) | |
| 8249 | 2-aminopyridin-6-yl-(CH₂)₂ | H | CH | CH | N | NHSO₂C₆H₂-(4-Ph-2,6-dimethyl) | |
| 8250 | 2-aminopyridin-6-yl-(CH₂)₂ | H | CH | CH | N | NHSO₂C₆H₂-(4-Ph-2,6-dichloro) | |
| 8251 | 2-aminopyridin-6-yl-(CH₂)₂ | CH₃ | CH | CH | N | NHSO₂C₆H₄-4-(4-pyridyl) | |
| 8252 | 2-aminopyridin-6-yl-(CH₂)₂ | CH₃ | CH | CH | N | NHSO₂C₆H₄-4-(4-pyridyl)-2,6-dimethyl | |
| 8253 | 2-aminopyridin-6-yl-(CH₂)₂ | H | N | CH | CH | NHSO₂C₆H₄-4-(4-pyridyl)- | |

TABLE 8-continued

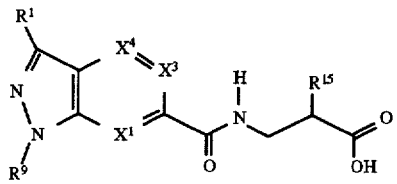

| Ex. No. | R¹ | R⁹ | X¹ | X³ | X⁴ | R¹⁵ | MS |
|---|---|---|---|---|---|---|---|
| 8254 | 2-aminopyridin-6-yl-(CH$_2$)$_2$ | CH$_3$ | CH | CH | N | NHSO$_2$C$_6$H$_4$-4-(2-oxazolyl)-2,6-dichloro | |
| 8255 | 2-aminopyridin-6-yl-(CH$_2$)$_2$ | CH$_3$ | CH | CH | N | NHSO$_2$C$_6$H$_4$-4-(2-oxazolyl)-2,6-dimethyl | |
| 8256 | 2-aminopyridin-6-yl-(CH$_2$)$_2$ | H | CH | CH | N | NHSO$_2$C$_6$H$_4$-4-(2-oxazolyl)-2,6-dichloro | |
| 8256a | 2-aminopyridin-6-yl-(CH$_2$)$_2$ | CH$_3$ | CH | CH | N | NHSO$_2$C$_6$H$_4$-4-(3-pyridyl)-2,6-dimethyl | |
| 8256b | 2-aminopyridin-6-yl-(CH$_2$)$_2$ | H | CH | CH | N | NHSO$_2$C$_6$H$_4$-4-(2-furyl)-2,6-dimethyl | |
| 8256c | 2-aminopyridin-6-yl-(CH$_2$)$_2$ | H | CH | CH | N | NHSO$_2$C$_6$H$_4$-4-(3-furyl)-2,6-dimethyl | |
| 8256d | 2-aminopyridin-6-yl-(CH$_2$)$_2$ | CH$_3$ | CH | CH | N | NHSO$_2$C$_6$H$_4$-4-(5-pyrazolyl)-2,6-dimethyl | |
| 8257 | 2-aminopyridin-6-yl-(CH$_2$)$_2$ | H | CH | CH | N | NHSO$_2$CH$_2$Ph | |
| 8258 | 2-aminopyridin-6-yl-(CH$_2$)$_2$ | H | N | N | CH | NHSO$_2$-n-Bu | |
| 8259 | 2-aminopyridin-6-yl-(CH$_2$)$_2$ | H | CH | CH | N | NHSO$_2$NHPh | |
| 8260 | 2-aminopyridin-6-yl-(CH$_2$)$_2$ | CH$_3$ | CH | N | CH | NHSO$_2$NHC$_6$H$_3$-(2,6-Me$_2$) | |
| 8261 | 2-aminopyridin-6-yl-(CH$_2$)$_2$ | H | CH | CH | N | NHSO$_2$NHC$_6$H$_2$-(2,4,6-Me$_3$) | |
| 8262 | 2-aminopyridin-6-yl-(CH$_2$)$_2$ | H | N | CH | CH | NHSO$_2$NH(2-naphthyl) | |
| 8263 | 2-aminopyridin-6-yl-(CH$_2$)$_2$ | CH$_3$ | CH | CH | N | NHSO$_2$NH(1-naphthyl) | |
| 8264 | 2-aminopyridin-6-yl-(CH$_2$)$_2$ | H | N | N | CH | NHSO$_2$NHC$_6$H$_4$-(4-Ph) | |
| 8265 | 2-aminopyridin-6-yl-(CH$_2$)$_2$ | H | CH | CH | N | NHSO$_2$NHC$_6$H$_2$-(4-Ph-2,6-dimethyl) | |
| 8266 | 2-aminopyridin-6-yl-(CH$_2$)$_2$ | CH$_3$ | CH | N | CH | NHSO$_2$NHC$_6$H$_2$-(4-Ph-2,6-dichloro) | |
| 8267 | 2-aminopyridin-6-yl-(CH$_2$)$_2$ | H | CH | CH | N | NHSO$_2$NHCH$_2$Ph | |
| 8268 | 2-aminopyridin-6-yl-(CH$_2$)$_2$ | H | N | CH | CH | NHSO$_2$NH-n-Bu | |
| 8269 | 2-aminopyridin-6-yl-(CH$_2$)$_2$ | H | CH | CH | N | NHSO$_2$NH-i-Bu | |
| 8270 | 2-aminopyridin-6-yl-(CH$_2$)$_2$ | CH$_3$ | N | N | CH | NHSO$_2$NH-t-Bu | |
| 8271 | imidazol-2-ylamino-CH$_2$(o-C$_6$H$_4$) | H | CH | CH | N | NHSO$_2$-(1-naphthyl) | |
| 8272 | imidazol-2-ylamino-CH$_2$(o-C$_6$H$_4$) | H | CH | CH | N | NHCO$_2$CH$_2$Ph | |
| 8273 | imidazol-2-ylamino-CH$_2$(o-C$_6$H$_4$) | H | CH | CH | N | NHSO$_2$C$_6$C$_2$-(2,4,6-Me$_3$) | |
| 8274 | pyridin-2-ylamino-CH$_2$(o-C$_6$H$_4$) | H | CH | CH | N | NHSO$_2$-(1-naphthyl) | |
| 8275 | pyridin-2-ylamino-CH$_2$(o-C$_6$H$_4$) | H | CH | CH | N | NHCO$_2$CH$_2$Ph | |
| 8276 | pyridin-2-ylamino-CH$_2$(o-C$_6$H$_4$) | H | CH | CH | N | NHSO$_2$C$_6$H$_2$-(2,4,6-Me$_3$) | |
| 8277 | imidazolin-2-ylamino-CH$_2$(o-C$_6$H$_4$) | H | CH | CH | N | NHSO$_2$-(1-naphthyl) | |
| 8278 | imidazolin-2-ylamino-CH$_2$(o-C$_6$H$_4$) | H | CH | CH | N | NHCO$_2$CH$_2$Ph | |
| 8279 | imidazolin-2-ylamino-CH$_2$(o-C$_6$H$_4$) | H | CH | CH | N | NHSO$_2$C$_6$C$_2$-(2,4,6-Me$_3$) | |
| 8280 | imidazolin-2-ylamino-(m-C$_6$H$_4$) | H | CH | CH | N | NHSO$_2$-(1-naphthyl) | |
| 8281 | imidazolin-2-ylamino-(m-C$_6$H$_4$) | H | CH | CH | N | NHCO$_2$CH$_2$Ph | |
| 8282 | imidazolin-2-ylamino-(m-C$_6$H$_4$) | H | CH | CH | N | NHSO$_2$C$_6$C$_2$-(2,4,6-Me$_3$) | |

What is claimed is:

1. A compound of Formula Ia:

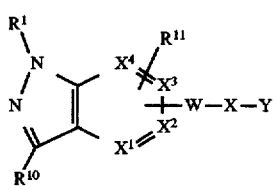

and pharmaceutically acceptable salt forms thereof, wherein:

X¹, X², X³, and X⁴ are independently selected from nitrogen or carbon provided that at least two of X¹, X², X³ and X⁴ are carbon;

R¹ is selected from:

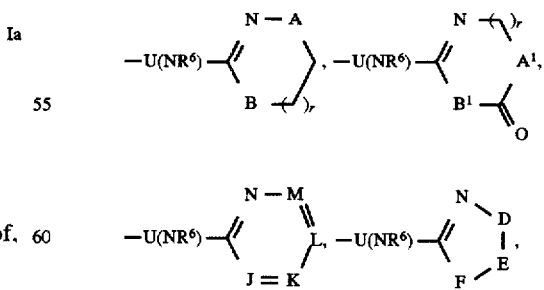

-continued

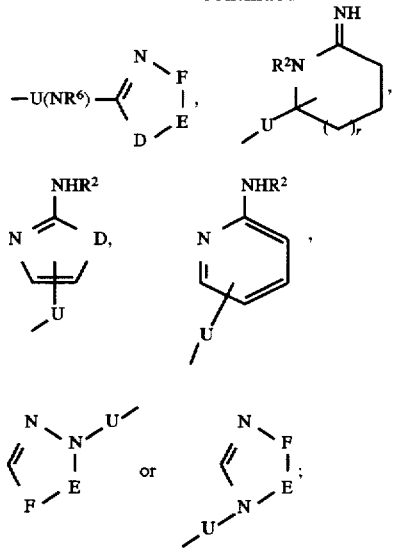

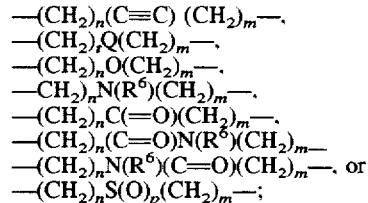

A and B are independently —CH$_2$—, —O—, —N(R$^2$)—, or —C(=O)—;

A$^1$ and B$^1$ are independently —CH$_2$— or —N(R$^3$)—;

D is —N(R$^2$)—, —O—, —S—, —C(=O)— or —SO$_2$—;

E—F is —C(R$^4$)=C(R$^5$)—, —N=C(R$^4$)—, —C(R$^4$)=N—, or —C(R$^4$)$_2$C(R$^5$)$_2$—;

J, K, L and M are independently selected from —C(R$^4$)—, —C(R$^5$)— or —N—, provided that at least one of J, K, L and M is not —N—;

R$^2$ is selected from: H, C$_1$-C$_6$ alkyl, (C$_1$-C$_6$ alkyl) carbonyl, (C$_1$-C$_6$ alkoxy)carbonyl; (C$_1$-C$_6$ alkyl) aminocarbonyl, C$_3$-C$_6$ alkenyl, C$_3$-C$_7$ cycloalkyl, C$_4$-C$_{11}$ cycloalkylalkyl, aryl, heteroaryl(C$_1$-C$_6$ alkyl) carbonyl, heteroarylcarbonyl, aryl(C$_1$-C$_6$ alkyl)-, (C$_1$-C$_6$ alkyl)darbonyl-, arylcarbonyl, C$_1$-C$_6$ alkylsulfonyl, arylsulfonyl, aryl(C$_1$-C$_6$ alkyl)sulfonyl, heteroarylsulfonyl, heteroaryl(C$_1$-C$_6$ alkyl)sulfonyl, aryloxycarbonyl, or aryl(C$_1$-C$_6$ alkoxy)carbonyl, wherein said aryl groups are substituted with 0-2 substituents selected from the group consisting of C$_1$-C$_4$ alkyl, C$_1$-C$_4$ alkoxy, halo, CF$_3$, and nitro;

R$^3$ is selected from: H, C$_1$-C$_6$ alkyl, C$_3$-C$_7$ cycloalkyl, C$_4$-C$_{11}$ cycloalkylalkyl, aryl, aryl(C$_1$-C$_6$ alkyl)-, or heteroaryl(C$_1$-C$_6$ alkyl)-;

R$^4$ and R$^5$ are independently selected from: H, C$_1$-C$_4$ alkoxy, NR$^2$R$^3$, halogen, NO$_2$, CN, CF$_3$, C$_1$-C$_6$ alkyl, C$_3$-C$_6$ alkenyl, C$_3$-C$_7$ cycloalkyl, C$_4$-C$_{11}$ cycloalkylalkyl, aryl, aryl (C$_1$-C$_6$ alkyl)-, (C$_1$-C$_6$ alkyl)carbonyl, (C$_1$-C$_6$ alkoxy)carbonyl, arylcarbonyl, or alternatively, when substituents on adjacent atoms, R$^4$ and R$^5$ can be taken together with the carbon atoms to which they are attached to form a 5-7 membered carbocyclic or 5-7 membered heterocyclic aromatic or non-aromatic ring system, said carbocyclic or heterocyclic ring being optionally substituted with 0-2 groups selected from: C$_1$-C$_4$ alkyl, C$_1$-C$_4$ alkoxy, halo, cyano, amino, CF$_3$, or NO$_2$;

U is selected from:
—(CH$_2$)$_n$—,
—(CH$_2$)$_n$(CR$^7$=CR$^8$) (CH$_2$)$_m$—,
—(CH$_2$)$_n$(C≡C) (CH$_2$)$_m$—,
—(CH$_2$)$_n$Q(CH$_2$)$_m$—,
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—,
—(CH$_2$)$_n$(C=O)N(R$^6$)(CH$_2$)$_m$—
—(CH$_2$)$_n$N(R$^6$)(C=O)(CH$_2$)$_m$—, or
—(CH$_2$)$_n$S(O)$_p$(CH$_2$)$_m$—;

wherein one or more of the methylene groups in U is optionally substituted with R$^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

R$^6$ is selected from: H, C$_1$-C$_4$ alkyl, or benzyl;

R$^7$ and R$^8$ are independently selected from: H, C$_1$-C$_6$ alkyl, C$_3$-C$_7$ cycloalkyl, C$_4$-C$_{11}$ cycloalkylalkyl, aryl, aryl(C$_1$-C$_6$ alkyl)-, or heteroaryl(C$_0$-C$_6$ alkyl)-;

R$^{10}$ is selected from: H, C$_1$-C$_4$ alkoxy substituted with 0-1 R$^{21}$, N(R$^6$)$_2$, halogen, NO$_2$, CN, CF$_3$, CO$_2$R$^{17}$, C(=O)R$^{17}$, CONR$^{17}$R$^{20}$, —SO$_2$R$^{17}$, —SO$_2$NR$^{17}$R$^{20}$, C$_1$-C$_6$ alkyl substituted with 0-1 R$^{15}$ or 0-1 R$^{21}$, C$_3$-C$_6$ alkenyl substituted with 0-1 R$^{15}$ or 0-1 R$^{21}$, C$_3$-C$_7$ cycloalkyl substituted with 0-1 R$^{15}$ or 0-1 R$^{21}$, C$_1$-C$_{11}$ cycloalkylalkyl substituted with 0-1 R$^{15}$ or 0-1 R$^{21}$, aryl substituted with 0-1 R$^{15}$ or 0-2 R$^{11}$ or 0-1 R$^{21}$, or aryl(C$_1$-C$_6$ alkyl)- substituted with 0-1 R$^{15}$ or 0-2 R$^{11}$ or 0-1 R$^{21}$;

R$^{11}$ is selected from H, halogen, CF$_3$, CN, NO$_2$, hydroxy, NR$^2$R$^3$, C$_1$-C$_4$ alkyl substituted with 0-1 R$^{21}$, C$_1$-C$_4$ alkoxy substituted with 0-1 R$^{21}$, aryl substituted with 0-1 R$^{21}$, aryl(C$_1$-C$_6$ alkyl)- substituted with 0-1 R$^{21}$, (C$_1$-C$_4$ alkoxy)carbonyl substituted with 0-1 R$^{21}$, (C$_1$-C$_4$ alkyl)carbonyl substituted with 0-1 R$^{21}$, C$_1$-C$_4$ alkylsulfonyl substituted with 0-1 R$^{21}$, or C$_1$-C$_4$ alkylaminosulfonyl substituted with 0-1 R$^{21}$;

W is selected from:
—(C(R$^{12}$)$_2$)$_q$C(=O)N(R$^{13}$)—, or
C(=O)—N(R$^{13}$)—(C(R$^{12}$)$_2$)$_q$—;

X is —C(R$^{12}$)(R$^{14}$)—C(R$^{12}$)(R$^{15}$)—; or alternatively, W and X can be taken together to be

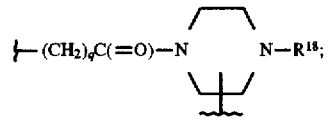

R$^{12}$ is selected from H, halogen, C$_1$-C$_6$ alkyl, C$_2$-C$_6$ alkenyl, C$_2$-C$_6$ alkynyl, C$_3$-C$_7$ cycloalkyl, C$_4$-C$_{10}$ cycloalkylalkyl, (C$_1$-C$_4$ alkyl)carbonyl, aryl, or aryl (C$_1$-C$_6$ alkyl)-;

R$^{13}$ is selected from H, C$_1$-C$_6$ alkyl, C$_3$-C$_7$ cycloalkylmethyl, or aryl(C$_1$-C$_6$ alkyl)-;

R$^{14}$ is selected from:

H, C$_1$-C$_6$ alkylthio(C$_1$-C$_6$ alkyl)-, aryl(C$_1$-C$_{10}$ alkylthioalkyl)-, aryl(C$_1$-C$_{10}$ alkoxyalkyl)-, C$_1$-C$_{10}$ alkyl, C$_1$-C$_{10}$ alkoxyalkyl, C$_1$-C$_6$ hydroxyalkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl(C$_1$-C$_6$ alkyl)-, heteroaryl(C$_1$-C$_6$ alkyl)-, aryl, heteroaryl, CO$_2$R$^{17}$, C(=O)R$^{17}$, or CONR$^{17}$R$^{20}$, provided that any of the above alkyl, cycloalkyl, aryl or heteroaryl groups may be unsubstituted or substituted independently with 0-1 R$^{16}$ or 0-2 R$^{11}$;

R$^{15}$ is selected from:

H, R$^{16}$, C$_1$-C$_{10}$ alkyl, C$_1$-C$_{10}$ alkoxyalkyl, C$_1$-C$_{10}$ alkylaminoalkyl, C$_1$-C$_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:
—$COR^{19}$, —$SO_3H$, —$PO_3H$, tetrazolyl, —$CONHNHSO_2CF_3$, —$CONHSO_2R^{17}$, —$CONHSO_2NHR^{17}$, —$NHCOCF_3$, —$NHCONHSO_2R^{17}$, —$NHSO_2R^{17}$, —$OP)_3H_2$, —$OSO_3H$, —$PO_3H_2$, —$SO_3H$, —$SO_2NHCOR^{17}$, —$SO_2NHCO_2R^{17}$,

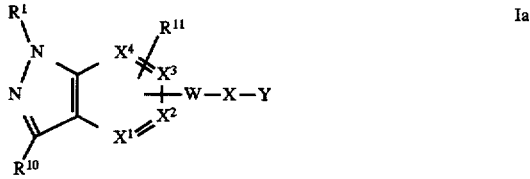

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R$—$R^{17}$, or
—$N(R^{20})SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:
H,
—$C(=O)$—$O$—$R^{17}$,
—$C(=O)$—$R^{17}$,
—$C(=O)$—$NH$—$R^{17}$,
—$SO_2$—$R^{17}$, or
—$SO_2$—$NR^{20}R^{17}$;

$R^{19}$ is selected from: hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$
alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or ($R^{11}$)($R^{12}$)N—($C_1$–$C_{10}$ alkoxy)-;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl ($C_1$–$C_6$ alkyl)-;

$R^{21}$ is selected from: COOH or $NR^6_2$;
m is 0–4;
n is 0–4;
t is 0–4;
p is 0–2;
q is 0–2; and
r is 0–2;

with the following provisos:
(1) t, n, m and q are chosen such that the number of atoms connecting $R^1$ and Y is in the range of 10–14; and
(2) n and m are chosen such that the value of n plus m is greater than one unless U is —($CH_2$)$_t$Q($CH_2$)$_m$—.

2. A compound of claim 1 of the Formula Ia:

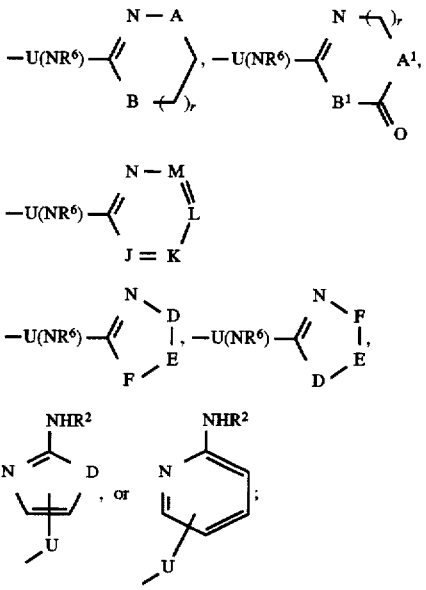

and pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

A and B are independently —$CH_2$—, —O—, —$N(R^2)$—, or —$C(=O)$—;

$A^1$ and $B^1$ are independently —$CH_2$— or —$N(R^3)$—;

D is —$N(R^2)$—, —O—, —S—, —$C(=)$— or —$SO_2$—;

E—F is —$C(R^4)=C(R^5)$—, —$N=C(R^4)$—, —$C(R^4)=N$—, or —$C(R^4)_2C(R^5)_2$—;

J, K, L and M are independently selected from —$C(R^4)$—, —$C(R^5)$— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$-$C_6$ alkyl)sulfonyl, aryloxycarbonyl, or aryl($C_1$-$C_6$ alkoxy)carbonyl, wherein said aryl groups are substituted with 0–2 substituents selected from the group consisting of $C_1$-$C_4$ alkyl, $C_1$-$C_4$ alkoxy, halo, $CF_3$, and nitro;

$R^3$ is selected from: H, $C_1$-$C_6$ alkyl, $C_3$-$C_7$ cycloalkyl, $C_4$-$C_{11}$ cycloalkylalkyl, aryl, aryl ($C_1$-$C_6$ alkyl)-, or heteroaryl($C_1$-$C_6$ alkyl)-;

$R^4$ and $R^5$ are independently selected from: H, $C_1$-$C_4$ alkoxy, $NR^2R^3$, halogen, $NO_2$, CN, $CF_3$, $C_1$-$C_6$ alkyl, $C_3$-$C_6$ alkenyl, $C_3$-$C_7$ cycloalkyl, $C_4$-$C_{11}$ cycloalkylalkyl, aryl, aryl($C_1$-$C_6$ alkyl)-, $C_2$-$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$-$C_4$ alkyl, $C_1$-$C_4$ alkoxy, halo, cyano, amino, $CF_3$, or $NO_2$;

U is selected from:
—$(CH_2)_n$—,
—$(CH_2)_n(CR^7$=$CR^8)(CH_2)_m$—,
—$(CH_2)_nQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—, or
—$(CH_2)_nS(O)_p(CH_2)_m$—;

wherein one or more of the methylene groups in U is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$-$C_4$ alkyl, or benzyl;

$R^7$ and $R^8$ are independently selected from: H, $C_1$-$C_6$ alkyl, $C_3$-$C_7$ cycloalkyl, $C_1$-$C_{11}$ cycloalkylalkyl, aryl, aryl($C_1$-$C_6$ alkyl)-, or heteroaryl($C_0$-$C_6$ alkyl)-;

$R^{10}$ is selected from: H, $C_1$-$C_4$ alkoxy substituted with 0–1 $R^{21}$, $N(R^6)_2$, halogen, $NO_2$, CN, $CF_3$, $CO_2R^{17}$, $C(=O)R^{17}$, $CONR^{17}R^{20}$, —$SO_2R^{17}$, —$SO_2NR^{17}R^{20}$, $C_1$-$C_6$ alkyl substituted with 0–1 $R^{15}$ or 0–1 $R^{21}$, $C_3$-$C_6$ alkenyl substituted with 0–1 $R^{15}$ or 0–1 $R^{21}$, $C_3$-$C_7$ cycloalkyl substituted with 0–1 $R^{15}$ or 0–1 $R^{21}$, $C_4$-$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$-$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$-$C_4$ alkyl substituted with 0–1 $R^{21}$, $C_1$-$C_4$ alkoxy substituted with 0–1 $R^{21}$, aryl substituted with 0–1 $R^{21}$, aryl($C_1$-$C_6$ alkyl)- substituted with 0–1 $R^{21}$, ($C_1$-$C_4$ alkoxy)carbonyl substituted with 0–1 $R^{21}$, ($C_1$-$C_4$ alkyl)carbonyl substituted with 0–1 $R^{21}$, $C_1$-$C_4$ alkylsulfonyl substituted with 0–1 $R^{21}$, or $C_1$-$C_4$ alkylaminosulfonyl substituted with 0–1 $R^{21}$;

W is —$C(=O)$—$N(R^{13})$—$(C(R^{12})_2)_2)_q$—;

X is —$C(R^{12})(R^{14})$—$C(R^{12})(R^{15})$—;

alternatively, W and X can be taken together to be

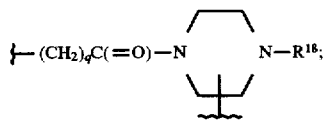

$R^{12}$ is H or $C_1$-$C_6$ alkyl;

$R^{13}$ is selected from: H, $C_1$-$C_6$ alkyl, $C_3$-$C_7$ cycloalkylmethyl, or aryl($C_1$-$C_6$ alkyl)-;

$R^{14}$ is selected from:
H, $C_1$-$C_6$ alkylthioalkyl, aryl($C_1$-$C_{10}$ alkylthioalkyl)-, aryl($C_1$-$C_{10}$ alkoxyalkyl)-, $C_1$-$C_{10}$ alkyl, $C_1$-$C_{10}$ alkoxyalkyl, $C_1$-$C_6$ hydroxyalkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl($C_1$-$C_6$ alkyl)-, heteroaryl ($C_1$-$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be substituted independently with 0–1 $R^{16}$ or 0–2 $R^{11}$;

$R^{15}$ is selected from:
H, $R^{16}$, $C_1$-$C_{10}$ alkyl, $C_1$-$C_{10}$ alkoxyalkyl, $C_1$-$C_{10}$ alkylaminoalkyl, $C_1$-$C_{10}$ dialkylaminoalkyl, $C_1$-$C_{10}$ alkylcarbonyl, aryl($C_0$-$C_6$ alkyl)carbonyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl($C_1$-$C_6$ alkyl)-, heteroaryl ($C_1$-$C_6$ alkyl)-, aryl, heteroaryl, $CO_2R^{17}$, $C(=O)R^{17}$, $CONR^{17}R^{20}$, $SO_2R^{17}$ or $SO_2NR^{17}R^{20}$, provided that any of the above alkyl, cycloalkyl, aryl or heteroaryl groups may be substituted independently with 0–2 $R^{11}$;

Y is selected from:

—$COR^{19}$, —$SO_3H$,

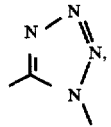

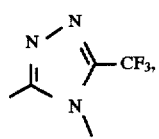

or

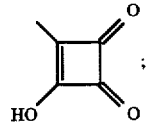

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from:
$C_1$-$C_{10}$ alkyl, $C_3$-$C_{11}$ cycloalkyl, aryl($C_1$-$C_6$ alkyl)-, ($C_1$-$C_6$ alkyl)aryl, heteroaryl($C_1$-$C_6$ alkyl)-, ($C_1$-$C_6$ alkyl)heteroaryl, biaryl($C_1$-$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:

H,
—C(=O)—O—$R^{17}$,
—C(=O)—$R^{17}$,
—C(=O)—NH—$R^{17}$,
—$SO_2$—$R^{17}$, or
—$SO_2$—$NR^{20}R^{17}$;

$R^{19}$ is selected from: hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N$—$(C_0$–$C_{10}$ alkoxy)-;

$R^{20}$ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

$R^{21}$ is selected from COOH or $NR^6_2$;

m is 0–4;

n is 0–4;

p is 0–2;

q is 0–2;

t is 0–4; and r is 0–2.

3. A compound of claim 1 of the Formula IIa or IIb:

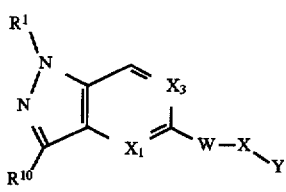

IIa or

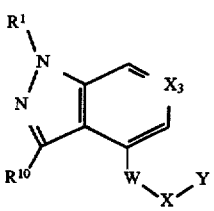

IIb and pharmaceutically acceptable salt forms thereof wherein:

$X_1$ and $X_3$ are independently selected from nitrogen or carbon;

$R^1$ is selected from:

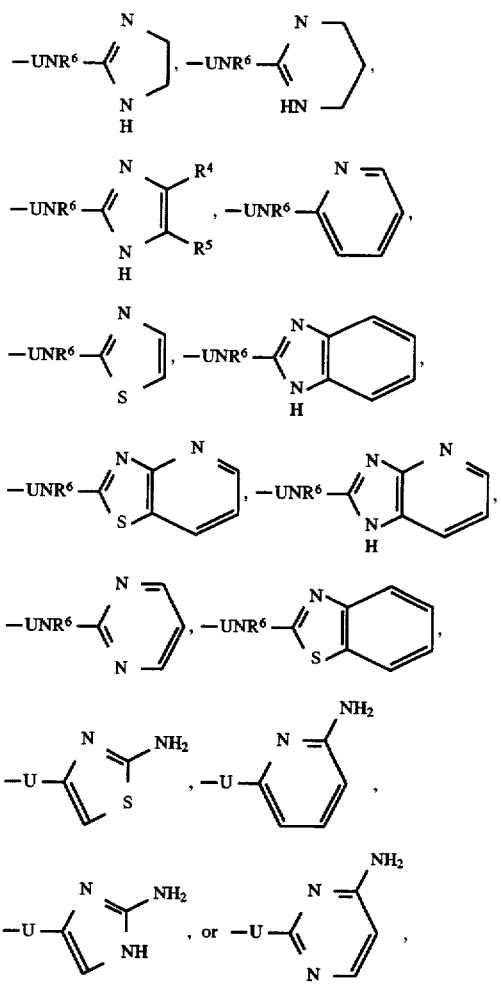

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_r Q(CH_2)_m$— or —C(=O) $(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, $C_1$–$C_4$ alkoxy substituted with 0–1 $R^{21}$, halogen, $CO_2R^{17}$, $CONR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl ($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —C(=O)—N($R^{13}$)—;

X is —CH($R^{14}$)—CH($R^{15}$)—;

$R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:

—NH($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—N($R^{20}$)$R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:

hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6_2$;

m is 0 or 1;

n is 1–4; and t is 0 or 1.

4. A compound of claim 1 of the Formula IIa or IIb:

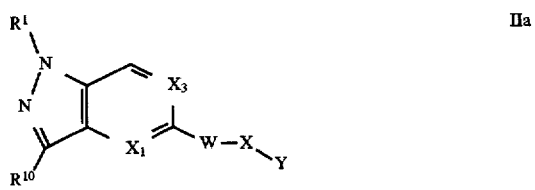

IIa or

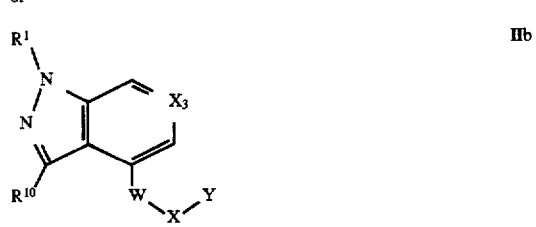

IIb and pharmaceutically acceptable salt forms thereof wherein:

$X_1$ and $X_3$ are independently selected from nitrogen or carbon, provided that at least one of $X_1$ and $X_3$ is carbon;

$R^1$ is selected from:

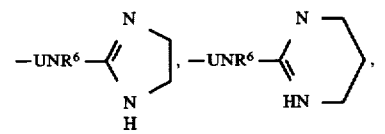

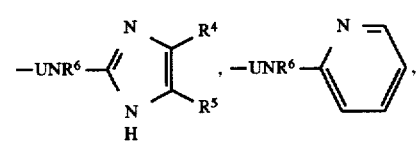

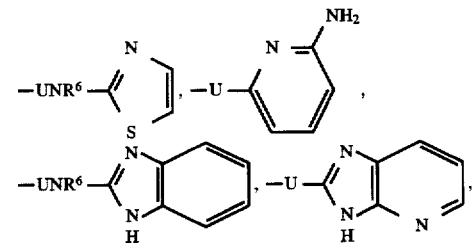

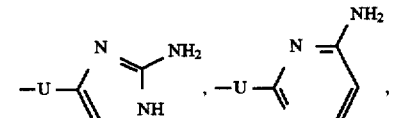

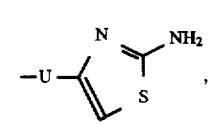

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is —$(CH_2)_n$—, —$(CH_2)_t Q(CH_2)_m$— or —C(=O)$(CH_2)_{n-1}$, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^{10}$ is selected from: H, $C_1$–$C_4$ alkoxy substituted with 0–1 $R^{21}$, halogen, $CO_2R^{17}$, $CONR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, or aryl ($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$ aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from:

H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—N($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or 1-(2-(2-methoxypropyl)carbonyloxy)ethoxy-;

$R^{20}$ is H or $CH_3$;

$R^{21}$ is selected from COOH or $NR^6{}_2$;

m is 0 or 1;

n is 1–4; and t is 0 or 1.

5. A compound of claim 1 of Formula Ia and enantiomeric or diasteriomeric forms thereof, and mixtures of enantiomeric or diasteriomeric forms thereof, and pharmaceutically acceptable salt forms thereof, selected from the group consisting of:

3-[1-[3-(imidazolin-2-ylamino)propyl]indazol-5-ylcarbonylamino]-2-(benzyloxycarbonylamino)propionic acid, 3-[1-[3-(imidazolin-2-ylamino)propyl]indazol-5-ylcarbonylamino]-2-(2,4,6-trimethylbenzenesulfonylamino)propionic acid, 3-[1-[3-(imidazolin-2-ylamino)propyl]indazol-5-ylcarbonylamino]-2-(benzenesulfonylamino)propionic acid, 3-[1-[3-(imidazolin-2-ylamino)propyl]indazol-5-ylcarbonylamino]-2-(2,6-dichlorobenzenesulfonylamino)propionic acid, 3-[1-[3-(imidazolin-2-ylamino)propyl]indazol-5-ylcarbonylamino]-2-(3,5-dimethylisoxazol-4-ylsulfonylamino)propionic acid, 3-[1-[3-(imidazolin-2-ylamino)propyl]indazol-5-ylcarbonylamino]-2-(2,6-dimethylbenzenesulfonylamino)propionic acid, 3-[1-[3-(imidazolin-2-ylamino)propyl]indazol-5-ylcarbonylamino]-2-(2,6-dimethyl-4-phenylbenzenesulfonylamino)propionic acid, 3-[1-[3-(imidazolin-2-ylamino)propyl]indazol-5-ylcarbonylamino]-2-(4-phenylbenzenesulfonylamino) propionic acid, 3-[1-[3-(tetrahydropyrimid-2-ylamino)propyl]indazol-5-ylcarbonylamino]-2-(benzyloxycarbonylamino)propionic acid, 3-[1-[3-(tetrahydropyrimid-2-ylamino)propyl]indazol-5-ylcarbonylamino]-2-(2,4,6-trimethylbenzenesulfonylamino)propionic acid, 3-[1-[3-(tetrahydropyrimid-2-ylamino)propyl]indazol-5-ylcarbonylamino]-2-(benzenesulfonylamino)propionic acid, 3-[1-[3-(tetrahydropyrimid-2-ylamino)propyl]indazol-5-ylcarbonylamino]-2-(2,6-dichlorobenzenesulfonylamino) propionic acid, 3-[1-[3-(tetrahydropyrimid-2-ylamino)propyl]indazol-5-ylcarbonylamino]-2-(3,5-dimethylisoxazol-4-ylsulfonylamino)propionic acid, 3-[1-[3-(tetrahydropyrimid-2-ylamino)propyl]indazol-5-ylcarbonylamino]-2-(2,6-dimethylbenzenesulfonylamino)propionic acid, 3-[1-[3-(tetrahydropyrimid-2-ylamino)propyl]indazol-5-ylcarbonylamino]-2-(2,6-dimethyl-4-phenylbenzenesulfonylamino)propionic acid, 3-[1-[3-(tetrahydropyrimid-2-ylamino)propyl]indazol-5-ylcarbonylamino]-2-(4-phenylbenzenesulfonylamino) propionic acid, 3-[1-[3-(imidazol-2-ylamino)propyl]indazol-5-ylcarbonylamino]-2-(benzyloxycarbonylamino)propionic acid, 3-[1-[3-(imidazol-2-ylamino)propyl]indazol-5-ylcarbonylamino]-2-(2,4,6-trimethylbenzenesulfonylamino)propionic acid, 3-[1-[3-(imidazol-2-ylamino)propyl]indazol-5-ylcarbonylamino]-2-(benzenesulfonylamino)propionic acid, 3-[1-[3-(imidazol-2-ylamino)propyl]indazol-5-ylcarbonylamino]-2-(2,6-dichlorobenzenesulfonylamino)propionic acid, 3-[1-[3-(imidazol-2-ylamino)propyl]indazol-5-ylcarbonylamino]-2-(3,5-dimethylisoxazol-4-ylsulfonylamino)propionic acid, 3-[1-[3-(imidazol-2-ylamino)propyl]indazol-5-ylcarbonylamino]-2-(2,6-dimethylbenzenesulfonylamino)propionic acid, 3-[1-[3-(imidazol-2-ylamino)propyl]indazol-5-ylcarbonylamino]-2-(2,6-dimethyl-4-phenylbenzenesulfonylamino)propionic acid, 3-[1-[3-(imidazol-2-ylamino)propyl]indazol-5-ylcarbonylamino]-2-(4-phenylbenzenesulfonylamino)propionic acid, 3-[1-[3-(pyridin-2-ylamino)propyl]indazol-5-ylcarbonylamino]-2-(benzyloxycarbonylamino)propionic acid, 3-[1-[3-(pyridin-2-ylamino)propyl]indazol-5-ylcarbonylamino]-2-(2,4,6-trimethylbenzenesulfonylamino)propionic acid, 3-[1-[3-(pyridin-2-ylamino)propyl]indazol-5-ylcarbonylamino]-2-(benzenesulfonylamino)propionic acid, 3-[1-[3-(pyridin-2-ylamino)propyl]indazol-5-ylcarbonylamino]-2-(2,6-dichlorobenzenesulfonylamino)propionic acid, 3-[1-[3-(pyridin-2-ylamino)propyl]indazol-5-ylcarbonylamino]-2-(3,5-dimethylisoxazol-4-ylsulfonylamino)propionic acid, 3-[1-[3-(pyridin-2-ylamino)propyl]indazol-5-ylcarbonylamino]-2-(2,6-dimethylbenzenesulfonylamino)propionic acid, 3-[1-[3-(pyridin-2-ylamino)propyl]indazol-5-ylcarbonylamino]-2-(2,6-dimethyl-4-phenylbenzenesulfonylamino)propionic acid, 3-[1-[3-(pyridin-2-ylamino)propyl]indazol-5-ylcarbonylamino]-2-(4-phenylbenzenesulfonylamino)propionic acid, 3-[1-[3-(imidazolin-2-ylamino)propyl]indazol-4-ylcarbonylamino]-2-(benzyloxycarbonylamino)propionic acid, 3-[1-[3-(imidazolin-2-ylamino)propyl]indazol-4-ylcarbonylamino]-2-(2,4,6-trimethylbenzenesulfonylamino)propionic acid, 3-[1-[3-(imidazolin-2-ylamino)propyl]indazol-4-ylcarbonylamino]-2-(benzenesulfonylamino)propionic acid, 3-[1-[3-(imidazolin-2-ylamino)propyl]indazol-4-ylcarbonylamino]-2-(2,6-dichlorobenzenesulfonylamino)propionic acid, 3-[1-[3-(imidazolin-2-ylamino)propyl]indazol-4-ylcarbonylamino]-2-(3,5-dimethylisoxazol-4-ylsulfonylamino)propionic acid, 3-[1-[3-(imidazolin-2-ylamino)propyl]indazol-4-ylcarbonylamino]-2-(2,6-dimethylbenzenesulfonylamino)propionic acid, 3-[1-[3-(imidazolin-2-ylamino)propyl]indazol-4-ylcarbonylamino]-2-(2,6-dimethyl-4-phenylbenzenesulfonylamino)propionic acid, 3-[1-[3-(imidazolin-2-ylamino)propyl]indazol-4-ylcarbonylamino]-2-(4-phenylbenzenesulfonylamino)propionic acid, 3-[1-[3-(tetrahydropyrimid-2-ylamino)propyl]indazol-4-ylcarbonylamino]-2-(benzyloxycarbonylamino)propionic acid, 3-[1-[3-(tetrahydropyrimid-2-ylamino)propyl]indazol-4-ylcarbonylamino]-2-(2,4,6-trimethylbenzenesulfonylamino)propionic acid, 3-[1-[3-(tetrahydropyrimid-2-ylamino)propyl]indazol-4-ylcarbonylamino]-2-(benzenesulfonylamino)propionic acid, 3-[1-[3-(tetrahydropyrimid-2-ylamino)propyl]indazol-4-ylcarbonylamino]-2-(2,6-dichlorobenzenesulfonylamino)propionic acid, 3-[1-[3-(tetrahydropyrimid-2-ylamino)propyl]indazol-4-ylcarbonylamino]-2-(3,5-dimethylisoxazol-4-ylsulfonylamino)propionic acid, 3-[1-[3-(tetrahydropyrimid-2-ylamino)propyl]indazol-4-ylcarbonylamino]-2-(2,6-dimethylbenzenesulfonylamino)propionic acid, 3-[1-[3-(tetrahydropyrimid-2-ylamino)propyl]indazol-4-ylcarbonylamino]-2-(2,6-dimethyl-4-phenylbenzenesulfonylamino)propionic acid, 3-[1-[3-(tetrahydropyrimid-2-ylamino)propyl]indazol-4-ylcarbonylamino]-2-(4-phenylbenzenesulfonylamino)propionic acid, 3-1-[3-(imidazol-2-ylamino)propyl]indazol-4-ylcarbonylamino]-2-(benzyloxycarbonylamino)propionic acid, 3-[1-[3-(imidazol-2-ylamino)propyl]indazol-4-ylcarbonylamino]-2-(2,4,6-trimethylbenzenesulfonylamino)propionic acid, 3-1-[3-(imidazol-2-ylamino)propyl]indazol-4-ylcarbonylamino]-2-(benzenesulfonylamino)propionic acid, 3-1-[3-(imidazol-2-ylamino)propyl]indazol-4-ylcarbonylamino]-2-(2,6-dichlorobenzenesulfonylamino)propionic acid, 3-[1-[3-(imidazol-2-ylamino)propyl]indazol-4-ylcarbonylamino]-2-(3,5-dimethylisoxazol-4-ylsulfonylamino)propionic acid, 3-[1-[3-(imidazol-2-ylamino)propyl]indazol-4-ylcarbonylamino]-2-(2,6-dimethylbenzenesulfonylamino)propionic acid, 3-[1-[3-(imidazol-2-ylamino)propyl]indazol-4-ylcarbonylamino]-2-(2,6-dimethyl-4-phenylbenzenesulfonylamino)propionic acid, 3-[1-[3-(imidazol-2-ylamino)propyl]indazol-4-ylcarbonylamino]-2-(4-phenylbenzenesulfonylamino)propionic acid, 3-[1-[3-(pyridin-2-ylamino)propyl]indazol-4-ylcarbonylamino]-2-(benzyloxycarbonylamino)propionic acid, 3-[1-[3-(pyridin-2-ylamino)propyl]indazol-4-ylcarbonylamino]-2-(2,4,6-trimethylbenzenesulfonylamino)propionic acid, 3-[1-[3-(pyridin-2-ylamino)propyl]indazol-4-ylcarbonylamino]-2-(benzenesulfonylamino)propionic acid, 3-[1-[3-(pyridin-2-ylamino)propyl]indazol-4-ylcarbonylamino]-2-(2,6-dichlorobenzenesulfonylamino)propionic acid, 3-[1-[3-(pyridin-2-ylamino)propyl]indazol-4-ylcarbonylamino]-2-(3,5-dimethylisoxazol-4-ylsulfonylamino)propionic acid, 3-[1-[3-(pyridin-2-ylamino)propyl]indazol-4-ylcarbonylamino]-2-(2,6-dimethylbenzenesulfonylamino)propionic acid, 3-[1-[3-(pyridin-2-ylamino)propyl]indazol-4-ylcarbonylamino]-2-(2,6-dimethyl-4-phenylbenzenesulfonylamino)propionic acid, and 3-[1-[3-(pyridin-2-ylamino)propyl]indazol-4-ylcarbonylamino]-2-(4-phenylbenzenesulfonylamino)propionic acid; and ester forms thereof, said ester being selected from the group consisting of:

methyl,
ethyl,
isopropyl,
n-butyl,
isobutyl,
benzyl,
methylcarbonyloxymethyl,
ethylcarbonyloxymethyl,
tert-butylcarbonyloxymethyl,
cyclohexylcarbonyloxymethyl,
tert-butyloxycarbonyloxymethyl,
dimethylaminoethyl,
diethylaminoethyl,
morpholinoethyl,
pyrrolidinoethyl, and
trimethylammonioethyl.

6. A compound of Formula Ib:

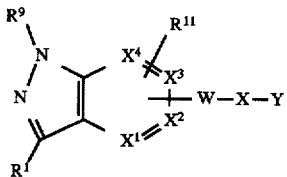

and pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

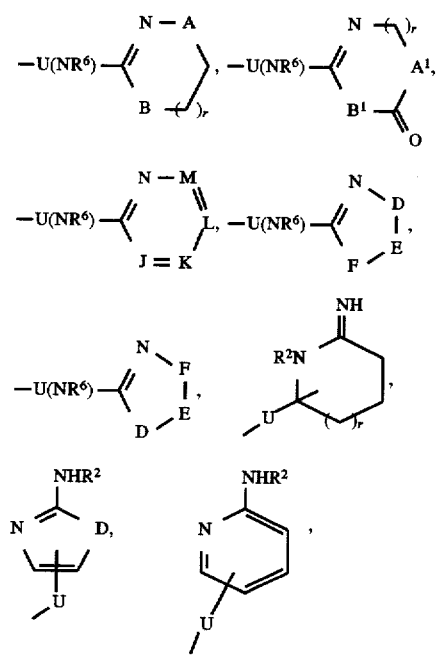

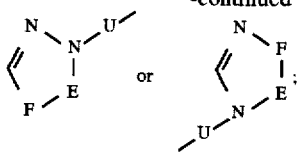

A and B are independently —$CH_2$—, —O—, —$N(R^2)$—, or —C(=O)—;

$A^1$ and $B^1$ are independently —$CH_2$— or —$N(R^3)$—;

D is —$N(R^2)$—, —O—, —S—, —C(=O)— or —$SO_2$—;

E—F is —$C(R^4)=C(R^5)$—, —$N=C(R^4)$—, —$C(R^4)=N$—, or —$C(R^4)_2C(R^5)_2$—;

J, K, L and M are independently selected from: —$C(R^4)$—, —$C(R^5)$— or —N—, provided that at least one of J, K, L and M is not —N—;

$R^2$ is selected from: H, $C_1$–$C_6$ alkyl, ($C_1$–$C_6$ alkyl) carbonyl, ($C_1$–$C_6$ alkoxy)carbonyl, ($C_1$–$C_6$ alkyl) aminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl $C_1$–$C_6$ alkyl, ($C_1$–$C_6$ alkyl)carbonyl, or arylcarbonyl, $C_1$–$C_6$ alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, or aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_1$–$C_{11}$ cycloalkylalkyl, aryl, aryl($C_1$–$C_6$ alkyl)-, ($C_1$–$C_6$ alkyl) carbonyl, ($C_1$–$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7=CR^8)(CH_2)_m$—
—$(CH_2)_n(C\equiv C)(CH_2)_m$—
—$(CH_2)_nQ(CH_2)_m$—
—$(CH_2)_nO(CH_2)_m$—,
—$(CH_2)_nN(R^6)(CH_2)_m$—,
—$(CH_2)_nC(=O)(CH_2)_m$—,
—$(CH_2)_n(C=O)N(R^6)(CH_2)_m$—
—$(CH_2)_nN(R^6)(C=O)(CH_2)_m$—, or
—$(CH_2)_nS(O)_p(CH_2)_m$—;

wherein one of the methylene groups is optionally substituted with $R^7$;

Q is selected from: 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

211

R⁹ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $N)_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:

—$(C(R^{12})_2)_qC(=O)N(R^{13})$—, or —$C(=O)$—$N(R^{13})$—$(C(R^{12})_2)_q$—;

X is —$C(R^{12})(R^{14})$—$C(R^{12})(R^{15})$—; or alternatively, W and X can be taken together to be

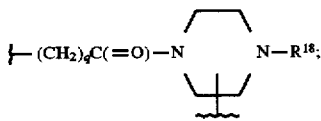

$R^{12}$ is selected from: H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl($C_1$–$C_6$ alkyl)-;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from:

H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from:

H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:

—$COR^{19}$, —$SO_3H$, —$PO_3H$, tetrazolyl, —$CONHNHSO_2CF_3$, —$CONHSO_2R^{17}$, —$CONHSO_2NHR^{17}$, —$NHCOCF_3$, —$NHCONHSO_2R^{17}$, —$NHSO_2R^{17}$, —$OPO_3H_2$, —$OSO_3H$, —$PO_3H_2$, —$SO_3H$, —$SO_2NHCOR^{17}$, —$SO_2NHCO_2R^{17}$

212

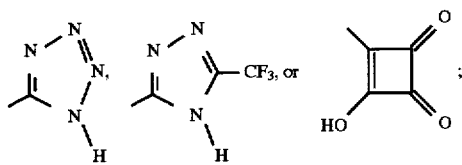

$R^{16}$ is selected from:
—$N(R^{20})$—$C(=O)$—O—$R^{17}$,
—$N(R^{20})$—$C(=O)$—$R^{17}$,
—$N(R^{20})$—$C(=O)$—NH—$R^{17}$,
—$N(R^{20})SO_2$—$R^{17}$, or
—$N(R^{20})SO_2$—$NR^{20}R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:
H,
—$C(=O)$—O—$R^{17}$,
—$C(=O)$—$R^{17}$,
—$C(=O)$—NH—$R^{17}$,
—$SO_2$—$R^{17}$, or
—$SO_2$—$NR^{20}R^{17}$;

$R^{19}$ is selected from hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N$—$(C_1$–$C_{10}$ alkoxy)-;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from COOH or $NR^6_2$;

m is 0–4;
n is 0–4;
t is 0–4;
p is 0–2;
q is 0–2; and
r is 0–2;

with the following provisos:

(1) t, n, m and q are chosen such that the number of atoms connecting $R^1$ and Y is in the range of 10–14; and (2) n and m are chosen such that the value of n plus m is greater than one unless U is —$(CH_2)_t Q(CH_2)_m$—.

7. A compound of claim 6 of Formula Ib:

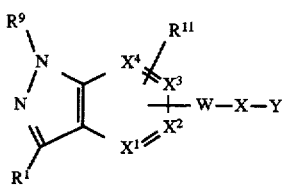

and pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

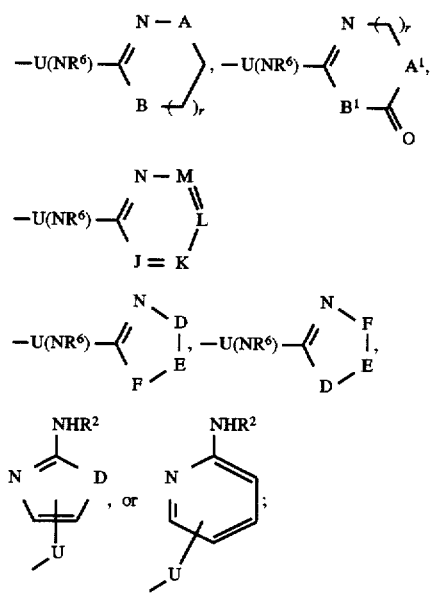

A and B are independently —CH$_2$—, —O—, —N(R$^2$)—, or —C(=O)—;

$A^1$ and $B^1$ are independently —CH$_2$— or —N(R$^3$)—;

D is —N(R$^2$)—, —O—, —S—, —C(=O)— or —SO$_2$—;

E—F is —C(R$^4$)=C(R$^5$)—, —N=C(R$^4$)—, —C(R$^4$)=N—, or —C(R$^4$)$_2$C(R$^5$)$_2$—;

J, K, L and M are independently selected from —C(R$^4$)—, —C(R$^5$)— or —N—, provided that at least one of J, K, L and M is not —N—;

$R^2$ is selected from: H, $C_1$–$C_6$ alkyl, ($C_1$–$C_6$ alkyl)carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl)carbonyl, heteroarylcarbonyl, aryl($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, CF$_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, NR$^2$R$^3$, halogen, NO$_2$, CN, CF$_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, CF$_3$, or NO$_2$;

U is selected from:
—(CH$_2$)$_n$—,
—(CH$_2$)$_n$(CR$^7$=CR$^8$)(CH$_2$)$_m$—
—(CH$_2$)$_n$Q(CH$_2$)$_m$—,
—(CH$_2$)$_n$O(CH$_2$)$_m$—,
—(CH$_2$)$_n$N(R$^6$)(CH$_2$)$_m$—,
—(CH$_2$)$_n$C(=O)(CH$_2$)$_m$—, or
—(CH$_2$)$_n$S(O)$_p$(CH$_2$)$_m$—;

wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_1$–$C_{11}$ cycloalkylalkyl, aryl, aryl($C_1$–$C_6$ alkyl)-, or heteroaryl($C_0$–$C_6$ alkyl)-;

$R^9$ is selected from: H, CO$_2$R$^{17}$C(=O)R$^{17}$, CONR$^{17}$R$^{20}$, —SO$_2$R$^{17}$, —SO$_2$NR$^{17}$R$^{20}$, $C_1$–$C_6$ alkyl substituted with 0–1 R$^{15}$ or 0–1 R$^{21}$, $C_3$–$C_6$ alkenyl substituted with 0–1 R$^{15}$ or 0–1 R$^{21}$, $C_3$–$C_7$ cycloalkyl substituted with 0–1 R$^{15}$ or 0–1 R$^{21}$, $C_4$–$C_{11}$ cycloalkylalkyl substituted with 0–1 R$^{15}$ or 0–1 R$^{21}$, aryl substituted with 0–1 R$^{15}$ or 0–2 R$^{11}$ or 0–1 R$^{21}$, or aryl($C_1$–$C_6$ alkyl)- substituted with 0–1 R$^{15}$ or 0–2 R$^{11}$ or 0–1 R$^{21}$;

$R^{11}$ is selected from: H, halogen, CF$_3$, CN, NO$_2$, hydroxy, NR$^2$R$^3$, $C_1$–$C_4$ alkyl substituted with 0–1 R$^{21}$, $C_1$–$C_4$ alkoxy substituted with 0–1 R$^{21}$, aryl substituted with 0–1 R$^{21}$, aryl($C_1$–$C_6$ alkyl)- substituted with 0–1 R$^{21}$, ($C_1$–$C_4$ alkoxy)carbonyl substituted with 0–1 R$^{21}$, ($C_1$–$C_4$ alkyl)carbonyl substituted with 0–1 R$^{21}$, $C_1$–$C_4$ alkylsulfonyl substituted with 0–1 R$^{21}$, or $C_1$–$C_4$ alkylaminosulfonyl substituted with 0–1 R$^{21}$;

W is —C(=O)—N(R$^{13}$)—(C(R$^{12}$)$_2$)$_q$—;

X is —C(R$^{12}$)(R$^{14}$)—C(R$^{12}$)(R$^{15}$)—;

alternatively, W and X can be taken together to be

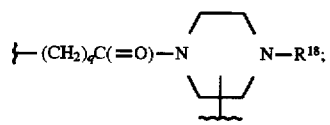

$R^{12}$ is H or $C_1$–$C_6$ alkyl;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from:

H, $C_1$–$C_6$ alkylthioalkyl, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl ($C_1$–$C_6$ alkyl)-, aryl, heteroaryl, CO$_2$R$^{17}$, C(=O) R$^{17}$, or CONR$^{17}$R$^{20}$, provided that any of the above alkyl, cycloalkyl, aryl or heteroaryl groups may be unsubstituted or substituted independently with 0–1 R$^{16}$ or 0–2 R$^{11}$;

$R^{15}$ is selected from:

H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl ($C_1$–$C_6$ alkyl)-, aryl, heteroaryl, $CO_2R^{17}$, $C(=O)$ $R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:

$-COR^{19}$, $-SO_3H$,

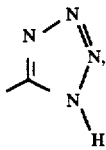

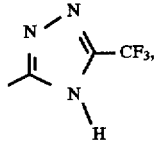

or

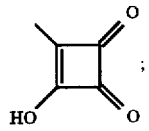

;

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:
H,
—$C(=O)$—$O$—$R^{17}$,
—$C(=O)$—$R^{17}$,
—$C(=O)$—$NH$—$R^{17}$,
—$SO_2$—$R^{17}$, or
—$SO_2$—$NR^{20}R^{17}$;

$R^{19}$ is selected from hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N$-($C_1$–$C_{10}$ alkoxy)-;

$R^{20}$ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

$R^{21}$ is selected from COOH or $NR^6_2$;

m is 0–4;

n is 0–4;

t is 0–4;

p is 0–2;

q is 0–2; and r is 0–2.

8. A compound of claim 6 of the Formula IIc or IId:

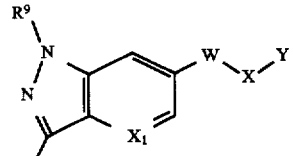 IIc or

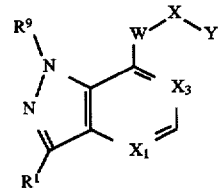 IId and pharmaceutically acceptable salt forms thereof, wherein:

$X_1$ and $X_3$ are independently selected from nitrogen or carbon;

$R^1$ is selected from:

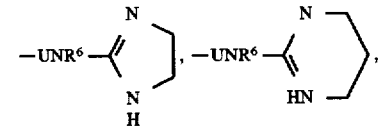

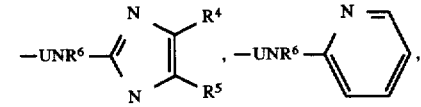

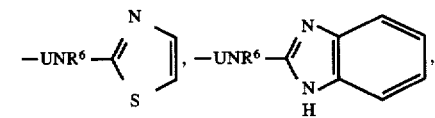

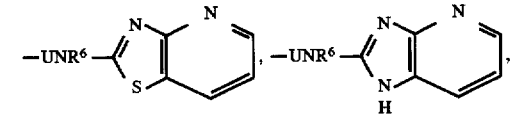

-continued

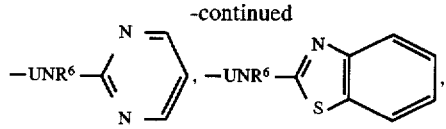

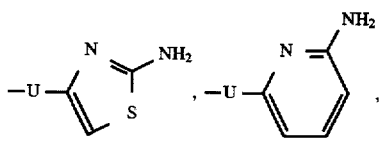

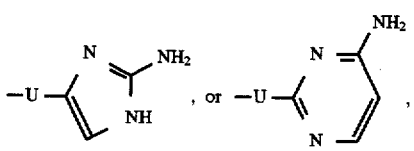

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is $-(CH_2)_n-$, $-(CH_2)_tQ(CH_2)_m-$ or $-C(=O)(CH_2)_{n-1}-$, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$ . $C_6$ alkyl);

$R^9$ is selected from: H, $-SO_2R^{17}$, $-SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is $-C(=O)-N(R^{13})-$;

X is $-CH(R^{14})-CH(R^{15})-$;

$R^{13}$ is H or $CH_3$;

$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is $-COR^{19}$;

$R^{16}$ is selected from:
$-NH(R^{20})-C(=O)-O-R^{17}$,
$-N(R^{20})-C(=O)-R^{17}$,
$-N(R^{20})-C(=O)-NH-R^{17}$,
$-N(R^{20})SO_2-R^{17}$, or
$-N(R^{20})SO_2-N(R^{20})R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
or
1-(2-(2-methoxypropyl)carbonyloxy)ethoxy-;

$R^{20}$ is H or $CH_3$;

$R^{21}$ is selected from COOH or $NR^6_2$; and m is 0 or 1;

n is 1–4; and t is 0 or 1.

9. A compound of claim 6 of the Formula IIc or IId:

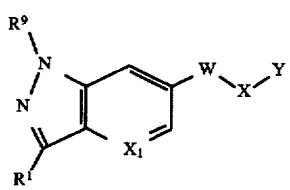

IIc or

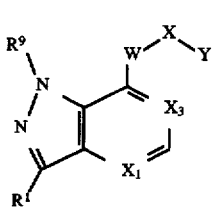

IId and pharmaceutically acceptable salt forms thereof, wherein:

$X_1$ and $X_3$ are independently selected from nitrogen or carbon, provided that at least one of $X_1$ and $X_3$ is carbon;

$R^1$ is selected from:

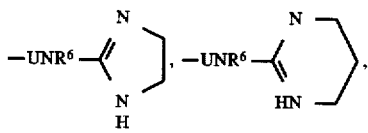

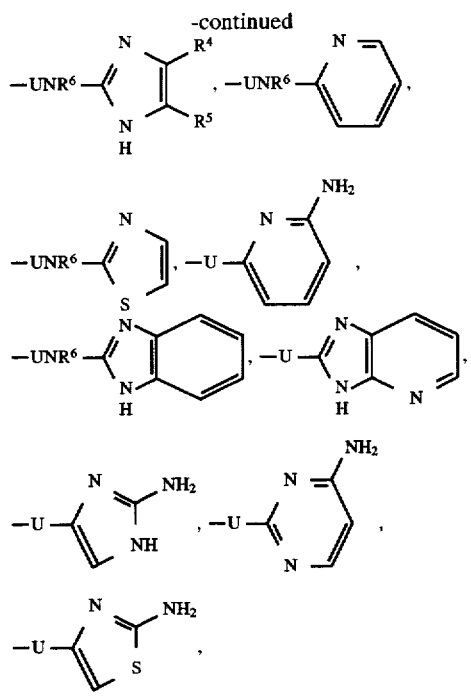

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl:

U is —$(CH_2)_n$—, —$(CH_2)_tQ(CH_2)_m$— or —C(=O)$(CH_2)_{n-1}$—, wherein one of the methylene groups is optionally substituted with $R^7$;

Q is selected from 1,2-phenylene, 1,3-phenlylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;
X is —CH($R^{14}$)—CH($R^{15}$);
$R^{13}$ is H or $CH_3$;
$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;
Y is —$COR^{19}$;
$R^{16}$ is selected from:
—N($R^{20}$)—C(=O)—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$ ;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;
$R^{21}$ is selected from COOH or $NR^6_2$; and
m is 0 or n 1;
n is 1–4; and
t is 0 or 1.

10. A compound of claim 6 of Formula Ib and enantiomeric or diasteriomeric forms thereof, and mixtures of enantiomeric or diasteriomeric forms thereof, and pharmaceutically acceptable salt forms thereof, selected from the group consisting of:

3-[3-[3-(imidazolin-2-ylamino)propyl]indazol-6-ylcarbonylamino]-2-(benzyloxycarbonylamino)propionic acid, 3-[1-methyl-3-[3-(imidazolin-2-ylamino)propyl]indazol-6-ylcarbonylamino]-2-(2,4,6-trimethylbenzenesulfonylamino)propionic acid, 3-[3-[3-(imidazolin-2-ylamino)propyl]indazol-6-ylcarbonylamino]-2-(benzenesulfonylamino)propionic acid, 3-[1-methyl-3-[3-(imidazolin-2-ylamino)propyl]indazol-6-ylcarbonylamino]-2-(2,6-dichlorobenzenesulfonylamino)propionic acid, 3-[3-[3-(imidazolin-2-ylamino)propyl]indazol-6-ylcarbonylamino]-2-(3,5-dimethylisoxazol-4-ylsulfonylamino)propionic acid, 3-[1-methyl-3-[3-(imidazolin-2-ylamino)propyl]indazol-6-ylcarbonylamino]-2-(2,6-dimethylbenzenesulfonylamino)propionic acid, 3-[3-[3-(imidazolin-2-ylamino)propyl]indazol-6-ylcarbonylamino]-2-(2,6-dimethyl-4-phenylbenzenesulfonylamino)propionic acid, 3-[1-methyl-3-[3-(imidazolin-2-ylamino)propyl]indazol-6-ylcarbonylamino]-2-(4-phenylbenzenesulfonylamino)propionic acid, 3-[3-[3-(tetrahydropyrimid-2-ylamino)propyl]indazol-6-ylcarbonylamino]-2-(benzyloxycarbonylamino)propionic acid, 3-[1-methyl-3-[3-(tetrahydropyrimid-2-ylamino)propyl]indazol-6-ylcarbonylamino]-2-(2,4,6-trimethylbenzenesulfonylamino)propionic acid, 3-[3-[3-(tetrahydropyrimid-2-ylamino)propyl]indazol-6-ylcarbonylamino]-2-(benzenesulfonylamino)propionic acid, 3-[1-methyl-3-[3-(tetrahydropyrimid-2-ylamino)propyl]indazol-6-ylcarbonylamino]-2-(2,6-dichlorobenzenesulfonylamino)propionic acid, 3-[3-[3-(tetrahydropyrimid-2-ylamino)propyl]indazol-6-ylcarbonylamino]-2-(3,5-dimethylisoxazol-4-ylsulfonylamino)propionic acid, 3-[1-methyl-3-[3-(tetrahydropyrimid-2-ylamino)propyl]indazol-6-ylcarbonylamino]-2-(2,6-dimethylbenzenesulfonylamino)propionic acid, 3-[3-[3-(tetrahydropyrimid-2-ylamino)propyl]indazol-6-ylcarbonylamino]-2-(2,6-dimethyl-4-phenylbenzenesulfonylamino)propionic acid, 3-[1-methyl-3-[3-(tetrahydropyrimid-2-ylamino)propyl]indazol-6-ylcarbonylamino]-2-(4-phenylbenzenesulfonylamino)propionic acid, 3-[3-[3-(imidazol-2-ylamino)propyl]indazol-6-ylcarbonylamino]-2-(benzyloxycarbonylamino)propionic acid, 3-[1-methyl-3-[3-(imidazol-2-ylamino)propyl]indazol-6-ylcarbonylamino]-2-(2,4,6-trimethylbenzenesulfonylamino)propionic acid, 3-[3-[3-(imidazol-2-ylamino)propyl]indazol-6-ylcarbonylamino]-2-(benzenesulfonylamino)propionic acid, 3-[1-methyl-3-[3-(imidazol-2-ylamino)propyl]indazol-6-ylcarbonylamino]-2-(2,6-dichlorobenzenesulfonylamino)propionic acid, 3-[3-[3-imidazol-2-ylamino)propyl]indazol-6-ylcarbonylamino]-2-(3,5-dimethylisoxazol-4-ylsulfonylamino)propionic acid, 3-[1-methyl-3-[3-(imidazol-2-ylamino)propyl]indazol-6-ylcarbonylamino]-2-(2,6-dimethylbenzenesulfonylamino)propionic acid, 3-[3-[3-(imidazol-2-ylamino)propyl]indazol-6-ylcarbonylamino]-2-(2,6-dimethyl-4-phenylbenzenesulfonylamino)propionic acid, 3-[1-methyl-3-[3-(imidazol-2-ylamino)propyl]indazol-6-ylcarbonylamino]-2-(4-phenylbenzenesulfonylamino)propionic acid, 3-[3-[3-(pyridin-2-ylamino)propyl]indazol-6-ylcarbonylamino]-2-(benzyloxycarbonylamino)propionic acid, 3-[1-methyl-3-[3-(pyridin-2-ylamino)propyl]indazol-6-ylcarbonylamino]-2-(2,4,6-trimethylbenzenesulfonylamino)propionic acid, 3-[3-[3-(pyridin-2-ylamino)propyl]indazol-6-ylcarbonylamino]-2-(benzenesulfonylamino)propionic acid, 3-[1-methyl-3-[3-(pyridin-2-ylamino)propyl]indazol-6-ylcarbonylamino]-2-(2,6-dichlorobenzenesulfonylamino)propionic acid, 3-[3-[3-(pyridin-2-ylamino)propyl]indazol-6-ylcarbonylamino]-2-(3,5-dimethylisoxazol-4-ylsulfonylamino)propionic acid, 3-[1-methyl-3-[3-(pyridin-2-ylamino)propyl]indazol-6-ylcarbonylamino]-2-(2,6-dimethylbenzenesulfonylamino)propionic acid, 3-[3-[3-(pyridin-2-ylamino)propyl]indazol-6-ylcarbonylamino]-2-(2,6-dimethyl-4-phenylbenzenesulfonylamino)propionic acid, 3-[1-methyl-3-[3-(pyridin-2-ylamino)propyl]indazol-6-ylcarbonylamino]-2-(4-phenylbenzenesulfonylamino)propionic acid, 3-[3-[3-(imidazolin-2-ylamino)propyl]indazol-7-ylcarbonylamino]-2-(benzyloxycarbonylamino)propionic acid, 3-[1-methyl-3-(3-(imidazolin-2-ylamino)propyl]indazol-7-ylcarbonylamino]-2-(2,4,6-trimethylbenzenesulfonylamino)propionic acid, 3-[3-[3-(imidazolin-2-ylamino)propyl]indazol-7-ylcarbonylamino]-2-(benzenesulfonylamino)propionic acid, 3-(1-methyl-3-[3-(imidazolin-2-ylamino)propyl]indazol-7-ylcarbonylamino]-2-(2,6-dichlorobenzenesulfonylamino)propionic acid, 3-[3-[3-(imidazolin-2-ylamino)propyl]indazol-7-ylcarbonylamino]-2-(3,5-dimethylisoxazol-4-ylsulfonylamino)propionic acid, 3-[1-methyl-3-[3-(imidazolin-2-ylamino)propyl]indazol-7-ylcarbonylamino]-2-(2,6-dimethylbenzenesulfonylamino)propionic acid, 3-[3-[3-(imidazolin-2-ylamino)propyl]indazol-7-ylcarbonylamino]-2-(2,6-dimethyl-4-phenylbenzenesulfonylamino)propionic acid, 3-[1-methyl-3-(3-(imidazolin-2-ylamino)propyl]indazol-7-ylcarbonylamino]-2-(4-phenylbenzenesulfonylamino)propionic acid, 3-[3-[3-(tetrahydropyrimid-2-ylamino)propyl]indazol-7-ylcarbonylamino]-2-(benzyloxycarbonylamino)propionic acid, 3-[1-methyl-3-[3-(tetrahydropyrimid-2-ylamino)propyl]indazol-7-ylcarbonylamino]-2-(2,4,6-trimethylbenzenesulfonylamino)propionic acid, 3-[3-[3-(tetrahydropyrimid-2-ylamino)propyl]indazol-7-ylcarbonylamino]-2-(benzenesulfonylamino)propionic acid, 3-[1-methyl-3-[3-(tetrahydropyrimid-2-ylamino)propyl]indazol-7-ylcarbonylamino]-2-(2,6-dichlorobenzenesulfonylamino)propionic acid, 3-[3-[3-(tetrahydropyrimid-2-ylamino)propyl]indazol-7-ylcarbonylamino]-2-(3,5-dimethylisoxazol-4-ylsulfonylamino)propionic acid, 3-[1-methyl-3-[3-(tetrahydropyrimid-2-ylamino)propyl]indazol-7-ylcarbonylamino]-2-(2,6-dimethylbenzenesulfonylamino)propionic acid, 3-[3-[3-(tetrahydropyrimid-2-ylamino)propyl]indazol-7-ylcarbonylamino]-2-(2,6-dimethyl-4phenylbenzenesulfonylamino)propionic acid, 3-[1-methyl-3-[3-(tetrahydropyrimid-2-ylamino)propyl]indazol-7-ylcarbonylamino]-2-(4-phenylbenzenesulfonylamino)propionic acid, 3-[3-[3-(imidazol-2-ylamino)propyl]indazol-7-ylcarbonylamino]-2-(benzyloxycarbonylamino)propionic acid, 3-[1-methyl-3-[3-(imidazol-2-ylamino)propyl]indazol-7-ylcarbonylamino]-2-(2,4,6-trimethylbenzenesulfonylamino)propionic acid, 3-[3-[3-(imidazol-2-ylamino)propyl]indazol-7-ylcarbonylamino]-2-(benzenesulfonylamino)propionic acid, 3-[1-methyl-3-[3-(imidazol-2-ylamino)propyl]indazol-7-ylcarbonylamino]-2-(2,6-dichlorobenzenesulfonylamino)propionic acid, 3-[3-[3-(imidazol-2-ylamino)propyl]indazol-7-ylcarbonylamino]-2-(3,5-dimethylisoxazol-4-ylsulfonylamino)propionic acid, 3-[1-methyl-3-[3-(imidazol-2-ylamino)propyl]indazol-7-ylcarbonylamino]-2-(2,6-dimethylbenzenesulfonylamino)propionic acid, 3-[3-[3-(imidazol-2-ylamino)propyl]indazol-7-ylcarbonylamino]-2-(2,6-dimethyl-4-phenylbenzenesulfonylamino)propionic acid, 3-[1-methyl-3-[3-(imidazol-2-ylamino)propyl]indazol-7-ylcarbonylamino]-2-(4-phenylbenzenesulfonylamino)propionic acid, 3-[3-[3-(pyridin-2-ylamino)propyl]indazol-7-ylcarbonylamino]-2-(benzyloxycarbonylamino)propionic acid, 3-[1-methyl-3-[3-(pyridin-2-ylamino)propyl]indazol-7-ylcarbonylamino]-2-(2,4,6-trimethylbenzenesulfonylamino)propionic acid, 3-[3-[3-(pyridin-2-ylamino)propyl]indazol-7-ylcarbonylamino]-2-(benzenesulfonylamino)propionic acid, 3-[1-methyl-3-[3-(pyridin-2-ylamino)propyl]indazol-7-ylcarbonylamino]-2-(2,6-dichlorobenzenesulfonylamino) propionic acid, 3-[3-[3-(pyridin-2-ylamino)propyl]indazol-7-ylcarbonylamino]-2-(3,5-dimethylisoxazol-4-ylsulfonylamino)propionic acid, 3-[1-methyl-3-[3-(pyridin-2-ylamino)propyl]indazol-7-ylcarbonylamino]-2-(2,6-dimethylbenzenesulfonylamino)propionic acid, 3-[3-[3-(pyridin-2-ylamino)propyl]indazol-7-ylcarbonylamino]-2-(2,6-dimethyl-4-phenylbenzenesulfonylamino)propionic acid, and 3-[1-methyl-3-[3-(pyridin-2-ylamino)propyl]indazol-7-ylcarbonylamino]-2-(4-phenylbenzenesulfonylamino) propionic acid;

and ester forms thereof, said esters being chosen from the group consisting of:

methyl,
ethyl,
isopropyl,
n-butyl,
isobutyl,
benzyl,
methylcarbonyloxymethyl,
ethylcarbonyloxymethyl,
tert-butylcarbonyloxymethyl,
cyclohexylcarbonyloxymethyl,
tert-butyloxycarbonyloxymethyl,
dimethylaminoethyl, and
diethylaminoethyl.

11. A compound of Formula Ic:

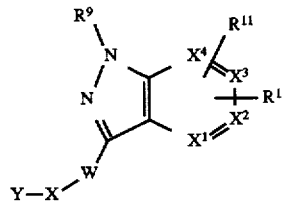

and pharmaceutically acceptable salt forms thereof, wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

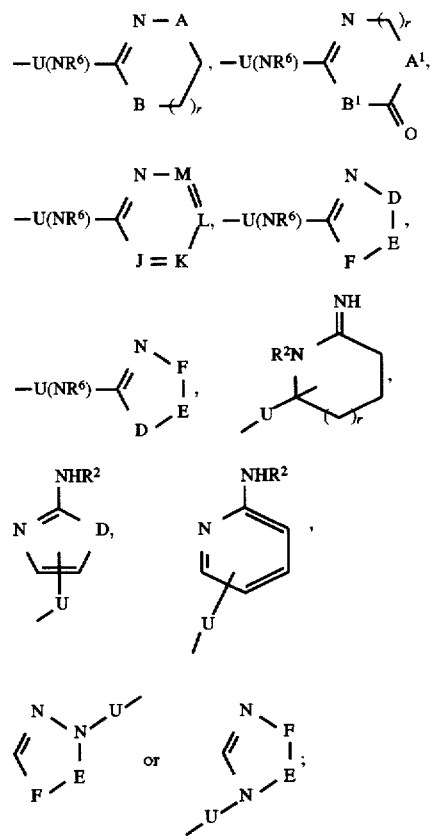

A and B are independently —$CH_2$—, —O—, —N($R^2$)—, or —C(=O)—;

$A^1$ and $B^1$ are independently —$CH_2$— or —N($R^3$)—;

D is —N($R^2$)—, —O—, —S—, —C(=O)— or —$SO_2$—;

E—F is —C($R^4$)=C($R^5$)—, —N=C($R^4$)—, —C($R^4$)=N—, or —C($R^4$)$_2$C($R^5$)$_2$—;

J, K, L and M are independently selected from —C($R^4$)—, —C($R^5$)— or —N—, provided that at least one of J, K, L and M is not —N—;

$R^2$ is selected from: H, $C_1$-$C_6$ alkyl, ($C_1$-$C_6$ alkyl) carbonyl, ($C_1$-$C_6$ alkoxy)carbonyl; ($C_1$-$C_6$ alkyl) aminocarbonyl, $C_3$-$C_6$ alkenyl, $C_3$-$C_7$ cycloalkyl, $C_4$-$C_{11}$ cycloalkylalkyl, aryl, heteroaryl($C_1$-$C_6$ alkyl) carbonyl, heteroarylcarbonyl, aryl $C_1$-$C_6$ alkyl, ($C_1$-$C_6$ alkyl)carbonyl, or arylcarbonyl, $C_1$-$C_6$ alkylsulfonyl, arylsulfonyl, aryl($C_1$-$C_6$ alkyl)sulfonyl, heteroarylsulfonyl, heteroaryl($C_1$-$C_6$ alkyl)sulfonyl, aryloxycarbonyl, or aryl($C_1$-$C_6$ alkoxy)carbonyl, wherein said aryl groups are substituted with 0-2 substituents selected from the group consisting of $C_1$-$C_4$ alkyl, $C_1$-$C_4$ alkoxy, halo, $CF_3$, and nitro;

$R^3$ is selected from: H, $C_1$-$C_6$ alkyl, $C_3$-$C_7$ cycloalkyl, $C_4$-$C_{11}$ cycloalkylalkyl, aryl, aryl($C_1$-$C_6$ alkyl)-, or heteroaryl($C_1$-$C_6$ alkyl)-;

$R^4$ and $R^5$ are independently selected from: H, $C_1$-$C_4$ alkoxy, $NR^2R^3$, halogen, $NO_2$, CN, $CF_3$, $C_1$-$C_6$ alkyl, $C_3$-$C_6$ alkenyl, $C_3$-$C_7$ cycloalkyl, $C_4$-$C_{11}$ cycloalkylalkyl, aryl, aryl($C_1$-$C_6$ alkyl)-, ($C_1$-$C_6$ alkyl) carbonyl, ($C_1$-$C_6$ alkoxy)carbonyl, arylcarbonyl, or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:
—$(CH_2)_n$—,
—$(CH_2)_n(CR^7$=$CR^8)(CH_2)_m$—
—$(CH_2)_n(C$≡$C)(CH_2)_m$—
—$(CH_2)_nQ(CH_2)_m$—
—$(CH_2)_nO(CH_2)_m$—,
—$(CH_2)_nN(R^6)(CH_2)_m$—,
—$(CH_2)_nC(=O)(CH_2)_m$—,
—$(CH_2)_n(C=O)N(R^6)(CH_2)_m$—
—$(CH_2)_nN(R^6)(C=O)(CH_2)_m$—, or
—$(CH_2)_nS(O)_p(CH_2)_m$—;

wherein one of the methylene groups is optionally substituted with $R^7$;

Q is selected from 1,2-cycloalkylene, 1,2-phenylene, 1,3-phenylene, 1,4-phenylene, 2,3-pyridinylene, 3,4-pyridinylene, 2,4-pyridinylene, or 3,4-pyridazinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is selected from:
—$(C(R^{12})_2)_qC(=O)N(R^{13})$—, or
—$C(=O)$—$N(R^{13})$—$(C(R^{12})_2)_q$—;

X is —$C(R^{12})(R^{14})$—$C(R^{12})(R^{15})$—; or alternatively, W and X can be taken together to be

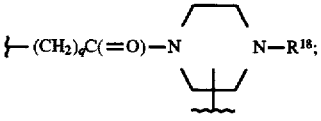

$R^{12}$ is selected from: H, halogen, $C_1$–$C_6$ alkyl, $C_2$–$C_6$ alkenyl, $C_2$–$C_6$ alkynyl, $C_3$–$C_7$ cycloalkyl, $C_4$–$C_{10}$ cycloalkylalkyl, ($C_1$–$C_4$ alkyl)carbonyl, aryl, or aryl ($C_1$–$C_6$ alkyl)-;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from:
H, $C_1$–$C_6$ alkylthio($C_1$–$C_6$ alkyl)-, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, or $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from:
H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, ($C_1$–$C_{10}$ alkyl)carbonyl, aryl($C_0$–$C_6$ alkyl)carbonyl, $C_1$–$C_{10}$ alkenyl, $C_1$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:
—$COR^{19}$, —$SO_3H$, —$PO_3H$, tetrazolyl, —$CONHNHSO_2CF_3$, —$CONHSO_2R^{17}$, —$CONHSO_2NHR^{17}$, —$NHCOCF_3$, —$NHCONHSO_2R^{17}$, —$NHSO_2R^{17}$, —$OPO_3H_2$, —$OSO_3H$, —$PO_3H_2$, —$SO_3H$, —$SO_2NHCOR^{17}$, —$SO_2NHCO_2R^{17}$,

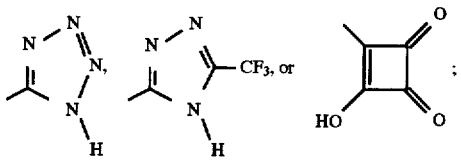

$R^{16}$ is selected from:
—$N(R^{20})$—$C(=O)$—$O$—$R^{17}$,
—$N(R^{20})$—$C(=O)$—$R^{17}$,
—$N(R^{20})$—$C(=O)$—$NH$—$R^{17}$,
—$N(R^{20})SO_2$—$R^{17}$, or
—$N(R^{20})SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:
H,
—$C(=O)$—$O$—$R^{17}$,
—$C(=O)$—$R^{17}$,
—$C(=O)$—$NH$—$R^{17}$,
—$SO_2$—$R^{17}$, or
—$SO_2$—$NR^{20}R^{17}$;

$R^{19}$ is selected from hydroxy, $C_1$–$C_{10}$ alkyloxy, $C_3$–$C_{11}$ cycloalkyloxy, aryloxy, aryl($C_1$–$C_6$ alkoxy)-, $C_3$–$C_{10}$ alkylcarbonyloxyalkyloxy, $C_3$–$C_{10}$
alkoxycarbonyloxyalkyloxy, $C_2$–$C_{10}$
alkoxycarbonylalkyloxy, $C_5$–$C_{10}$
cycloalkylcarbonyloxyalkyloxy, $C_5$–$C_{10}$
cycloalkoxycarbonyloxyalkyloxy, $C_5$–$C_{10}$
cycloalkoxycarbonylalkyloxy, $C_7$–$C_{11}$
aryloxycarbonylalkyloxy, $C_8$–$C_{12}$
aryloxycarbonyloxyalkyloxy, $C_8$–$C_{12}$
arylcarbonyloxyalkyloxy, $C_5$–$C_{10}$
alkoxyalkylcarbonyloxyalkyloxy, $C_5$–$C_{10}$ (5-alkyl-1,3- dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N$—$(C_1$–$C_{10}$ alkoxy)-;

$R^{20}$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^{21}$ is selected from COOH or $NR^6{}_2$;

m is 0–4;

n is 0–4;

p is 0–2;

q is 0–2; and r is 0–2;

with the following provisos:

(1) t, n, m and q are chosen such that the number of atoms connecting $R^1$ and Y is in the range of 10–14; and (2) n and m are chosen such that the value of n plus m is greater than one unless U is —$(CH_2)_nQ(CH_2)_m$—.

12. A compound of claim 11 of the Formula Ic:

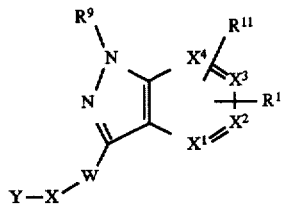

Ic and pharmaceutically acceptable salt forms thereof wherein:

$X^1$, $X^2$, $X^3$, and $X^4$ are independently selected from nitrogen or carbon provided that at least two of $X^1$, $X^2$, $X^3$ and $X^4$ are carbon;

$R^1$ is selected from:

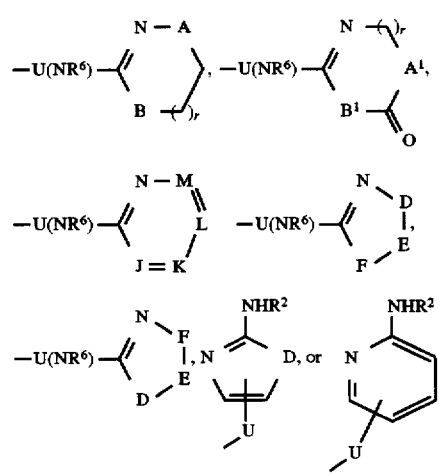

A and B are independently —$CH_2$—, —O—, —$N(R^2)$—, or —$C(=O)$—;

$A^1$ and $B^1$ are independently —$CH_2$— or —$N(R^3)$—;

D is —$N(R^2)$—, —O—, —S—, —$C(=O)$— or —$SO_2$—;

E—F is —$C(R^4)=C(R^5)$—, —$N=C(R^4)$—, —$C(R^4)=N$—, or —$C(R^4)_2C(R^5)_2$—;

J, K, L and M are independently selected from: —$C(R^4)$—, —$C(R^5)$— or —N—, provided that at least one of J, K, L and M is not —N—;

$R^2$ is selected from: H, $C_1$–$C_6$ alkyl, ($C_1$–$C_6$ alkyl) carbonyl, ($C_1$–$C_6$ alkoxy)carbonyl, $C_1$–$C_6$ alkylaminocarbonyl, $C_3$–$C_6$ alkenyl, $C_3$–$C_7$ cycloalkyl, $C_4$–$C_{11}$ cycloalkylalkyl, aryl, heteroaryl($C_1$–$C_6$ alkyl) carbonyl, heteroarylcarbonyl, aryl($C_1$–$C_6$ alkyl)-, ($C_1$–$C_6$ alkyl)carbonyl, arylcarbonyl, alkylsulfonyl, arylsulfonyl, aryl($C_1$–$C_6$ alkyl)sulfonyl, heteroarylsulfonyl, heteroaryl($C_1$–$C_6$ alkyl)sulfonyl, aryloxycarbonyl, aryl($C_1$–$C_6$ alkoxy)carbonyl, wherein said aryl groups are substituted with 0–2 substituents selected from the group consisting of $C_1$–$C_4$ alkyl, $C_1$–$C_4$ alkoxy, halo, $CF_3$, and nitro;

$R^3$ is selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_1$–$C_6$ alkyl)-;

$R^4$ and $R^5$ are independently selected from: H, $C_1$–$C_4$ alkoxy, $NR^2R^3$, halogen, $NO_2$, CN, $CF_3$, $C_1$–$C_6$ alkyl, $C_3$–$C_6$ alkenyl, $C_3$–$C_7$ cycloalkyl, $C_4$–$C_{11}$ cycloalkylalkyl, aryl, aryl($C_1$–$C_6$ alkyl)-, $C_2$–$C_7$ alkylcarbonyl, arylcarbonyl or alternatively, when substituents on adjacent atoms, $R^4$ and $R^5$ can be taken together with the carbon atoms to which they are attached to form a 5–7 membered carbocyclic or 5–7 membered heterocyclic aromatic or non-aromatic ring system, said carbocyclic or heterocyclic ring being optionally substituted with 0–2 groups selected from: $C_1$–$C_4$ alkyl, $C_1$–$C_4$ alkoxy, halo, cyano, amino, $CF_3$, or $NO_2$;

U is selected from:

—$(CH_2)_n$—,
—$(CH_2)_n(CR^7=CR^8)(CH_2)_m$—
—$(CH_2)_nQ(CH_2)_m$—,
—$(CH_2)_nO(CH_2)_m$—,
—$(CH_2)_nN(R^6)(CH_2)_m$—,
—$(CH_2)_nC(=O)(CH_2)_m$—, or
—$(CH_2)_nS(O)_p(CH_2)_m$—;

wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ and $R^8$ are independently selected from: H, $C_1$–$C_6$ alkyl, $C_3$–$C_7$ cycloalkyl, $C_4$–$C_{11}$ cycloalkylalkyl, aryl, aryl($C_1$–$C_6$ alkyl)-, or heteroaryl($C_0$–$C_6$ alkyl)-;

$R^9$ is selected from: H, $CO_2R^{17}$, $C(=O)R^{17}$, $CONR^{17}R^{20}$, —$SO_2R^{17}$, —$SO_2NR^{17}R^{20}$, $C_1$–$C_6$ alkyl substituted with 0–1 $R^{15}$ or 0–1 $R^{21}$, $C_3$–$C_6$ alkenyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from: H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is —$C(=O)$—$N(R^{13})$—$(C(R^{12})_2)_q$—;

X is —$C(R^{12})(R^{14})$—$C(R^{12})(R^{15})$—;

alternatively, W and X can be taken together to be

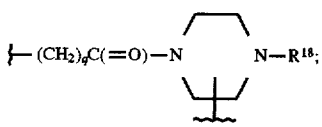

$R^{12}$ is H or $C_1$–$C_6$ alkyl;

$R^{13}$ is selected from: H, $C_1$–$C_6$ alkyl, $C_3$–$C_7$ cycloalkylmethyl, or aryl($C_1$–$C_6$ alkyl)-;

$R^{14}$ is selected from:

H, $C_1$–$C_6$ alkylthioalkyl, aryl($C_1$–$C_{10}$ alkylthioalkyl)-, aryl($C_1$–$C_{10}$ alkoxyalkyl)-, $C_1$–$C_{10}$ alkyl, $C_1$–$C_{10}$ alkoxyalkyl, $C_1$–$C_6$ hydroxyalkyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl ($C_1$–$C_6$ alkyl)-, aryl, heteroaryl, $CO_2R^{17}$, $C(=O)R^{17}$, $CONR^{17}R^{20}$, provided that any of the above alkyl, cycloalkyl, aryl or heteroaryl groups may be unsubstituted or substituted independently with 0–1 $R^{16}$ or 0–2 $R^{11}$;

$R^{15}$ is selected from:

H, $R^{16}$, $C_1$–$C_{10}$ alkyl, $C_1$–$C_{10}$ alkoxyalkyl, $C_1$–$C_{10}$ alkylaminoalkyl, $C_1$–$C_{10}$ dialkylaminoalkyl, $C_1$–$C_{10}$ alkylcarbonyl, aryl($C_0$–$C_6$ alkyl)carbonyl, $C_2$–$C_{10}$ alkenyl, $C_2$–$C_{10}$ alkynyl, $C_3$–$C_{10}$ cycloalkyl, $C_3$–$C_{10}$ cycloalkylalkyl, aryl($C_1$–$C_6$ alkyl)-, heteroaryl ($C_1$–$C_6$ alkyl)-, aryl, heteroaryl, $CO_2R^{17}$, $C(=O)R^{17}$, $CONR^{17}R^{20}$, $SO_2R^{17}$, or $SO_2NR^{17}R^{20}$, provided that any of the above alkyl, cycloalkyl, aryl or heteroaryl groups may be unsubstituted or substituted independently with 0–2 $R^{11}$;

Y is selected from:

—$COR^{19}$, —$SO_3H$,

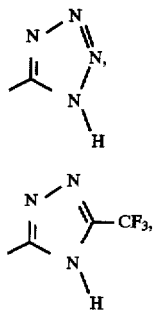

or

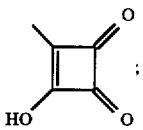

$R^{16}$ is selected from:
—$N(R^{20})$—$C(=O)$—O—$R^{17}$,
—$N(R^{20})$—$C(=O)$—$R^{17}$,
—$N(R^{20})$—$C(=O)$—NH—$R^{17}$,
—$N(R^{20})SO_2$—$R^{17}$, or
—$N(R^{20})SO_2$—$NR^{20}R^{17}$;

$R^{17}$ is selected from:

$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{18}$ is selected from:

H,
—$C(=O)$—O—$R^{17}$,
—$C(=O)$—$R^{17}$,
—$C(=O)$—NH—$R^{17}$,
—$SO_2$—$R^{17}$, or
—$SO_2$—$NR^{20}R^{17}$;

$R^{19}$ is selected from: hydroxy, $C_1$–$C_{10}$ alkyloxy, $C_3$–$C_{11}$ cycloalkyloxy, $C_6$–$C_{10}$ aryloxy, $C_7$–$C_{11}$ aralkyloxy, $C_3$–$C_{10}$ alkylcarbonyloxyalkyloxy, $C_3$–$C_{10}$ alkoxycarbonyloxyalkyloxy, $C_2$–$C_{10}$ alkoxycarbonylalkyloxy, $C_5$–$C_{10}$ cycloalkylcarbonyloxyalkyloxy, $C_5$–$C_{10}$ cycloalkoxycarbonyloxyalkyloxy, $C_5$–$C_{10}$ cycloalkoxycarbonylalkyloxy, $C_7$–$C_{11}$ aryloxycarbonylalkyloxy, $C_8$–$C_{12}$ aryloxycarbonyloxyalkyloxy, $C_8$–$C_{12}$ arylcarbonyloxyalkyloxy, $C_5$–$C_{10}$ alkoxyalkylcarbonyloxyalkyloxy, $C_5$–$C_{10}$ (5-alkyl-1,3-dioxa-cyclopenten-2-one-yl)methyloxy, $C_{10}$–$C_{14}$ (5-aryl-1,3-dioxa-cyclopenten-2-one-yl)methyloxy, or $(R^{11})(R^{12})N$—($C_1$–$C_{10}$ alkoxy)-;

$R^{20}$ selected from: H, $C_1$–$C_6$ alkyl, $C_3$–$C_7$ cycloalkyl, $C_4$–$C_{11}$ cycloalkylalkyl, aryl($C_1$–$C_6$ alkyl)-, or heteroaryl($C_1$–$C_6$ alkyl)-;

$R^{21}$ is selected from COOH or $NR^6_2$;

m is 0–4;

n is 0–4;

t is 0–4;

p is 0–2;

q is 0–2; and r is 0–2.

13. A compound of claim 11 of the Formula IIe or IIf:

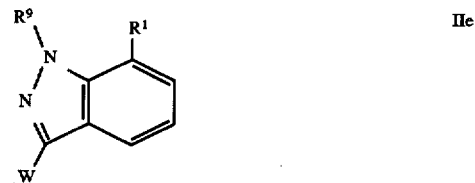

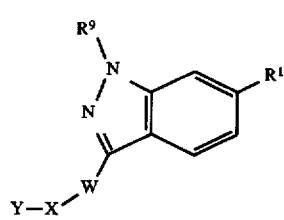

and pharmaceutically acceptable salt forms thereof, wherein:

$R^1$ is selected from:

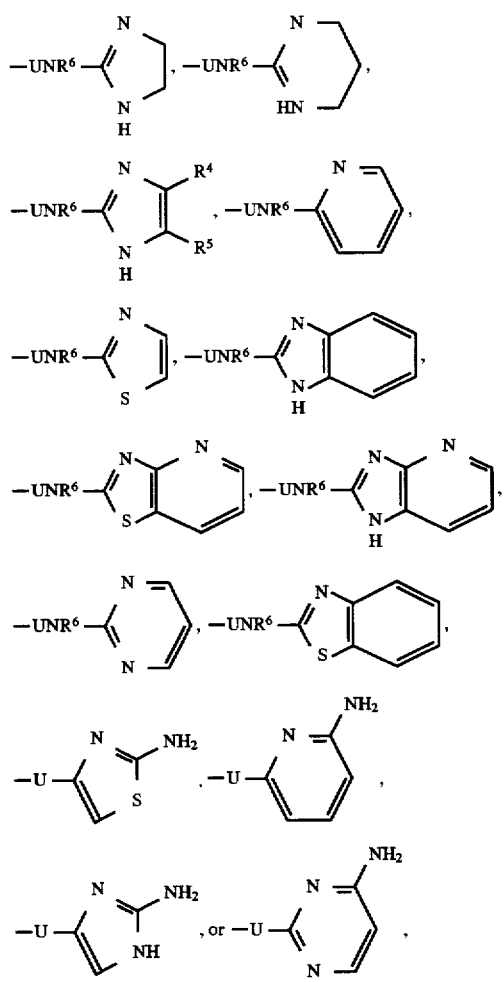

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl;

U is $-(CH_2)_n-$, $-(CH_2)_tQ(CH_2)_m-$ or $-(=O)(CH_2)_{n-1}-$, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ is selected from: H, $C_1$–$C_4$ alkyl, or benzyl;

$R^7$ is selected from: $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, $-SO_2R^{17}$, $-SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$;

W is $-C(=O)-N(R^{13})-$;

X is $-CH(R^{14})-CH(R^{15})-$;

$R^{13}$ is H or $CH_3$;

$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

is $-COR^{19}$;

$R^{16}$ is selected from:
$-NH(R^{20})-C(=O)-O-R^{17}$,
$-N(R^{20})-C(=O)-R^{17}$,
$-N(R^{20})-C(=O)-NH-R^{17}$,
$-N(R^{20})SO_2-R^{17}$, or
$-N(R^{20})SO_2-N(R^{20})R^{17}$;

$^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6{}_2$; and m is 0 or 1;

n is 1–4; and t is 0 or 1.

14. A compound of claim 11 of the Formula IIe or IIf:

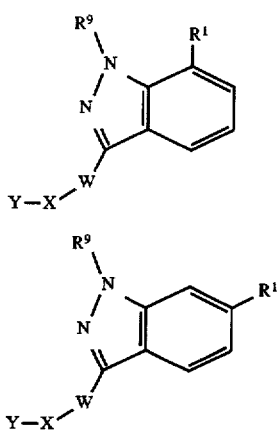

and pharmaceutically acceptable salt forms thereof, wherein:

$R^1$ is selected from:

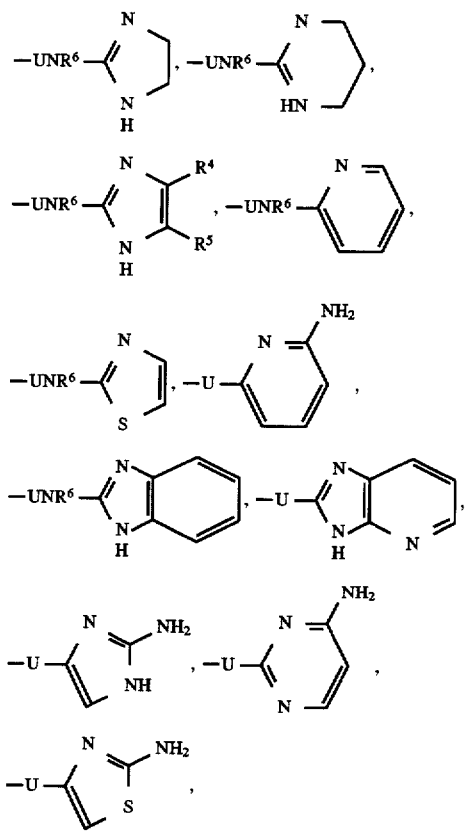

wherein the above heterocycles are optionally substituted with 0–2 substituents selected from the group consisting of: $NH_2$, halogen, $NO_2$, CN, $CF_3$, $C_1$–$C_4$ alkoxy, $C_1$–$C_6$ alkyl, and $C_3$–$C_7$ cycloalkyl:

U is —$(CH_2)_n$—, —$(CH_2)_nQ(CH_2)_m$— or —C(=O)$(CH_2)_{n-1}$—, wherein one of the methylene groups is optionally substituted with $R^7$;

Q is selected from 1,2-phenylene, 1,3-phenylene, 2,3-pyridinylene, 3,4-pyridinylene, or 2,4-pyridinylene;

$R^6$ selected from: H, $C_1$–$C_4$ alkyl, or benzyl;

$R^7$ is selected from $C_1$–$C_6$ alkyl, $C_3$–$C_7$ cycloalkyl, $C_4$–$C_{11}$ cycloalkylalkyl, aryl, aryl($C_1$–$C_6$ alkyl), heteroaryl, or heteroaryl($C_1$–$C_6$ alkyl);

$R^9$ is selected from: H, —$SO_2R^{17}$, —$SO_2NR^{17}R^{20}$, $C_1$–$C_6$ alkyl substituted with 0–1 $R^{15}$ or 0–1 $R^{21}$, $C_3$–$C_7$ cycloalkyl substituted with 0–1 $R^{15}$ or 0–1 $R^{21}$, $C_4$–$C_{11}$ cycloalkylalkyl substituted with 0–1 $R^{15}$ or 0–1 $R^{21}$, aryl substituted with 0–1 $R^{15}$ or 0–2 $R^{11}$ or 0–1 $R^{21}$, or aryl($C_1$–$C_6$ alkyl)- substituted with 0–1 $R^{15}$ or 0–2 $R^{11}$ or 0–1 $R^{21}$;

$R^{11}$ is selected from H, halogen, $CF_3$, CN, $NO_2$, hydroxy, $NR^2R^3$, $C_1$–$C_4$ alkyl substituted with 0–1 $R^{21}$, $C_1$–$C_4$ alkoxy substituted with 0–1 $R^{21}$, aryl substituted with 0–1 $R^{21}$, aryl($C_1$–$C_6$ alkyl)- substituted with 0–1 $R^{21}$, ($C_1$–$C_4$ alkoxy)carbonyl substituted with 0–1 $R^{21}$, ($C_1$–$C_4$ alkyl)carbonyl substituted with 0–1 $R^{21}$, $C_1$–$C_4$ alkylsulfonyl substituted with 0–1 $R^{21}$, or $C_1$–$C_4$ alkylaminosulfonyl substituted with 0–1 $R^{21}$; W is —C(=O)—N($R^{13}$)—;

W is —C(=O)—N($R^{13}$)—;

X is —CH($R^{14}$)—CH($R^{15}$)—;

$R^{13}$ is H or $CH_3$;

$R^{14}$ is selected from:
H, $C_1$–$C_{10}$ alkyl, aryl, or heteroaryl, wherein said aryl or heteroaryl groups are optionally substituted with 0–3 substituents selected from the group consisting of: $C_1$–$C_4$ alkyl, $C_1$–$C_4$ alkoxy, aryl, halo, cyano, amino, $CF_3$, and $NO_2$;

$R^{15}$ is H or $R^{16}$;

Y is —$COR^{19}$;

$R^{16}$ is selected from:
—NH($R^{20}$)—C(=O—O—$R^{17}$,
—N($R^{20}$)—C(=O)—$R^{17}$,
—N($R^{20}$)—C(=O)—NH—$R^{17}$,
—N($R^{20}$)$SO_2$—$R^{17}$, or
—N($R^{20}$)$SO_2$—$NR^{20}R^{17}$;

$R^{17}$ is selected from:
$C_1$–$C_{10}$ alkyl, $C_3$–$C_{11}$ cycloalkyl, aryl($C_1$–$C_6$ alkyl)-, ($C_1$–$C_6$ alkyl)aryl, heteroaryl($C_1$–$C_6$ alkyl)-, ($C_1$–$C_6$ alkyl)heteroaryl, biaryl($C_1$–$C_6$ alkyl)-, heteroaryl, or aryl, wherein said aryl or heteroaryl groups are optionally substituted with 0–3 substituents selected from the group consisting of: $C_1$–$C_4$ alkyl, $C_1$–$C_4$ alkoxy, aryl, heteroaryl, halo, cyano, amino, $CF_3$, and $NO_2$;

$R^{19}$ is selected from:
hydroxy, $C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-, or
1-(2-(2-methoxypropyl)carbonyloxy)ethoxy-;

$R^{20}$ is H or $CH_3$;

$R^{21}$ is selected from COOH or $NR^6{}_2$; and m is 0 or 1;

n is 1–4; and t is 0 or 1.

15. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of any one of claims 1–14.

16. A pharmaceutical composition comprising a pharmaceutically acceptable carrier and a compound of any one of claims 1–14.

* * * * *